(12) United States Patent
Johnson et al.

(10) Patent No.: US 12,084,415 B2
(45) Date of Patent: Sep. 10, 2024

(54) BIOMOLECULE-POLYMER-PHARMACEUTICAL AGENT CONJUGATES FOR DELIVERING THE PHARMACEUTICAL AGENT

(71) Applicant: Massachusetts Institute of Technology, Cambridge, MA (US)

(72) Inventors: Jeremiah A. Johnson, Boston, MA (US); Hung Vanthanh Nguyen, Braintree, MA (US); Peyton Shieh, Cambridge, MA (US); Wencong Wang, Cambridge, MA (US); Bin Liu, Hopkinton, MA (US); Valerie Lensch, Cambridge, MA (US); Landon Kilgallon, Cambridge, MA (US); Yutong Dai, Somerville, MA (US); Samantha Lynn Kristufek, Lubbock, TX (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/970,533

(22) Filed: Oct. 20, 2022

(65) Prior Publication Data

US 2023/0192610 A1    Jun. 22, 2023

Related U.S. Application Data

(60) Provisional application No. 63/291,937, filed on Dec. 20, 2021.

(51) Int. Cl.
| | | |
|---|---|---|
| C08G 61/08 | (2006.01) | |
| C07C 233/60 | (2006.01) | |
| C07C 301/02 | (2006.01) | |
| C07D 207/277 | (2006.01) | |
| C07D 257/08 | (2006.01) | |

(52) U.S. Cl.
CPC ........ *C07D 207/277* (2013.01); *C07C 233/60* (2013.01); *C07C 301/02* (2013.01); *C07D 257/08* (2013.01); *C08G 61/08* (2013.01); *C08G 2261/136* (2013.01); *C08G 2261/1424* (2013.01); *C08G 2261/1432* (2013.01); *C08G 2261/1646* (2013.01); *C08G 2261/354* (2013.01); *C08G 2261/418* (2013.01)

(58) Field of Classification Search
USPC ....................................................... 528/423
See application file for complete search history.

(56) References Cited

U.S. PATENT DOCUMENTS

| | | | |
|---|---|---|---|
| 3,256,308 A | 6/1966 | Pawloski et al. | |
| 3,337,598 A | 8/1967 | Pawloski et al. | |
| 4,359,425 A | 11/1982 | Totani et al. | |
| 4,510,136 A | 4/1985 | Moberg | |
| 5,811,515 A | 9/1998 | Grubbs et al. | |
| 6,812,238 B1 | 11/2004 | Fukuda et al. | |
| 7,183,059 B2 | 2/2007 | Verdine et al. | |
| 8,067,505 B2 | 11/2011 | Harris et al. | |
| 8,968,920 B2 | 3/2015 | Lee et al. | |
| 9,381,253 B2 | 7/2016 | Johnson et al. | |
| 9,447,129 B2 | 9/2016 | Johnson et al. | |
| 9,822,216 B2 | 11/2017 | Mahanthappa et al. | |
| 10,023,536 B2 | 7/2018 | Johnson et al. | |
| 10,105,449 B2 | 10/2018 | Johnson et al. | |
| 10,153,513 B2 | 12/2018 | Grubbs et al. | |
| 10,159,749 B2 | 12/2018 | Johnson et al. | |
| 10,683,387 B2 | 6/2020 | Johnson et al. | |
| 10,716,858 B2 | 7/2020 | Johnson et al. | |
| 10,792,373 B2 | 10/2020 | Johnson et al. | |
| 10,793,683 B2 | 10/2020 | Johnson et al. | |
| 10,799,594 B2 | 10/2020 | Johnson et al. | |
| 10,961,338 B2 | 3/2021 | Johnson et al. | |
| 10,973,847 B2 | 4/2021 | Johnson et al. | |
| 10,988,491 B2 | 4/2021 | Johnson et al. | |
| 11,752,221 B2 | 9/2023 | Johnson et al. | |
| 2002/0183473 A1 | 12/2002 | Matyjaszewski et al. | |
| 2002/0198328 A1 | 12/2002 | L'alloret | |
| 2003/0004364 A1 | 1/2003 | Yaghi et al. | |
| 2003/0065023 A1 | 4/2003 | Swindell et al. | |
| 2005/0109976 A1 | 5/2005 | Fuchs et al. | |
| 2008/0063937 A1 | 3/2008 | Lee et al. | |
| 2011/0166128 A1 | 7/2011 | Remenar et al. | |
| 2011/0243848 A1 | 10/2011 | Appel et al. | |
| 2011/0300219 A1 | 12/2011 | Lippard et al. | |

(Continued)

FOREIGN PATENT DOCUMENTS

| | | | |
|---|---|---|---|
| CN | 101412792 A | 4/2009 | |
| CN | 103819486 A | 5/2014 | |

(Continued)

OTHER PUBLICATIONS

U.S. Appl. No. 17/751,540, filed May 23, 2022, Johnson et al.
U.S. Appl. No. 17/970,533, filed Oct. 20, 2022, Johnson et al.
Extended European Search Report for EP 14782253.0, mailed Nov. 11, 2016.
International Search Report and Written Opinion for PCT/US2014/033554, mailed Aug. 29, 2014.
International Preliminary Report on Patentability for PCT/US2014/033554, mailed Oct. 22, 2015.
International Search Report for PCT/US2017/036447, mailed Sep. 7, 2017.
International Preliminary Report on Patentability for Application No. PCT/US2017/036447 mailed Dec. 20, 2018.
International Search Report and Written Opinion for PCT/US2017/055145, mailed Jan. 23, 2018.

(Continued)

*Primary Examiner* — Terressa Boykin
(74) *Attorney, Agent, or Firm* — Wolf, Greenfield & Sacks, P.C.

(57) ABSTRACT

The present disclosure provides enynes, end-functionalized polymers, conjugates, methods of preparation, compositions, kits, and methods of use. The conjugates comprise at least (1) a peptide (e.g., an antibody), protein, nucleoprotein, mucoprotein, lipoprotein, glycoprotein, or polynucleotide; and (2) a polymer comprising a pharmaceutical agent. The conjugates may be useful in delivering (e.g., targeted delivering) the pharmaceutical agent to a subject in need thereof or cell or treating, preventing, or diagnosing a disease.

30 Claims, 82 Drawing Sheets

(56) References Cited

U.S. PATENT DOCUMENTS

| | | |
|---|---|---|
| 2013/0296491 A1 | 11/2013 | Xia et al. |
| 2013/0324666 A1 | 12/2013 | Xia et al. |
| 2014/0024137 A1 | 1/2014 | Arya et al. |
| 2014/0142249 A1 | 5/2014 | Cho et al. |
| 2014/0308234 A1 | 10/2014 | Johnson et al. |
| 2015/0225438 A1 | 8/2015 | Johnson et al. |
| 2015/0291562 A1 | 10/2015 | Crew et al. |
| 2016/0024246 A1 | 1/2016 | Mahanthappa et al. |
| 2016/0289392 A1 | 10/2016 | Grubbs et al. |
| 2016/0296631 A1 | 10/2016 | Johnson et al. |
| 2016/0361702 A1 | 12/2016 | Cohen et al. |
| 2017/0000909 A1 | 1/2017 | Gianneschi et al. |
| 2017/0073311 A1 | 3/2017 | Johnson et al. |
| 2017/0348431 A1 | 12/2017 | Johnson et al. |
| 2018/0030213 A1 | 2/2018 | Johnson et al. |
| 2018/0036415 A9 | 2/2018 | Johnson et al. |
| 2018/0094099 A1 | 4/2018 | Johnson et al. |
| 2018/0312634 A1 | 11/2018 | Chung |
| 2019/0030067 A1 | 1/2019 | Johnson et al. |
| 2019/0038751 A1 | 2/2019 | Johnson et al. |
| 2019/0038782 A1 | 2/2019 | Johnson et al. |
| 2019/0054187 A1 | 2/2019 | Johnson et al. |
| 2019/0192672 A1 | 6/2019 | Johnson et al. |
| 2020/0055879 A1 | 2/2020 | Johnson et al. |
| 2020/0123297 A1 | 4/2020 | Johnson et al. |
| 2020/0239626 A1 | 7/2020 | Miyake et al. |
| 2020/0261596 A1 | 8/2020 | Ali et al. |
| 2020/0362095 A1 | 11/2020 | Johnson et al. |
| 2020/0369685 A1 | 11/2020 | Johnson et al. |
| 2021/0023224 A1 | 1/2021 | Johnson et al. |
| 2021/0113701 A1 | 4/2021 | Johnson et al. |
| 2021/0147598 A1 | 5/2021 | Johnson et al. |
| 2021/0220391 A1 | 7/2021 | Johnson et al. |
| 2021/0284664 A1 | 9/2021 | Johnson et al. |
| 2021/0317143 A9 | 10/2021 | Johnson et al. |
| 2021/0386861 A1 | 12/2021 | Johnson et al. |
| 2022/0370628 A9 | 11/2022 | Johnson et al. |
| 2023/0068959 A1 | 3/2023 | Johnson et al. |

FOREIGN PATENT DOCUMENTS

| | | |
|---|---|---|
| CN | 108727581 A | 11/2018 |
| DE | 2263509 A1 | 7/1974 |
| EP | 3315126 A1 | 5/2018 |
| EP | 3584245 A1 | 12/2019 |
| JP | H05-112739 A | 5/1993 |
| KR | 20120113694 A | 10/2012 |
| WO | WO 2001/032652 A2 | 5/2001 |
| WO | WO 2010/047765 A2 | 4/2010 |
| WO | WO 2011/084846 A1 | 7/2011 |
| WO | WO 2013/010676 A2 | 1/2013 |
| WO | WO 2013/169739 A1 | 11/2013 |
| WO | WO 2014/004884 A1 | 1/2014 |
| WO | WO 2014/169073 A1 | 10/2014 |
| WO | WO 2016/023036 A1 | 2/2016 |
| WO | WO 2016/172386 A1 | 10/2016 |
| WO | WO 2017/180834 A1 | 10/2017 |
| WO | WO 2018/106738 A1 | 6/2018 |
| WO | WO 2018/149359 A1 | 8/2018 |
| WO | WO 2019/006426 A2 | 1/2019 |
| WO | WO 2019/200367 A1 | 10/2019 |
| WO | WO 2019/201123 A1 | 10/2019 |

OTHER PUBLICATIONS

International Preliminary Report on Patentability for PCT/US2017/055145, mailed Apr. 18, 2019.
International Search Report and Written Opinion for PCT/US2017/064784, mailed Mar. 1, 2018.
International Preliminary Report on Patentability for PCT/US2017/064784, mailed Jun. 20, 2019.
International Search Report and Written Opinion for PCT/US2017/48641, mailed Nov. 9, 2017.
International Preliminary Report on Patentability for PCT/US2017/48641 mailed Mar. 7, 2019.
International Search Report and Written Opinion for PCT/US2018/040488, mailed Oct. 15, 2018.
International Preliminary Report on Patentability for PCT/US2018/040488, mailed Jan. 9, 2020.
International Search Report and Written Opinion for PCT/US2018/040494, mailed Oct. 10, 2018.
International Preliminary Report on Patentability for PCT/US2018/040494, mailed Jan. 9, 2020.
Invitation to Pay Additional Fees for PCT/US2018/040496, mailed on Nov. 21, 2018.
International Search Report and Written Opinion for Application No. PCT/US2018/040496 mailed Jan. 14, 2019.
International Preliminary Report on Patentability for PCT/US2018/040496, mailed Jan. 9, 2020.
International Search Report and Written Opinion for PCT/US2019/027414, mailed on Sep. 12, 2019.
International Preliminary Report on Patentability for PCT/US2019/027414, mailed on Oct. 22, 2020.
International Search Report and Written Opinion for PCT/US2019/046872, mailed on Oct. 29, 2019.
International Preliminary Report on Patentability for PCT/US2019/046872, mailed on Mar. 4, 2021.
International Search Report and Written Opinion for PCT/US2020/023836, mailed on Jul. 7, 2020.
International Preliminary Report on Patentability for PCT/US2020/023836, mailed on Dec. 2, 2021.
Invitation to Pay Additional Fees for PCT/US2020/059827 mailed Feb. 4, 2021.
International Search Report and Written Opinion for PCT/US2020/059827 mailed Mar. 15, 2021.
International Preliminary Report on Patentability for PCT/US2020/059827 mailed Jul. 21, 2022.
Invitation to Pay Additional Fees for PCT/US2020/055862, mailed on Feb. 12, 2021.
International Search Report and Written Opinion for PCT/US2020/055862 mailed May 6, 2021.
International Preliminary Report on Patentability for PCT/US2020/055862 mailed Apr. 28, 2022.
International Search Report and Written Opinion for PCT/US2022/047333 mailed Jan. 25, 2023.
[No Author Listed], 2-Propen-1-amine, 3-(2-methoxyphenyl)-N-2-propyn-1-yl. CAS Registry File RN 1883141-01-2. STN Entry Date Mar. 10, 2016.
Aguirre-Chagala et al., Phenylboronic Acid-Installed Polycarbonates for the ph-Dependent Release of Diol-Containing Molecules. ACS Macro Letters. Nov. 20, 2014;3(12):1249-1253.
Ahn et al., Two-photon fluorescence microscopy imaging of cellular oxidative stress using profluorescent nitroxides. J Am Chem Soc. Mar. 14, 2012;134(10):4721-30. doi: 10.1021/ja210315x. Epub Mar. 1, 2012.
Aime et al., Lanthanide(III) chelates for NMR biomedical applications. Chem Soc Rev. 1998;27:19-29. doi: 10.1039/A827019Z.
Aime et al., Pushing the sensitivity envelope of lanthanide-based magnetic resonance imaging (MRI) contrast agents for molecular imaging applications. Acc Chem Res. Jul. 21, 2009;42(7):822-31. doi: 10.1021/ar800192p.
Alge et al., Synthetically tractable click hydrogels for three-dimensional cell culture formed using tetrazine-norbornene chemistry. Biomacromolecules. Apr. 8, 2013;14(4):949-53. doi: 10.1021/bm4000508. Epub Mar. 8, 2013.
Altintas et al., Constructing star polymersvia modular ligation strategies. Polym. Chem., 2012;3:34-45. DOI: 10.1039/C1PY00249J.
Alvaredejo et al., Polyoxazoline-Based Bottlebrush and Brush-Arm Star Polymers via ROMP: Syntheses and Applications as Organic Radical Contrast Agents. ACS Macro Lett. Apr. 16, 2019;8(4):473-478. doi: 10.1021/acsmacrolett.9b00016. Epub Apr. 4, 2019.
Amouri et al., Host-guest interactions: design strategy and structure of an unusual cobalt cage that encapsulates a tetrafluoroborate anion. Angew Chem Int Ed Engl. Jul. 18, 2005;44(29):4543-6.

(56) References Cited

OTHER PUBLICATIONS

Anderson, Late Transition Metal Complexes of Pentafluorophenylphosphino-Pincer Ligands. Doctoral Thesis. Victoria University of Wellington. 2012:ii, iii, 32.
Angelov et al., EPR and rheological study of hybrid interfaces in gold-clay-epoxy nanocomposites. Langmuir. Nov. 11, 2014;30(44):13411-21. doi: 10.1021/la503361k. Epub Oct. 30, 2014.
Angot et al., Living Radical Polymerization Immobilized on Wang Resins: Synthesis and Harvest of Narrow Polydispersity Poly(methacrylate)s. Macromolecules, 2001;34(4):768-774. DOI: 10.1021/ma0011690.
Anraku et al., Size-controlled long-circulating PICsome as a ruler to measure critical cut-off disposition size into normal and tumor tissues. Chem Commun (Camb). Jun. 7, 2011;47(21):6054-6. doi: 10.1039/c1cc11465d. Epub Apr. 26, 2011.
Arvizo et al., Modulating pharmacokinetics, tumor uptake and biodistribution by engineered nanoparticles. PLoS One. 2011;6(9):e24374. doi: 10.1371/journal.pone.0024374. Epub Sep. 13, 2011.
Aryal et al., Polymeric nanoparticles with precise ratiometric control over drug loading for combination therapy. Mol Pharm. Aug. 1, 2011;8(4):1401-7. doi: 10.1021/mp200243k. Epub Jul. 6, 2011.
Bapat et al., Dynamic-covalent nanostructures prepared by Diels-Alder reactions of styrene-maleic anhydride-derived copolymers obtained by one-step cascade block copolymerization. Polym. Chem., 2012;3:3112-3120. DOI: 10.1039/C2PY20351K.
Bapat et al., Redox-Responsive Dynamic-Covalent Assemblies: Stars and Miktoarm Stars. Macromolecules, 2013;46(6):2188-2198. DOI: 10.1021/ma400169m.
Bar-Shir et al., Single 19F Probe for Simultaneous Detection of Multiple Metal Ions Using miCEST MRI. J. Am. Chem. Soc., 2015;137(1):78-81. DOI: 10.1021/ja511313k.
Barbour et al., An intermolecular (H2O)10 cluster in a solid-state supramolecular complex. Nature. 1998;393(6686): 671-673.
Barner-Kowollik et al., Synthesis of core-shell poly(divinylbenzene) microspheres via reversible addition fragmentation chain transfer graft polymerization of styrene. J. Polym. Sci. A Polym. Chem., 2006;42:5067-5076. doi:10.1002/pola.20328.
Barnes et al., Using an RNAi Signature Assay To Guide the Design of Three-Drug-Conjugated Nanoparticles with Validated Mechanisms, In Vivo Efficacy, and Low Toxicity. J Am Chem Soc. Sep. 28, 2016;138(38):12494-501. doi: 10.1021/jacs.6b06321. Epub Sep. 14, 2016.
Barrett et al., pH-Based Regulation of Hydrogel Mechanical Properties Through Mussel-Inspired Chemistry and Processing. Advanced Functional Materials. Mar. 6, 2013;23(9):1111-1119.
Bates et al., Polarity-switching top coats enable orientation of sub-10-nm block copolymer domains. Science. Nov. 9, 2012;338(6108):775-9. doi: 10.1126/science.1226046.
Beck et al., Multistimuli, multiresponsive metallo-supramolecular polymers. J Am Chem Soc. Nov. 19, 2003;125(46):13922-3.
Bender et al., Site-isolated luminescent europium complexes with polyester macroligands: metal-centered heteroarm stars and nanoscale assemblies with labile block junctions. J Am Chem Soc. Jul. 24, 2002;124(29):8526-7.
Blencowe et al., Core cross-linked star polymers via controlled radical polymerisation. Polymer Jan. 2009;50(1):5-32.
Blencowe et al., Ring-opening metathesis polymerization with the second generation Hoveyda-Grubbs catalyst: an efficient approach toward high-purity functionalized macrocyclic oligo(cyclooctene)s. J Am Chem Soc. Apr. 17, 2013;135(15):5717-25. doi: 10.1021/ja312418z. Epub Apr. 8, 2013.
Blinco et al., Profluorescent Nitroxides as Sensitive Probes of Oxidative Change and Free Radical Reactions. Australian Journal of Chemistry 2010;64(4):373-389. https://doi.org/10.1071/CH10442.
Boase et al., Molecular imaging with polymers. Polym. Chem., 2012,3, 1384-1389. DOI: 10.1039/C2PY20132A.
Bobko et al., Reversible reduction of nitroxides to hydroxylamines: roles for ascorbate and glutathione. Free Radic Biol Med. Feb. 1, 2007;42(3):404-12. Epub Nov. 10, 2006.
Bohbot-Raviv et al., Discovering new ordered phases of block copolymers. Phys Rev Lett. Oct. 16, 2000;85(16):3428.
Bolton et al., Synthesis and Melt Self-Assembly of PS-PMMA-PLA Triblock Bottlebrush Copolymers. Macromolecules, 2014;47(9):2864-74. DOI: 10.1021/ma500625k.
Borke et al., Poly(glyceryl glycerol): A multi-functional hydrophilic polymer for labeling with boronic acids. Polym Chem. Jun. 1, 2017;55(11):1822-30. doi: 10.1002/pola.28497.
Brasch et al., Work in progress: nuclear magnetic resonance study of a paramagnetic nitroxide contrast agent for enhancement of renal structures in experimental animals. Radiology. Jun. 1983;147(3):773-9.
Brasch, Work in progress: methods of contrast enhancement for NMR imaging and potential applications. A subject review. Radiology. Jun. 1983;147(3):781-8.
Brummelhuis et al., Stimuli-responsive star polymers through thiol-yne core functionalization/crosslinking of block copolymer micelles. Polym. Chem., 2011;2:1180-1184. DOI: 10.1039/C1PY00002K.
Budil et al., Nonlinear-Least-Squares Analysis of Slow-Motion EPR Spectra in One and Two Dimensions Using a Modified Levenberg-Marquardt Algorithm. Elsevier. Journal of Magnetic Resonance, Series A. Jun. 1996;120(2):155-189.
Buerkle et al., Supramolecular gels formed from multi-component low molecular weight species. Chem Soc Rev. Sep. 21, 2012;41(18):6089-102. doi: 10.1039/c2cs35106d. Epub Jun. 7, 2012.
Bunzen et al., Self-assembly of M24L48 polyhedra based on empirical prediction. Angew Chem Int Ed Engl. Mar. 26, 2012;51(13):3161-3. doi: 10.1002/anie.201108731.
Burdynska et al., Synthesis of Star Polymers Using ARGET ATRP. Macromolecules, 2010;43(22):9227-9229. DOI: 10.1021/ma101971z.
Burnworth et al., Decoupling Optical Properties in Metallo-Supramolecular Poly (p-phenylene ethynylene)s. Macromolecules. 2008;41(6):2157-2163.
Burts et al., Brush-first and click: efficient synthesis of nanoparticles that degrade and release doxorubicin in response to light. Photochem Photobiol. Mar.-Apr. 2014;90(2):380-5. doi: 10.1111/php.12182. Epub Nov. 25, 2013.
Burts et al., Brush-first synthesis of core-photodegradable miktoarm star polymers via ROMP: towards photoresponsive self-assemblies. Macromol Rapid Commun. Jan. 2014;35(2):168-173. doi: 10.1002/marc.201300618. Epub Nov. 22, 2013.
Burts et al., Using EPR to Compare PEG-branch-nitroxide "Bivalent-Brush Polymers" and Traditional PEG Bottle—Brush Polymers: Branching Makes a Difference. Macromolecules. 2012;45(20):8310-18.
Cabral et al., Accumulation of sub-100 nm polymeric micelles in poorly permeable tumours depends on size. Nat Nanotechnol. Oct. 23, 2011;6(12):815-23. doi: 10.1038/nnano.2011.166.
Caiolfa et al., Polymer-bound camptothecin: initial biodistribution and antitumour activity studies. J Control Release. Mar. 1, 2000;65(1-2):105-19.
Campos-Fernández et al., A One-Pot, High-Yield Synthesis of a Paramagnetic Nickel Square from Divergent Precursors by Anion Template Assembly. Angewandte Chemie International Edition. Dec. 3, 1999;38(23):3477-3479.
Campos-Fernández et al., Fine-tuning the ring-size of metal-lacyclophanes: a rational approach to molecular pentagons. J Am Chem Soc. Jan. 31, 2001;123(4):773-4.
Cannon, J.G., Analog Design. In: Burger's Medicinal Chemistry and Drug Discovery, Fifth Edition, vol. I: Principles and Practice. 1995. Burger, Ed. Wiley Interscience. Chapter 19:783-802.
Caravan et al., Gadolinium(III) Chelates as MRI Contrast Agents: Structure, Dynamics, and Applications. Chem Rev. Sep. 8, 1999;99(9):2293-352.
Castilla et al., Stereochemistry in subcomponent self-assembly. Acc Chem Res. Jul. 15, 2014;47(7):2063-73. doi: 10.1021/ar5000924. Epub May 2, 2014.
Chambron et al., Topologically complex molecules obtained by transition metal templation: it is the presentation that determines the synthesis strategy. New Journal of Chemistry. 2013;37(1):49-57.

(56) References Cited

OTHER PUBLICATIONS

Chand et al., Self-assembly of a novel macrotricyclic Pd(II) metallocage encapsulating a nitrate ion. Chem Commun (Camb). Sep. 7, 2001;(17):1652-3.

Chang et al., Dose-dense chemotherapy improves mechanisms of antitumor immune response. Cancer Res. Jan. 1, 2013;73(1):119-27. doi: 10.1158/0008-5472.CAN-12-2225. Epub Oct. 29, 2012.

Chen et al., Polymeric phosphorylcholine-camptothecin conjugates prepared by controlled free radical polymerization and click chemistry. Bioconjug Chem. Dec. 2009;20(12):2331-41. doi: 10.1021/bc900339x.

Chen et al., Synthesis of superporous hydrogels: hydrogels with fast swelling and superabsorbent properties. J Biomed Mater Res. Jan. 1999;44(1):53-62.

Cheng et al., Well-defined diblock macromonomer with a norbornene group at block junction: anionic living linking synthesis and ring-opening metathesis polymerization. Macromol. Mar. 4, 2010;43(7):3153-5.

Cheon et al., Synergistically integrated nanoparticles as multimodal probes for nanobiotechnology. Acc Chem Res. Dec. 2008;41(12):1630-40. doi: 10.1021/ar800045c.

Chiang et al., Vitamin D for the prevention and treatment of pancreatic cancer. World J Gastroenterol. Jul. 21, 2009;15(27):3349-54.

Chifotides et al., Anion-π interactions in supramolecular architectures. Acc Chem Res. Apr. 16, 2013;46(4):894-906. doi: 10.1021/ar300251k. Epub Mar. 11, 2013.

Choi et al., Self-confirming "AND" logic nanoparticles for fault-free MRI. J Am Chem Soc. Aug. 18, 2010;132(32):11015-7. doi: 10.1021/ja104503g.

Chou et al., In vitro and in vivo studies of FePt nanoparticles for dual modal CT/MRI molecular imaging. J Am Chem Soc. Sep. 29, 2010;132(38):13270-8. doi: 10.1021/ja1035013.

Clark et al., Dynamically Restructuring Hydrogel Networks Formed with Reversible Covalent Crosslinks. Advanced Materials. 2007;19:2503-2507. 10.1002/adma.200602649.

Clever et al., Inclusion of anionic guests inside a molecular cage with palladium(II) centers as electrostatic anchors. Angew Chem Int Ed Engl. 2009;48(38):7010-2. doi: 10.1002/anie.200902717.

Cok et al., Synthesis of Model Network Hydrogels via Tetrazine-Olefin Inverse Electron Demand Diels-Alder Cycloaddition. Macromolecular Symposia. Jul. 2013;329(1):108-112.

Collins et al., Chemical approaches to targeted protein degradation through modulation of the ubiquitin-proteasome pathway. Biochem J. Mar. 15, 2017;474(7):1127-1147. doi: 10.1042/BCJ20160762.

Conrad et al., Tunable, temperature-responsive polynorbornenes with side chains based on an elastin peptide sequence. Angew Chem Int Ed Engl. 2009;48(44):8328-30. doi: 10.1002/anie.200903888.

Cordier et al., Self-healing and thermoreversible rubber from supramolecular assembly. Nature. Feb. 21, 2008;451(7181):977-80. doi: 10.1038/nature06669.

Corey et al., Diisopropylsilyl ditriflate and di-tert-butysilyl ditriflate: new reagents for the protection of diols. Tetrahedron Letters. 1982;23(47):4871-4874.

Dag et al., Three-arm star ring opening metathesis polymers via alkyne-azide click reaction. J. Polym. Sci. A Polym. Chem., 2009;47:2344-2351. doi:10.1002/pola.23324.

Dalsin et al., Bottlebrush block polymers: Quantitative theory and experiments. ACS Nano. Nov. 6, 2015;9(12):12233-45.

Davies et al., Environmentally responsive MRI contrast agents. Chem Commun (Camb). Oct. 28, 2013;49(84):9704-21. doi: 10.1039/c3cc44268c.

Davis et al., A novel nitroxide is an effective brain redox imaging contrast agent and in vivo radioprotector. Free Radic Biol Med. Aug. 1, 2011;51(3):780-90. doi: 10.1016/j.freeradbiomed.2011.05.019. Epub May 25, 2011.

Davis et al., Atom transfer radical polymerization of tert-butyl acrylate and preparation of block copolymers. Macromol. May 30, 2000;33(11):4039-47.

Davis et al., Nanoparticle therapeutics: an emerging treatment modality for cancer. Nat Rev Drug Discov. Sep. 2008;7(9):771-82. doi: 10.1038/nrd2614.

Desmarets et al., Design, Self-Assembly, and Molecular Structures of 3D Copper(II) Capsules Templated by BF4-Guest Anions. European Journal of Inorganic Chemistry. Oct. 2009;(29-30):4396-4400. doi: 10.1002/ejic.200900606.

Detappe et al., Advanced multimodal nanoparticles delay tumor progression with clinical radiation therapy. J Control Release. Sep. 28, 2016;238:103-113. doi: 10.1016/j.jconrel.2016.07.021. Epub Jul. 14, 2016.

Dhar et al., Polyvalent oligonucleotide gold nanoparticle conjugates as delivery vehicles for platinum(IV) warheads. J Am Chem Soc. Oct. 21, 2009;131(41):14652-3. doi: 10.1021/ja9071282.

Dhar et al., Targeted delivery of a cisplatin prodrug for safer and more effective prostate cancer therapy in vivo. Proc Natl Acad Sci U S A. Feb. 1, 2011;108(5):1850-5. doi: 10.1073/pnas.1011379108. Epub Jan. 13, 2011.

Dhar et al., Targeted delivery of cisplatin to prostate cancer cells by aptamer functionalized Pt(IV) prodrug-PLGA-PEG nanoparticles. Proc Natl Acad Sci U S A. Nov. 11, 2008;105(45):17356-61. doi: 10.1073/pnas.0809154105. Epub Oct. 31, 2008.

Doane et al., The unique role of nanoparticles in nanomedicine: imaging, drug delivery and therapy. Chem Soc Rev. Apr. 7, 2012;41(7):2885-911. doi: 10.1039/c2cs15260f. Epub Jan. 27, 2012.

Duncan, The dawning era of polymer therapeutics. Nat Rev Drug Discov. May 2003;2(5):347-60.

Durr et al., Mild and Efficient Modular Synthesis of Poly(acrylonitrile-co-butadiene) Block and Miktoarm Star Copolymer Architectures. Macromolecules, 2013;46(1):49-62. DOI: 10.1021/ma302017c.

Elliott et al., Metabolism of brain tissue slices and suspensions from various mammals. J Neurophysiol. Nov. 1948;11(6):473-84.

Eryazici et al., Two Large-Pore Metal-Organic Frameworks Derived from a Single Polytopic Strut. Crystal Growth & Design. Mar. 7, 2012;12(3):1075-1080.

Evans, R.A., The Rise of Azide-Alkyne 1,3-Dipolar 'Click' Cycloaddition and its Application to Polymer Science and Surface Modification. Aust J Chem. Jun. 18, 2007;60(6):384-95. doi: 10.1071/CH06457.

Feng et al., A metabonomic analysis of organ specific response to USPIO administration. Biomaterials. Sep. 2011;32(27):6558-69. doi: 10.1016/j.biomaterials.2011.05.035.

Fenlon et al., The Thread & Cut Method: Syntheses of Molecular Knot Precursors. Eur J Org Chem. Jun. 2008;2008(18):3065-3068.

Ferrauto et al., Frequency-encoded MRI-CEST agents based on paramagnetic liposomes/RBC aggregates. Nano Lett. Dec. 10, 2014;14(12):6857-62. doi: 10.1021/nl5026612. Epub Nov. 10, 2014.

Ferrauto et al., Lanthanide-loaded erythrocytes as highly sensitive chemical exchange saturation transfer MRI contrast agents. J Am Chem Soc. Jan. 15, 2014;136(2):638-41. doi: 10.1021/ja411793u. Epub Dec. 30, 2013.

Fiers et al., Orthogonal Synthesis of Xeno Nucleic Acids. Chemistry. Dec. 12, 2016;22(50):17945-17948. doi: 10.1002/chem.201604386. Epub Nov. 3, 2016.

Forgan et al., Chemical topology: complex molecular knots, links, and entanglements. Chem Rev. Sep. 14, 2011;111(9):5434-64. doi: 10.1021/cr200034u. Epub Jun. 21, 2011.

Foster et al., Differentially Addressable Cavities within Metal-Organic Cage-Cross-Linked Polymeric Hydrogels. J Am Chem Soc. Aug. 5, 2015;137(30):9722-9. doi: 10.1021/jacs.5b05507. Epub Jul. 23, 2015.

Fox et al., Soluble polymer carriers for the treatment of cancer: the importance of molecular architecture. Acc Chem Res. Aug. 18, 2009;42(8):1141-51. doi: 10.1021/ar900035f.

Frechet. Functional polymers and dendrimers: reactivity, molecular architecture, and interfacial energy. Science. Mar. 25, 1994;263(5154):1710-5.

Fullenkamp et al., Mussel-Inspired Histidine-Based Transient Network Metal Coordination Hydrogels. Macromolecules. Jan. 18, 2013;46(3):1167-1174.

Furstner et al., Alkyne metathesis: development of a novel molybdenum-based catalyst system and its application to the total synthesis of

(56) References Cited

OTHER PUBLICATIONS epothilone A and C. Chem Eur J. Dec. 17, 2001;7(24):5299-317. doi: 10.1002/1521-3765(20011217)7:24<5299::aid-chem5299>3.0.co;2-x.

Furstner et al., Mo[N(t-Bu)(Ar)]$_3$ Complexes as Catalyst Precursors: In Situ Activation and Application to Metathesis Reactions of Alkynes and Diynes. J Am Chem Soc. Sep. 23, 1999;121(40):9453-4. doi: 10.1021/ja991340r.

Gallivan et al., A neutral, water-soluble olefin metathesis catalyst based on an N-heterocyclic carbene ligand. Tetrahedron Lett. Apr. 11, 2005;46(15):2577-80. doi: 10.1016/j.tetlet.2005.02.096.

Gao et al., Development of star polymers as unimolecular containers for nanomaterials. Macromol Rapid Commun. May 14, 2012;33(9):722-34. doi: 10.1002/marc.201200005. Epub Mar. 14, 2012.

Gao et al., Modular Approaches to Star and Miktoarm Star Polymers by ATRP of Cross-Linkers. Macromol. Symp., 291-292: 12-16. doi:10.1002/masy.201050502.

Gao et al., Synthesis of Acid-Labile PEG and PEG-Doxorubicin-Conjugate Nanoparticles via Brush-First ROMP. ACS Macro Lett. Sep. 16, 2014;3(9):854-857. Epub Aug. 13, 2014.

Gao et al., Synthesis of functional polymers with controlled architecture by CRP of monomers in the presence of cross-linkers: From stars to gels. Progress in Polymer Science Apr. 2009;34(4):317-350.

Gao et al., Synthesis of Star Polymers by a New "Core-First" Method: Sequential Polymerization of Cross-Linker and Monomer. Macromolecules, 2008;41(4):1118-1125.

Ge et al., A Pyrene-functionalized Polynorbornene for Ratiometric Fluorescence Sensing of Pyrophosphate. Chem. Asian J. 2016;11:687.

Gestwicki et al., Influencing receptor-ligand binding mechanisms with multivalent ligand; architecture. J Am Chem Soc. Dec. 18, 2002;124(50):14922-33.

Gilgorich et al., Palladium-catalyzed reductive coupling of styrenes and organostannanes under aerobic conditions. J Am Chem Soc. Nov. 21, 2007;129(46):14193-5. Epub Oct. 27, 2007.

Glunde et al., Magnetic resonance spectroscopy in metabolic and molecular imaging and diagnosis of cancer. Chem Rev. May 12, 2010;110(5):3043-59. doi: 10.1021/cr9004007.

Godugu et al., Abstract 2139: Effect of telmisartan on triple negative breast cancer (TNBC) and lung cancer tumor progression and intratumoral distribution of nanoparticles. Cancer Res. 2013;73(8).

Goh et al., Highly efficient synthesis of low polydispersity core cross-linked star polymers by Ru-catalyzed living radical polymerization. Macromol Rapid Commun. Mar. 2, 2011;32(5):456-61. doi: 10.1002/marc.201000641. Epub Jan. 7, 2011.

Grahovac et al., Abstract B41: The angiotensin receptor blocker telmisartan inhibits the growth of pancreatic ductal adenocarcinoma and improves survival. Cancer Res. 2016;76(24).

Grason et al., Geometric theory of diblock copolymer phases. Phys Rev Lett. Jul. 31, 2003;91(5):058304.

Greenwald et al., Effective drug delivery by PEGylated drug conjugates. Adv Drug Deliv Rev. Feb. 10, 2003;55(2):217-50.

Grubbs et al., Ring-Closing Metathesis and Related Processes in Organic Synthesis. Acc Chem Res. Nov. 1, 1995;28(11):446-52. doi: 10.1021/ar00059a002.

Gu et al., Mechanism of the reactions of dimethylsilylene with oxetanes. J. Am. Chem. Soc. 1980, 102, 5, 1641-1644.

Gumbley et al., Photoresponsive Polymers Containing Nitrobenzyl Esters via Ring-Opening Metathesis Polymerization. Macromolecules. 2011;44(20):7956-61.

Gupta et al., Cell protective, ABC triblock polymer-based thermoresponsive hydrogels with ROS-triggered degradation and drug release. J Am Chem Soc. Oct. 22, 2014;136(42):14896-902. doi: 10.1021/ja507626y. Epub Oct. 7, 2014.

Hackelbusch et al., Chain Dynamics in Supramolecular Polymer Networks. Macromolecules. 2013;46(15):6273-6286.

Hackelbusch et al., Multiresponsive Polymer Hydrogels by Orthogonal Supramolecular Chain Cross-Linking. Macromolecules. 2014;47(12):4028-4036.

Haddleton et al., Well-defined oligosaccharide-terminated polymers from living radical polymerization. Biomacromolecules. 2000 Summer;1(2):152-6.

Hafkamp et al., Organogel formation and molecular imprinting by functionalized gluconamides and their metal complexes. Chemical Communications. 1997;6:545-546. doi: 10.1039/A608266A.

Hall et al., Platinum(IV) antitumour compounds: their bioinorganic chemistry. Coord Chem Rev. 2002;232:49-67.

Hall et al., The cellular distribution and oxidation state of platinum(II) and platinum(IV) antitumour complexes in cancer cells. J Biol Inorg Chem. Sep. 2003;8(7):726-32. Epub Jul. 12, 2003.

Hamblett et al., Effects of drug loading on the antitumor activity of a monoclonal antibody drug conjugate. Clin Cancer Res. Oct. 15, 2004;10(20):7063-70. doi: 10.1158/1078-0432.CCR-04-0789.

Han et al., Recent Development of Peptide Coupling Reagents in Organic Synthesis. Tetrahedron, 2004;60:2447-2467.

Hansell et al., Additive-free clicking for polymer functionalization and coupling by tetrazine-norbornene chemistry. J Am Chem Soc. Sep. 7, 2011;133(35):13828-31. doi: 10.1021/ja203957h. Epub Aug. 11, 2011.

Hao et al., Dendrimers as scaffolds for multifunctional reversible addition-fragmentation chain transfer agents: Syntheses and polymerization. J. Polym. Sci. A Polym. Chem., 2004;42:5877-5890. doi: 10.1002/pola.20434.

Harrington et al., Holdfast heroics: comparing the molecular and mechanical properties of Mytilus californianus byssal threads. J Exp Biol. Dec. 2007;210(Pt 24):4307-18.

Harrington et al., Iron-clad fibers: a metal-based biological strategy for hard flexible coatings. Science. Apr. 9, 2010;328(5975):216-20. doi: 10.1126/science.1181044. Epub Mar. 4, 2010.

Harris et al., Giant hollow M(n)L(2n) spherical complexes: structure, functionalisation and applications. Chem Commun (Camb). Aug. 4, 2013;49(60):6703-12. doi: 10.1039/c3cc43191f.

Harrison et al., A multimeric MR-optical contrast agent for multimodal imaging. Chem Commun (Camb). Oct. 9, 2014;50(78):11469-71. doi: 10.1039/c4cc05651e.

Harrison et al., Multimeric Near IR-MR Contrast Agent for Multimodal In Vivo Imaging. J Am Chem Soc. Jul. 22, 2015;137(28):9108-16. doi: 10.1021/jacs.5b04509. Epub Jul. 14, 2015.

Harvey et al., Lanthanide Complexes as Paramagnetic Probes for 19F Magnetic Resonance. Eur. J. Inorg. Chem., 2012: 2015-2022. doi: 10.1002/ejic.201100894.

Hatje et al., Increases in Anthropogenic Gadolinium Anomalies and Rare Earth Element Concentrations in San Francisco Bay over a 20 Year Record. Environ Sci Technol. Apr. 19, 2016;50(8):4159-68. doi: 10.1021/acs.est.5b04322. Epub Jan. 25, 2016.

Hawker et al., Preparation of polymers with controlled molecular architecture. A new convergent approach to dendritic macromolecules. J Am Chem Soc. Oct. 1990;112(21):7638-47.

Hedrick et al., Dendrimer-like Star Block and Amphiphilic Copolymers by Combination of Ring Opening and Atom Transfer Radical Polymerization. Macromolecules, 1998;31(25):8691-8705. DOI: 10.1021/ma980932b.

Hein et al., Copper-catalyzed azide-alkyne cycloaddition (CuAAC) and beyond: new reactivity of copper(I) acetylides. Chem Soc Rev. Apr. 2010;39(4):1302-15. doi: 10.1039/b904091a. Epub Mar. 4, 2010.

Helms et al., One-Pot Reaction Cascades Using Star Polymers with Core-Confined Catalysts. Angewandte Chemie, 2005;44:6384-6387. doi:10.1002/ange.200502095.

Heroguez et al., Novel Styrene-Butadiene Copolymers by Ring-Opening Metathesis Polymerization. Macromol. Oct. 3, 2000;33(20):7241-8.

Hirakawa et al., Removal of Perchlorate Anion from an Aqueous Solution by Encapsulation in an Anion-templated Self-assembled Molecular Capsule. Chemistry Letters. 2009;38(3):290-291.

Holbrook et al., Gd(III)-Dithiolane Gold Nanoparticles for T1-Weighted Magnetic Resonance Imaging of the Pancreas. Nano Lett. May 11, 2016;16(5):3202-9. doi: 10.1021/acs.nanolett.6b00599. Epub Apr. 20, 2016.

Holliday et al., Strategies for the Construction of Supramolecular Compounds through Coordination Chemistry. Angew Chem Int Ed Engl. Jun. 1, 2001;40(11):2022-2043.

(56) References Cited

OTHER PUBLICATIONS

Holten-Andersen et al., Metal-coordination: using one of nature's tricks to control soft material mechanics. J. Mater. Chem. B. 2014;2:2467-2472.

Holten-Andersen et al., pH-induced metal-ligand cross-links inspired by mussel yield self-healing polymer networks with near-covalent elastic moduli. PNAS. Feb. 15, 2011;108:2651-2655.

Hoogenboom et al., 1-Lactide Polymerization Utilizing a Hydroxy-Functionalized 3,6-Bis(2-pyridyl)pyridazine as Supramolecular (Co)initiator: Construction of Polymeric [2×2] Grids. Macromolecules, 2003;36(13):4743-9. DOI: 10.1021/ma034119e.

Hoye et al., Silicon tethered ring-closing metathesis reactions for self- and cross-coupling of alkenols. Tetrahedron Letters. Feb. 19, 1999;40(8):1429-1432.

Hu et al., Enhancing Gelation of Doubly Thermosensitive Hydrophilic ABC Linear Triblock Copolymers in Water by Thermoresponsive Hairy Nanoparticles. Macromolecules, 2016;49(15):5502-13. DOI: 10.1021/acs.macromol.6b01156.

Hu et al., Nanoparticle-based combination therapy toward overcoming drug resistance in cancer. Biochem Pharmacol. Apr. 15, 2012;83(8):1104-11. doi: 10.1016/j.bcp.2012.01.008. Epub Jan. 18, 2012.

Huang et al., Polymer-Stabilized Perfluorobutane Nanodroplets for Ultrasound Imaging Agents. J Am Chem Soc. Jan. 11, 2017;139(1):15-18. doi: 10.1021/jacs.6b08800. Epub Dec. 29, 2016.

Huinink et al., Topotecan versus paclitaxel for the treatment of recurrent epithelial ovarian cancer. J Clin Oncol. Jun. 1997;15(6):2183-93.

Huynh, Novel Polymeric Micelles via RAFT Polymerization for Platinum Drug Delivery. Doctoral Thesis. The University of New South Wales. 2012:i, 57-58.

Hyodo et al., Assessment of tissue redox status using metabolic responsive contrast agents and magnetic resonance imaging. J Pharm Pharmacol. Aug. 2008;60(8):1049-60. doi: 10.1211/jpp.60.8.0011.

Hyodo et al., Brain redox imaging using blood-brain barrier-permeable nitroxide MRI contrast agent. J Cereb Blood Flow Metab. Jun. 2008;28(6):1165-74. doi: 10.1038/jcbfm.2008.5. Epub Feb. 13, 2008.

Hyodo et al., Probing the intracellular redox status of tumors with magnetic resonance imaging and redox-sensitive contrast agents. Cancer Res. Oct. 15, 2006;66(20):9921-8.

Iha et al., Applications of Orthogonal "Click" Chemistries in the Synthesis of Functional Soft Materials. Chem. Rev., 2009;109(11):5620-5686. DOI: 10.1021/cr900138t.

Inglis et al., Well-defined star shaped polymer-fullerene hybrids via click chemistry. Soft Matter, 2010;6:82-84. DOI: 10.1039/B920806M.

Jackson et al., pH triggered self-assembly of core cross-linked star polymers possessing thermoresponsive cores. Chem. Commun., 2011;47:6807-6809. DOI: 10.1039/C1CC11785H.

Jakubowski et al., Activators regenerated by electron transfer for atom transfer radical polymerization of styrene. Macromol. Jan. 10, 2006;39(1):39-45.

Jamieson et al., Structure, Recognition, and Processing of Cisplatin-DNA Adducts. Chem Rev. Sep. 8, 1999;99(9):2467-98.

Jeong et al., Highly tunable self-assembled nanostructures from a poly (2-vinylpyridine-b-dimethylsiloxane) block copolymer. Nano Lett. Sep. 27, 2011;11(10):4095-101.

Jesberger et al., Hyperbranched polymers as scaffolds for multifunctional reversible addition-fragmentation chain-transfer agents: A route to polystyrene-core-polyesters and polystyrene-block-poly(butyl acrylate)-core-polyesters. J. Polym. Sci. A Polym. Chem., 2003;41:3847-3861. doi:10.1002/pola.10976.

Jiang et al., Morphology and Phase Diagram of Comb Block Copolymer Am+1 (BC)m. J Phys Chem B. May 7, 2009;113(21):7462-7.

Johnson et al., Core-clickable PEG-branch-azide bivalent-bottle-brush polymers by ROMP: grafting-through and clicking-to. J Am Chem Soc. Jan. 26, 2011;133(3):559-66. doi: 10.1021/ja108441d. Epub Dec. 13, 2010.

Johnson et al., Drug-loaded, bivalent-bottle-brush polymers by graft-through ROMP. Macromolecules. Dec. 28, 2010;43(24):10326-10335.

Johnson et al., Efficient Synthesis of Doxorubicin Releasing Brush Polymers by Graft-Through Romp. Polymer Preprints. 2010;51(2):96-97.

Jokerst et al., Molecular imaging with theranostic nanoparticles. Acc Chem Res. Oct. 18, 2011;44(10):1050-60. doi: 10.1021/ar200106e. Epub Sep. 15, 2011.

Jokerst et al., Nanoparticle PEGylation for imaging and therapy. Nanomedicine (Lond). Jun. 2011;6(4):715-28. doi: 10.2217/nnm.11.19.

Joralemon et al., PEGylated polymers for medicine: from conjugation to self-assembled systems. Chem Commun (Camb). Mar. 7, 2010;46(9):1377-93. doi: 10.1039/b920570p. Epub Jan. 28, 2010.

Jung et al., Orientation-controlled self-assembled nanolithography using a polystyrene-polydimethylsiloxane block copolymer. Nano Lett. Jul. 11, 2007;7(7):2046-50.

Kale et al., Supramolecular assemblies of amphiphilic homopolymers. Langmuir. May 19, 2009;25(17):9660-70.

Kalyani et al., Oxidatively intercepting Heck intermediates: Pd-catalyzed 1,2- and 1,1-arylhalogenation of alkenes. J Am Chem Soc. Feb. 20, 2008;130(7):2150-1. doi: 10.1021/ja0782798. Epub Jan. 30, 2008.

Kauffman et al., Fluorescence-Based Assays for Measuring oxorubicin in Biological Systems. React Oxyg Species (Apex). 2016;2(6):432-439. doi: 10.20455/ros.2016.873. PMID: 29707647; PMCID: PMC5921830.

Kawamoto et al., Graft-through Synthesis and Assembly of Janus Bottlebrush Polymers from A-Branch-B Diblock Macromonomers. J Am Chem Soc. Sep. 14, 2016;138(36):11501-4. doi: 10.1021/jacs.6b07670. Epub Sep. 1, 2016.

Kawamoto et al., Loops versus branch functionality in model click hydrogels. Macromol. Dec. 1, 2015;48(24):8980-8.

Kean et al., Increasing the maximum achievable strain of a covalent polymer gel through the addition of mechanically invisible cross-links. Adv Mater. Sep. 10, 2014;26(34):6013-8. doi: 10.1002/adma.201401570. Epub Jul. 17, 2014.

Keana et al., Nitroxides as potential contrast enhancing agents for MRI application: influence of structure on the rate of reduction by rat hepatocytes, whole liver homogenate, subcellular fractions, and ascorbate. Magn Reson Med. Dec. 1987;5(6):525-36.

Khanna et al., Designing Miktoarm Polymers Using a Combination of "Click" Reactions in Sequence with Ring-Opening Polymerization. Macromolecules, 2010;43(13):5688-5698. DOI: 10.1021/ma100845a.

Kim et al., Anion-directed self-assembly of coordination polymer into tunable secondary structure. J Am Chem Soc. Jun. 9, 2004;126(22):7009-14.

Kim et al., Supporting Information Experimental Section. J Am Chem Soc. Jun. 9, 2004;126(22):7009-14. Available at: http://pubs.acs.org/doi/suppl/10.1021/ja049799v/suppl_file/ja049799vsi20040219_113203.pdf Retrieved Apr. 24, 2015.

Kirchhoff et al., Boronic acids: new coupling partners in room-temperature Suzuki reactions of alkyl bromides. Crystallographic characterization of an oxidative-addition adduct generated under remarkably mild conditions. J Am Chem Soc. Nov. 20, 2002;124(46):13662-3.

Kishi et al., An M2L4 molecular capsule with an anthracene shell: encapsulation of large guests up to 1 nm. J Am Chem Soc. Aug. 3, 2011;133(30):11438-41. doi: 10.1021/ja2037029. Epub Jul. 8, 2011.

Kokuryo et al., SPIO-PICsome: development of a highly sensitive and stealth-capable MRI nano-agent for tumor detection using SPIO-loaded unilamellar polyion complex vesicles (PICsomes). J Control Release. Aug. 10, 2013;169(3):220-7. doi: 10.1016/j.jconrel.2013.03.016. Epub Mar. 29, 2013.

Kolb et al., Click Chemistry: Diverse Chemical Function from a Few Good Reactions. Angew Chem Int Ed Engl. Jun. 1,

(56) References Cited

OTHER PUBLICATIONS

2001;40(11):2004-2021. doi: 10.1002/1521-3773(20010601)40:11<2004::AID-ANIE2004>3.0.CO;2-5.
Kolishetti et al., Engineering of self-assembled nanoparticle platform for precisely controlled combination drug therapy. Proc Natl Acad Sci U S A. Oct. 19, 2010;107(42):17939-44. doi: 10.1073/pnas.1011368107. Epub Oct. 4, 2010.
Kreutzer et al., Water-Soluble, Unimolecular Containers Based on Amphiphilic Multiarm Star Block Copolymers. Macromolecules, 2006;39(13):4507-4516. DOI: 10.1021/ma060548b.
Kumar et al., Multivalency in the recognition and antagonism of a HIV TAR RNA-TAT assembly using an aminoglycoside benzimidazole scaffold. Org Biomol Chem. Feb. 14, 2016;14(6):2052-6. doi: 10.1039/c5ob02016f.
Kwon et al., Block copolymer micelles as long-circulating drug vehicles. Adv Drug Delivery Rev. 1995;16:295-309.
Lambert et al., Ado-trastuzumab Emtansine (T-DM1): an antibody-drug conjugate (ADC) for HER2-positive breast cancer. J Med Chem. Aug. 28, 2014;57(16):6949-64. doi: 10.1021/jm500766w. Epub Jul. 10, 2014.
Lammers et al., Simultaneous delivery of doxorubicin and gemcitabine to tumors in vivo using prototypic polymeric drug carriers. Biomaterials. Jul. 2009;30(20):3466-75. doi: 10.1016/j.biomaterials.2009.02.040. Epub Mar. 20, 2009.
Lee et al., Multifunctional nanoparticles for multimodal imaging and theragnosis. Chem Soc Rev. Apr. 7, 2012;41(7):2656-72. doi: 10.1039/c2cs15261d. Epub Dec. 21, 2011.
Lee et al., Mussel-Inspired Adhesives and Coatings. Annu Rev Mater Res. Aug. 1, 2011;41:99-132.
Lee et al., Novel phase morphologies in a microphase-separated dendritic polymer melt. Macromol. Jan. 12, 2009;42(3):849-59.
Lee et al., Single-molecule mechanics of mussel adhesion. Proc Natl Acad Sci U S A. Aug. 29, 2006;103(35):12999-3003. Epub Aug. 18, 2006.
Lee et al., Stimuli-responsive molecular brushes. Progress in Polymer Science (Oxford), 35(1-2), 24-44. DOI: 10.1016/j.progpolymsci.2009.11.002.
Leininger et al., Self-assembly of discrete cyclic nanostructures mediated by transition metals. Chem Rev. Mar. 8, 2000;100(3):853-908.
Li et al., Polycatechol Nanoparticle MRI Contrast Agents. Small, 2016;12(5):668-677. https://doi.org/10.1002/smll.201502754.
Li et al., A magnetic switch for spin-catalyzed interconversion of nuclear spin isomers. J Am Chem Soc. Mar. 31, 2010;132(12):4042-3. doi: 10.1021/ja910282p.
Li et al., Crosslinking-induced morphology change of latex nanoparticles: A study of RAFT-mediated polymerization in aqueous dispersed media using amphiphilic double-brush copolymers as reactive surfactants. J Polym Sci Part A: Polym Chem. Nov. 15, 2014;52(22):3250-9.
Li et al., Distance-Dependent Paramagnet-Enhanced Nuclear Spin Relaxation of H2@C60 Derivatives Covalently Linked to a Nitroxide Radical. J. Phys. Chem. Lett., 2010;1(14):2135-2138. DOI: 10.1021/jz100645w.
Li et al., Dynamic cylindrical assembly of triblock copolymers by a hierarchical process of covalent and supramolecular interactions. J Am Chem Soc. Jan. 4, 2011;133(5):1228-31.
Li et al., Efficient synthesis of narrowly dispersed amphiphilic double-brush copolymers through the polymerization reaction of macromonomer micelle emulsifiers at the oil-water interface. Polym Chem. 2016;7(27):4476-85.
Li et al., Facile syntheses of cylindrical molecular brushes by a sequential RAFT and ROMP "grafting-through" methodology. J Polym Sci A Polym Chem. Oct. 15, 2009;47(20):5557-5563.
Li et al., Highly fluorescent M2L4 molecular capsules with anthracene shells. Chem Commun (Camb). Aug. 14, 2011;47(30):8605-7. doi: 10.1039/c1cc12946e. Epub Jun. 28, 2011.

Li et al., Isostructural M2L4 molecular capsules with anthracene shells: synthesis, crystal structures, and fluorescent properties. Chemistry. Jul. 2, 2012;18(27):8358-65. doi: 10.1002/chem.201200155. Epub May 25, 2012.
Li et al., Pinpointing the extent of electronic delocalization in the Re(I)-to-tetrazine charge-separated excited state using time-resolved infrared spectroscopy. J Am Chem Soc. Aug. 26, 2009;131(33):11656-7. doi: 10.1021/ja903901n.
Li et al., Star Polymers via Cross-Linking Amphiphilic Macroinitiators by AGET ATRP in Aqueous Media. J. Am. Chem. Soc., 2009;131(30):10378-10379. DOI: 10.1021/ja904204g.
Li et al., Surface Properties of Bottlebrush Polymer Thin Films. Macromolecules. 2012;45(17):7118-7127.
Li et al., Synthesis of Hetero-Grafted Amphiphilic Diblock Molecular Brushes and Their Self-Assembly in Aqueous Medium. Macromolecules. 2010;43(3):1182-1184.
Li et al., Well-defined amphiphilic double-brush copolymers and their performance as emulsion surfactants. Macromol. May 18, 2012;45(11):4623-9.
Liang et al., The copper(I)-catalyzed alkyne-azide cycloaddition (CuAAC) "click" reaction and its applications. An overview. Coordination Chemistry Reviews Dec. 2011;255(23-24):2933-2945.
Liao et al., A convergent synthetic platform for single-nanoparticle combination cancer therapy: ratiometric loading and controlled release of cisplatin, doxorubicin, and camptothecin. J Am Chem Soc. Apr. 23, 2014;136(16):5896-9. doi: 10.1021/ja502011g. Epub Apr. 11, 2014.
Liao et al., A palladium-catalyzed three-component cross-coupling of conjugated dienes or terminal alkenes with vinyl triflates and boronic acids. J Am Chem Soc. Apr. 20, 2011;133(15):5784-7. doi: 10.1021/ja201358b. Epub Mar. 30, 2011.
Liao et al., Palladium-catalyzed hydroarylation of 1,3-dienes with boronic esters via reductive formation of pi-allyl palladium intermediates under oxidative conditions. J Am Chem Soc. Aug. 4, 2010;132(30):10209-11. doi: 10.1021/ja105010t.
Liao et al., Two-component control of guest binding in a self-assembled cage molecule. Chem Commun (Camb). Jul. 21, 2010;46(27):4932-4. doi: 10.1039/c0cc00234h. Epub Jun. 2010.
Lim et al., Multiplexed imaging of therapeutic cells with multispectrally encoded magnetofluorescent nanocomposite emulsions. J Am Chem Soc. Dec. 2, 2009;131(47):17145-54. doi: 10.1021/ja904472z.
Liu et al., "Brush-first" method for the parallel synthesis of photocleavable, nitroxide-labeled poly(ethylene glycol) star polymers. J Am Chem Soc. Oct. 3, 2012;134(39):16337-44. doi: 10.1021/ja3067176. Epub Sep. 24, 2012.
Liu et al., Aqueous Dispersion Polymerization of 2-Methoxyethyl Acrylate for the Synthesis of Biocompatible Nanoparticles Using a Hydrophilic RAFT Polymer and a Redox Initiator. Macromolecules, 2011;44(13):5237-5245. DOI: 10.1021/ma200984h.
Liu et al., Assembly of trigonal and tetragonal prismatic cages from octahedral metal ions and a flexible molecular clip. Inorg Chem. Jul. 23, 2007;46(15):5814-6. Epub Jan. 26, 2007.
Liu et al., Discrete M2L2 metallacycle and M2L4 cage frameworks and anion competitive reactions of Cu2L4 type receptor. Inorganic Chemistry Communications. Jun. 2009;12(6):457-460.
Liu et al., Nuts and bolts of chemical exchange saturation transfer MRI. NMR Biomed. Jul. 2013;26(7):810-28. doi: 10.1002/nbm.2899. Epub Jan. 10, 2013.
Liu et al., Particles without a box: brush-first synthesis of photodegradable PEG star polymers under ambient conditions. J Vis Exp. Oct. 10, 2013;(80):50874. doi: 10.3791/50874.
Liu et al., Synthesis of functional core, star polymers via RAFT polymerization for drug delivery applications. Macromol Rapid Commun. May 14, 2012;33(9):760-6. doi: 10.1002/marc.201200029. Epub Apr. 12, 2012.
Lock et al., One-Component Supramolecular Filament Hydrogels as Theranostic Label-Free Magnetic Resonance Imaging Agents. ACS Nano. Jan. 24, 2017;11(1):797-805.
Love et al., A practical and highly active ruthenium-based catalyst that effects the cross metathesis of acrylonitrile. Angew Chem Int Ed Engl. Nov. 4, 2002;41(21):4035-7.

(56) References Cited

OTHER PUBLICATIONS

Loveless et al., Chemoresponsive viscosity switching of a metallo-supramolecular polymer network near the percolation threshold. J. Mater Chem. 2007;17:56-61.
Loveless et al., Rational Control of Viscoelestic Properties in Multicomponent Associative Polymer Networks. Macromolecules. 2005;38(24):10171-10177.
Luginbuhl et al., One-week glucose control via zero-order release kinetics from an injectable depot of glucagon-like peptide-1 fused to a thermosensitive biopolymer. Nat Biomed Eng. 2017;1:0078. doi: 10.1038/s41551-017-0078. Epub Jun. 5, 2017.
Luo et al., Toroidal structures from brush amphiphiles. Chem Commun. 2014;50(5):536-8.
Ma et al., Hierarchical Responsive Nanoplatform with Two-Photon Aggregation-Induced Emission Imaging for Efficient Cancer Theranostics. ACS Appl Mater Interfaces. Dec. 18, 2019;11(50):47259-47269. doi: 10.1021/acsami.9b17587. Epub Dec. 9, 2019. PMID: 31769279.
Ma et al., Nanoparticles for combination drug therapy. ACS Nano. Nov. 26, 2013;7(11):9518-25. doi: 10.1021/nn405674m.
Machida et al., Efficient approach to medium-sized cyclic molecules containing (E)-Alkene via Z to E photochemical isomerization in the presence of $AgNO_3$-impregnated silica gel. Chemistry Lett. Jan. 11, 2018;47(2):186-8. doi: https://doi.org/10.1246/cl.170937.
MacKay et al., Self-assembling chimeric polypeptide-doxorubicin conjugate nanoparticles that abolish tumours after a single injection. Nat Mater. Dec. 2009;8(12):993-9. doi: 10.1038/nmat2569. Epub Nov. 8, 2009.
MacRenaris et al., Cell-Permeable Esterase-Activated Ca(II)-Sensitive MRI Contrast Agent. Bioconjug Chem. Feb. 17, 2016;27(2):465-73. doi: 10.1021/acs.bioconjchem.5b00561. Epub Jan. 6, 2016.
Maeda et al., Polymeric drugs for efficient tumor-targeted drug delivery based on EPR-effect. Eur J Pharm Biopharm. Mar. 2009;71(3):409-19. doi: 10.1016/j.ejpb.2008.11.010. Epub Dec. 3, 2008.
Manyeruke et al., Synthesis and evaluation of 3-hydroxy-3-phenylpropanoate ester-AZT conjugates as potential dual-action HIV-1 Integrase and Reverse Transcriptase inhibitors. Bioorg Med Chem. Dec. 15, 2015;23(24):7521-8. doi: 10.1016/j.bmc.2015.10.039.
Mastarone et al., A modular system for the synthesis of multiplexed magnetic resonance probes. J Am Chem Soc. Apr. 13, 2011;133(14):5329-37. doi: 10.1021/ja1099616. Epub Mar. 17, 2011.
Matson et al., Synthesis of fluorine-18 functionalized nanoparticles for use as in vivo molecular imaging agents. J Am Chem Soc. May 28, 2008;130(21):6731-3. doi: 10.1021/ja802010d. Epub May 2, 2008.
Matsumoto et al., High-resolution mapping of tumor redox status by magnetic resonance imaging using nitroxides as redox-sensitive contrast agents. Clin Cancer Res. Apr. 15, 2006;12(8):2455-62.
Matsumura et al., A new concept for macromolecular therapeutics in cancer chemotherapy: mechanism of tumoritropic accumulation of proteins and the antitumor agent smancs. Cancer Res. Dec. 1986;46(12 Pt 1):6387-92.
McCammant et al., Palladium-catalyzed 1,4-difunctionalization of butadiene to form skipped polyenes. J Am Chem Soc. Mar. 20, 2013;135(11):4167-70. doi: 10.1021/ja3110544. Epub Mar. 12, 2013.
McKenzie et al., Highly Efficient and Versatile Formation of Biocompatible Star Polymers in Pure Water and Their Stimuli-Responsive Self-Assembly. Macromolecules, 2014;47(22):7869-7877. DOI: 10.1021/ma502008j.
McKenzie et al., Visible Light Mediated Controlled Radical Polymerization in the Absence of Exogenous Radical Sources or Catalysts. Macromolecules, 2015;48(12):3864-3872. DOI: 10.1021/acs.macromol.5b00965.
Medarova et al., In vivo imaging of siRNA delivery and silencing in tumors. Nat Med. Mar. 2007;13(3):372-7. Epub Feb. 25, 2007.
Mendichovszky et al., Gadolinium and nephrogenic systemic fibrosis: time to tighten practice. Pediatr Radiol. May 2008;38(5):489-96; quiz 602-3. Epub Oct. 18, 2007.
Menyo et al., Versatile tuning of supramolecular hydrogels through metal complexation of oxidation-resistant catechol-inspired ligands. Soft Matter. 2013;9:10314-10323.
Meyer et al., The dynamic chemistry of molecular borromean rings and Solomon knots. Chemistry. Nov. 8, 2010;16(42):12570-81. doi: 10.1002/chem.201001806.
Mi et al., A pH-activatable nanoparticle with signal-amplification capabilities for non-invasive imaging of tumour malignancy. Nat Nanotechnol. Aug. 2016;11(8):724-30. doi: 10.1038/nnano.2016.72. Epub May 16, 2016.
Mi et al., Hydrothermally synthesized PEGylated calcium phosphate nanoparticles incorporating Gd-DTPA for contrast enhanced MRI diagnosis of solid tumors. Journal of Controlled Release Jan. 2014;174(28):63-71.
Miyake et al., Precisely tunable photonic crystals from rapidly self-assembling brush block copolymer blends. Angew Chem Int Ed Engl. Nov. 5, 2012;51(45):11246-8. doi: 10.1002/anie.201205743. Epub Sep. 13, 2012.
Moghimi et al., Long-circulating and target-specific nanoparticles: theory to practice. Pharmacol Rev. Jun. 2001;53(2):283-318.
Mukherjee et al., Oximes as reversible links in polymer chemistry: dynamic macromolecular stars. Polym. Chem., 2014;5:6923-6931. DOI: 10.1039/C4PY01282H.
Mukherjee et al., pH-Sensitive Nanoaggregates for Site-Specific Drug-Delivery as Well as Cancer Cell Imaging. ACS Omega, 2016;1(5):755-764. DOI: 10.1021/acsomega.6b00167.
Mukherjee et al., Site-Specific Amphiphilic Magnetic Copolymer Nanoaggregates for Dual Imaging. Macromolecules, 2015;48(19):6791-6800. DOI: 10.1021/acs.macromol.5b01716.
Muthukrishnan et al., Synthesis and Characterization of Glycomethacrylate Hybrid Stars from Silsesquioxane Nanoparticles. Macromolecules, 2005;38(26):10631-10642. DOI: 10.1021/ma051949e.
Na et al., Development of a T1 contrast agent for magnetic resonance imaging using MnO nanoparticles. Angew Chem Int Ed Engl. 2007;46(28):5397-401.
Na et al., Inorganic Nanoparticles for MRI Contrast Agents. Adv. Mater. 2009;21:2133-2148. doi:10.1002/adma.200802366.
Nair et al., Modulating mechanical properties of self-assembled polymer networks by multi-functional complementary hydrogen bonding. Soft Matter. 2011;7(2):553-559.
Nair et al., Multiresponsive Reversible Polymer Networks Based on Hydrogen Bonding and Metal Coordination. Macromolecules. 2011;44(9):3346-3357.
Nardone et al., Pediatric nephrogenic systemic fibrosis is rarely reported: a RADAR report. Pediatr Radiol. Feb. 2014;44(2):173-80. doi: 10.1007/s00247-013-2795-x. Epub Sep. 21, 2013.
Nguyen et al., Nitroxide-Based Macromolecular Contrast Agents with Unprecedented Transverse Relaxivity and Stability for Magnetic Resonance Imaging of Tumors. ACS Cent. Sci., 2017;3(7):800-811. DOI: 10.1021/acscentsci.7b00253.
Nguyen et al., Pro-organic radical contrast agents ("pro-ORCAs") for real-time MRI of pro-drug activation in biological systems. Polym Chem. Aug. 7, 2020;11(29):4768-4779. doi: 10.1039/d0py00558d. Epub Jun. 26, 2020.
Nguyen et al., Scalable Synthesis of Multivalent Macromonomers for ROMP. ACS Macro Lett. Apr. 17, 2018;7(4):472-476. doi: 10.1021/acsmacrolett.8b00201. Epub Mar. 26, 2018.
Nguyen et al., Triply Loaded Nitroxide Brush-Arm Star Polymers Enable Metal-Free Millimetric Tumor Detection by Magnetic Resonance Imaging. ACS Nano. Nov. 27, 2018;12(11):11343-11354. doi: 10.1021/acsnano.8b06160. Epub Nov. 2, 2018.
Nicholls et al., DNA-gadolinium-gold nanoparticles for in vivo T1 MR imaging of transplanted human neural stem cells. Biomaterials. Jan. 2016;77:291-306. doi: 10.1016/j.biomaterials.2015.11.021. Epub Nov. 14, 2015.
Nishimura et al., Rhodium-Catalyzed Asymmetric Cycloisomerization of 1,6-Ene-ynamides. Adv Synth Catal. May 3, 2013;355(7):1374-82. doi: 10.1002/adsc.201300148.

(56) References Cited

OTHER PUBLICATIONS

Nishiyama et al., Novel cisplatin-incorporated polymeric micelles can eradicate solid tumors in mice. Cancer Res. Dec. 15, 2003;63(24):8977-83.

Nomura et al., Facile Controlled Synthesis of Soluble Star Shape Polymers by Ring-Opening Metathesis Polymerization (ROMP). Macromolecules, 2009;42(4):899-901. DOI: 10.1021/ma8027529.

Nomura et al., Use of Pyridine-Coated Star-Shaped ROMP Polymer as the Supporting Ligand for Ruthenium-Catalyzed Chemoselective Hydrogen Transfer Reduction of Ketones. Organometallics, 2012;31(14):5074-5080. DOI: 10.1021/om300417v.

Ohno et al., Synthesis of well-defined cyclodextrin-core star polymers. J. Polym. Sci. A Polym. Chem. 2001;39:2206-2214. doi:10.1002/pola.1197.

Ohwada et al., Design, synthesis and antifungal activity of a novel water soluble prodrug of antifungal triazole. Bioorg Med Chem Lett. Jan. 20, 2003;13(2):191-6. doi: 10.1016/s0960-894x(02)00892-2.

Paletta et al., Synthesis and Reduction Kinetics of Sterically Shielded Pyrrolidine Nitroxides. Org. Lett., 2012;14(20):5322-5325. DOI: 10.1021/ol302506f.

Panchamoorthy et al., Targeting the human MUC1-C oncoprotein with an antibody-drug conjugate. JCI Insight. Jun. 21, 2018;3(12):e99880. doi: 10.1172/jci.insight.99880.

Park et al., Star Synthesis Using Macroinitiators via Electrochemically Mediated Atom Transfer Radical Polymerization. Macromolecules, 2013;46(15):5856-5860 DOI: 10.1021/ma401308e.

Patel et al., Synthesis and cell adhesive properties of linear and cyclic RGD functionalized polynorbornene thin films. Biomacromolecules. Aug. 13, 2012;13(8):2546-53. doi: 10.1021/bm300795y. Epub Jul. 27, 2012.

Patrick et al., Intracellular pH measurements using perfluorocarbon nanoemulsions. J Am Chem Soc. Dec. 11, 2013;135(49):18445-57. doi: 10.1021/ja407573m. Epub Nov. 22, 2013.

Peer et al., Nanocarriers as an emerging platform for cancer therapy. Nat Nanotechnol. Dec. 2007;2(12):751-60. doi: 10.1038/nnano.2007.387.

Perez-Salvia et al., Bromodomain inhibitors and cancer therapy: From structures to applications. Epigenetics. May 4, 2017;12(5):323-339. doi: 10.1080/15592294.2016.1265710. Epub Dec. 2, 2016.

Pesek et al., Synthesis of bottlebrush copolymers based on poly(dimethylsiloxane) for surface active additives. Polymer. Aug. 19, 2016;98(19):495-504.

Petros et al., Strategies in the design of nanoparticles for therapeutic applications. Nat Rev Drug Discov. Aug. 2010;9(8):615-27. doi: 10.1038/nrd2591. Epub Jul. 9, 2010.

Plummer et al., A Phase I clinical study of cisplatin-incorporated polymeric micelles (NC-6004) in patients with solid tumours. Br J Cancer. Feb. 15, 2011;104(4):593-8. doi: 10.1038/bjc.2011.6. Epub Feb. 1, 2011.

Prevost et al., Strained organosilacyclic compounds:synthesis of anti-Bredt olefins and trans-dioxasilacyclooctenes. Dalton Trans. Oct. 21, 2010;39(39):9275-81. doi: 10.1039/c003227a. Epub Jul. 8, 2010.

Qi et al., A brush-polymer conjugate of exendin-4 reduces blood glucose for up to five days and eliminates poly(ethylene glycol) antigenicity. Nat Biomed Eng. 2016;1:0002. doi: 10.1038/s41551-016-0002. Epub Nov. 28, 2016.

Qiu et al., Efficient and versatile synthesis of star polymers in water and their use as emulsifiers. Chem. Commun., 2011;47:12685-12687. DOI: 10.1039/C1CC15679A.

Qiu et al., Oxidation-Responsive Polymer-Drug Conjugates with a Phenylboronic Ester Linker. Macromol Rapid Commun. Nov. 2015;36(22):2012-8. doi: 10.1002/marc.201500349. Epub Aug. 22, 2015. PMID: 26297612.

Rajca et al., Correction to organic radical contrast agents for magnetic resonance imaging. J Am Chem Soc. Feb. 26, 2014;136(8):3318. doi: 10.1021/ja413028d. Epub Feb. 17, 2014.

Rajca et al., Organic radical contrast agents for magnetic resonance imaging. J Am Chem Soc. Sep. 26, 2012;134(38):15724-7. Epub Sep. 17, 2012.

Rangadurai et al., Temporal and triggered evolution of host-guest characteristics in amphiphilic polymer assemblies. J Am Chem Soc. Jun. 10, 2016;138(24):7508-11.

Rasmussen et al., Improved numerical algorithm for exploring block copolymer mesophases. J Polym Sci Part B: Poly Phys. Aug. 15, 2002;40(16):1777-83.

Ratnakar et al., Modulation of CEST images in vivo by T1 relaxation: a new approach in the design of responsive PARACEST agents. J Am Chem Soc. Oct. 9, 2013;135(40):14904-7. doi: 10.1021/ja406738y. Epub Sep. 25, 2013.

Ren et al., Organic Catalyst-Mediated Ring-Opening Polymerization for the Highly Efficient Synthesis of Polyester-Based Star Polymers. ACS Macro Lett., 2012;1(6):681-686. DOI: 10.1021/mz300169m.

Ren et al., Star Polymers. Chem Rev. Jun. 22, 2016;116(12):6743-836. doi: 10.1021/acs.chemrev.6b00008. Epub Jun. 14, 2016.

Ren et al., Synthetic Strategies towards Well-Defined Complex Polymeric Architectures through Covalent Chemistry. Chemie Ingenieur Technik. 2014;86:2195-2214. doi:10.1002/cite.201400088.

Rizzo et al., In vivo nanotoxicity testing using the zebrafish embryo assay. J. Mater. Chem. B, 2013,1, 3918-3925. DOI: 10.1039/C3TB20528B.

Rolfe et al., Multimodal polymer nanoparticles with combined 19F magnetic resonance and optical detection for tunable, targeted, multimodal imaging in vivo. J Am Chem Soc. Feb. 12, 2014;136(6):2413-9. doi: 10.1021/ja410351h. Epub Jan. 29, 2014.

Ronson et al., Metal-organic container molecules through subcomponent self-assembly. Chem Commun (Camb). Mar. 28, 2013;49(25):2476-90. doi: 10.1039/c2cc36363a.

Rowan et al., Metal-ligand induced supramolecular polymerization: a route to responsive materials. Faraday Discuss. 2005;128:43-53.

Roy et al., Cyclic-Peptoids. Org. Lett., 2008;10(5):921-924. DOI: 10.1021/ol7030763.

Runge et al., Synthesis and Self-Assembly of Bottlebrush Block Copolymers. PMSEPreprints, 2005, 92, 5-6.

Rzayev et al., Molecular Bottlebrushes: New Opportunities in Nanomaterials Fabrication. ACS Macro Lett., 2012;1(9):1146-1149. DOI: 10.1021/mz300402x.

Rzayev, Synthesis of polystyrene-polylactide bottlebrush block copolymers and their melt self-assembly into large domain nanostructures. Macromol. Feb. 20, 2009;42(6):2135-41.

Saini et al., Pd(0)-catalyzed 1,1-diarylation of ethylene and allylic carbonates. Org Lett. Oct. 4, 2013;15(19):5008-11. doi: 10.1021/ol4023358. Epub Sep. 18, 2013.

Sakamoto et al., Protacs: chimeric molecules that target proteins to the Skp1-Cullin-F box complex for ubiquitination and degradation. Proc Natl Acad Sci U S A. Jul. 17, 2001;98(15):8554-9. doi: 10.1073/pnas.141230798. Epub Jul. 3, 2001.

Samuni et al., Factors influencing nitroxide reduction and cytotoxicity in vitro. Antioxid Redox Signal. Jun. 2004;6(3):587-95.

Sancey et al., Long-term in vivo clearance of gadolinium-based AGuIX nanoparticles and their biocompatibility after systemic injection. ACS Nano. Mar. 24, 2015;9(3):2477-88. doi: 10.1021/acsnano.5b00552. Epub Feb. 26, 2015.

Sanders et al., Metal-free sequential [3+2]-dipolar cycloadditions using cyclooctynes and 1,3-dipoles of different reactivity. J Am Chem Soc. Feb. 2, 2011;133(4):949-57. doi: 10.1021/ja1081519. Epub Dec. 23, 2010.

Sartori et al., Nitroxide paramagnet-induced para-ortho conversion and nuclear spin relaxation of H2 in organic solvents. J Am Chem Soc. Sep. 24, 2008;130(38):12752-6. doi: 10.1021/ja8037195. Epub Aug. 20, 2008.

Saunders et al., Synthesis of amphiphilic star block copolymers using ring-opening metathesis polymerization. Macromolecules, 1992;25(7):2055-2057. DOI: 10.1021/ma00033a035.

Schmidt et al., Supramolecular three-armed star polymers via cyclodextrin host-guest self-assembly. Polym. Chem., 2012;3:3139-3145. DOI: 10.1039/C2PY20293J.

Schrock et al., Tungsten(VI) neopentylidyne complexes. Organometallics. Dec. 1, 1982;1(12):1645-51. doi: 10.1021/om00072a018.

(56) References Cited

OTHER PUBLICATIONS

Sengupta et al., Temporal targeting of tumour cells and neovasculature with a nanoscale delivery system. Nature. Jul. 28, 2005;436(7050):568-72.

Sheiko et al., Cylindrical molecular brushes: Synthesis, characterization, and properties. Progress in Polymer Science (Oxford), 33(7), 759-785. DOI: 10.1016/j.progpolymsci.2008.05.001.

Shellock et al., Safety of magnetic resonance imaging contrast agents. J Magn Reson Imaging. Sep. 1999;10(3):477-84.

Shi et al., Core cross-linked star (CCS) polymers with tunable polarity: synthesis by RAFT dispersion polymerization, self-assembly and emulsification. Polym. Chem., 2013;4:1950-1959. DOI: 10.1039/C3PY21120G.

Shibata et al., Quantitative Synthesis of Star-Shaped Poly(vinyl ether)s with a Narrow Molecular Weight Distribution by Living Cationic Polymerization. J. Am. Chem. Soc., 2006;128(23):7497-7504. DOI: 10.1021/ja057611h.

Shin et al., Recent advances in magnetic nanoparticle-based multimodal imaging. Chem Soc Rev. Jul. 21, 2015;44(14):4501-16. doi: 10.1039/c4cs00345d.

Sides et al., Parallel algorithm for numerical self-consistent field theory simulations of block copolymer structure. Polymer. Sep. 1, 2003;44(19):5859-66.

Sinturel et al., High-low N block polymers: how far can we go? ACS Macro Lett. Sep. 2, 2015;4:1044-50.

Skomski et al., Redox-active on-surface assembly of metal-organic chains with single-site Pt(II). J Am Chem Soc. Jul. 16, 2014;136(28):9862-5. doi: 10.1021/ja504850f. Epub Jul. 1, 2014.

Smith et al., Modular synthesis of biologically active phosphatidic acid probes using click chemistry. Mol Biosyst. Sep. 2009;5(9):962-72. doi: 10.1039/b901420a. Epub May 7, 2009.

Smith et al., Nanomaterials for In Vivo Imaging. Chem Rev. Feb. 8, 2017;117(3):901-986. doi: 10.1021/acs.chemrev.6b00073. Epub Jan. 3, 2017.

Smulders et al., Building on architectural principles for three-dimensional metallosupramolecular construction. Chem Soc Rev. Feb. 21, 2013;42(4):1728-54. doi: 10.1039/c2cs35254k. Epub Oct. 2, 2012.

Sowers et al., Redox-responsive branched-bottlebrush polymers for in vivo MRI and fluorescence imaging. Nature Communications. 2014;5:Article No. 5460.

Spiniello et al., Synthesis and characterization of fluorescently labeled core cross-linked star polymers. J. Polym. Sci. A Polym. Chem., 2008;46:2422-2432. doi:10.1002/pola.22576.

Stenzel-Rosenbaum et al., Synthesis of Poly(styrene) Star Polymers Grown from Sucrose, Glucose, and Cyclodextrin Cores via Living Radical Polymerization Mediated by a Half-Metallocene Iron Carbonyl Complex. Macromolecules, 2001;34(16):5433-5438. DOI: 10.1021/ma0021803.

Su et al., Catechol polymers for pH-responsive, targeted drug delivery to cancer cells. J Am Chem Soc. Aug. 10, 2011;133(31):11850-3. doi: 10.1021/ja203077x. Epub Jul. 19, 2011. PMID: 21751810; PMCID: PMC3149454.

Su et al., Coordination-directed assembly of trigonal and tetragonal molecular boxes encapsulating anionic guests. Journal of the Chemical Society, Dalton Transactions. 2001:359-361. doi: 10.1039/B0101180.

Sulistio et al., Star polymers composed entirely of amino acid building blocks: a route towards stereospecific, biodegradable and hierarchically functionalized stars. Chem. Commun., 2011;47:1151-1153. DOI: 10.1039/C0CC03541F.

Sun et al., Multicomponent metal-ligand self-assembly. Curr Opin Chem Biol. Dec. 2002;6(6):757-64.

Sun et al., Self-assembled M24L48 polyhedra and their sharp structural switch upon subtle ligand variation. Science. May 28, 2010;328(5982):1144-7. doi:10.1126/science.1188605. Epub Apr. 29, 2010.

Sveinbjornsson et al., Rapid self-assembly of brush block copolymers to photonic crystals. Proc Natl Acad Sci U S A. Sep. 4, 2012;109(36):14332-6. doi: 10.1073/pnas.1213055109. Epub Aug. 21, 2012.

Swaminathan et al., Nephrogenic systemic fibrosis, gadolinium, and iron mobilization. N Engl J Med. Aug. 16, 2007;357(7):720-2.

Takamizu et al., Synthesis of oligo(thiophene)-coated star-shaped ROMP polymers: unique emission properties by the precise integration of functionality. Journal of the American Chemical Society 2012;134(18):7892-7895.

Tam et al., Recent advances in metallogels. Chem Soc Rev. Feb. 21, 2013;42(4):1540-67. doi: 10.1039/c2cs35354g. Epub Jan. 8, 2013.

Tanino et al., Control of Stereochemistry by sigma-Participation of a Silyl Group. A Novel Method for Diastereoselective Polyol Synthesis. J Org Chem. Jun. 27, 1997;62(13):4206-4207. doi: 10.1021/jo9703515.

Terashima et al., Star-Polymer-Catalyzed Living Radical Polymerization: Microgel-Core Reaction Vessel by Tandem Catalyst Interchange. Angew. Chem., 2011;50:7892-7895. doi:10.1002/anie.201101381.

Terreno et al., Challenges for molecular magnetic resonance imaging. Chem Rev. May 12, 2010;110(5):3019-42. doi: 10.1021/cr100025t.

Theodorakis et al., Interplay between chain collapse and microphase separation in bottle-brush polymers with two types of side chains. Macromol. May 4, 2010;43(11):5137-48.

Thompson et al., Labelling polymers and micellar nanoparticles via initiation, propagation and termination with ROMP. Polym. Chem., 2014;5:1954-1964.

Tinworth et al., Small molecule-mediated protein knockdown as a new approach to drug discovery. Med Chem Commun. Jul. 26, 2016;7:2206-16. doi: 10.1039/C6MD00347H.

Tirotta et al., (19)F magnetic resonance imaging (MRI): from design of materials to clinical applications. Chem Rev. Jan. 28, 2015;115(2):1106-29. doi: 10.1021/cr500286d. Epub Oct. 20, 2014.

Tolmasoff et al., Superoxide dismutase: correlation with life-span and specific metabolic rate in primate species. Proc Natl Acad Sci U S A. May 1980;77(5):2777-81.

Tominaga et al., Finite, spherical coordination networks that self-organize from 36 small components. Angew Chem Int Ed Engl. Oct. 25, 2004;43(42):5621-5.

Tomooka et al., Planar chiral dialkoxysilane:introduction of inherent chirality and high reactivity in conventional achiral alkene. Chemistry. Jun. 16, 2014;20(25):7598-602. doi: 10.1002/chem.201402434. Epub May 6, 2014.

Torchilin, Tumor delivery of macromolecular drugs based on the EPR effect. Adv Drug Deliv Rev. Mar. 18, 2011;63(3):131-5. doi: 10.1016/j.addr.2010.03.011. Epub Mar. 18, 2010.

Trail et al., Cure of xenografted human carcinomas by BR96-doxorubicin immunoconjugates. Science. Jul. 9, 1993;261(5118):212-5. doi: 10.1126/science.8327892. Erratum in: Science Feb. 25, 1994;263(5150):1076.

Tsuji et al., Facile Palladium catalyzed decarboxylative allylation of active methylene compounds under neutral conditions using allylic carbonates. Tetrahedron Letters. 1982;23(46):4809-12.

Tu et al., Multimodal magnetic-resonance/optical-imaging contrast agent sensitive to NADH. Angew Chem Int Ed Engl. 2009;48(35):6547-51. doi: 10.1002/anie.200900984.

Tunca et al., Novel miktofunctional initiator for the preparation of an ABC-type miktoarm star polymer via a combination of controlled polymerization techniques. J. Polym. Sci. A Polym. Chem., 42: 4228-4236. doi:10.1002/pola.20284.

Valeur et al., Amide bond formation: beyond the myth of coupling reagents. Chem. Soc. Rev., 2009;38:606-631. DOI: 10.1039/B701677H.

Venkatesh et al., Role of the development scientist in compound lead selection and optimization. J Pharm Sci. Feb. 2000;89(2):145-54. doi: 10.1002/(SICI)1520-6017(200002)89:2<145::AID-JPS2>3.0.CO;2-6.

Verduzco et al., Correction: Structure, function, self-assembly, and applications of bottlebrush copolymers. Chem Soc Rev. Nov. 7, 2015;44(21):7916. doi: 10.1039/c5cs90099a.

(56) References Cited

OTHER PUBLICATIONS

Verduzco et al., Structure, function, self-assembly, and applications of bottlebrush copolymers. Chem. Soc. Rev., 2015;44:2405-20.
Verwilst et al., Recent advances in Gd-chelate based bimodal optical/MRI contrast agents. Chem Soc Rev. Apr. 7, 2015;44(7):1791-806. doi: 10.1039/c4cs00336e. Epub Jan. 27, 2015.
Villaraza et al., Macromolecules, dendrimers, and nanomaterials in magnetic resonance imaging: the interplay between size, function, and pharmacokinetics. Chem Rev. May 12, 2010;110(5):2921-59. doi: 10.1021/cr900232t.
Wang et al., Advances of cancer therapy by nanotechnology. Cancer Res Treat. Mar. 2009;41(1):1-11. doi: 10.4143/crt.2009.41.1.1. Epub Mar. 31, 2009.
Wang et al., Synthesis of Unnatural Amino Acids Functionalized with Sterically Shielded Pyrroline Nitroxides. Org Lett. Oct. 17, 2014;16(20): 5298-5300. Published online Sep. 16, 2014. doi: [10.1021/ol502449r].
Wei et al., Exceedingly small iron oxide nanoparticles as positive MRI contrast agents. Proc. Natl. Acad. Sci. USA 2017;114(9):2325-2330.
Weng et al., Control of Gel Morphology and Properties of a Class of Metallo-Supramolecular Polyers by Good/Poor Solvent Environments. Macromolecules. 2009;42(1):236-246.
Weng et al., Effect of monomer structure on the gelation of a class of metallo-supramolecular polymers. Soft Matter. 2009;5(23):4647-4657.
Weng et al., Structural origin of the thixotropic behavior of a class of metallosupramolecular gels. Tetrahedron. Jul. 30, 2007;63(31):7419-7431.
Weng et al., Understanding the mechanism of gelation and stimuli-responsive nature of a class of metallo-supramolecular gels. J Am Chem Soc. Sep. 6, 2006;128(35):11663-72.
Westhaus et al., Triggered release of calcium from lipid vesicles: a bioinspired strategy for rapid gelation of polysaccharide and protein hydrogels. Biomaterials. Mar. 2001;22(5):453-62.
Wilkinson et al., Electrophilic fluorocyclization of allyl silanes. Angew Chem Int Ed Engl. 2009;48(38):7083-7086. doi:10.1002/anie.200901795.
Wollinsky et al., Therapeutic and diagnostic applications of dendrimers for cancer treatment. Adv Drug Deliv Rev. Jun. 10, 2008;60(9):1037-55. doi: 10.1016/j.addr.2008.02.012. Epub Mar. 4, 2008.
Wong et al., Quantitative formation of core cross-linked star polymers via a one-pot two-step single electron transfer-living radical polymerization. Polym. Chem., 2013;4:4562-4565. DOI: 10.1039/C3PY00726J.
Worrell et al., Direct evidence of a dinuclear copper intermediate in Cu(I)-catalyzed azide-alkyne cycloadditions. Science. Apr. 26, 2013;340(6131):457-60. doi: 10.1126/science.1229506. Epub Apr. 4, 2013.
Wurz et al., A "Click Chemistry Platform" for the Rapid Synthesis of Bispecific Molecules for Inducing Protein Degradation. J Med Chem. Jan. 25, 2018;61(2):453-461. doi: 10.1021/acs.jmedchem.6b01781. Epub Apr. 17, 2017.
Xia et al., Efficient synthesis of narrowly dispersed brush copolymers and study of their assemblies: the importance of side chain arrangement. J Am Chem Soc. Dec. 30, 2009;131(51):18525-32. doi: 10.1021/ja908379q.
Xia et al., Efficient Synthesis of Narrowly Dispersed Brush Polymers via Living Ring-Opening Metathesis Polymerization of Macromonomers. Macromolecules, 2009;42(11):3761-3766. DOI: 10.1021/ma900280c.
Xia et al., EPR study of spin labeled brush polymers in organic solvents. J Am Chem Soc. Dec. 14, 2011;133(49):19953-9. doi: 10.1021/ja2085349. Epub Nov. 21, 2011.
Xiao et al., Precision glycocalyx editing as a strategy for cancer immunotherapy. Proc Natl Acad Sci U S A. Sep. 13, 2016;113(37):10304-9. doi: 10.1073/pnas.1608069113. Epub Aug. 22, 2016.
Xiao et al., The use of polymeric platinum(IV) prodrugs to deliver multinuclear platinum(II) drugs with reduced systemic toxicity and enhanced antitumor efficacy. Biomaterials. Nov. 2012;33(33):8657-69. doi: 10.1016/j.biomaterials.2012.08.015. Epub Aug. 28, 2012.
Xing et al., A stable metal coordination polymer gel based on a calix[4]arene and its 'uptake' of non-ionic organic molecules from the aqueous phase. Chem Commun (Camb). Feb. 21, 2002;(4):362-3.
Xing et al., Design of coordination polymer as stable catalytic systems. Chemistry. Nov. 4, 2002;8(21):5028-32.
Xing et al., Spontaneous Enrichment of Organic Molecules from Aqueous and Gas Phases into a Stable Metallogel. Langmuir. 2002;18:9654-9658.
Xu et al., Mechanism of Shear Thickening in Reversibly Cross-linked Supramolecular Polymer Networks. Macromolecules. Apr. 13, 2010;43(7):3556-3565.
Xu et al., Scaling Laws in Supramolecular Polymer Networks. Macromolecules. 2011;44(13):5465-5472.
Xu et al., Strain Hardening and Strain Softening of Reversibly Cross-linked Supramolecular Polymer Networks. Macromolecules. Sep. 27, 2011;44(18):7478-7488.
Yan et al., Hierarchical self-assembly: well-defined supramolecular nanostructures and metallohydrogels via amphiphilic discrete organoplatinum(II) metallacycles. J Am Chem Soc. Sep. 25, 2013;135(38):14036-9. doi: 10.1021/ja406877b. Epub Aug. 8, 2013.
Yan et al., Particle carriers for combating multidrug-resistant cancer. ACS Nano. Nov. 26, 2013;7(11):9512-7. doi: 10.1021/nn405632s. Epub Nov. 11, 2013.
Yan et al., Responsive supramolecular polymer metallogel constructed by orthogonal coordination-driven self-assembly and host/guest interactions. J Am Chem Soc. Mar. 26, 2014;136(12):4460-3. doi: 10.1021/ja412249k. Epub Mar. 12, 2014.
Yan et al., Supramolecular polymers with tunable topologies via hierarchical coordination-driven self-assembly and hydrogen bonding interfaces. Proc Natl Acad Sci U S A. Sep. 24, 2013;110(39):15585-90. doi: 10.1073/pnas.1307472110. Epub Sep. 9, 2013.
Yan et al., The relationship among pKa, pH, and binding constants in the interactions between boronic acids and diols-it is not as simple as it appears. Tetrahedron. Nov. 29, 2004;60(49):11205-11209.
Yang et al., Luminescent chemodosimeters for bioimaging. Chem Rev. Jan. 9, 2013;113(1):192-270. doi: 10.1021/cr2004103. Epub Jun. 18, 2012.
Yi et al., Telmisartan attenuates hepatic fibrosis in bile ductligated; rats. Acta Pharmacol Sin. Dec. 2012;33(12):1518-24. doi: 10.1038/aps.2012.115. Epub Oct. 29, 2012.
Yoneya et al., Coordination-directed self-assembly of M12L24 nanocage: effects of kinetic trapping on the assembly process. ACS Nano. Feb. 25, 2014;8(2):1290-6. doi: 10.1021/nn404595j. Epub Jan. 31, 2014.
Yoneya et al., Simulation of metal-ligand self-assembly into spherical complex M6L8. J Am Chem Soc. Sep. 5, 2012;134(35):14401-7. doi: 10.1021/ja303542r. Epub Aug. 22, 2012.
Yoshizawa et al., Molecular architectures of multi-anthracene assemblies. Chem Soc Rev. Mar. 21, 2014;43(6):1885-98. doi: 10.1039/c3cs60315f.
You et al., Manganese displacement from Zinpyr-1 allows zinc detection by fluorescence microscopy and magnetic resonance imaging. Chem Commun (Camb). Jun. 21, 2010;46(23):4139-41. doi: 10.1039/c0cc00179a. Epub May 10, 2010.
Yount et al., Small-molecule dynamics and mechanisms underlying the macroscopic mechanical properties of coordinatively cross-linked polymer networks. J Am Chem Soc. Oct. 19, 2005;127(41):14488-96.
Yount et al., Strong means slow: dynamic contributions to the bulk mechanical properties of supramolecular networks. Angew Chem Int Ed Engl. Apr. 29, 2005;44(18):2746-8.
Yuan et al., One-pot syntheses of amphiphilic centipede-like brush copolymers via combination of ring-opening polymerization and "click" chemistry. Macromol. Jan. 27, 2010;43(4):1739-46.
Yue et al., Macrocyclic and lantern complexes of palladium(II) with bis(amidopyridine) ligands: synthesis, structure, and host-guest chemistry. Inorg Chem. Nov. 29, 2004;43(24):7671-81.

(56) References Cited

OTHER PUBLICATIONS

Yurkovetskiy et al., Fully degradable hydrophilic polyals for protein modification. Biomacromolecules. Sep.-Oct. 2005;6(5):2648-58. doi: 10.1021/bm049210k.

Zhang et al., Active cross-linkers that lead to active gels. Angew Chem Int Ed Engl. Oct. 25, 2013;52(44):11494-8. doi: 10.1002/anie.201304437. Epub Sep. 12, 2013.

Zhang et al., Convergent Synthesis of Branched Metathesis Polymers with Enyne Reagents. Macromolecules. Sep. 28, 2021;54(18):8435-8442. doi: 10.1021/acs.macromol.1c01051. Epub Sep. 8, 2021.

Zhang et al., Cyclodextrin-centred star polymers synthesized via a combination of thiol-ene click and ring opening polymerization. Chem Commun (Camb). Aug. 21, 2012;48(65):8063-5. doi: 10.1039/c2cc33742h. Epub Jul. 6, 2012.

Zhang et al., Dual-functional gadolinium-based copper(II) probe for selective magnetic resonance imaging and fluorescence sensing. Inorg Chem. Feb. 20, 2012;51(4):2325-31. doi: 10.1021/ic202322f. Epub Feb. 8, 2012.

Zhang et al., One-pot RAFT synthesis of core cross-linked star polymers of polyPEGMA in water by sequential homogeneous and heterogeneous polymerizations. Polym. Chem., 2012;3:2656-2664. DOI: 10.1039/C2PY20442H.

Zhang et al., polyMOFs: A Class of Interconvertible Polymer-Metal-Organic-Framework Hybrid Materials. Angew Chem Int Ed Engl. May 18, 2015;54(21):6152-7. doi: 10.1002/anie.201502733. Epub Apr. 29, 2015.

Zhang et al., Redox-Responsive, Core Cross-Linked Polyester Micelles. ACS Macro Lett., 2013;2(1):40-44. DOI: 10.1021/mz300522n.

Zhao et al., Polystyrene-Polylactide Bottlebrush Block Copolymer at the Air/Water Interface. Macromol. Sep. 28, 2009;42(22):9027-33.

Zhao et al., Rheological Behavoir of Shear-Responsive Metallo-Supramolecular Gels. Macromolecules. 2004;37(10):3529-3531.

Zhelev et al., Imaging of superoxide generation in the dopaminergic area of the brain in Parkinson's disease, using mito-TEMPO. ACS Chem Neurosci. Nov. 20, 2013;4(11):1439-45. doi: 10.1021/cn400159h. Epub Sep. 16, 2013.

Zhelev et al., Nitroxyl radicals as low toxic spin-labels for non-invasive magnetic resonance imaging of blood-brain barrier permeability for conventional therapeutics. Chem Commun (Camb). Jan. 7, 2009;(1):53-5. doi: 10.1039/b816878d. Epub Nov. 13, 2008.

Zhelev et al., Nitroxyl radicals for labeling of conventional therapeutics and noninvasive magnetic resonance imaging of their permeability for blood-brain barrier: relationship between structure, blood clearance, and MRI signal dynamic in the brain. Mol Pharm. Mar.-Apr. 2009;6(2):504-12. doi: 10.1021/mp800175k.

Zheng et al., Construction of Smart Supramolecular Polymeric Hydrogels Cross-linked by Discrete Organoplatinum(II) Metallacycles via Post-Assembly Polymerization. J. Am. Chem. Soc., 2016;138(14):4927-37. DOI: 10.1021/jacs.6b01089.

Zheng et al., Morphology of ABC triblock copolymers. Macromol. Oct. 1995;28(21):7215-23.

Zhou et al., Counting primary loops in polymer gels. Proc Natl Acad Sci U S A. Nov. 20, 2012;109(47):19119-24. doi: 10.1073/pnas.1213169109. Epub Nov. 6, 2012.

Zhou et al., Efficient formation of multicompartment hydrogels by stepwise self-assembly of thermoresponsive ABC triblock terpolymers. J Am Chem Soc. Jun. 27, 2012;134(25):10365-8. doi: 10.1021/ja303841f. Epub Jun. 13, 2012.

Zhou et al., Photo-controlled growth of telechelic polymers and end-linked polymer gels. Angew Chem Int Ed Engl. Feb. 18, 2013;52(8):2235-8. doi: 10.1002/anie.201207966. Epub Jan. 17, 2013.

Baslé et al., Protein chemical modification on endogenous amino acids. Chem Biol. Mar. 26, 2010;17(3):213-27. doi: 10.1016/j.chembiol.2010.02.008.

Beck et al., Strategies and challenges for the next generation of antibody-drug conjugates. Nat Rev Drug Discov. May 2017;16(5):315-337. doi: 10.1038/nrd.2016.268. Epub Mar. 17, 2017.

Dennler et al., Antibody Conjugates: From Heterogeneous Populations to Defined Reagents. Antibodies. Aug. 3, 2015;4(3):197-224. doi: 10.3390/antib4030197.

Fu et al., Relay Conjugation of Living Metathesis Polymers. J Am Chem Soc. Sep. 26, 2018;140(38):12181-12188. doi: 10.1021/jacs.8b07315. Epub Sep. 11, 2018.

Knall et al., Inverse electron demand Diels-Alder (iEDDA)-initiated conjugation: a (high) potential click chemistry scheme. Chem Soc Rev. Jun. 21, 2013;42(12):5131-42. doi: 10.1039/c3cs60049a.

Lyon et al., Reducing hydrophobicity of homogeneous antibody-drug conjugates improves pharmacokinetics and therapeutic index. Nat Biotechnol. Jul. 2015;33(7):733-5. doi: 10.1038/nbt.3212. Epub Jun. 15, 2015.

Tolcher et al., Randomized phase II study of BR96-doxorubicin conjugate in patients with metastatic breast cancer. J Clin Oncol. Feb. 1999;17(2):478-84. doi: 10.1200/JCO.1999.17.2.478.

Xu et al., Site-specific labeling of an anti-MUC1 antibody: probing the effects of conjugation and linker chemistry on the internalization process. RSC Adv. Jan. 15, 2019;9(4):1909-1917. doi: 10.1039/c8ra09902b.

Yurkovetskiy et al., A Polymer-Based Antibody-Vinca Drug Conjugate Platform: Characterization and Preclinical Efficacy. Cancer Res. Aug. 15, 2015;75(16):3365-72. doi: 10.1158/0008-5472.CAN-15-0129. Epub Jun. 25, 2015.

Zhang et al., Practical Synthesis of Functional Metathesis Initiators Using Enynes. Macromol. Aug. 16, 2018;51(16):6497-503. doi: 10.1021/acs.macromol.8b00866.

[No Author Listed], CAS Abstract of S. Masuoka et al., JP05112739 (1993). CAS Registry File RN 150076-39-4. 2023. 7 pages.

Amass, A.J., Ring-opening metathesis polymerization of cyclic alkenes. In: New Methods of Polymer Synthesis. 1991. J.R. Ebdon, Ed. Blackie & Son Ltd., Glasgow, Scotland. Chapter 3:209 pages.

Burke et al., Development of Novel Quaternary Ammonium Linkers for Antibody-Drug Conjugates. Mol Cancer Ther. May 2016;15(5):938-45. doi: 10.1158/1535-7163.MCT-16-0038. Epub Mar. 4, 2016.

Dutta et al., Dilute solution structure of bottlebrush polymers. Soft Matter. Apr. 3, 2019;15(14):2928-2941. doi: 10.1039/c9sm00033j.

Ekladious et al., Polymer-drug conjugate therapeutics: advances, insights and prospects. Nat Rev Drug Discov. Apr. 2019;18(4):273-294. doi: 10.1038/s41573-018-0005-0.

Foster et al., Getting into Shape: Reflections on a New Generation of Cylindrical Nanostructures' Self-Assembly Using Polymer Building Blocks. J Am Chem Soc. Feb. 20, 2019;141(7):2742-2753. doi: 10.1021/jacs.8b08648. Epub Feb. 8, 2019.

Kodger, T., Mechanical Failure in Colloidal Gels. Dissertation. Harvard University. Dec. 2014. 255 pages.

Li et al., Thermoresponsive PNIPAAM bottlebrush polymers with tailored side-chain length and end-group structure. Soft Matter. Mar. 28, 2014;10(12):2008-15. doi: 10.1039/c3sm52614c.

Qiu et al., ROMP synthesis of benzaldehyde-containing amphiphilic block polynorbornenes used to conjugate drugs for pH-responsive release. React Func Polym. Jul. 2018;128:1-15. doi: 10.1016/j.reactfunctpolym.2018.03.010.

Shibuya et al., Mikto-Brush-Arm Star Polymers via Cross-Linking of Dissimilar Bottlebrushes: Synthesis and Solution Morphologies. ACS Macro Lett. Sep. 19, 2017;6(9):963-968. doi: 10.1021/acsmacrolett.7b00529. Epub Aug. 21, 2017.

Shieh et al., Tailored silyl ether monomers enable backbone-degradable polynorbornene-based linear, bottlebrush and star copolymers through ROMP. Nat Chem. Dec. 2019;11(12):1124-1132. doi: 10.1038/s41557-019-0352-4. Epub Oct. 28, 2019.

Sowers et al., Redox-responsive branched-bottlebrush polymers for in vivo MRI and fluorescence imaging. Nat Commun. Nov. 18, 2014;5:5460. doi: 10.1038/ncomms6460.

Staben et al., Targeted drug delivery through the traceless release of tertiary and heteroaryl amines from antibody-drug conjugates. Nat Chem. Dec. 2016;8(12):1112-1119. doi: 10.1038/nchem.2635. Epub Oct. 17, 2016.

(56) References Cited

OTHER PUBLICATIONS

Tian et al., Selective esterase-ester pair for targeting small molecules with cellular specificity. Proc Natl Acad Sci U S A. Mar. 27, 2012;109(13):4756-61. doi: 10.1073/pnas.1111943109. Epub Mar. 12, 2012.

Tu et al., Recent advances towards applications of molecular bottlebrushes and their conjugates. Curr Opin Solid State Mater Sci. Feb. 2019;23(1):50-61. doi: 10.1016/j.cossms.2019.01.003.

Vohidov et al., Design of BET Inhibitor Bottlebrush Prodrugs with Superior Efficacy and Devoid of Systemic Toxicities. J Am Chem Soc. Mar. 31, 2021;143(12):4714-4724. doi: 10.1021/jacs.1c00312. Epub Mar. 19, 2021. Author Manuscript, 18 pages.

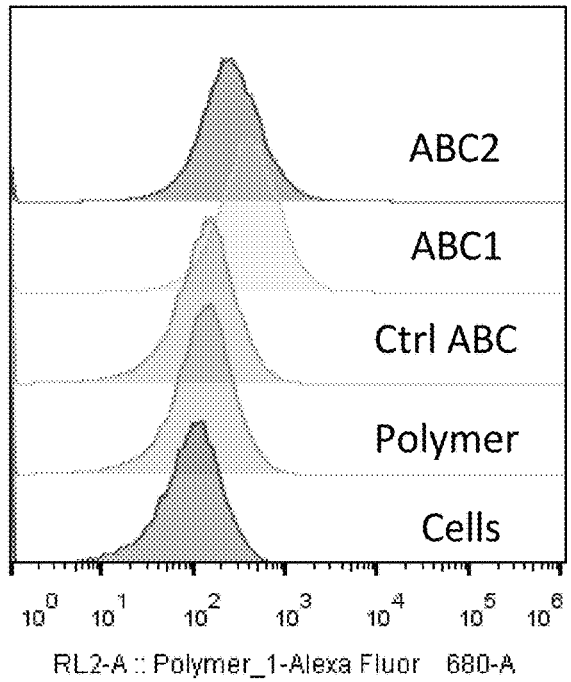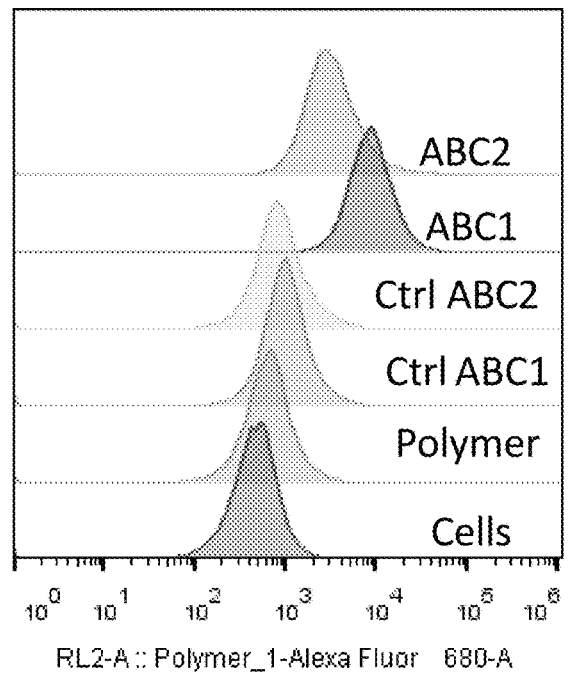
FIG. 9A
FIG. 9B

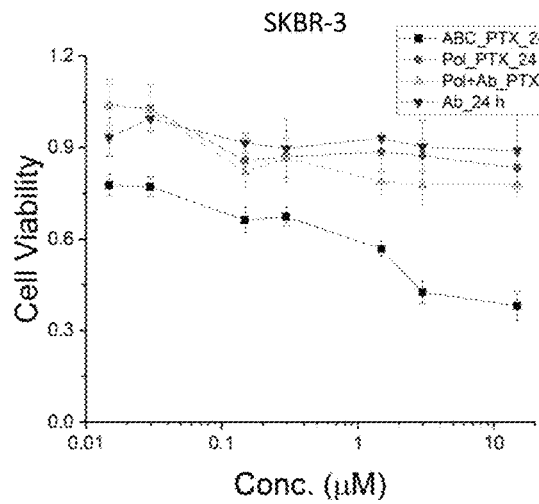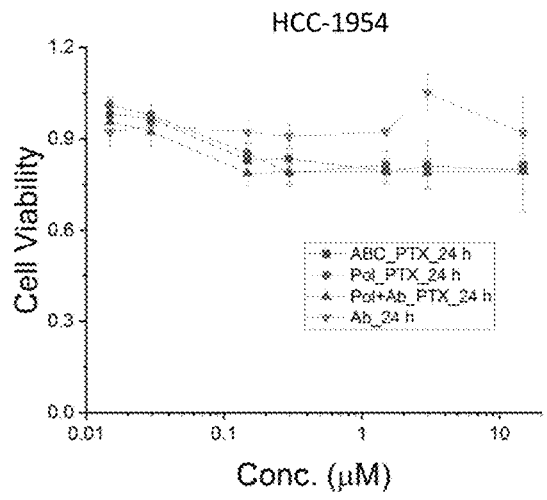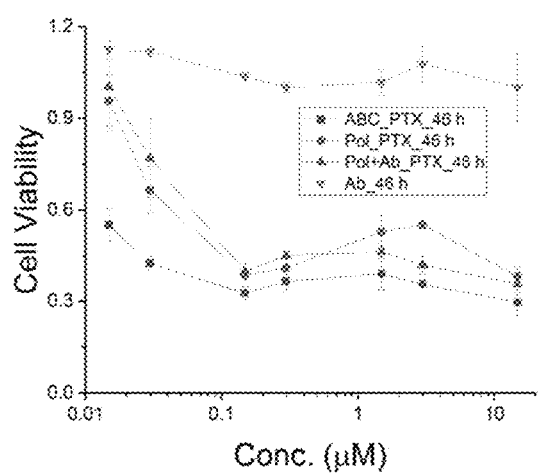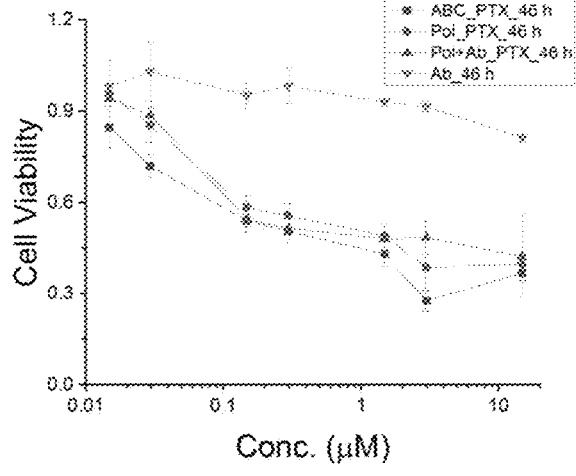
FIG. 15A
FIG. 15B
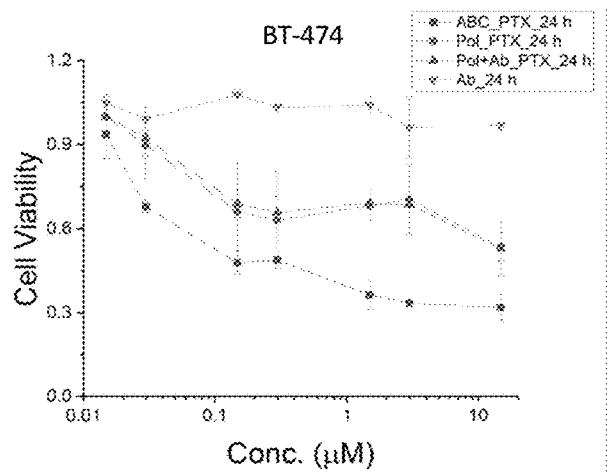
FIG. 15C

Kinetics study

Different antibodies

SN-38

PTX

PTX 60

Survival curve

PROTAC-azide

PROTAC-MM

BIOMOLECULE-POLYMER-PHARMACEUTICAL AGENT CONJUGATES FOR DELIVERING THE PHARMACEUTICAL AGENT

RELATED APPLICATIONS

This application claims priority to U.S. Provisional Patent Application No. 63/291,937, filed Dec. 20, 2021, which is incorporated herein by reference in its entirety.

GOVERNMENT SUPPORT

This invention was made with government support under CA220468 awarded by the National Institutes of Health. The government has certain rights in the invention.

BACKGROUND

Known antibody-drug conjugates (ADCs) may have low drug-to-antibody ratios (DARs), may only be applicable to very high potency drugs and may need a certain hydrophilicity to achieve aqueous conjugation to the antibody. Moreover, ADCs may need specific design and synthesis for each drug to which they are applied. Further, drugs may be exposed to the biological environment, resulting in premature release. There is a need for improved ADCs.

SUMMARY OF THE DISCLOSURE

In one aspect, the present disclosure provides enyne of Formula (I):

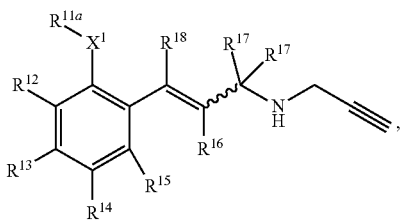

or a tautomer, isotopically labeled compound, salt, solvate, polymorph, or co-crystal thereof.

In certain embodiments, an enyne is a compound comprising at least one non-aromatic C=C bond and at least one non-aromatic CC bond.

In another aspect, the present disclosure provides a enyne of Formula (II):

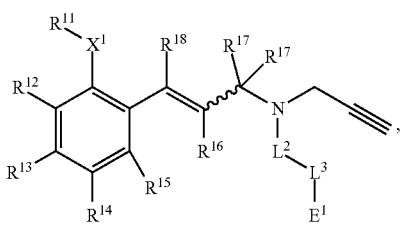

or a tautomer, isotopically labeled compound, salt, solvate, polymorph, or co-crystal thereof.

In another aspect, the present disclosure provides an end-functionalized polymer of Formula (III):

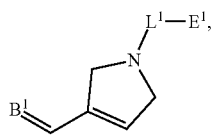

or a tautomer, isotopically labeled polymer, or salt thereof.

In another aspect, the present disclosure provides a method of preparing an end-functionalized polymer of Formula (III), or a tautomer, isotopically labeled polymer, or salt thereof.

In another aspect, the present disclosure provides a conjugate of Formula (IV'):

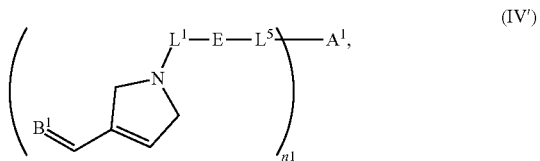

or a tautomer, isotopically labeled conjugate, or salt thereof.

In another aspect, the present disclosure provides a conjugate of Formula (IV):

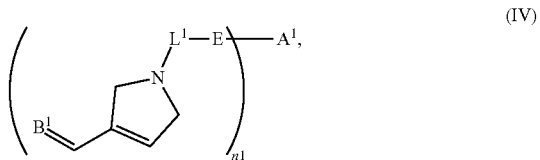

or a tautomer, isotopically labeled conjugate, or salt thereof.

In another aspect, the present disclosure provides a method of preparing a conjugate of Formula (IV'), or a tautomer, isotopically labeled conjugate, or salt thereof.

In another aspect, the present disclosure provides a method of preparing a conjugate of Formula (IV), or a tautomer, isotopically labeled conjugate, or salt thereof.

In other aspects, the present disclosure provides compositions and kits that comprise the enyne, end-functionalized polymer, or conjugate.

In other aspects, the present disclosure provides certain methods of using the enynes, end-functionalized polymers, conjugates, or compositions.

The enynes may be useful in preparing the conjugates. The end-functionalized polymers may be useful in preparing the conjugates.

The conjugates comprise at least (1) $A^1$, which is a peptide, protein, nucleoprotein, mucoprotein, lipoprotein, glycoprotein, or polynucleotide; and (2) $B^1$, which is a polymer, wherein each instance of the polymer comprises independently one or more pharmaceutical agents (e.g., a drug). In certain embodiments, $A^1$ is an antibody, $B^1$ is a brush polymer, and the conjugate is an antibody-brush polymer conjugate (ABC). The conjugates may be useful in delivering a pharmaceutical agent to a subject in need thereof or cell. The delivering may be targeted delivering at least because the peptide, protein, nucleoprotein, mucoprotein, lipoprotein, glycoprotein, or polynucleotide selectively binds a target organ or target tissue in the subject in need thereof. The conjugates may be useful in treating, preventing, or diagnosing a disease. The conjugates may be advantageous over the pharmaceutical agent because the former may show higher potency, efficacy, bioavailability, safety, and/or subject compliance; wider therapeutic window; fewer and/or less severe side effects; and/or lower toxicity and/or resistance to treatment than the latter. One or more of the advantages may be at least in part because the peptide, protein, nucleoprotein, mucoprotein, lipoprotein, glycoprotein, or polynucleotide selectively binds a target (e.g., a target peptide, target protein, target nucleoprotein, target mucoprotein, target lipoprotein, target glycoprotein, target polynucleotide, target cell, target issue, target organ) that is associated with the disease. The conjugates may be advantageous over known antibody-drug conjugates (ADCs) because the former: (1) may show higher drug-to-antibody ratios (DARs); (2) may be applicable to a broader range of pharmaceutical agents; (3) may be applicable to pharmaceutical agents with lower limitations on the pharmaceutical agents' potency and/or hydrophilicity; (4) may have a more general synthesis strategy for different pharmaceutical agents; (5) may show long circulation times (e.g., at least because of the higher protection by the brush chains (e.g., PEG); and/or (6) may have a more controllable release of the pharmaceutical agents (e.g., at least because of the linkers (e.g., L)).

Definitions

Other than in the operating examples, or where otherwise indicated, all numbers expressing quantities of ingredients or reaction conditions used herein should be understood as modified in all instances by the term "about." "About" and "approximately" shall generally mean an acceptable degree of error for the quantity measured given the nature or precision of the measurements. Exemplary degrees of error are within 20 percent (%), typically, within 10%, and more typically, within 5%, 4%, 3%, 2% or 1% of a given value or range of values.

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, N Y, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values ("range") is listed, it is intended to encompass each value and sub-range within the range. A range is inclusive of the values at the two ends of the range unless otherwise provided. For example, "an integer between 1 and 4" refers to 1, 2, 3, and 4. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "alkyl" refers to a radical of a $C_1$-$C_{1000}$ straight-chain or branched saturated hydrocarbon group. In some embodiments, an alkyl group has 3 to 400 carbon atoms ("$C_3$-$C_{400}$ alkyl"), 20 to 200 carbon atoms ("$C_{20}$-$C_{200}$ alkyl"), 1 to 20 carbon atoms ("$C_{1}$-$C_{20}$ alkyl"), 1 to 10 carbon atoms ("$C_1$-$C_{10}$ alkyl"), 1 to 9 carbon atoms ("$C_1$-$C_9$ alkyl"), 1 to 8 carbon atoms ("$C_1$-$C_8$ alkyl"), 1 to 7 carbon atoms ("$C_1$-$C_7$ alkyl"), 1 to 6 carbon atoms ("$C_1$-$C_6$ alkyl"), 1 to 5 carbon atoms ("$C_1$-$C_5$ alkyl"), 1 to 4 carbon atoms ("$C_1$-$C_4$ alkyl"), 1 to 3 carbon atoms ("$C_1$-$C_3$ alkyl"), 1 to 2 carbon atoms ("$C_1$-$C_2$ alkyl"), or 1 carbon atom ("$C_1$ alkyl"). Examples of $C_1$-$C_6$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. $C_{30}$-$C_{1000}$ alkyl may be obtained from polymerization. Unless otherwise specified, each instance of an alkyl group is independently unsubstituted (an "unsubstituted alkyl") or substituted (a "substituted alkyl") with one or more substituents.

The term "alkenyl" refers to a radical of a straight-chain or branched hydrocarbon group having from 2 to 1000 carbon atoms and one or more carbon-carbon double bonds (e.g., 1, 2, 3, or 4 double bonds). In some embodiments, an alkenyl group has 2 to 400 carbon atoms ("$C_{2-400}$ alkenyl") or 20 to 200 carbon atoms ("$C_{20}$-$C_{200}$ alkenyl"). In some embodiments, an alkenyl group has 2 to 20 carbon atoms ("$C_{2-20}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. $C_{30}$-$C_{1000}$ alkenyl may be obtained from polymerization. Unless otherwise specified, each instance of an alkenyl group is independently unsubstituted (an "unsubstituted alkenyl") or substituted (a "substituted alkenyl") with one or more substituents. In an alkenyl group, a C═C double bond for which the stereochemistry is not specified (e.g., —CH═CHCH$_3$,

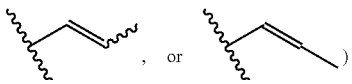

may be in the (E)- or (Z)-configuration.

The term "alkynyl" refers to a radical of a straight-chain or branched hydrocarbon group having from 2 to 1000 carbon atoms and one or more carbon-carbon triple bonds (e.g., 1, 2, 3, or 4 triple bonds) ("$C_{2-10}$ alkynyl"). In some embodiments, an alkynyl group has 2 to 400 carbon atoms ("$C_{2-400}$ alkynyl"), 20 to 200 carbon atoms ("$C_{20}$-$C_{200}$ alkynyl"), 2 to 20 carbon atoms ("$C_{2-20}$ alkynyl"), 2 to 9 carbon atoms ("$C_{2-9}$ alkynyl"), 2 to 8 carbon atoms ("$C_{2-8}$ alkynyl"), 2 to 7 carbon atoms ("$C_{2-7}$ alkynyl"), 2 to 6 carbon atoms ("$C_{2-6}$ alkynyl"), 2 to 5 carbon atoms ("$C_{2-5}$ alkynyl"), 2 to 4 carbon atoms ("$C_{2-4}$ alkynyl"), 2 to 3 carbon atoms ("$C_{2-3}$ alkynyl"), or 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. $C_{30}$-$C_{1000}$ alkynyl may be obtained from polymerization. Unless otherwise specified, each instance of an alkynyl group is independently unsubstituted (an "unsubstituted alkynyl") or substituted (a "substituted alkynyl") with one or more substituents.

The term "heteroalkyl" refers to an alkyl group which further includes at least one heteroatom (e.g., 1, 2, 3, 4, or more heteroatoms, as valency permits) selected from oxygen, nitrogen, phosphorus, or sulfur within (i.e., inserted between adjacent carbon atoms of) and/or placed at one or more terminal position(s) of the parent chain. In certain embodiments, a heteroalkyl group refers to a saturated group having from 1 to 1000 carbon atoms and 1 or more heteroatoms within the parent chain ("$C_1$-$C_{100}$ heteroalkyl" or "$C_{1-1000}$ heteroalkyl"), 2 to 400 carbon atoms and 1 or more heteroatoms within the parent chain ("$C_2$-$C_{400}$ heteroalkyl"), 1 to 20 carbon atoms and 1 or more heteroatoms within the parent chain ("$C_1$-$C_{20}$ heteroalkyl"), 1 to 10 carbon atoms and 1 or more heteroatoms within the parent chain ("$C_1$-$C_{10}$ heteroalkyl"), 1 to 9 carbon atoms and 1 or more heteroatoms within the parent chain ("$C_1$-$C_9$ heteroalkyl"), 1 to 8 carbon atoms and 1 or more heteroatoms within the parent chain ("$C_1$-$C_8$ heteroalkyl"), 1 to 7 carbon atoms and 1 or more heteroatoms within the parent chain ("$C_1$-$C_7$ heteroalkyl"), 1 to 6 carbon atoms and 1 or more heteroatoms within the parent chain ("$C_1$-$C_6$ heteroalkyl"), 1 to 5 carbon atoms and 1 or more heteroatoms within the parent chain ("$C_1$-$C_5$ heteroalkyl"), 1 to 4 carbon atoms and for more heteroatoms within the parent chain ("$C_1$-$C_4$ heteroalkyl"), 1 to 3 carbon atoms and 1 or more heteroatoms within the parent chain ("$C_1$-$C_3$ heteroalkyl"), 1 to 2 carbon atoms and 1 heteroatom within the parent chain ("$C_1$-$C_2$ heteroalkyl"), or 1 carbon atom and 1 heteroatom ("$C_1$ heteroalkyl").

$C_{30}$-$C_{1000}$ heteroalkyl may be obtained from polymerization. Unless otherwise specified, each instance of a heteroalkyl group is independently unsubstituted (an "unsubstituted heteroalkyl") or substituted (a "substituted heteroalkyl") with one or more substituents.

The term "heteroalkenyl" refers to an alkenyl group, which further includes at least one heteroatom (e.g., 1, 2, 3, 4, or more heteroatoms, as valency permits) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 1000 carbon atoms, at least one double bond, and 1 or more heteroatoms within the parent chain ("hetero$C_{2-1000}$ alkenyl" or "$C_{2-1000}$ heteroalkenyl"), or 40 to 400 carbon atoms, at least one double bond, and 1 or more heteroatoms within the parent chain ("hetero$C_{40-400}$ alkenyl"). In certain embodiments, a heteroalkenyl group refers to a group having from 2 to 20 carbon atoms, at least one double bond, and 1 or more heteroatoms within the parent chain ("hetero$C_{2-20}$ alkenyl"). In certain embodiments, a heteroalkenyl group refers to a group having from 2 to 10 carbon atoms, at least one double bond, and 1 or more heteroatoms within the parent chain ("hetero$C_{2-10}$ alkenyl"). In some embodiments, a heteroalkenyl group has 2 to 9 carbon atoms at least one double bond, and 1 or more heteroatoms within the parent chain ("hetero$C_{2-9}$ alkenyl"). In some embodiments, a heteroalkenyl group has 2 to 8 carbon atoms, at least one double bond, and 1 or more heteroatoms within the parent chain ("hetero$C_{2-8}$ alkenyl"). In some embodiments, a heteroalkenyl group has 2 to 7 carbon atoms, at least one double bond, and 1 or more heteroatoms within the parent chain ("hetero$C_{2-7}$ alkenyl"). In some embodiments, a heteroalkenyl group has 2 to 6 carbon atoms, at least one double bond, and 1 or more heteroatoms within the parent chain ("hetero$C_{2-6}$ alkenyl"). In some embodiments, a heteroalkenyl group has 2 to 5 carbon atoms, at least one double bond, and 1 or 2 heteroatoms within the parent chain ("hetero$C_{2-5}$ alkenyl"). In some embodiments, a heteroalkenyl group has 2 to 4 carbon atoms, at least one double bond, and for 2 heteroatoms within the parent chain ("hetero$C_{2-4}$ alkenyl"). In some embodiments, a heteroalkenyl group has 2 to 3 carbon atoms, at least one double bond, and 1 heteroatom within the parent chain ("hetero$C_{2-3}$ alkenyl"). In some embodiments, a heteroalkenyl group has 2 to 6 carbon atoms, at least one double bond, and 1 or 2 heteroatoms within the parent chain ("hetero$C_{2-6}$ alkenyl"). $C_{30}$-$C_{1000}$ heteroalkenyl may be obtained from polymerization. Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted hetero$C_{2-10}$ alkenyl. In certain embodiments, the heteroalkenyl group is a substituted hetero$C_{2-10}$ alkenyl.

The term "heteroalkynyl" refers to an alkynyl group, which further includes at least one heteroatom (e.g., 1, 2, 3, 4, or more heteroatoms, as valency permits) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 1000 carbon atoms, at least one triple bond, and 1 or more heteroatoms within the parent chain ("hetero$C_{2-1000}$ alkynyl" or "$C_{2-1000}$ heteroalkynyl"), or 40 to 400 carbon atoms, at least one double bond, and 1 or more heteroatoms within the parent chain ("hetero$C_{40-400}$ alkynyl"). In certain embodiments, a heteroalkynyl group refers to a group having from 2 to 20 carbon atoms, at least one triple bond, and 1 or more heteroatoms within the parent chain ("heteroC$_{2-20}$ alkynyl"). In certain embodiments, a heteroalkynyl group refers to a group having from 2 to 10 carbon atoms, at least one triple bond, and 1 or more heteroatoms within the parent chain ("heteroC$_{2-10}$ alkynyl"). In some embodiments, a heteroalkynyl group has 2 to 9 carbon atoms, at least one triple bond, and 1 or more heteroatoms within the parent chain ("heteroC$_{2-9}$ alkynyl"). In some embodiments, a heteroalkynyl group has 2 to 8 carbon atoms, at least one triple bond, and 1 or more heteroatoms within the parent chain ("heteroC$_{2-8}$ alkynyl"). In some embodiments, a heteroalkynyl group has 2 to 7 carbon atoms, at least one triple bond, and 1 or more heteroatoms within the parent chain ("heteroC$_{2-7}$ alkynyl"). In some embodiments, a heteroalkynyl group has 2 to 6 carbon atoms, at least one triple bond, and 1 or more heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and for 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). C$_{30}$-C$_{1000}$ heteroalkynyl may be obtained from polymerization. Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

The term "carbocyclyl" or "carbocyclic" or "cycloalkyl" refers to a radical of a non-aromatic cyclic hydrocarbon group having from 3 to 10 ring carbon atoms ("C$_{3-10}$ carbocyclyl") and zero heteroatoms in the non-aromatic ring system. In some embodiments, a carbocyclyl group has 3 to 8 ring carbon atoms ("C$_{3-8}$ carbocyclyl"), 3 to 7 ring carbon atoms ("C$_{3-7}$ carbocyclyl"), 3 to 6 ring carbon atoms ("C$_{3-6}$ carbocyclyl"), 4 to 6 ring carbon atoms ("C$_{4-6}$ carbocyclyl"), 5 to 6 ring carbon atoms ("C$_{2-6}$ carbocyclyl"), or 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents.

The term "heterocyclyl" or "heterocyclic" refers to a radical of a 3- to 14-membered non-aromatic ring system having ring carbon atoms and 1 to 4 ring heteroatoms, wherein each heteroatom is independently selected from nitrogen, oxygen, phosphorus, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon-carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents.

In some embodiments, a heterocyclyl group is a 5-10 membered non-aromatic ring system having ring carbon atoms and 1-4 ring heteroatoms, wherein each heteroatom is independently selected from nitrogen, oxygen, phosphorus, and sulfur ("5-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorus, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorus, and sulfur ("5-6 membered heterocyclyl"). In some embodiments, the 5-6 membered heterocyclyl has 1-3 ring heteroatoms selected from nitrogen, oxygen, phosphorus, and sulfur. In some embodiments, the 5-6 membered heterocyclyl has 1-2 ring heteroatoms selected from nitrogen, oxygen, phosphorus, and sulfur. In some embodiments, the 5-6 membered heterocyclyl has 1 ring heteroatom selected from nitrogen, oxygen, phosphorus, and sulfur.

Exemplary 3-membered heterocyclyl groups containing 1 heteroatom include, without limitation, azirdinyl, oxiranyl, and thiiranyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl, and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, and dioxanyl. Exemplary 6-membered heterocyclyl groups containing 3 heteroatoms include, without limitation, triazinanyl. Exemplary 7-membered heterocyclyl groups containing 1 heteroatom include, without limitation, azepanyl, oxepanyl, and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

The term "aryl" refers to a radical of a monocyclic or polycyclic (e.g., bicyclic or tricyclic) 4n+2 aromatic ring system (e.g., having 6, 10, or 14 r electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents.

The term "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen, and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group be monovalent or may have more than one point of attachment to another moiety (e.g., it may be divalent, trivalent, etc), although the valency may be specified directly in the name of the group. For example, "triazoldiyl" refers to a divalent triazolyl moiety.

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

As understood from the above, alkyl, alkenyl, alkynyl, carbocyclyl, aryl, and heteroaryl groups are, in certain embodiments, optionally substituted. Optionally substituted refers to a group which may be substituted or unsubstituted (e.g., "substituted" or "unsubstituted" alkyl). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Affixing the suffix "ene" to a group indicates the group is a polyvalent (e.g., bivalent, trivalent, tetravalent, or pentavalent) moiety. In certain embodiments, affixing the suffix "ene" to a group indicates the group is a bivalent moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)(R$^{aa}$)$_2$, —P(=O)(OR$^{cc}$)$_2$, —OP(=O)(R$^{aa}$)$_2$, —OP(=O)(OR$^{cc}$)$_2$, —P(=O)(N(R$^{bb}$)$_2$)$_2$, —OP(=O)(N(R$^{bb}$)$_2$)$_2$, —NR$^{bb}$P(=O)(R$^{aa}$)$_2$, —NR$^{bb}$P(=O)(OR$^{cc}$)$_2$, —NR$^{bb}$P(=O)(N(R$^{bb}$)$_2$)$_2$, —P(R$^{cc}$)$_2$, —P(OR$^{cc}$)$_2$, —P(R$^{cc}$)$_3$$^+$X$^-$, —P(OR$^{cc}$)$_3$$^+$X$^-$, —P(R$^{cc}$)$_4$, —P(OR$^{cc}$)$_4$, —OP(R$^{cc}$)$_2$, —OP(R$^{cc}$)$_3$$^+$X$^-$, —OP(OR$^{cc}$)$_2$, —OP(OR$^{cc}$)$_3$$^+$X$^-$, —OP(R$^{cc}$)$_4$, —OP(OR$^{cc}$)$_4$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)(R$^{aa}$)$_2$, —P(=O)(OR$^{cc}$)$_2$, —P(=O)(N(R$^{cc}$)$_2$)$_2$, C$_{1-10}$ alkyl, C$_{1-10}$ perhaloalkyl, C$_{2-10}$ alkenyl, C$_{2-10}$ alkynyl, heteroC$_{1-10}$alkyl, heteroC$_{2-10}$alkenyl, heteroC$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, heteroC$_{1-10}$ alkyl, heteroC$_{2-10}$ alkenyl, heteroC$_{2-10}$ alkynyl, C$_{3-10}$ carbocyclyl, 3-14 membered heterocyclyl, C$_{6}$-14 aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{cc}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)(OR$^{ee}$)$_2$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, heteroC$_{1-6}$ alkyl, heteroC$_{2-6}$ alkenyl, heteroC$_{2-6}$ alkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_3$-10 carbocyclyl, 3-10 membered heterocyclyl, $C_{6-10}$ aryl and 5-10 membered heteroaryl, or two $R^{ff}$ groups are joined to form a 3-10 membered heterocyclyl or 5-10 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups;

each instance of $R^{gg}$ is, independently, halogen, —CN, —$NO_2$, —$N_3$, —$SO_2H$, —$SO_3H$, —OH, —$OC_{1-6}$ alkyl, —ON($C_{1-6}$ alkyl)$_2$, —N($C_{1-6}$ alkyl), —N($C_{1-6}$ alkyl)$_3$$^+X^-$, —NH($C_{1-6}$ alkyl)$^+X^-$, —$NH_2$($C_{1-6}$ alkyl)$^+X^-$, —$NH_3^+X^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(=O)($C_{1-6}$ alkyl), —$CO_2H$, —$CO_2$($C_{1-6}$ alkyl), —OC(=O)($C_{1-6}$ alkyl), —OCO$_2$($C_{1-6}$ alkyl), —C(=O)$NH_2$, —C(=O)N($C_{1-6}$ alkyl)$_2$, —OC(=O)NH($C_{1-6}$ alkyl), —NHC(=O)($C_{1-6}$ alkyl), —N($C_{1-6}$ alkyl)C(=O)($C_{1-6}$ alkyl), —NHCO$_2$($C_{1-6}$ alkyl), —NHC(=O)N($C_{1-6}$ alkyl)$_2$, —NHC(=O)NH($C_{1-6}$ alkyl), —NHC(=O)$NH_2$, —C(=NH)O($C_{1-6}$ alkyl), —OC(=NH)($C_{1-6}$ alkyl), —OC(=NH)O$C_{1-6}$ alkyl, —C(=NH)N($C_{1-6}$ alkyl), —C(=NH)NH($C_{1-6}$ alkyl), —C(=NH)$NH_2$, —OC(=NH)N($C_{1-6}$ alkyl)$_2$, —OC(NH)NH($C_{1-6}$ alkyl), —OC(NH)$NH_2$, —NHC(NH)N($C_{1-6}$ alkyl), —NHC(=NH)$NH_2$, —NHSO$_2$($C_{1-6}$ alkyl), —SO$_2$N($C_{1-6}$ alkyl), —SO$_2$NH($C_{1-6}$ alkyl), —SO$_2NH_2$, —SO$_2C_{1-6}$ alkyl, —SO$_2$O$C_{1-6}$ alkyl, —OSO$_2C_{1-6}$ alkyl, —SO$C_{1-6}$ alkyl, —Si($C_{1-6}$ alkyl)$_3$, —OSi($C_{1-6}$ alkyl)$_3$ —C(=S)N($C_{1-6}$ alkyl), C(=S)NH($C_{1-6}$ alkyl), C(=S)$NH_2$, —C(=O)S($C_{1-6}$ alkyl), —C(=S)S$C_{1-6}$ alkyl, —SC(=S)S$C_{1-6}$ alkyl, —P(=O)(O$C_{1-6}$ alkyl), —P(=O)($C_{1-6}$ alkyl)$_2$, —OP(=O)($C_{1-6}$ alkyl), —OP(=O)(O$C_{1-6}$ alkyl), $C_{1-6}$ alkyl, $C_{1-6}$ perhaloalkyl, $C_{2-6}$ alkenyl, $C_{2-6}$ alkynyl, hetero$C_{1-6}$ alkyl, hetero$C_{2-6}$ alkenyl, hetero$C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form =O or =S; and each $X^-$ is a counterion.

In certain embodiments, the carbon atom substituents are independently halogen, substituted or unsubstituted, $C_{1-6}$ alkyl, —$OR^{aa}$, —$SR^{aa}$, —$N(R^{bb})_2$, —CN, —SCN, —$NO_2$, —C(=O)$R^{aa}$, —$CO_2R^{aa}$, —C(=O)N($R^{bb}$)$_2$, —OC(=O)$R^{aa}$, —OCO$_2R^{aa}$, —OC(=O)N($R^{bb}$)$_2$, —$NR^{bb}$C(=O)$R^{aa}$, —$NR^{bb}CO_2R^{aa}$, or —$NR^{bb}$C(=O)N($R^{bb}$)$_2$. In certain embodiments, the carbon atom substituents are independently halogen, substituted or unsubstituted, $C_{1-6}$ alkyl, —$OR^{aa}$, —$SR^{aa}$, —$N(R^{bb})_2$, —CN, —SCN, or —$NO_2$.

Nitrogen atoms can be substituted or unsubstituted as valency permits, and include primary, secondary, tertiary, and quaternary nitrogen atoms. Exemplary nitrogen atom substituents include, but are not limited to, hydrogen, —OH, —$OR^{aa}$, —N($R^{cc}$)$_2$, —CN, —C(=O)$R^{aa}$, —C(=O)N($R^{cc}$)$_2$, —$CO_2R^{aa}$, —$SO_2R^{aa}$, —C(=$NR^{bb}$)$R^{aa}$, —C(=$NR^{cc}$)$OR^{aa}$, —C(=$NR^{cc}$)N($R^{cc}$)$_2$, —$SO_2$N($R^{cc}$)$_2$, —$SO_2R^{cc}$, —$SO_2OR^{cc}$, —$SOR^{aa}$, —C(=S)N($R^{cc}$)$_2$, —C(=O)$SR^{cc}$, —C(=S)$_5R^{cc}$, —P(=O)($OR^{cc}$)$_2$, —P(=O)($R^{aa}$)$_2$, —P(=O)(N($R^{cc}$)$_2$)$_2$, $C_{1-10}$ alkyl, $C_{1-10}$ perhaloalkyl, $C_{2-10}$ alkenyl, $C_{2-10}$ alkynyl, hetero$C_{1-10}$alkyl, hetero$C_{2-10}$alkenyl, hetero$C_{2-10}$ alkynyl, $C_{3-10}$ carbocyclyl, 3-14 membered heterocyclyl, $C_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is a nitrogen protecting group (also referred to herein as an "amino protecting group"). Nitrogen protecting groups include, but are not limited to, —OH, —$OR^{aa}$, —N($R^{cc}$)$_2$, —C(=O)$R^{aa}$, —C(=O)N($R^{cc}$)$_2$, —$CO_2R^{aa}$, —$SO_2R^{aa}$, —C(=$NR^{cc}$)$R^{aa}$, —C(=$NR^{cc}$)$OR^{aa}$, —C(=$NR^{cc}$)N($R^{cc}$)$_2$, —$SO_2$N($R^{cc}$)$_2$, —$SO_2R^{cc}$, —$SO_2OR^{cc}$, —$SOR^{aa}$, —C(=S)N($R^{cc}$)$_2$, —C(=O)$SR^{cc}$, —C(=S)$SR^{cc}$, $C_{1-10}$ alkyl (e.g., aralkyl, heteroaralkyl), $C_{2-10}$ alkenyl, $C_{2-10}$ alkynyl, hetero$C_{1-10}$ alkyl, hetero$C_{2-10}$ alkenyl, hetero$C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in Protecting Groups in Organic Synthesis, T. W. Greene and P. G. M. Wuts, $3^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)$OR^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluorenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl) methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC or Boc), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo) benzyl carbamate, 2,4,6-tri-t-butylphenyl carbamate, 4-(trimethylammonium)benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3{}^+$X$^-$, —P(OR$^{cc}$)$_2$, —P(OR$^{cc}$)$_3{}^+$X$^-$, —P(=O)(R$^{aa}$)$_2$, —P(=O)(OR$^{cc}$)$_2$, and —P(=O)(N(R$^{bb}$)$_2$)$_2$, wherein X$^-$, R$^{aa}$, R$^{bb}$, and R$^{cc}$ are as defined herein. Oxygen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC or Boc), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3{}^+X^-$, $-P(OR^{cc})_2$, $-P(OR^{cc})_3{}^+X^-$, $-P(=O)(R^{aa})_2$, $-P(=O)(OR^{cc})_2$, and $-P(=O)(N(R^{bb})_2)_2$, wherein $R^{aa}$, $R^{bb}$, and $R^{cc}$ are as defined herein. Sulfur protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

The term "halo" or "halogen" refers to fluorine (fluoro, —F), chlorine (chloro, —Cl), bromine (bromo, —Br), or iodine (iodo, —I).

The term "hydroxyl" or "hydroxy" refers to the group —OH.

The term "thiol" or "thio" refers to the group —SH.

The term "amine" or "amino" refers to the group —NH— or —NH$_2$.

A "counterion" or "anionic counterion" is a negatively charged group associated with a positively charged group in order to maintain electronic neutrality. An anionic counterion may be monovalent (i.e., including one formal negative charge). An anionic counterion may also be multivalent (i.e., including more than one formal negative charge), such as divalent or trivalent. Exemplary counterions include halide ions (e.g., F$^-$, Cl$^-$, Br$^-$, I$^-$), NO$_3{}^-$, ClO$_4{}^-$, OH$^-$, H$_2$PO$_4{}^-$, HCO$_3{}^-$, HSO$_4{}^-$, sulfonate ions (e.g., methansulfonate, trifluoromethanesulfonate (triflate), p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), carboxylate ions (e.g., acetate, propanoate, benzoate, glycerate, lactate, tartrate, glycolate, gluconate, and the like), BF$_4{}^-$, PF$_4{}^-$, PF$_6{}^-$, AsF$_6{}^-$, SbF$_6{}^-$, B[3,5-(CF$_3$)$_2$C$_6$H$_3$]$_4{}^-$, B(C$_6$F$_5$)$_4{}^-$, BPh$_4{}^-$, Al(OC(CF$_3$)$_3$)$_4{}^-$, and carborane anions (e.g., CB$_{11}$H$_{12}{}^-$ or (HCB$_{11}$Me$_5$Br$_6$)$^-$). Exemplary counterions which may be multivalent include CO$_3{}^{2-}$, HPO$_4{}^{2-}$, PO$_4{}^{3-}$, B$_4$O$_7{}^{2-}$, SO$_4{}^{2-}$, S$_2$O$_3{}^{2-}$, carboxylate anions (e.g., tartrate, citrate, fumarate, maleate, malate, malonate, gluconate, succinate, glutarate, adipate, pimelate, suberate, azelate, sebacate, salicylate, phthalates, aspartate, glutamate, and the like), and carboranes. In certain embodiments, the counterion is triflate.

The term "leaving group" is given its ordinary meaning in the art of synthetic organic chemistry and refers to an atom or a group capable of being displaced by a nucleophile. Examples of suitable leaving groups include halogen (such as F, Cl, Br, or I (iodine)), alkoxycarbonyloxy, aryloxycarbonyloxy, alkanesulfonyloxy, arenesulfonyloxy, alkyl-carbonyloxy (e.g., acetoxy), arylcarbonyloxy, aryloxy, methoxy, N,O-dimethylhydroxylamino, pixyl, and haloformates. In some cases, the leaving group is a sulfonic acid ester, such as toluenesulfonate (tosylate, —OTs), methanesulfonate (mesylate, —OMs), p-bromobenzenesulfonyloxy (brosylate, —OBs), —OS(=O)$_2$(CF$_2$)$_3$CF$_3$ (nonaflate, —ONf), or trifluoromethanesulfonate (triflate, —OTf). In some cases, the leaving group is a brosylate, such as p-bromobenzenesulfonyloxy. In some cases, the leaving group is a nosylate, such as 2-nitrobenzenesulfonyloxy. In some embodiments, the leaving group is a sulfonate-containing group. In some embodiments, the leaving group is a tosylate group. The leaving group may also be a phosphineoxide (e.g., formed during a Mitsunobu reaction) or an internal leaving group such as an epoxide or cyclic sulfate. Other examples of leaving groups are water, ammonia, alcohols, ether moieties, thioether moieties, zinc halides, magnesium moieties, diazonium salts, and copper moieties.

The term "small molecule" refers to molecules, whether naturally-occurring or artificially created (e.g., via chemical synthesis) that have a relatively low molecular weight. Typically, a small molecule is an organic compound (i.e., it contains carbon). The small molecule may contain multiple carbon-carbon bonds, stereocenters, and other functional groups (e.g., amines, hydroxyl, carbonyls, and heterocyclic rings, etc.). In certain embodiments, the molecular weight of a small molecule is not more than 2,000 g/mol. In certain embodiments, the molecular weight of a small molecule is not more than 1,500 g/mol. In certain embodiments, the molecular weight of a small molecule is not more than 1,000 g/mol, not more than 900 g/mol, not more than 800 g/mol, not more than 700 g/mol, not more than 600 g/mol, not more than 500 g/mol, not more than 400 g/mol, not more than 300 g/mol, not more than 200 g/mol, or not more than 100 g/mol. In certain embodiments, the molecular weight of a small molecule is at least 100 g/mol, at least 200 g/mol, at least 300 g/mol, at least 400 g/mol, at least 500 g/mol, at least 600 g/mol, at least 700 g/mol, at least 800 g/mol, or at least 900 g/mol, or at least 1,000 g/mol. Combinations of the above ranges (e.g., at least 200 g/mol and not more than 500 g/mol) are also possible. In certain embodiments, the small molecule is a therapeutically active agent such as a drug (e.g., a molecule approved by the U.S. Food and Drug Administration as provided in the Code of Federal Regulations (C.F.R.)). The small molecule may also be complexed with one or more metal atoms and/or metal ions. In this instance, the small molecule is also referred to as a "small organometallic molecule." Preferred small molecules are biologically active in that they produce a biological effect in animals, preferably mammals, more preferably humans. Small molecules include radionuclides and imaging agents. In certain embodiments, the small molecule is a drug. Preferably, though not necessarily, the drug is one that has already been deemed safe and effective for use in humans or animals by the appropriate governmental agency or regulatory body. For example, drugs approved for human use are listed by the FDA under 21 C.F.R. §§ 330.5, 331 through 361, and 440 through 460, incorporated herein by reference; drugs for veterinary use are listed by the FDA under 21 C.F.R. §§ 500 through 589, incorporated herein by reference. All listed drugs are considered acceptable for use in accordance with the present invention.

The term "polymer" refers to a compound comprising eleven or more covalently connected repeating units. In certain embodiments, a polymer is naturally occurring. In certain embodiments, a polymer is synthetic (e.g., not naturally occurring). In certain embodiments, the number average molecular weight of the polymer (e.g., as determined by gel permeation chromatography) is between 1,000 and 3,000, between 3,000 and 10,000, between 10,000 and 30,000, between 30,000 and 100,000, between 100,000 and 300,000, or between 300,000 and 1,000,000, g/mol, inclusive. In certain embodiments, the dispersity of the polymer is between 1 and 1.2, between 1.2 and 1.5, between 1.5 and 2, between 2 and 4, between 4 and 10, inclusive.

A "protein," "peptide," or "polypeptide" comprises a polymer of amino acid residues linked together by peptide bonds. The term refers to proteins, polypeptides, and peptides of any size, structure, or function. A protein may refer to an individual protein or a collection of proteins. Proteins preferably contain only natural amino acids, although non-natural amino acids (i.e., compounds that do not occur in nature but that can be incorporated into a polypeptide chain) and/or amino acid analogs as are known in the art may alternatively be employed. In certain embodiments, the amino acid residues of a peptide are alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and/or valine, in D and/or L form. In certain embodiments, the amino acid residues of a peptide are alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and/or valine, in L form. One or more of the amino acids in a protein may be protected. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these. In certain embodiments, a protein comprises (e.g., consists essentially of) between 3 and 10, between 10 and 30, between 30 and 100, between 100 and 300, between 300 and 1,000, between 1,000 and 3,000, or between 3,000 and 10,000, inclusive, amino acids. In certain embodiments, the amino acids in a protein are natural amino acids. In certain embodiments, the amino acids in a protein are unnatural amino acids. In certain embodiments, the amino acids in a protein are a combination of natural amino acids and unnatural amino acids (e.g., unnatural alpha-amino acids).

The term "salt" refers to ionic compounds that result from the neutralization reaction of an acid and a base. A salt is composed of one or more cations (positively charged ions) and one or more anions (negative ions) so that the salt is electrically neutral (without a net charge). Salts of the compounds of this invention include those derived from inorganic and organic acids and bases. Examples of acid addition salts are salts of an amino group formed with inorganic acids such as hydrochloric acid, hydrobromic acid, phosphoric acid, sulfuric acid, and perchloric acid, or with organic acids such as acetic acid, oxalic acid, maleic acid, tartaric acid, citric acid, succinic acid, or malonic acid or by using other methods known in the art such as ion exchange. Other salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further salts include ammonium, quaternary ammonium, and amine cations formed using counterions such as halide, hydroxide, carboxylate, sulfate, phosphate, nitrate, lower alkyl sulfonate, and aryl sulfonate.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids, such as hydrochloric acid, hydrobromic acid, phosphoric acid, sulfuric acid, and perchloric acid or with organic acids, such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium, and $N^+(C_{1-4}\text{ alkyl})_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

The term "solvate" refers to forms of the compound, or a salt thereof, that are associated with a solvent, usually by a solvolysis reaction. This physical association may include hydrogen bonding. Conventional solvents include water, methanol, ethanol, acetic acid, DMSO, THF, diethyl ether, and the like. The compounds described herein may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolatable solvates. Representative solvates include hydrates, ethanolates, and methanolates.

The term "hydrate" refers to a compound that is associated with water. Typically, the number of the water molecules contained in a hydrate of a compound is in a definite ratio to the number of the compound molecules in the hydrate. Therefore, a hydrate of a compound may be represented, for example, by the general formula $R \cdot xH_2O$, wherein R is the compound, and x is a number greater than 0. A given compound may form more than one type of hydrate, including, e.g., monohydrates (x is 1), lower hydrates (x is a number greater than 0 and smaller than 1, e.g., hemihydrates ($R \cdot 0.5H_2O$)), and polyhydrates (x is a number greater than 1, e.g., dihydrates ($R \cdot 2H_2O$) and hexahydrates ($R \cdot 6H_2O$)).

The term "tautomers" or "tautomeric" refers to two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol, amide-to-imide, lactam-to-lactim, enamine-to-imine, and enamine-to-(a different enamine) tautomerizations.

Compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers," and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture."

The term "prodrug" refers to a compound that becomes active, e.g., by solvolysis, reduction, oxidation, or under physiological conditions, to provide a pharmaceutically active compound, e.g., in vivo. A prodrug can include a derivative of a pharmaceutically active compound, such as, for example, to form an ester by reaction of the acid, or acid anhydride, or mixed anhydrides moieties of the prodrug moiety with the hydroxyl moiety of the pharmaceutical active compound. See, Bundgard, H., *Design of Prodrugs*, pp. 7-9, 21-24, Elsevier, Amsterdam 1985.

"Click chemistry" reaction includes Huisgen alkyne-azide cycloaddition. Any "click chemistry" reaction known in the art can be used to this end. Click chemistry is a chemical approach introduced by Sharpless in 2001 and describes chemistry tailored to generate substances quickly and reliably by joining small units together. See, e.g., Kolb, Finn and Sharpless *Angewandte Chemie International Edition* (2001) 40: 2004-2021; Evans, *Australian Journal of Chemistry* (2007) 60: 384-395). Exemplary coupling reactions (some of which may be classified as "click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgen cycloaddition; thiol-yne addition; imine formation; Michael additions (e.g., maleimide addition); and Diels-Alder reactions (e.g., tetrazine [4+2] cyclo addition).

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In certain embodiments, the non-human animal is a mammal (e.g., primate (e.g., cynomolgus monkey or rhesus monkey), commercially relevant mammal (e.g., cattle, pig, horse, sheep, goat, cat, or dog), or bird (e.g., commercially relevant bird, such as chicken, duck, goose, or turkey)). In certain embodiments, the non-human animal is a fish, reptile, or amphibian. The non-human animal may be a male or female at any stage of development. The non-human animal may be a transgenic animal or genetically engineered animal.

The term "administer," "administering," or "administration" refers to implanting, absorbing, ingesting, injecting, inhaling, or otherwise introducing a compound described herein, or a composition thereof, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen). Treatment may also be continued after symptoms have resolved, for example, to delay and/or prevent recurrence.

The term "prevent," "preventing," or "prevention" refers to a prophylactic treatment of a subject who is not and was not with a disease but is at risk of developing the disease or who was with a disease, is not with the disease, but is at risk of regression of the disease. In certain embodiments, the subject is at a higher risk of developing the disease or at a higher risk of regression of the disease than an average healthy member of a population of subjects.

The terms "condition," "disease," and "disorder" are used interchangeably.

An "effective amount" of a compound described herein refers to an amount sufficient to elicit the desired biological response. An effective amount of a compound described herein may vary depending on such factors as the desired biological endpoint, the pharmacokinetics of the compound, the condition being treated, the mode of administration, and the age and health of the subject. In certain embodiments, an effective amount is a therapeutically effective amount. In certain embodiments, an effective amount is a prophylactically effective amount. In certain embodiments, an effective amount is the amount of a compound or pharmaceutical composition described herein in a single dose. In certain embodiments, an effective amount is the combined amounts of a compound or pharmaceutical composition described herein in multiple doses.

A "therapeutically effective amount" of a compound described herein is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of a compound described herein is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The term "therapeutic agent" includes an agent that is capable of providing a local or systemic biological, physiological, or therapeutic effect in the biological system to which it is applied. For example, a therapeutic agent can act to control tumor growth, control infection or inflammation, act as an analgesic, promote anti-cell attachment, and enhance bone growth, among other functions. Other suitable therapeutic agents can include anti-viral agents, hormones, antibodies, or therapeutic proteins. Other therapeutic agents include prodrugs, which are agents that are not biologically active when administered but, upon administration to a subject are converted to biologically active agents through metabolism or some other mechanism.

Additional terms may be defined in other sections of this disclosure.

BRIEF DESCRIPTION OF THE DRAWINGS

The figures are exemplary and do not limit the scope of the present disclosure.

FIG. 4A shows a scheme of the antibody lysine modification. Mass spectra were obtained for IgG (FIG. 4B), NHS (N-hydroxysuccinimide) small molecule with PEG12 (PEG12) (FIG. 4C) and NHS small molecule with PEG8 (PEG8) (FIG. 4D). "Ab" refers to antibody.

FIGS. 9A to 9B show anti-HER2 ABCs in HCC-1954 (HER2 medium expression) and BT-474 cell line (HER2 high expression). Results show that ABCs can also significantly enhance cell uptake toward the other HER2 expression cell lines.

FIGS. 15A to 15C show cell toxicity studies in SKBR-3 (FIG. 15A), HCC-1954 (FIG. 15B) and BT-474 (FIG. 15C) cell lines with the free antibody (Ab) as a control. Results show that the antibody itself has no toxicity toward these cell lines. The brush polymer (Pol) and the physical mixture of antibody and brush polymer (Pol+Ab) have similar toxicity, significantly lower than ABCs.

FIG. 16A shows a conjugation and delivery process (FG: functional group). FIG. 16B shows efficient conjugation between TCO functionalized antibodies and Tz terminated bottle brush polymers based on SDS PAGE gel. FIG. 16C shows enhanced cell uptake for the ABC comparing to the bottle brush polymer prodrug (BPD) by flow cytometry in MM.1S cell line. FIG. 16D shows enhanced cell uptake for ABC comparing to BPD by flow cytometry in KMS cell line.

FIG. 17A: an azide-DBCO conjugation. FIGS. 17B to 17C: a Tz-TCO conjugation. FIGS. 17B and 17D: another azide-DBCO conjugation. FIG. 17E: another Tz-TCO conjugation. Tz: tetrazine. TCO: trans-cyclooctene. G3: the third generation Grubbs catalyst. DBCO:

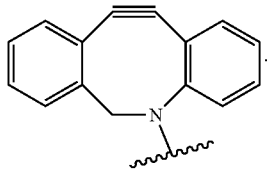 [SMILES: *N1Cc2ccccc2C#Cc2ccccc21]

Figure 17A:
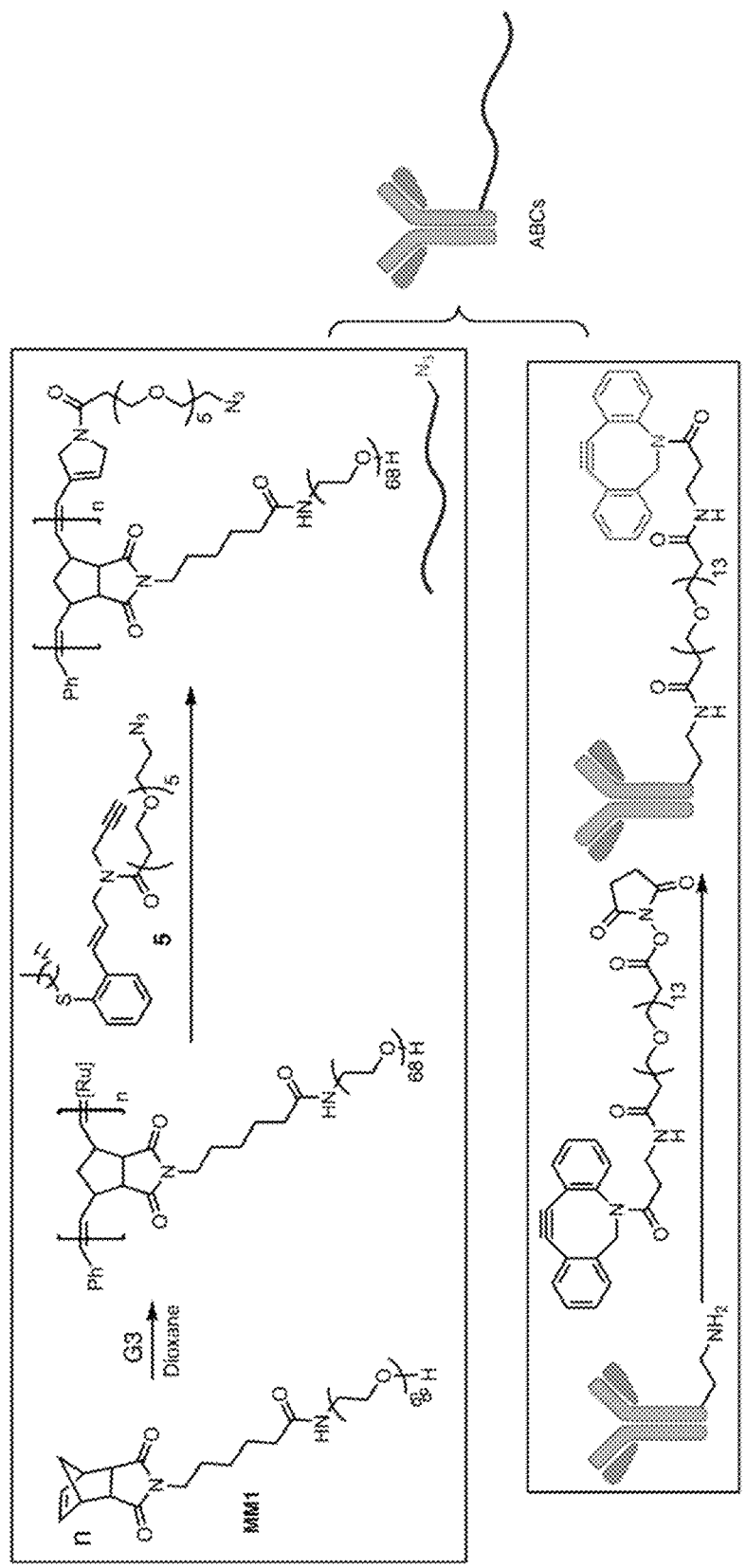
FIGS. 17A to 17E show schemes of four strategies for antibody-polymer conjugation prepared thorough click reactions between the antibody and polymer.
Figure 18A:
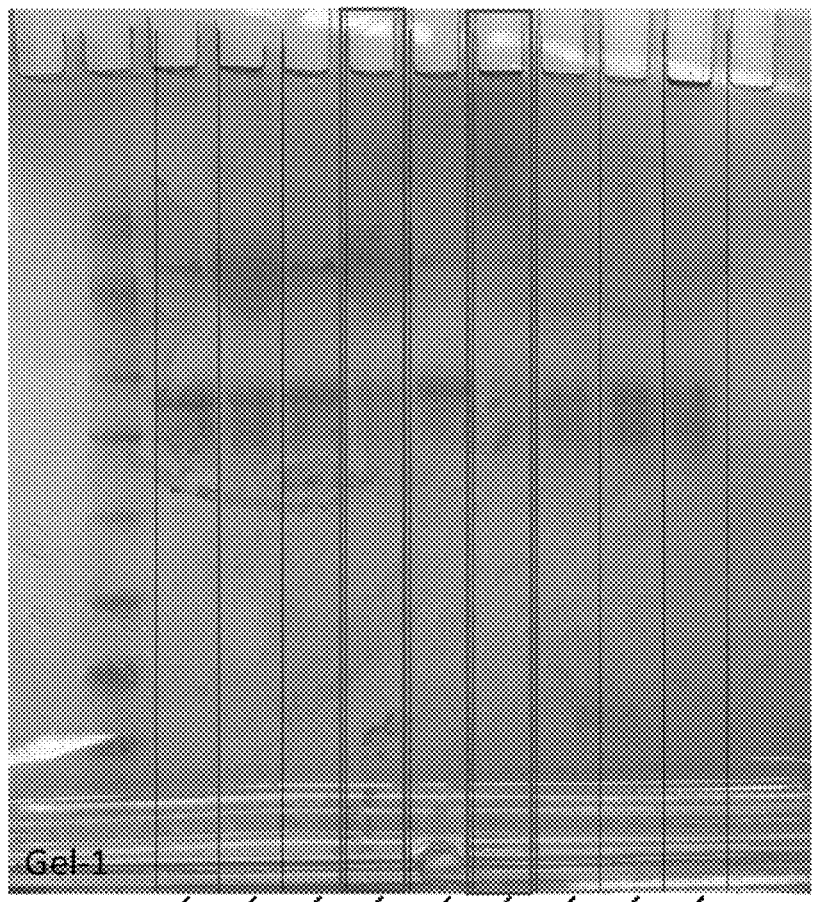
Figure 18B:
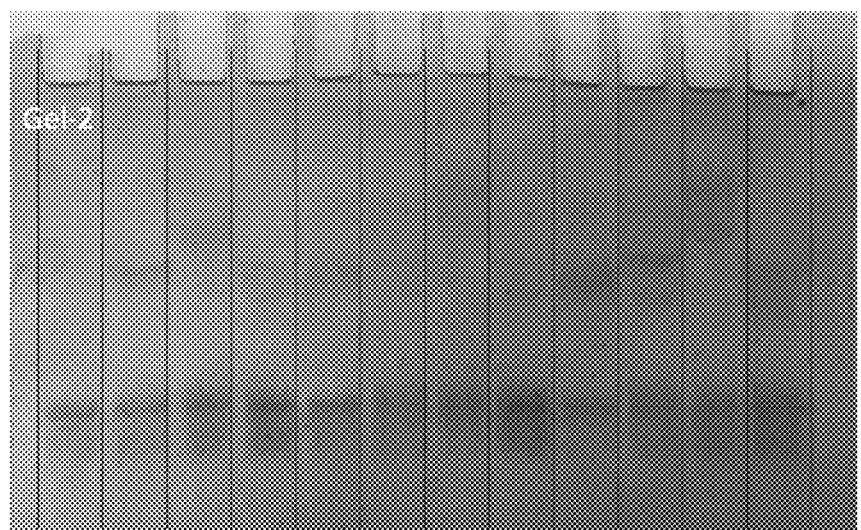
Figure 18C:
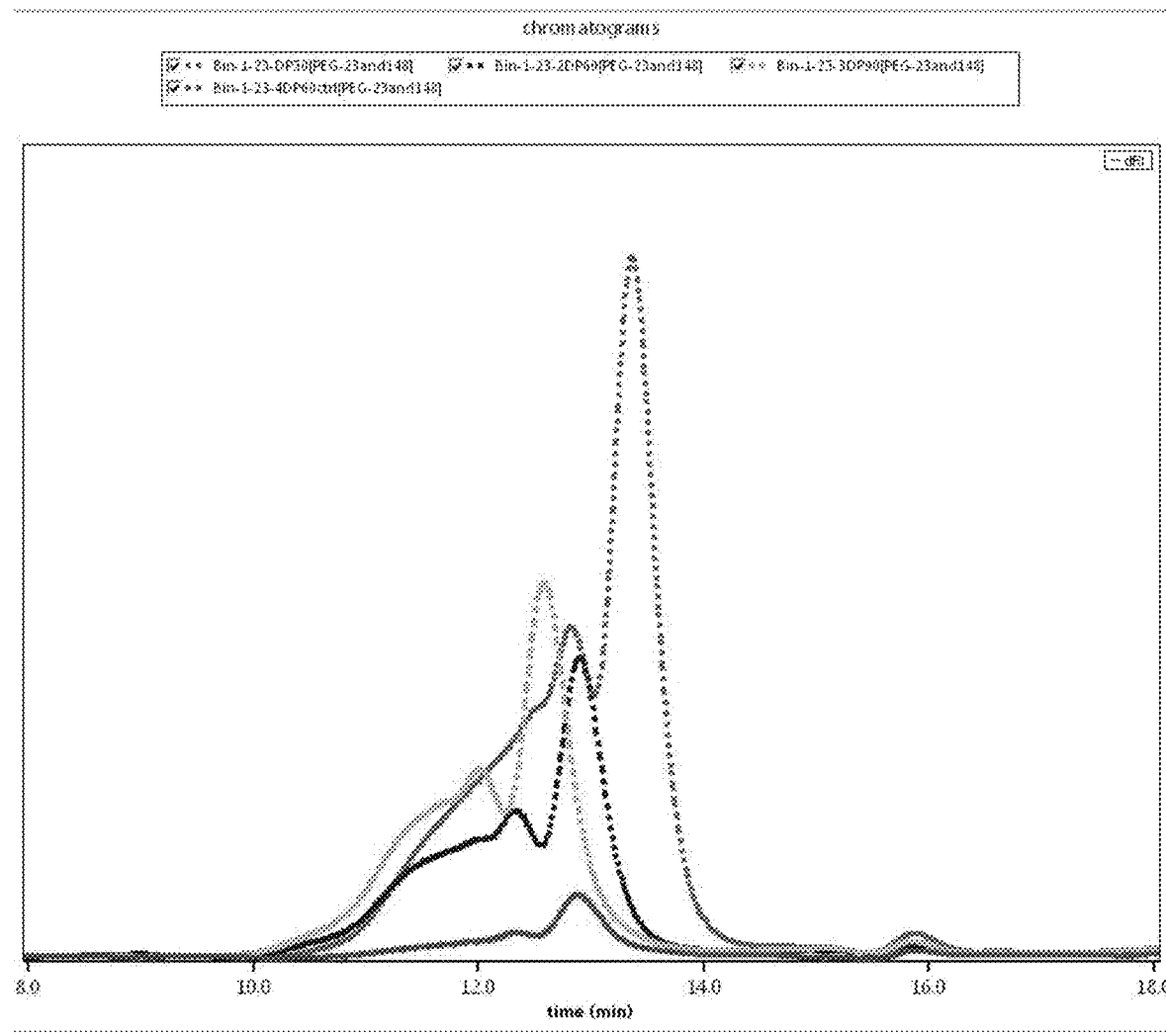
Figure 18D:
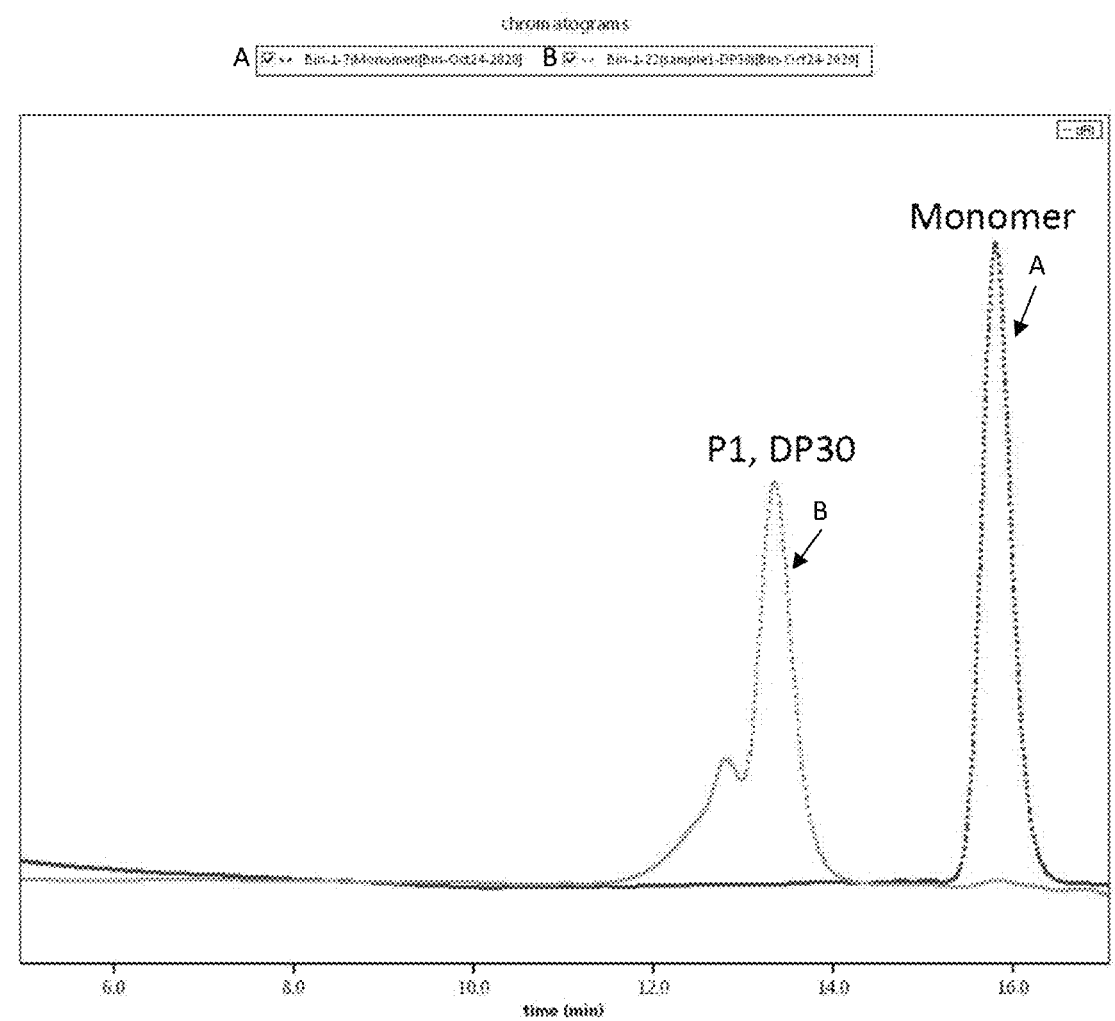
Figure 18E:
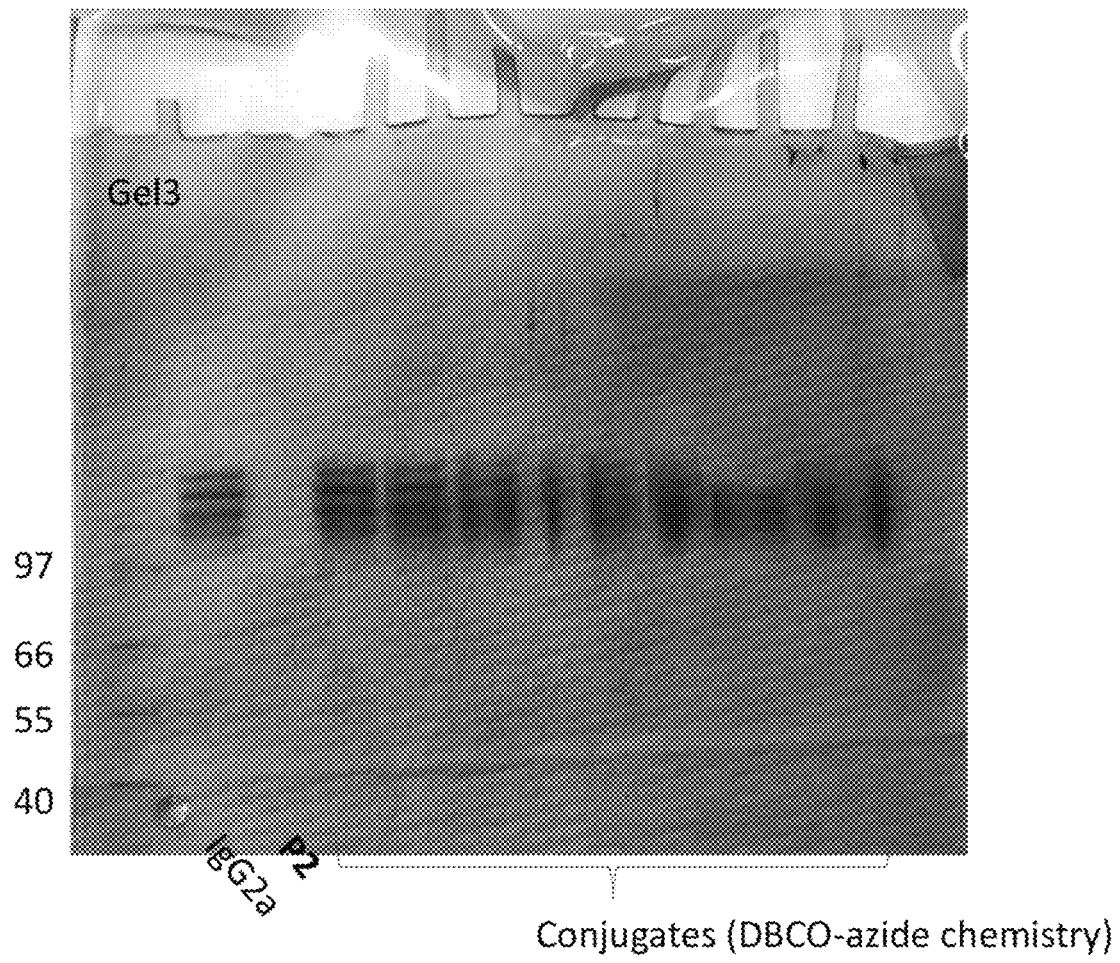

FIGS. 18A to 18E show an antibody-polymer conjugation using the strategy shown in FIG. 17A. *P4: control polymer; IgG1: 1:5 linker reaction (1 mg scale, 1 mL); IgG2: 1:10 linker reaction (1 mg scale, 1 mL); IgG3: 1:15 linker reaction (1 mg scale, 1 mL). "DP" refers to degree of polymerization. FIG. 18A shows conjugation efficiency between DBCO functionalized IgG antibody and azide functionalized bottle brush polymer with different DPs at different ratios. FIG. 18B shows conjugation efficiency between DBCO functionalized IgG antibody and azide functionalized bottle brush polymer with different DPs at a ratio of 1:2. FIG. 18C shows GPC traces of the bottle brush polymers with different DPs. FIG. 18D shows comparison of GPC traces for the bottle brush polymers with DP=30 and macromonomer. FIG. 18E shows SDS PAGE gel data from azide terminated bottle brush polymers with short linker.

Figure 17B:
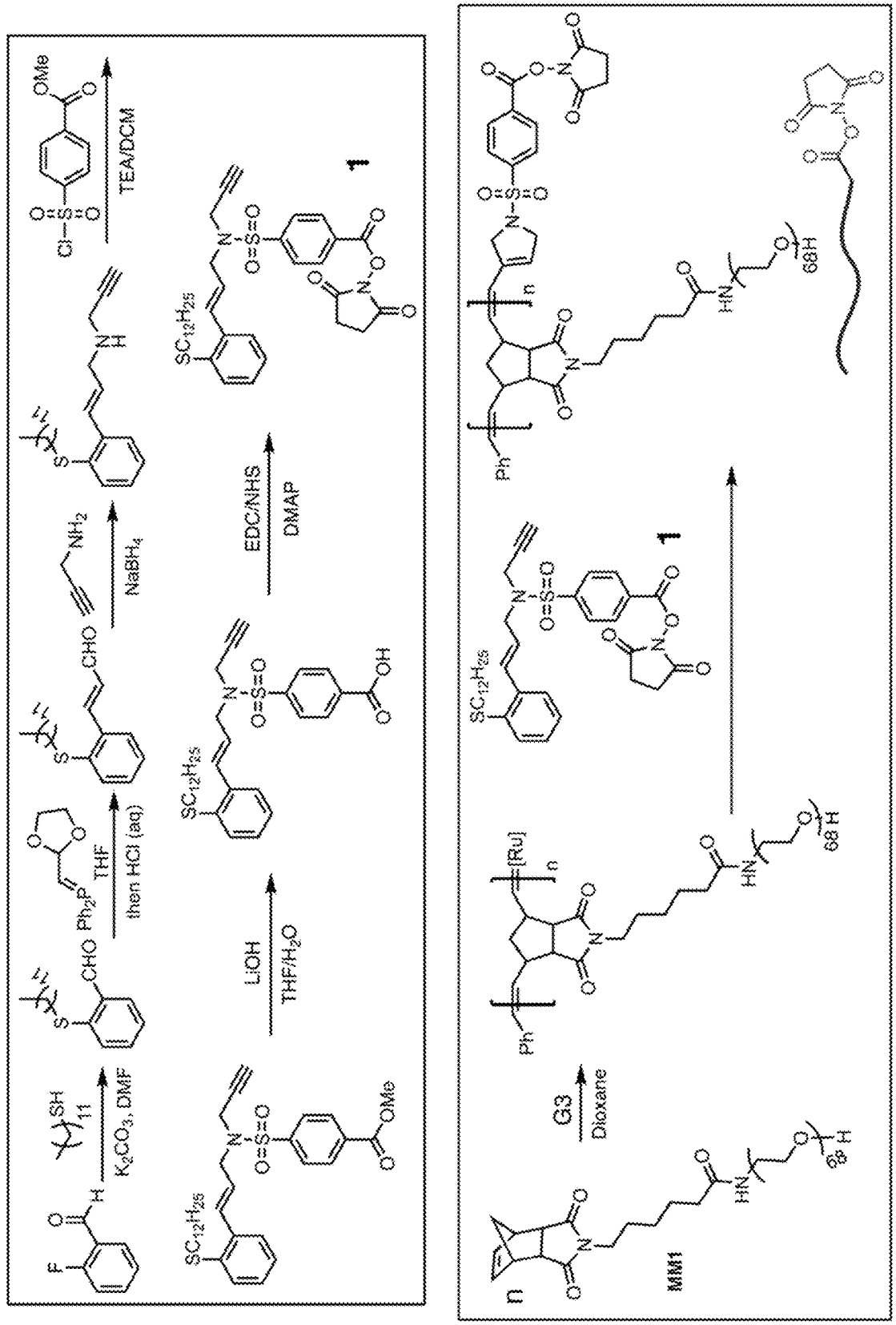
Figure 17C:
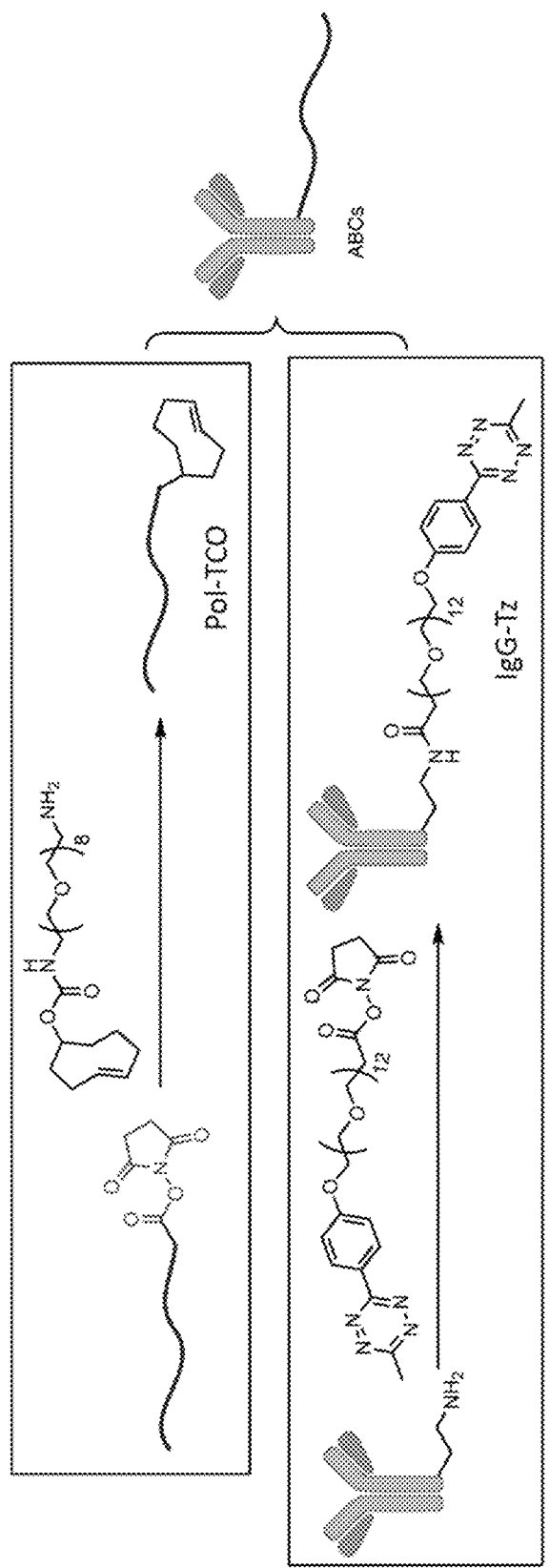
Figure 19A:
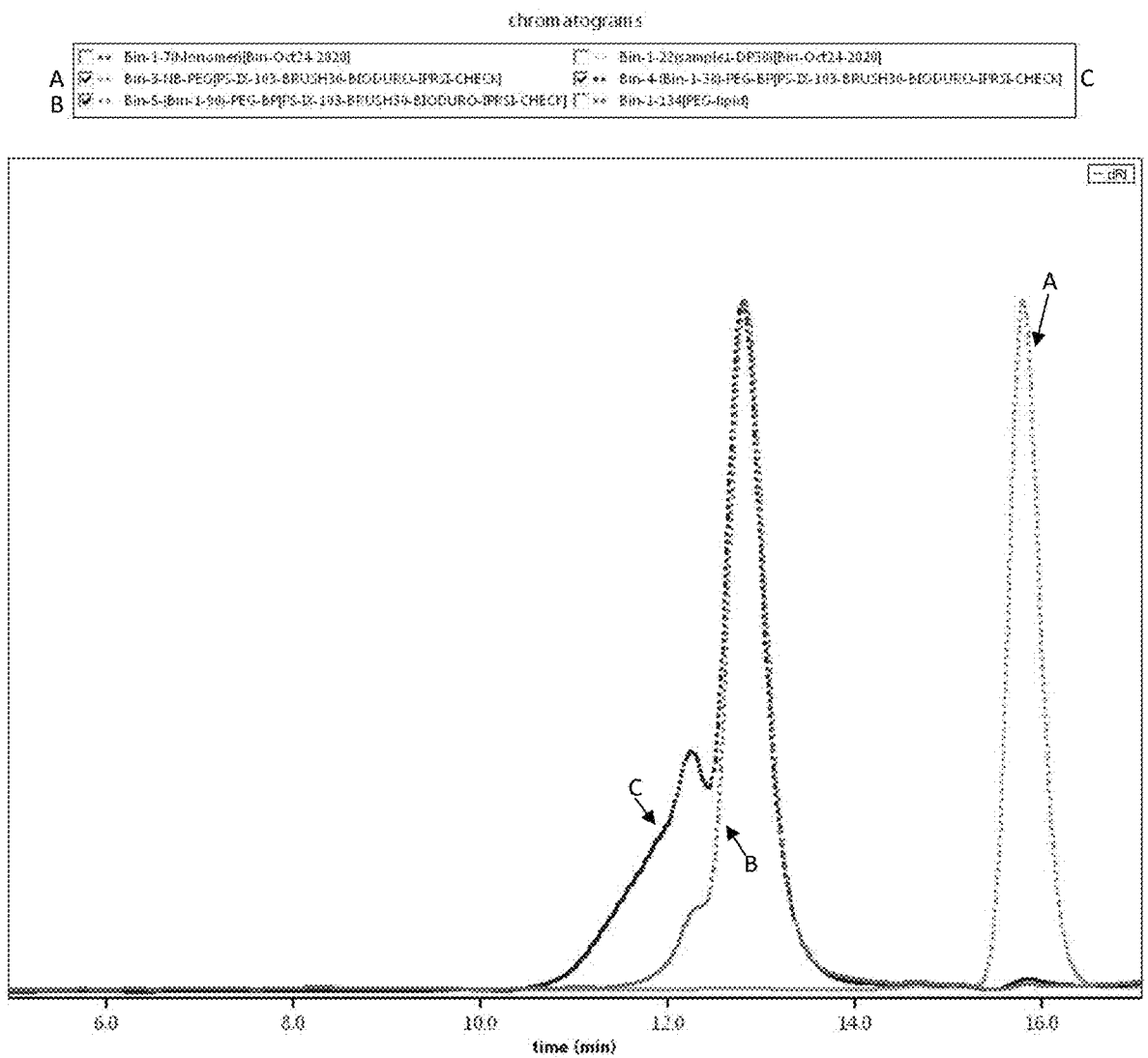
Figure 19B:
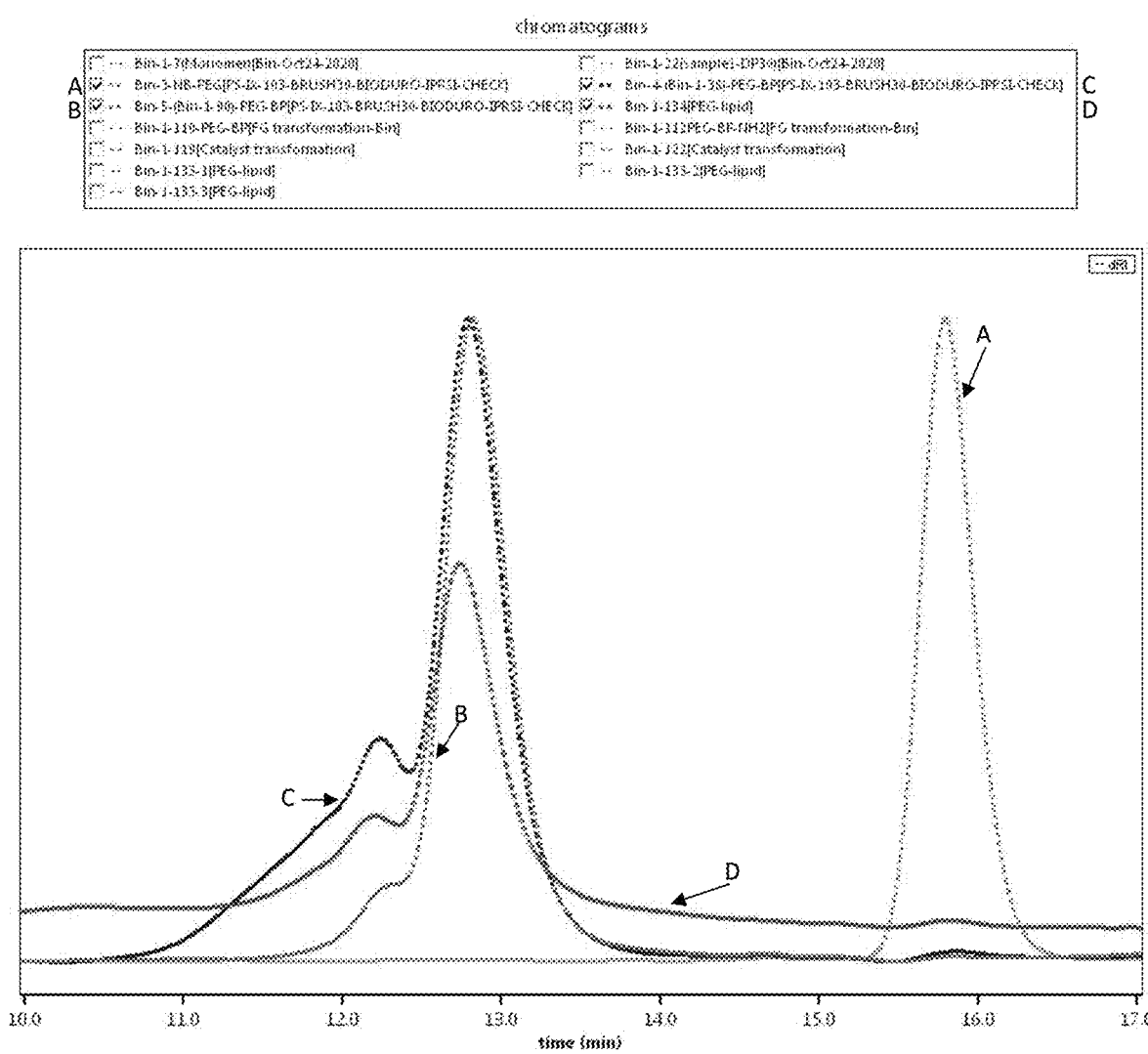

FIGS. 19A to 19B show an antibody-polymer conjugation using the strategy shown in FIGS. 17B to 17C. FIG. 19A shows GPC traces of NHS functional group terminated bottle brush polymers: green color is macromonomer; blue color is bottle brush polymer with DP=60; blue color is dye labelled bottle brush polymer with DP=60. FIG. 19B shows GPC traces of terminal functional group transformation for NHS terminated bottle brush polymers.

Figure 17D:
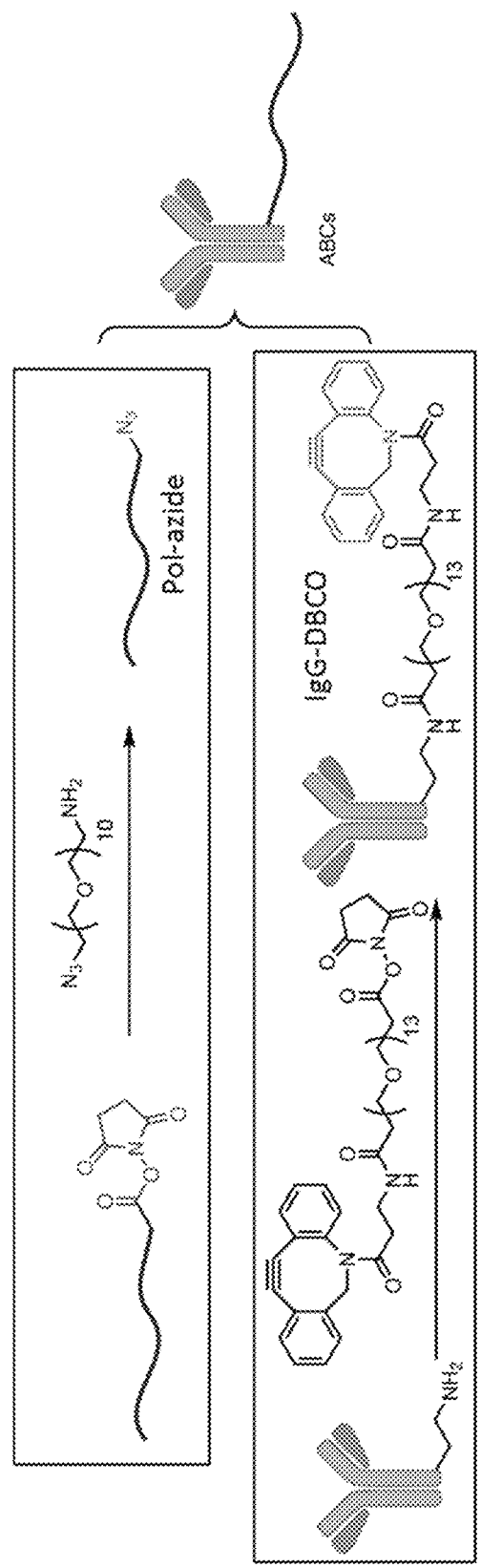
Figure 20A:
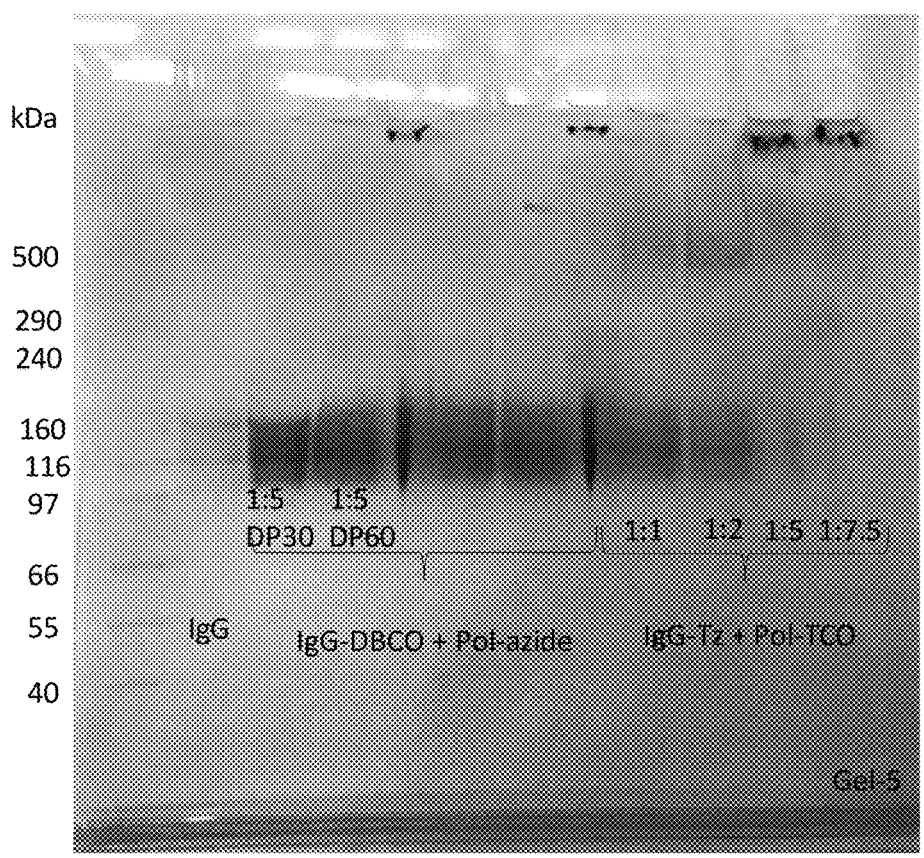
Figure 20B:
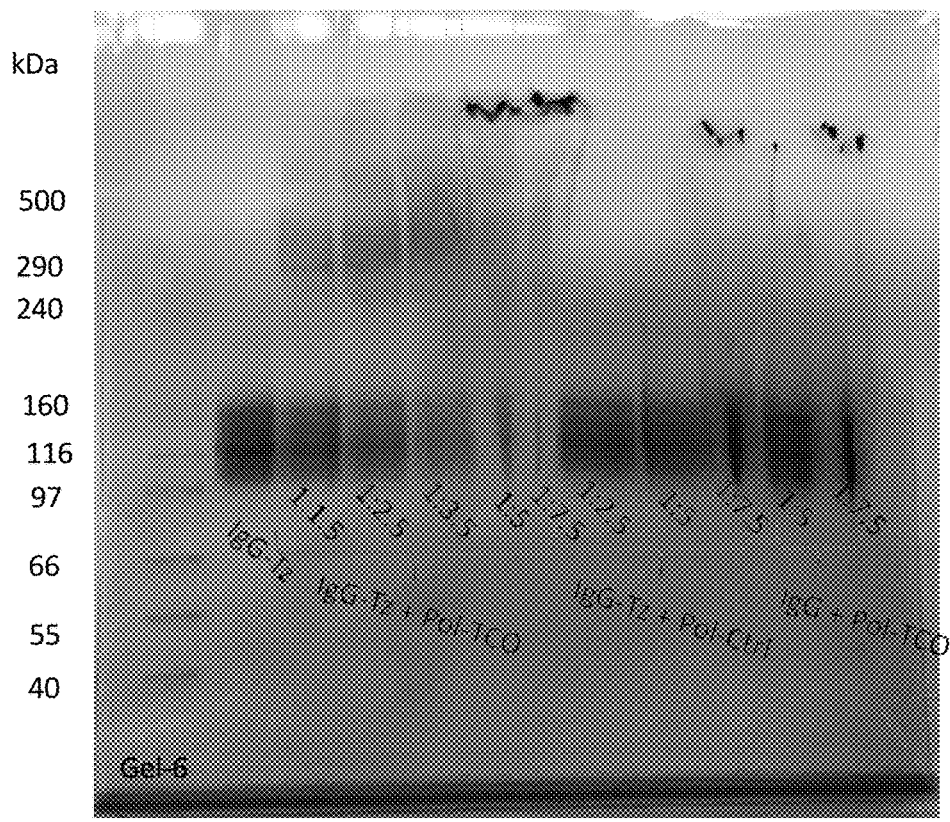
Figure 20C:
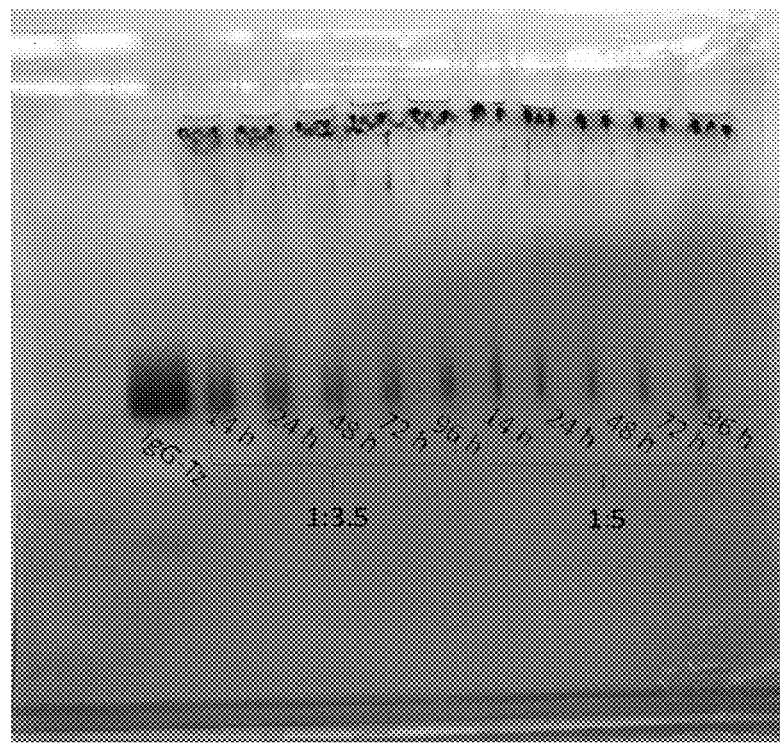
Figure 20D:
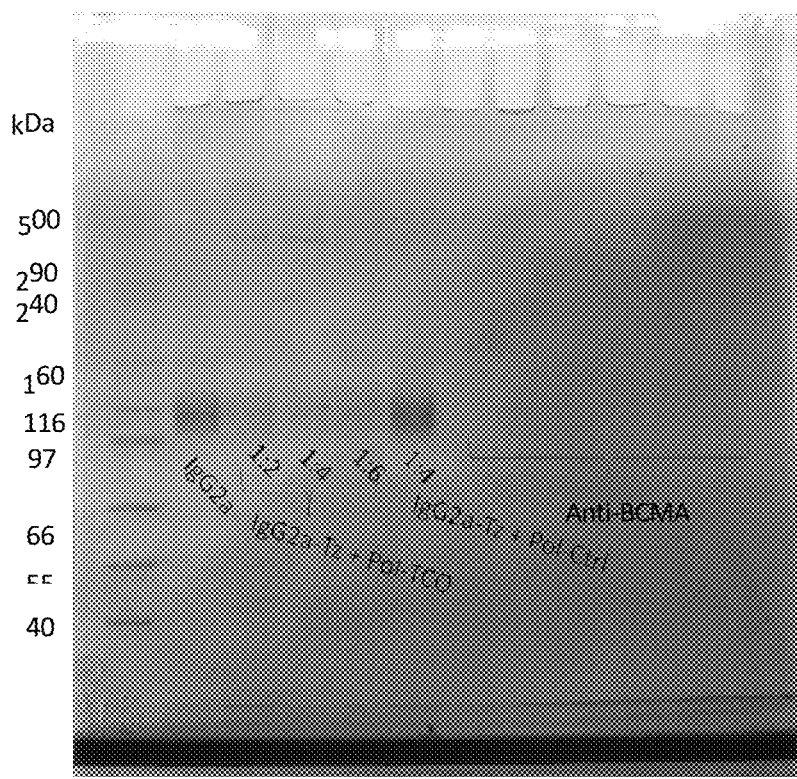

FIGS. 20A to 20D show antibody-polymer conjugations using the strategy shown in FIGS. 17B and 17D (IgG-DBCO+Pol-azide) or the strategy shown in FIGS. 17B and 17C (IgG-Tz+Pol-TCO). FIG. 20A shows SDS PAGE gel for efficiency of conjugation between antibody and bottle brush polymer. The conjugation is much more efficient based on Tz-TCO reaction than DBCO-azide reaction. FIG. 20B shows SDS PAGE gel for conjugation between TCO functionalized IgG antibody and Tz functionalized bottle brush polymer. IgG+Pol-TCO and IgG-Tz+Pol-Ctrl were controls. FIG. 20C shows SDS PAGE gel for conjugation kinetics between TCO functionalized IgG antibody and Tz functionalized bottle brush polymer. The reaction was efficient, which was finished in 14 h. FIG. 20D shows SDS PAGE gel for conjugation between TCO functionalized antibodies (IgG2a and anti-BCMA) and Tz functionalized bottle brush polymer.

Figure 21A:
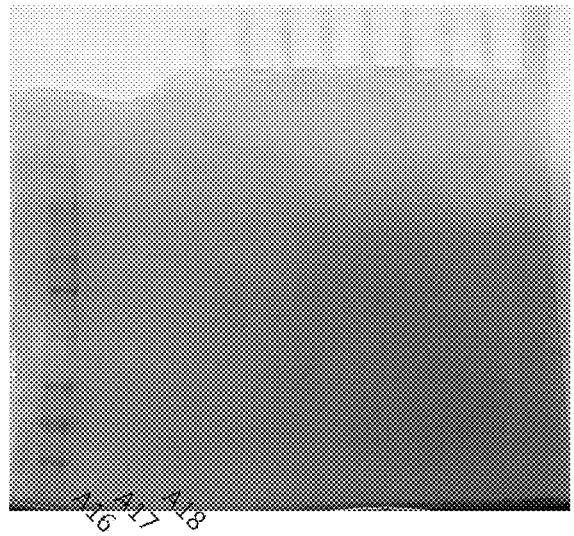
Figure 21B:
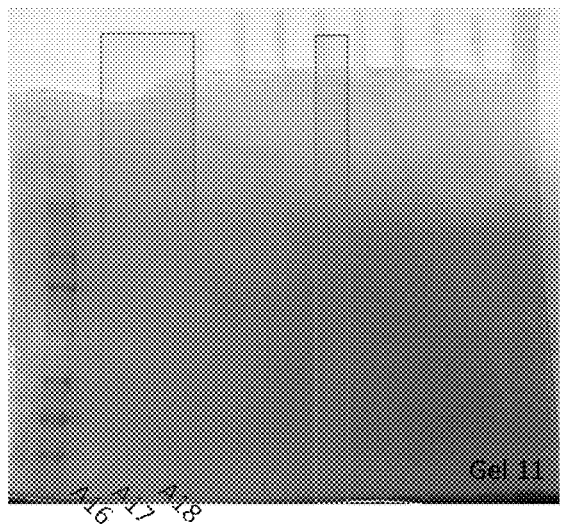
Figure 21C:
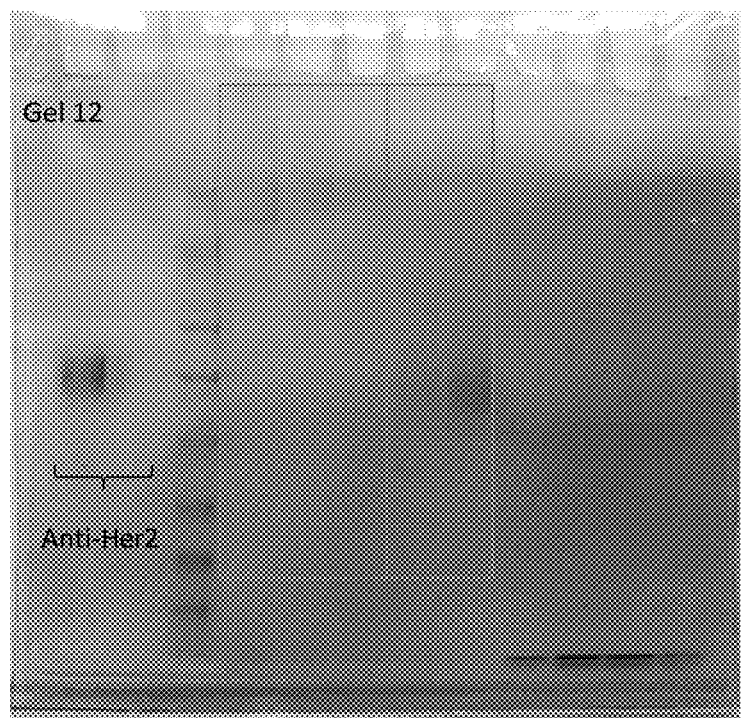

FIGS. 21A to 21C show SDS PAGE gels for different fractions of the conjugates after FPLC separation.

Figure 22A:
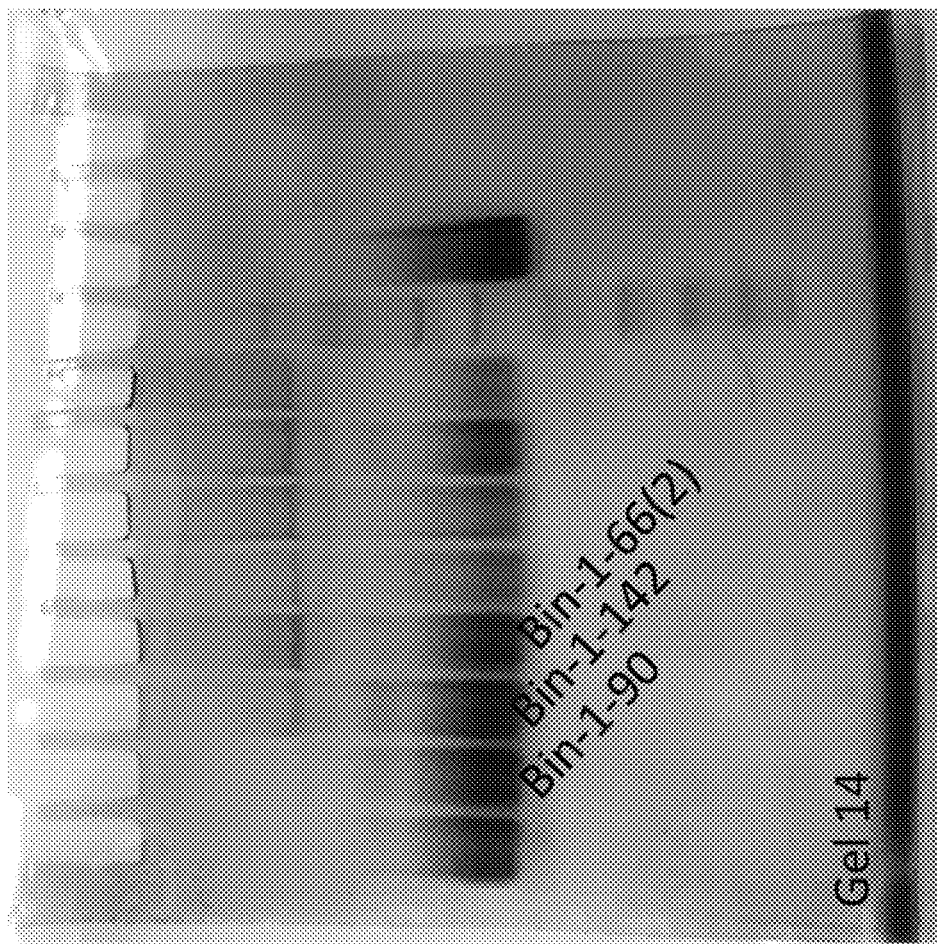
Figure 22A:
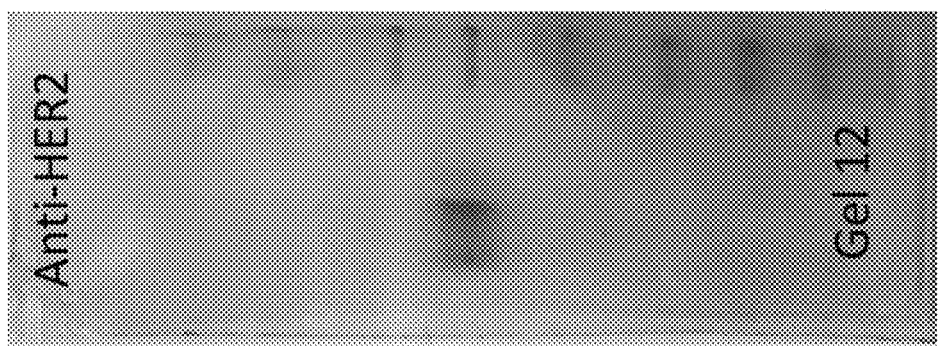
Figure 22B:
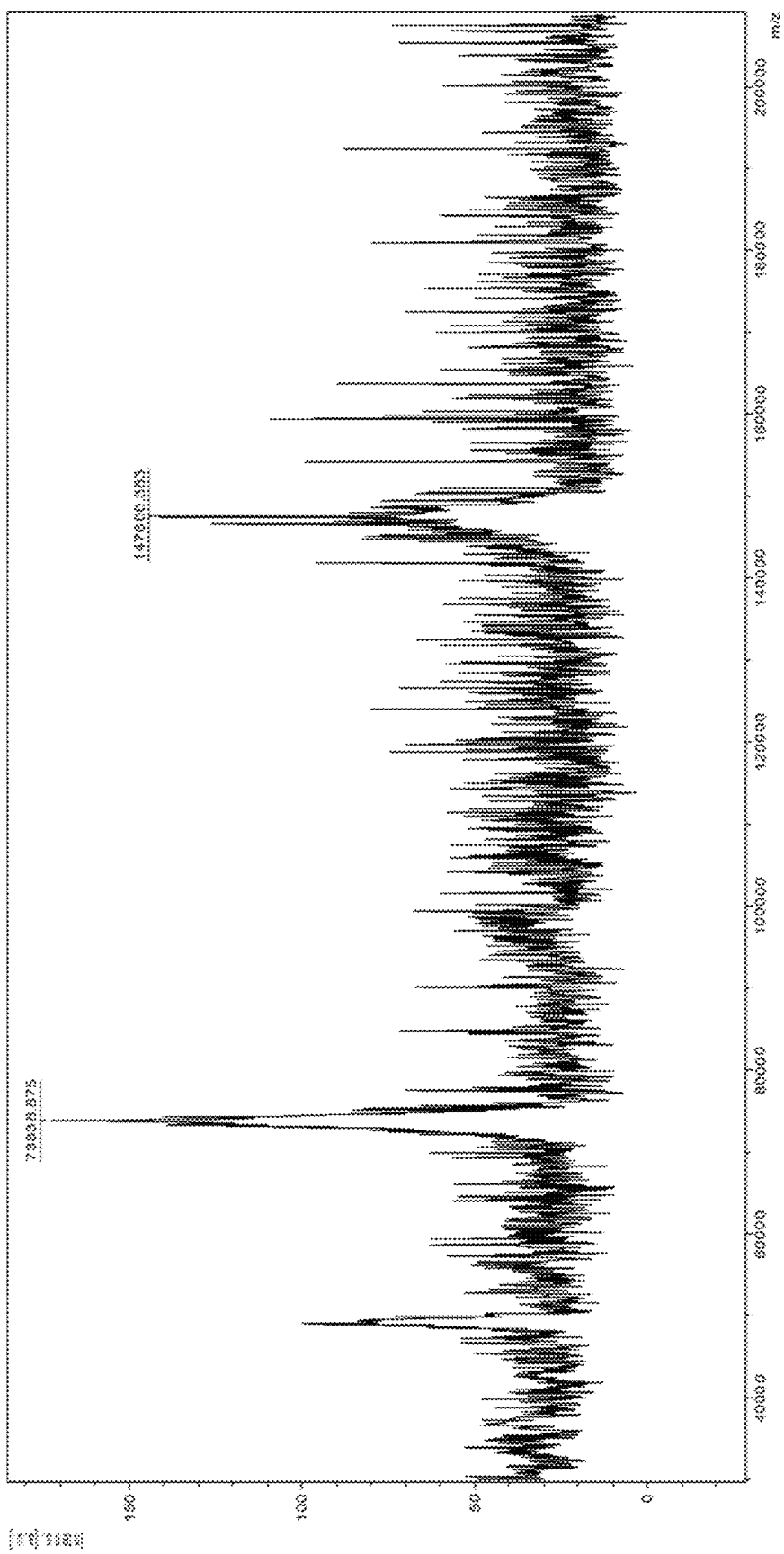
Figure 22C:
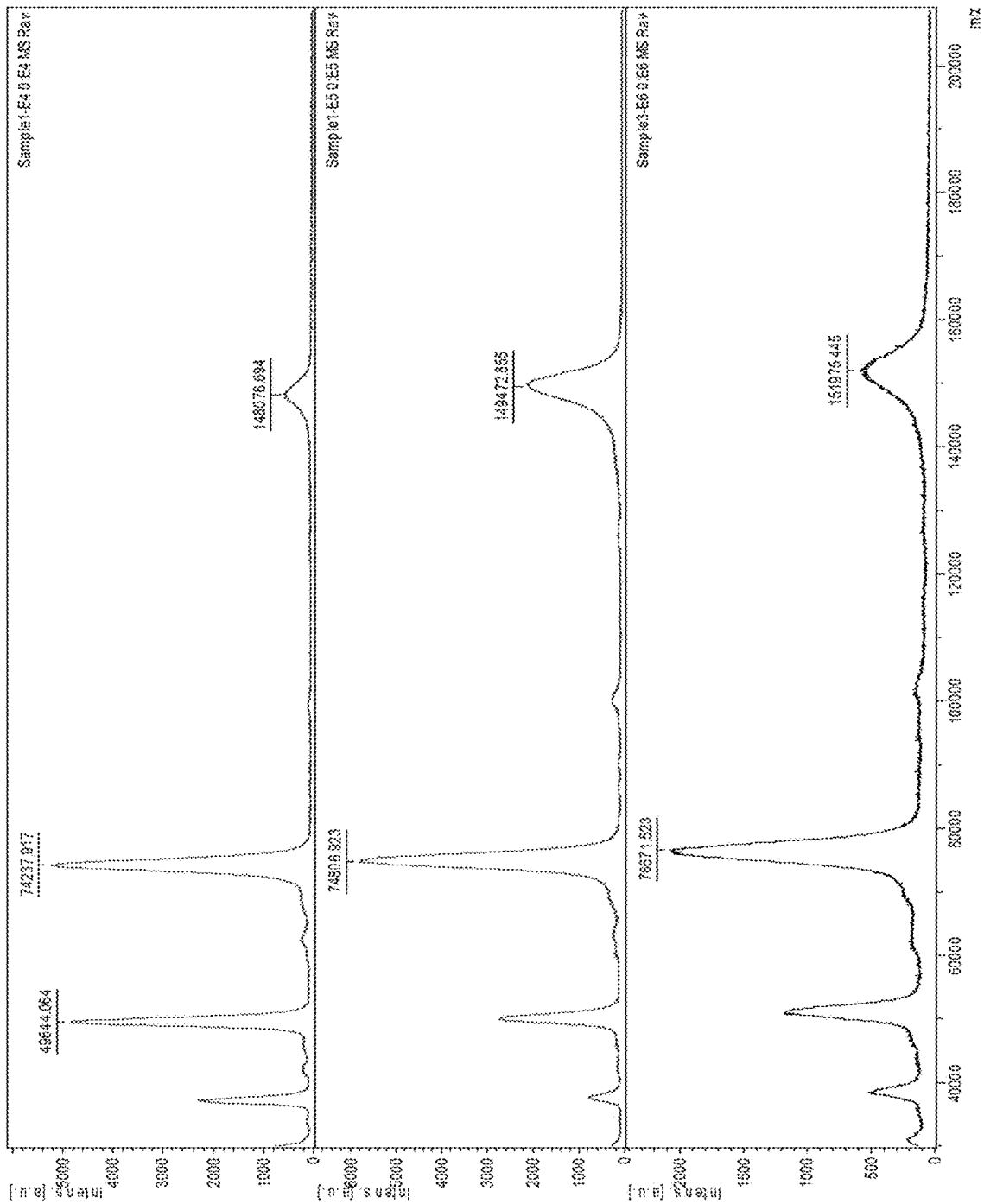

FIGS. 22A to 22C show synthesis of dye labeled polymers for conjugation. FIG. 22A shows SDS PAGE gel for conjugation between different dye labelled polymers and antibodies. FIG. 22B shows MALDI-TOF mass spectrometry of IgG antibody. FIG. 22C shows MALDI-TOF mass spectrometry of different amounts of TCO functional group modified IgG antibody.

Figure 23A:
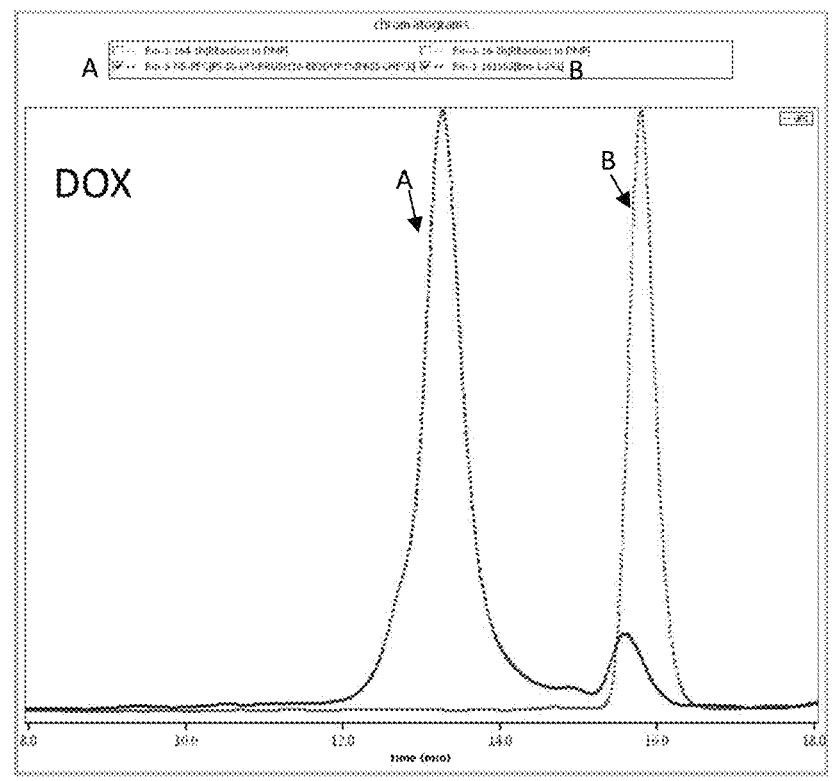
Figure 23B:
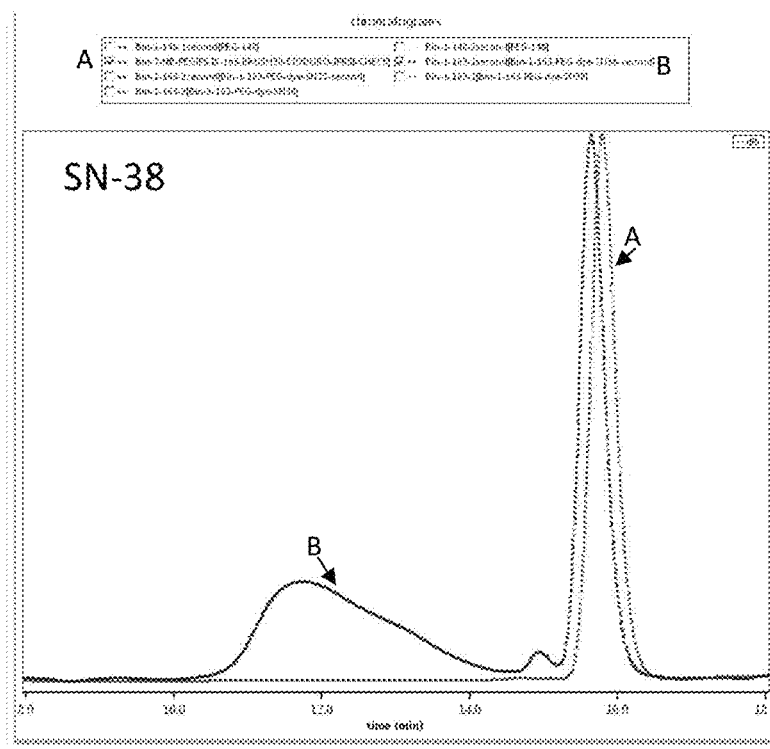
Figure 23C:
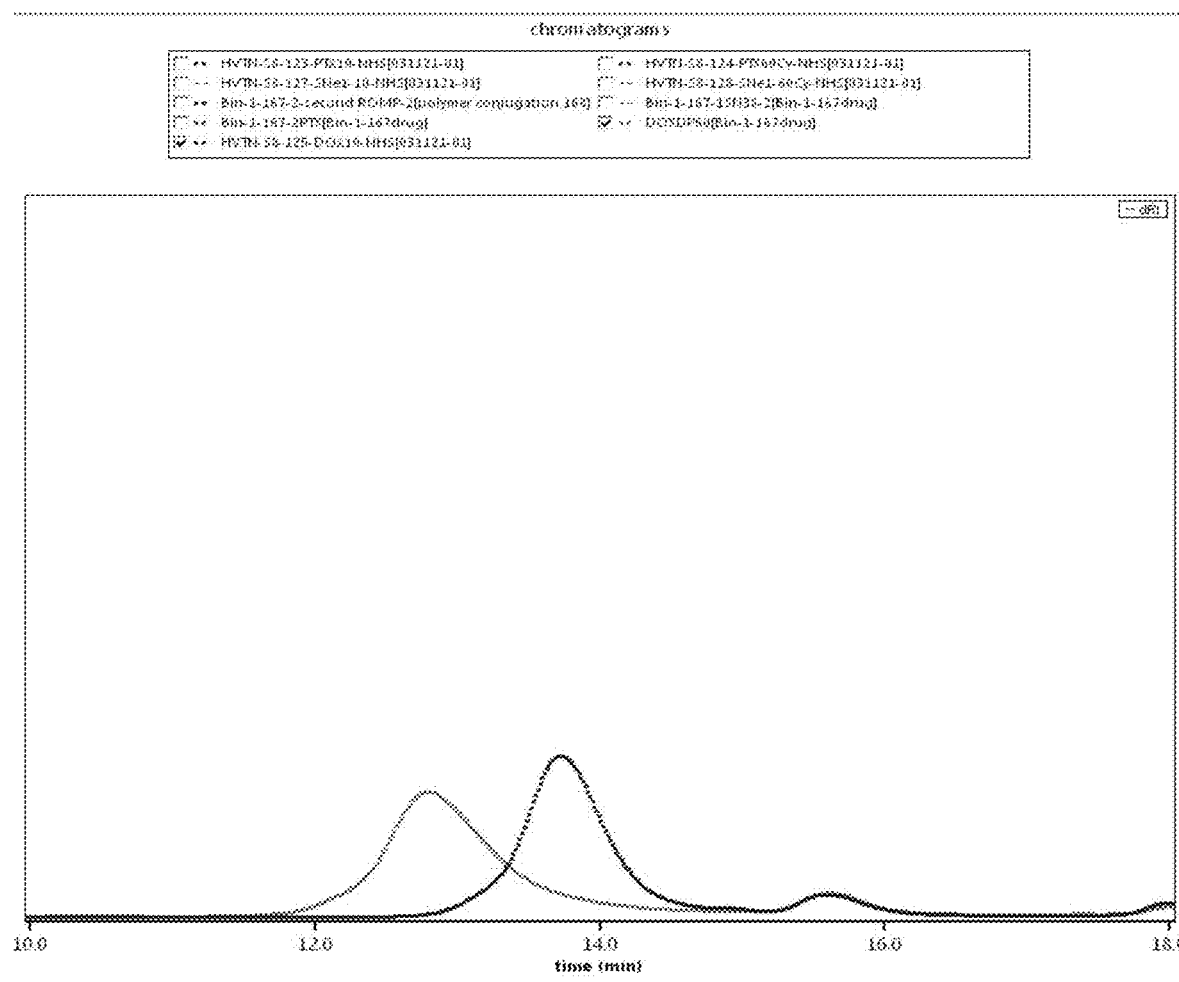
Figure 23D:
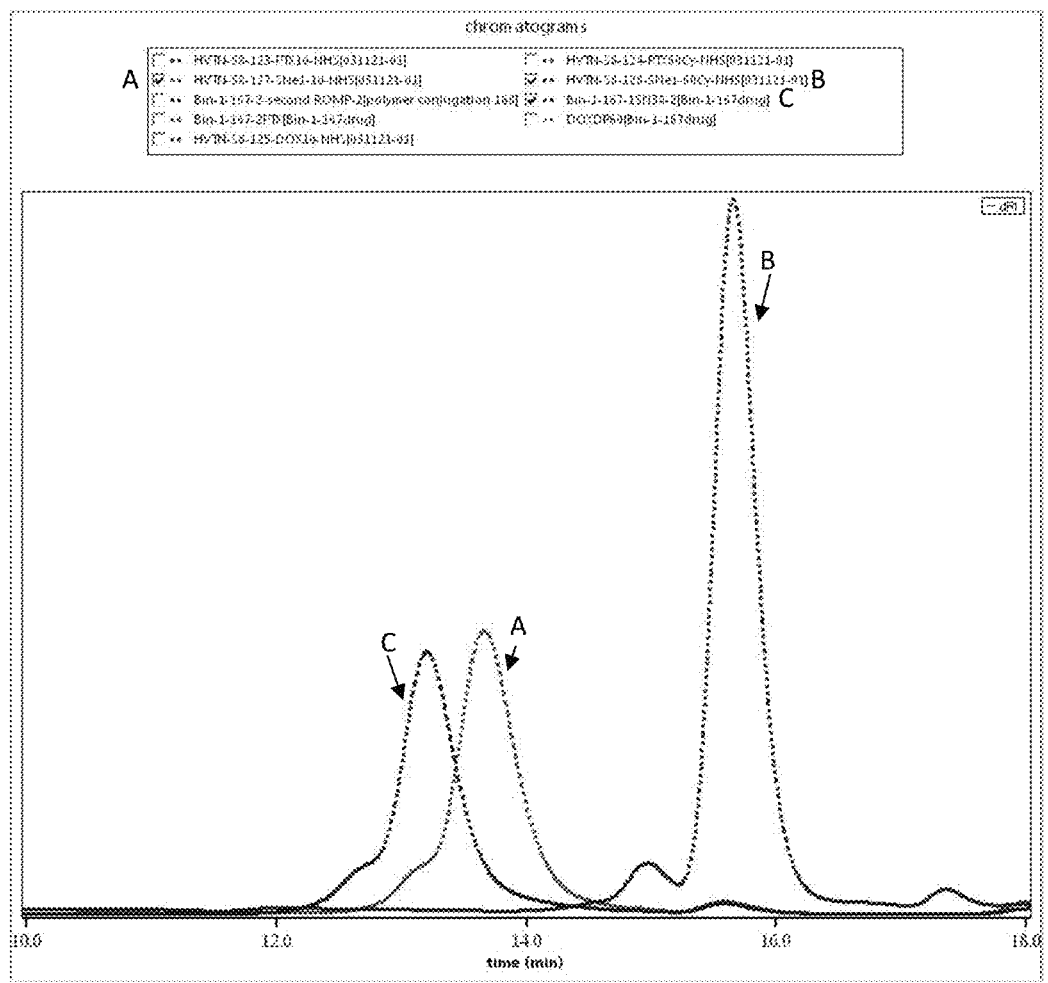
Figure 23E:
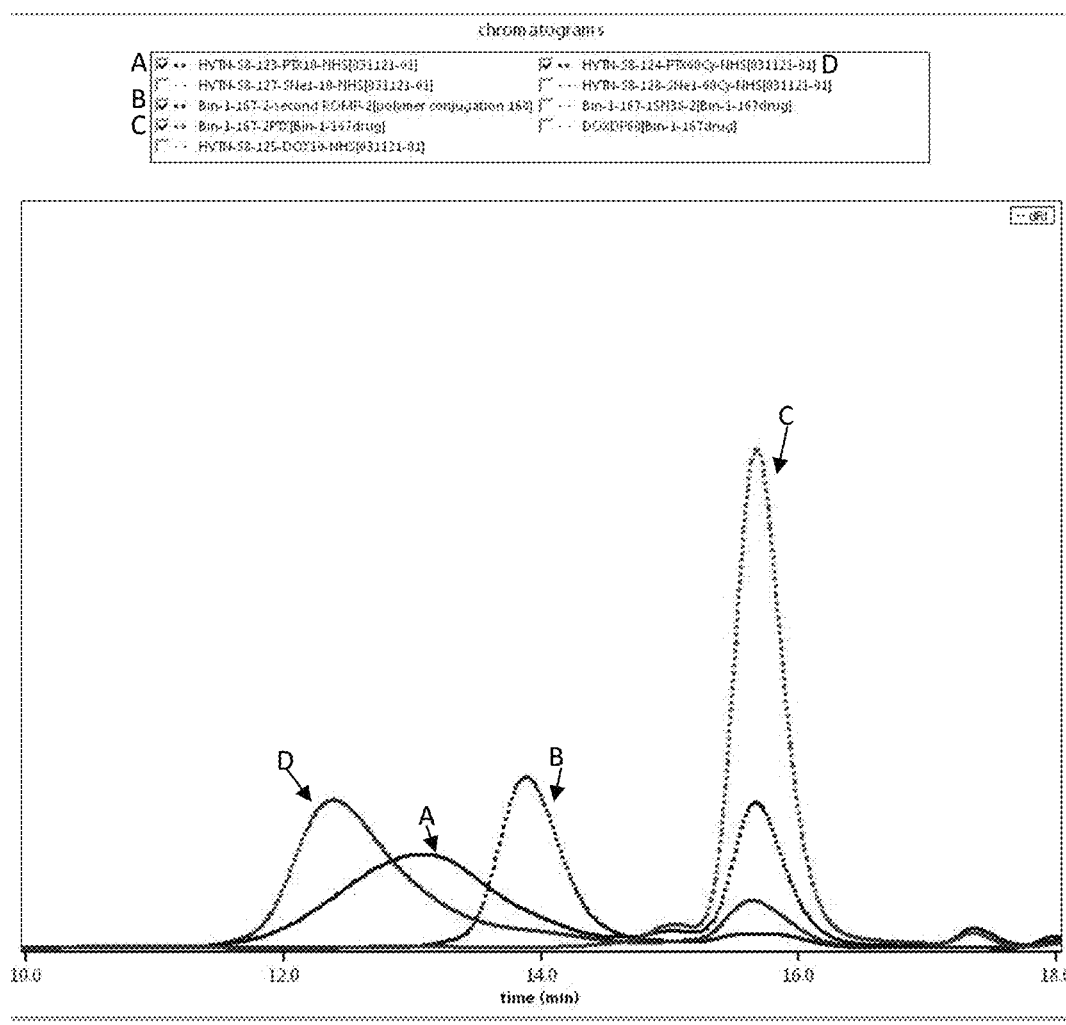

FIGS. 23A to 23E show ROMP for drug conjugated MMs (macromonomers). FIG. 23A shows GPC trace of DOX loaded bottle brush polymer with NHS functional terminal group. FIG. 23B shows GPC trace of SN38 loaded bottle brush polymer with NHS functional terminal group. FIG. 23C shows GPC traces of DOX loaded bottle brush polymer with different DPs (10 and 60). FIG. 23D shows GPC traces of SN38 loaded bottle brush polymer with different DPs (10, 30, and 60). FIG. 23E shows GPC traces of PTX loaded bottle brush polymer with different DPs (10 and 60). There polymers are homopolymerized and the results showed unreacted monomers.

Figure 24A:
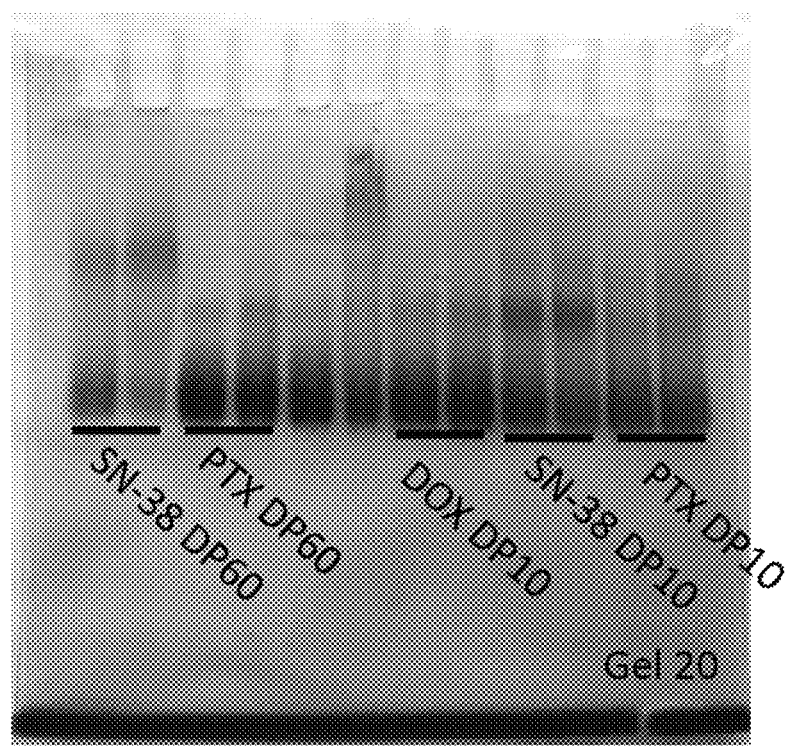
Figure 24B:
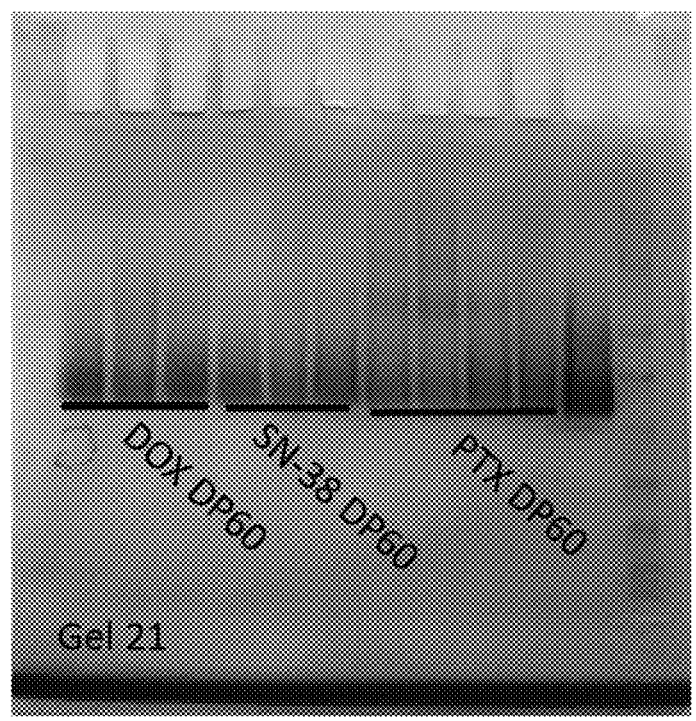
Figure 24C:
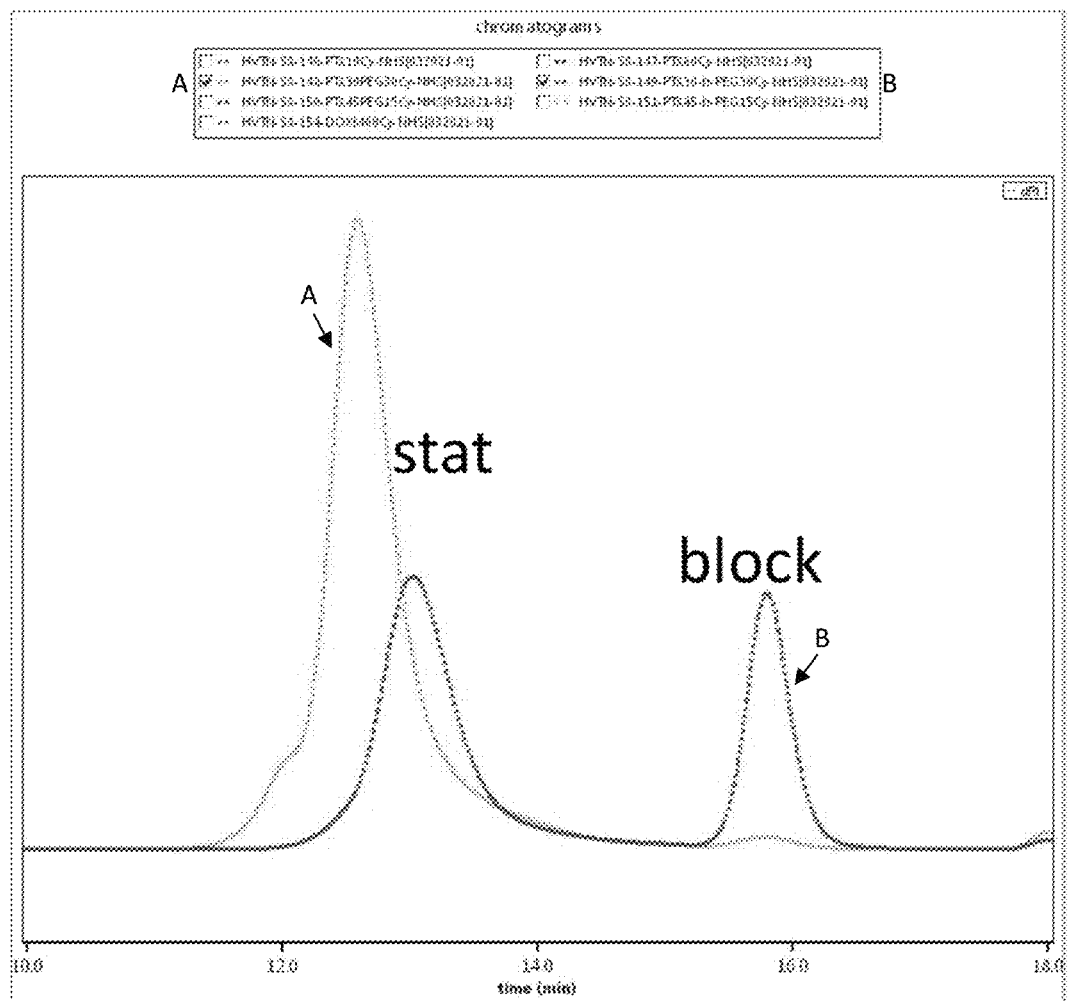
Figure 24D:
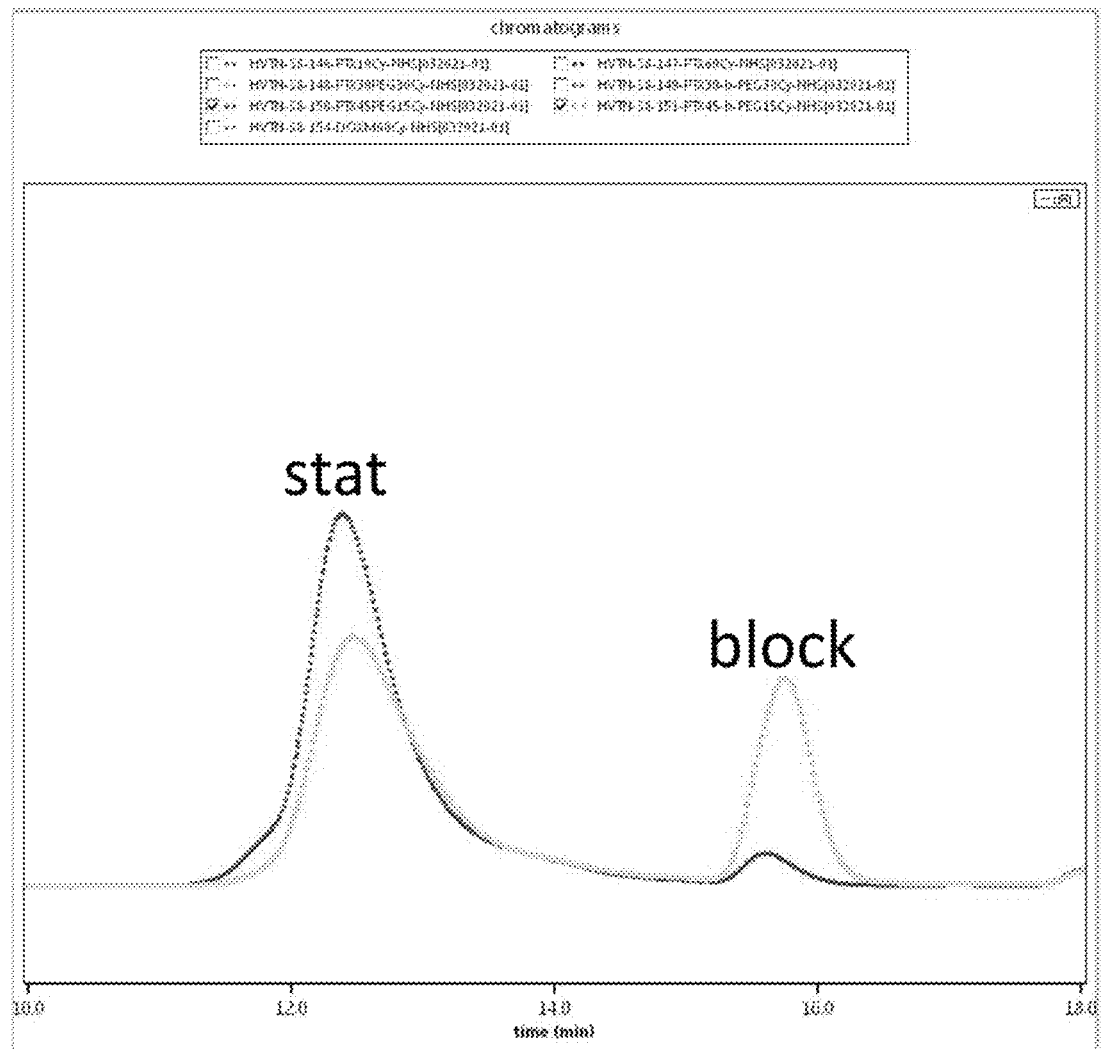
Figure 24E:
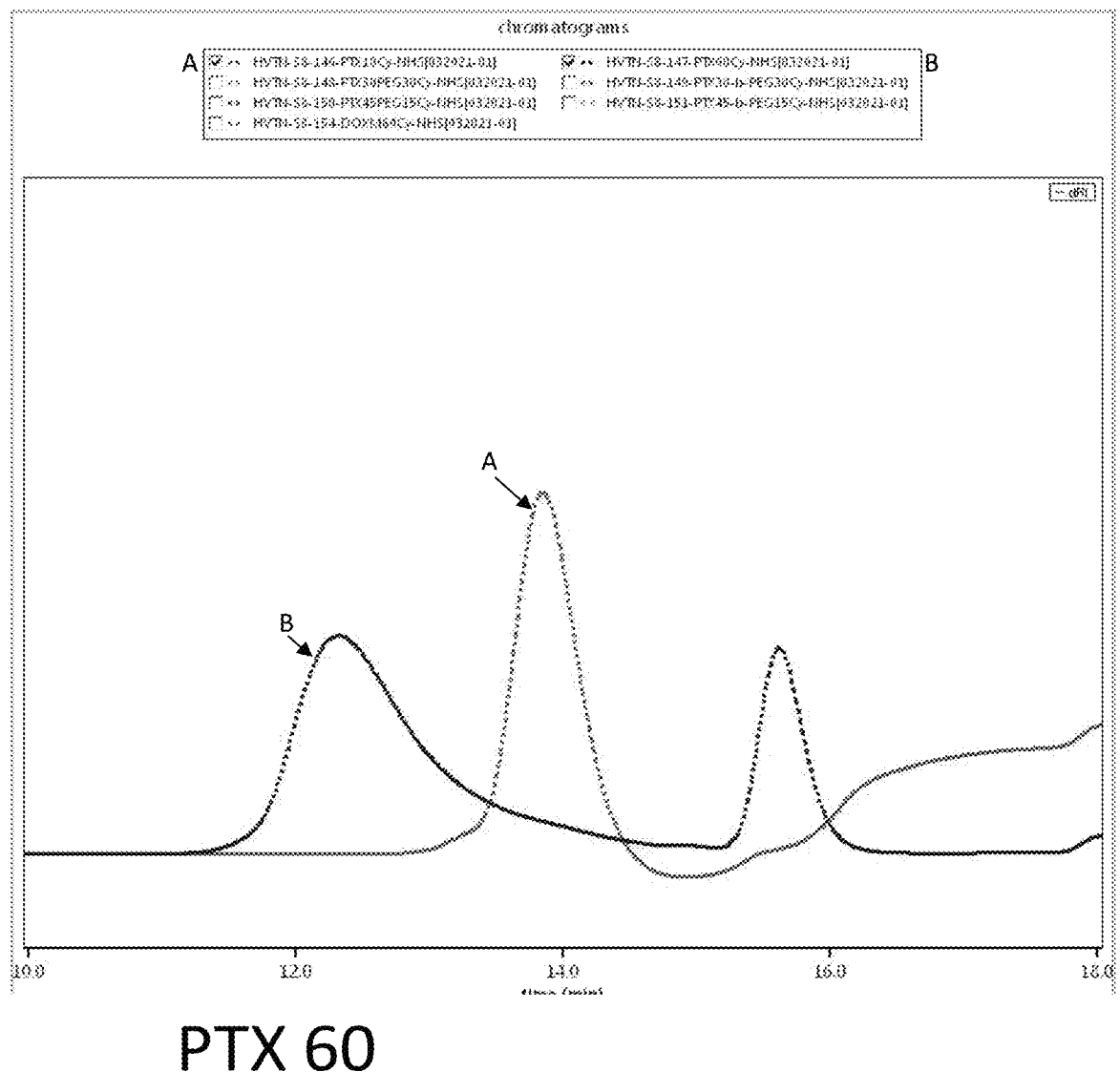
Figure 24F:
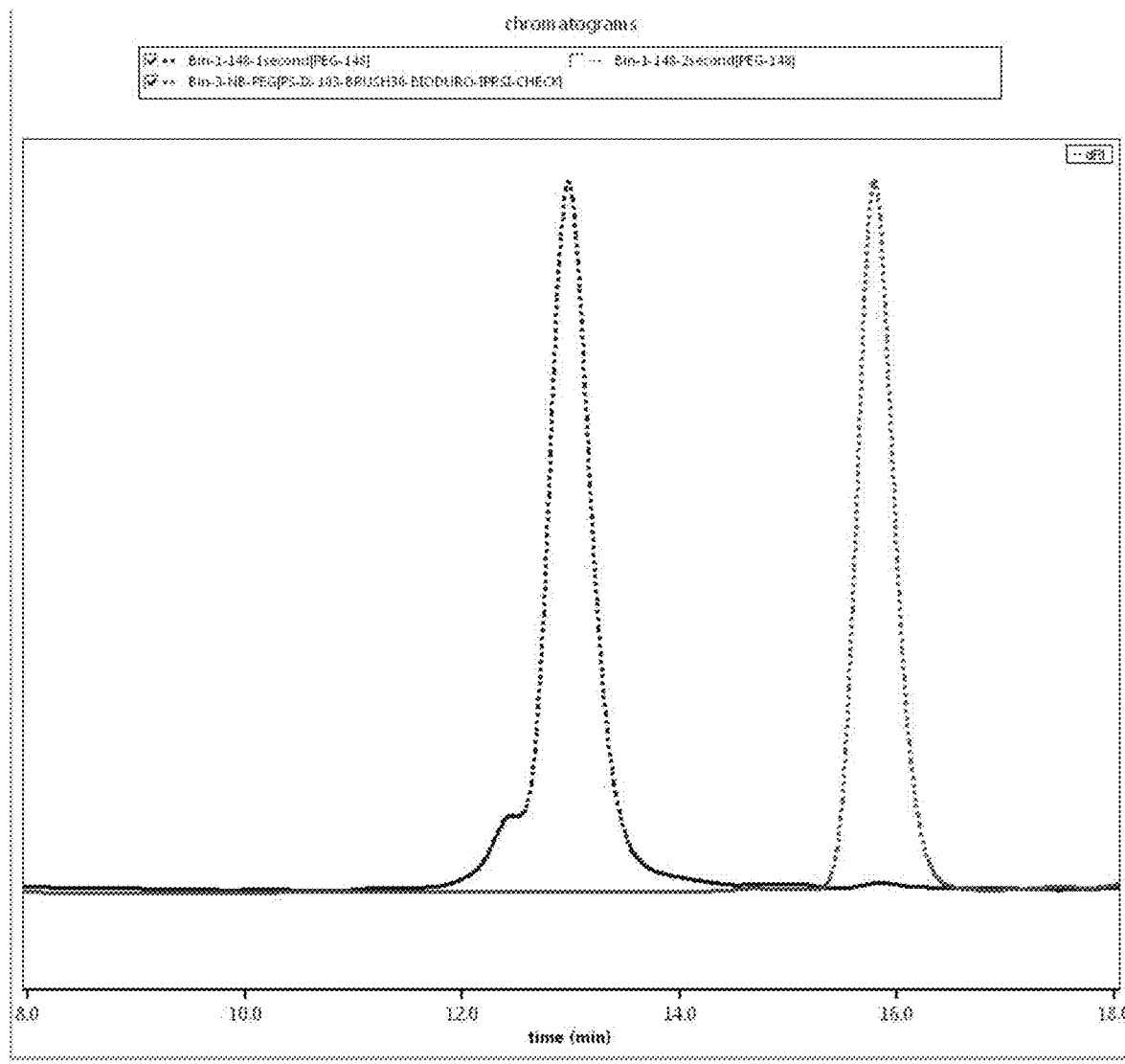
Figure 24G:
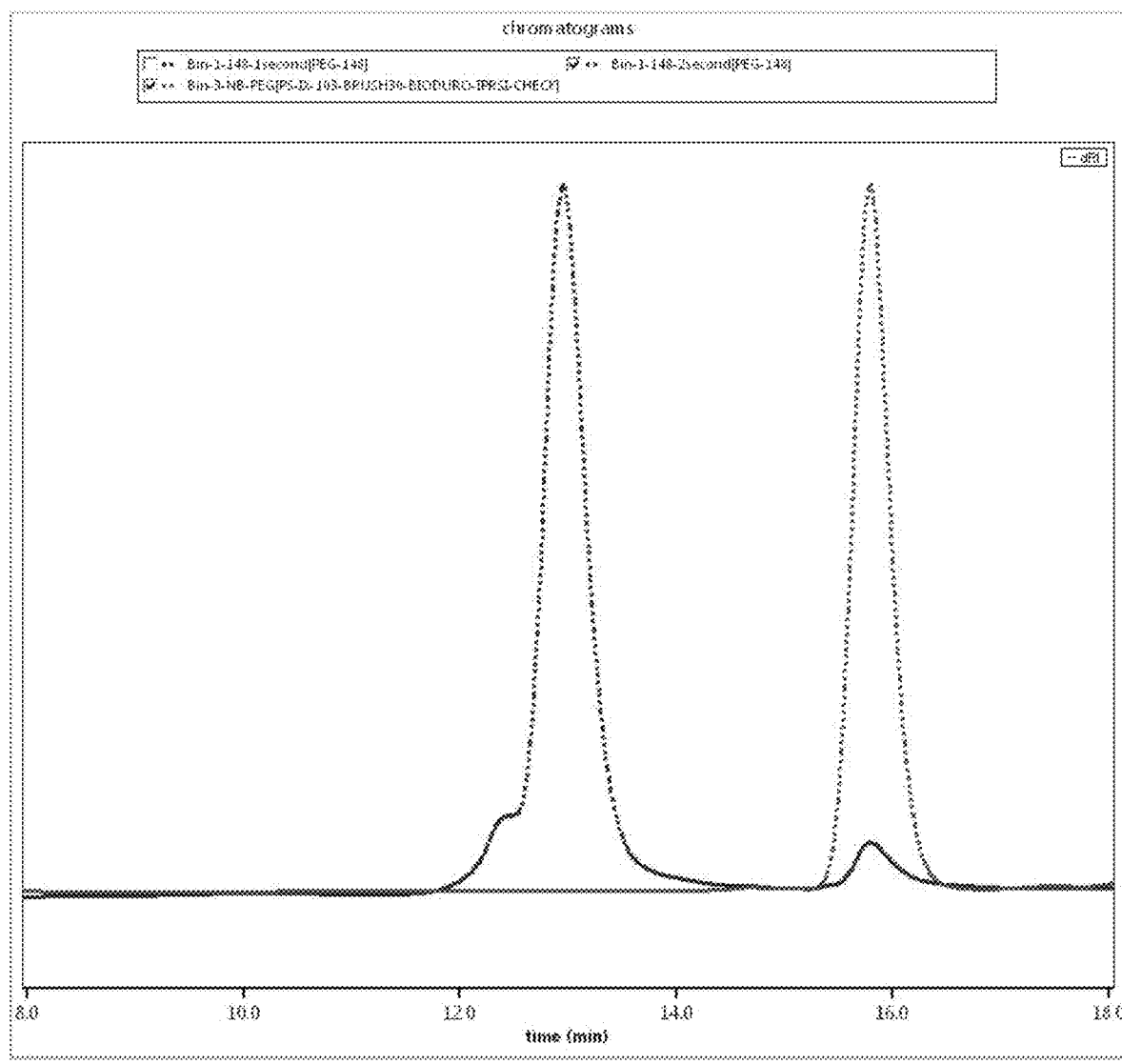
Figure 24H:
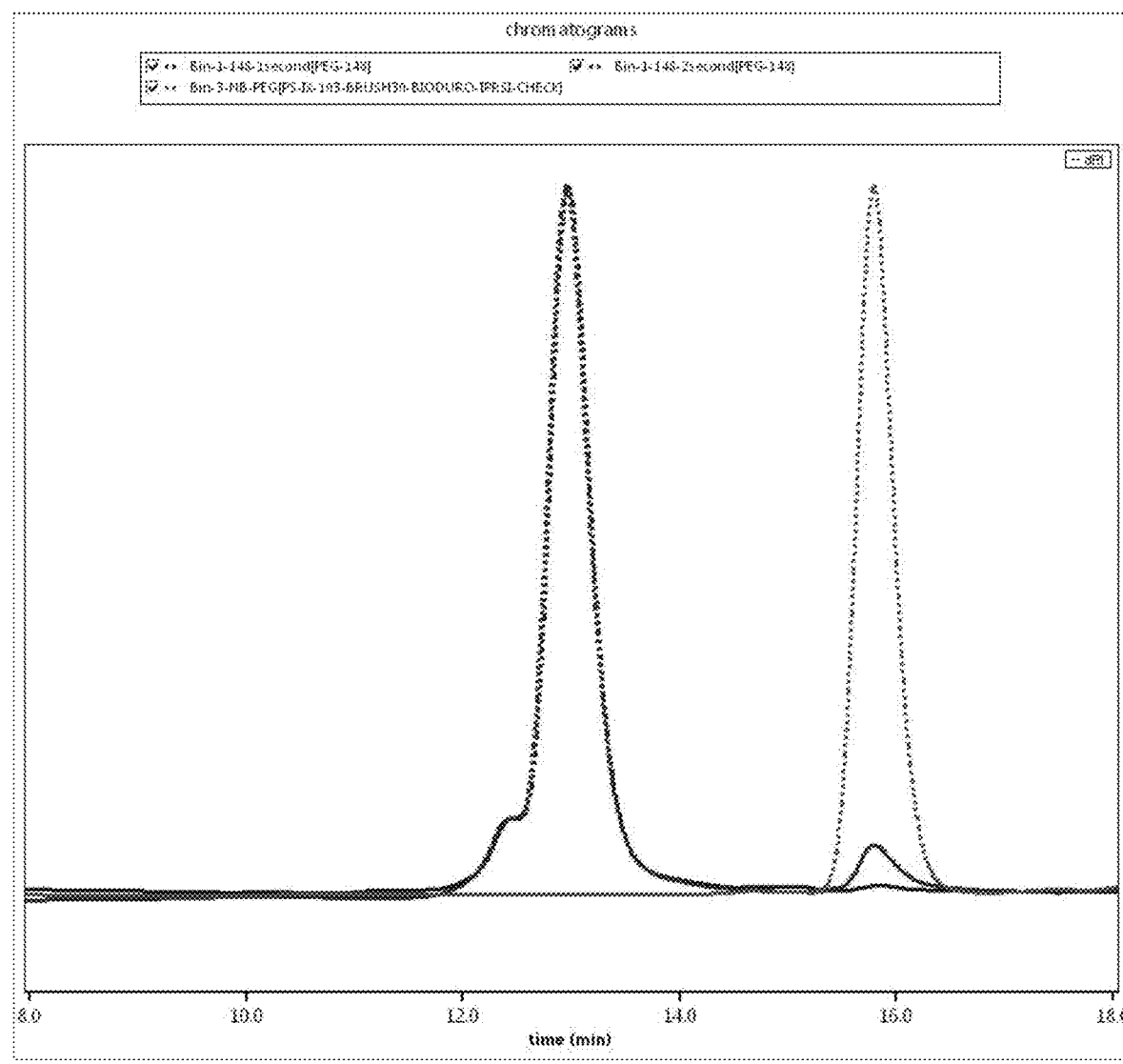
Figure 24I:
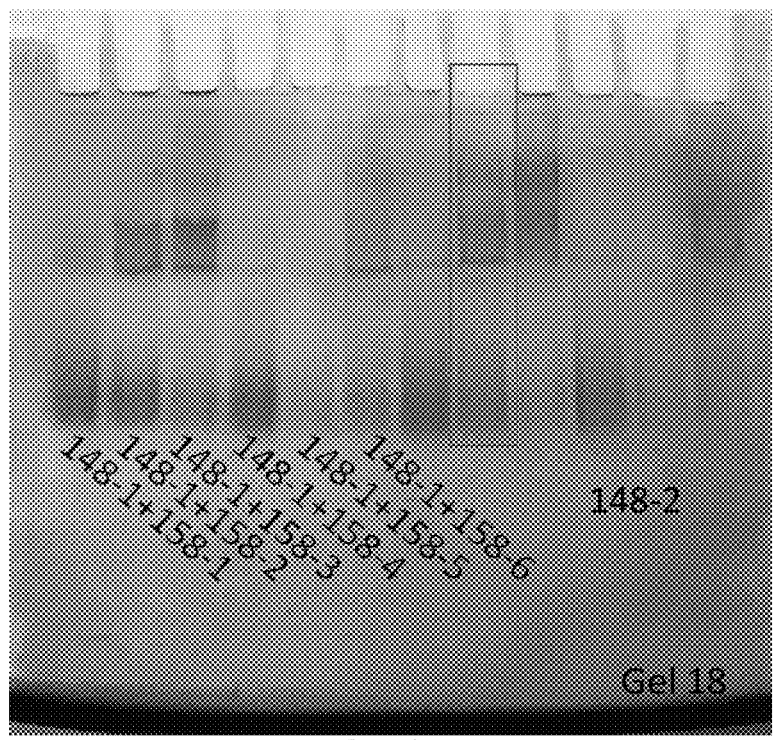

FIGS. 24A to 24I show block or statistic polymerization for ROMP of drug conjugated MMs using an antibody-polymer conjugation using the strategy shown in FIGS. 17B and 17C. FIG. 24A and FIG. 24B show SDS PAGE gel of conjugates between drug loaded polymers with different DPs and IgG antibody from a post modification strategy in FIG. 17C. FIG. 24C shows GPC traces of polymers from copolymerization of PEG based MMs and PTX loaded MMs at 1:1 ratio with statistic or blocky strategies. FIG. 24D shows GPC traces of polymers from copolymerization of PEG based MMs and PTX loaded MMs at 1:3 ratio with statistic or blocky strategies. FIG. 24E shows GPC traces of polymers from homopolymerization of PTX loaded MM. FIG. 24F, FIG. 24G, and FIG. 24H show GPC traces of homopolymerization of PEG based MM. FIG. 24I shows SDS PAGE gel of conjugates between drug loaded polymers with different DPs and IgG antibody using strategy in FIG. 17E.

Figure 25A:
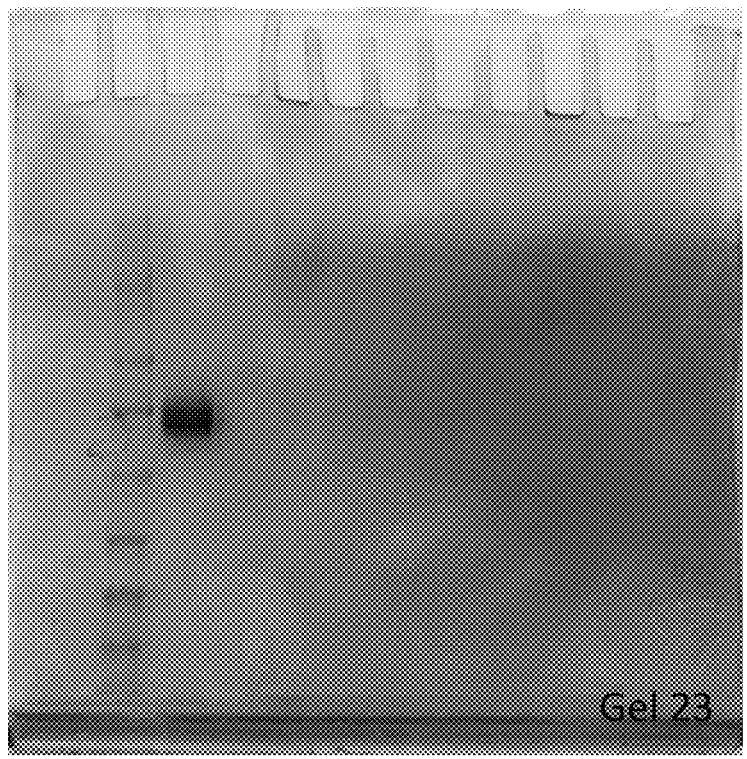
Figure 25B:
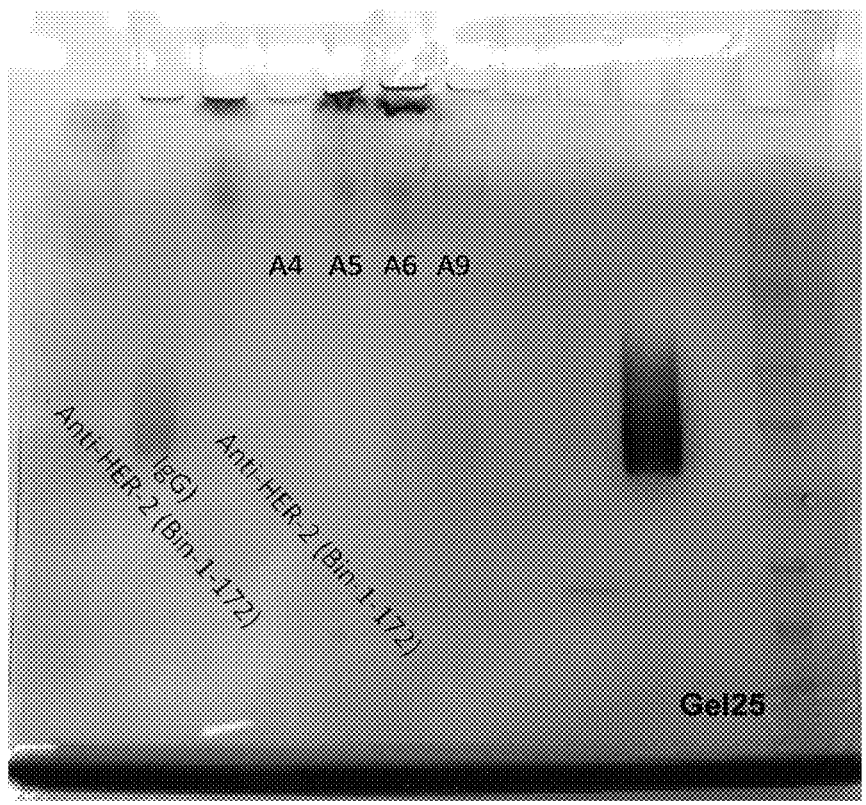

FIG. 25A shows anti-HER-2 ABCs using the strategy shown in FIGS. 17B and 17C after FPLC purification. FIG. 25B shows anti-HER-2 and IgG ABCs using the strategy shown in FIG. 17E before and after FPLC purification.

Figure 26:
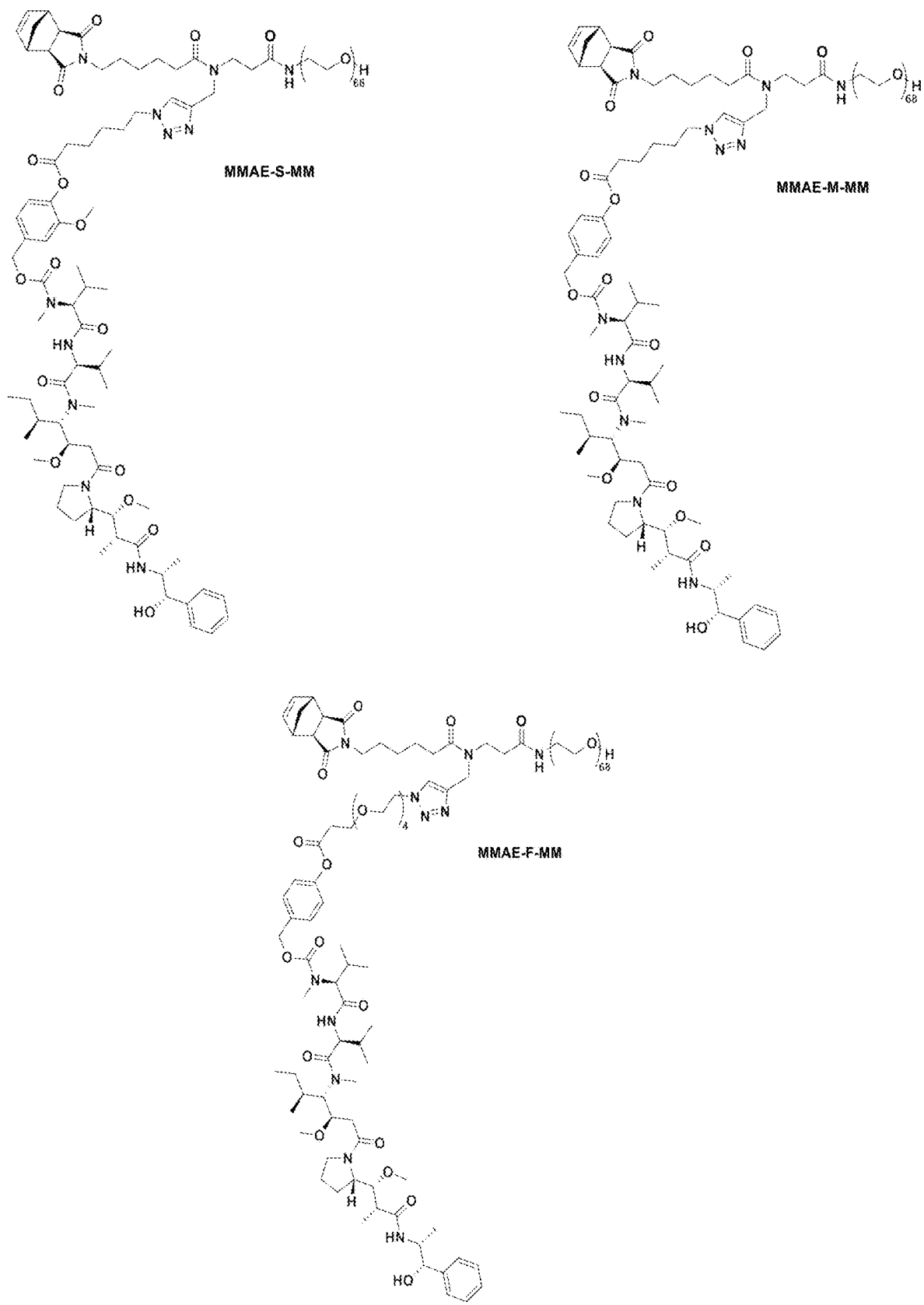

FIG. 26 shows the structures of MMAE-S-MM, MMAE-M-MM, and MMAE-F-MM.

Figure 27:
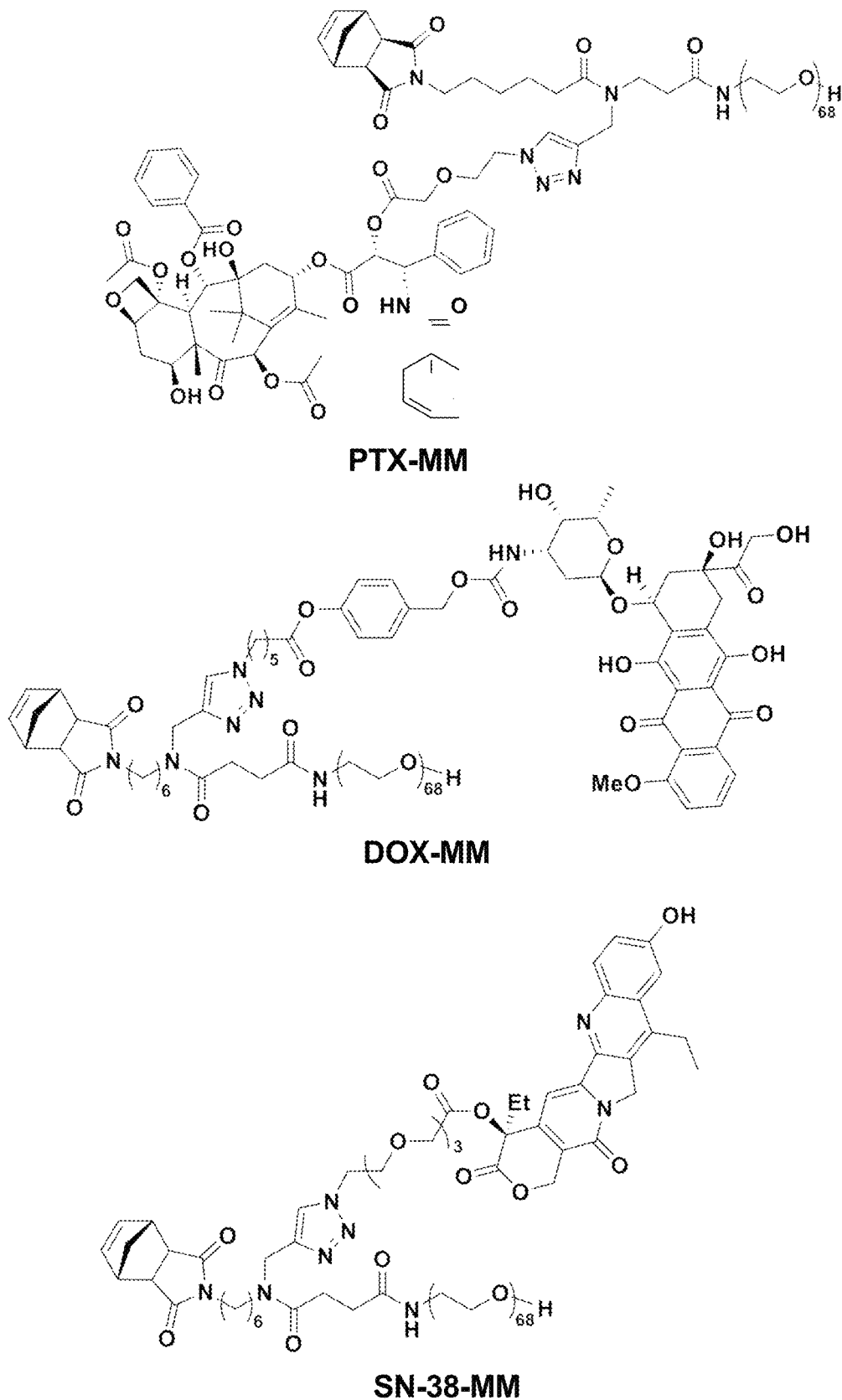

FIG. 27 shows the structures of drug conjugated MMs.

Figure 28:
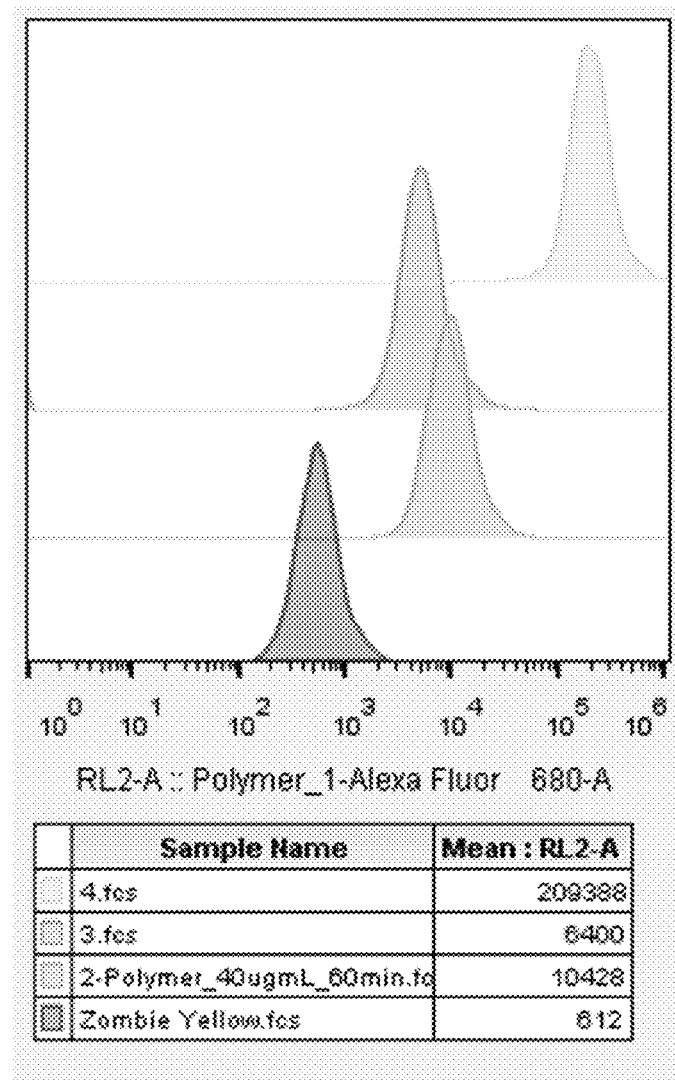

FIG. 28 shows cell uptake of BPD, ctrl-ABC (ctrl ABC, Ctrl-ABC, Ctrl ABC, CtrlABC, control ABC, non-binding ABC, or NB-ABC), and ABCs from flow cytometry. The anti-HER2 antibody was used for targeting moiety for ABCs and BT474 cell line was chosen with high surface HER2 expression. 2 represents the BPD treatment; 3 represents ctrl-ABC treatment; 4 represents ABC treatment. The ABC treatment group showed much higher cell uptake comparing to BPD and ctrl-ABC treatment groups, meaning the higher targeting efficiency of the ABC treatment group.

Figure 29:
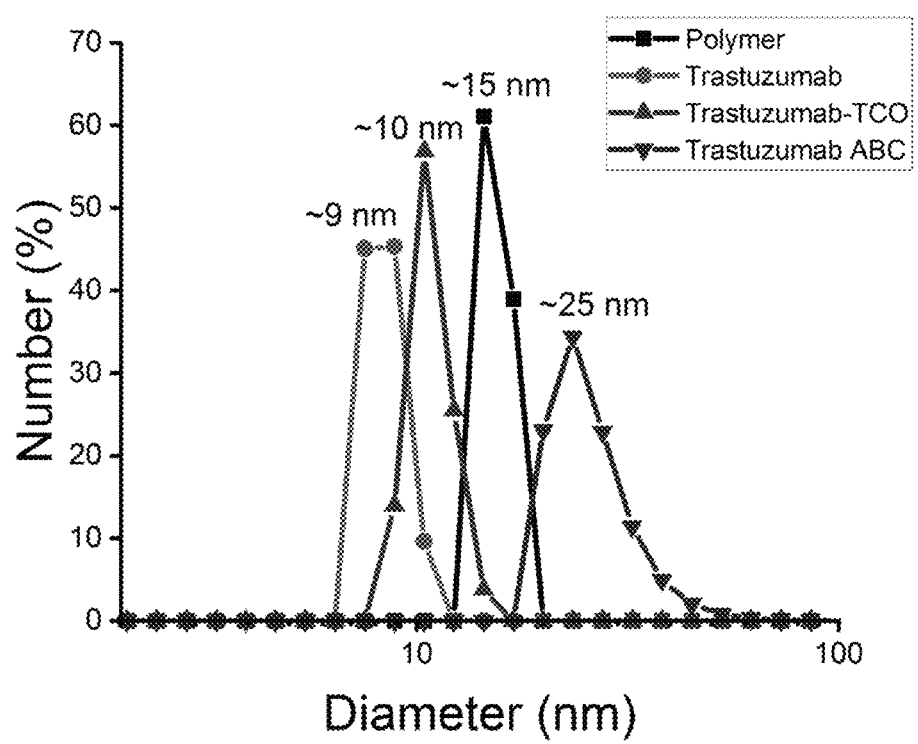

FIG. 29 shows DLS measurements of brush polymer ("Polymer"), antibody ("Trastuzumab"), antibody-TCO ("Trastuzumab-TCO"), and ABCs ("Trastuzumab ABC"). The size of the Trastuzumab is ~9 nm. After TCO surface modification, the size is increased to ~10 nm for Trastuzumab-TCO. The size of brush polymer with DP60 is 15 nm. The size of the ABCs is 25 nm, which is significant bigger than Trastuzumab-TCO and BPD. These results suggested the successful conjugation between antibody and brush polymer.

Figure 30:
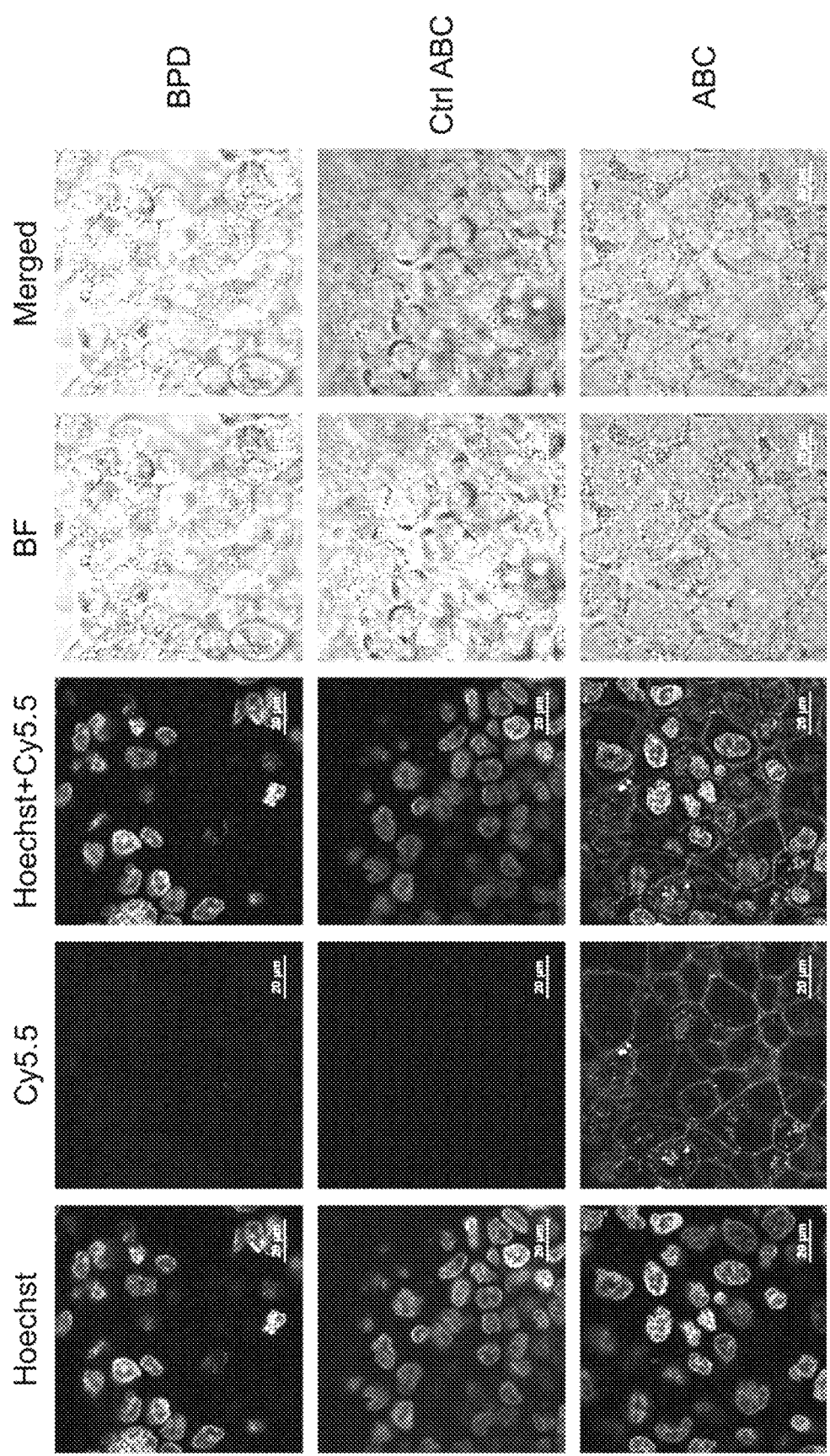

FIG. 30 shows confocal images for cell uptake. There was almost no cell uptake after 4 h incubation for BPD and ctrl ABC as their high PEGylation. In contrast, the ABCs showed very high cell uptake. There were a lot of signals from the cell membrane and also significant amount of the signal from the intracellular environment, suggesting efficient cell binding between ABCs and cells with subsequent cell uptake.

Figure 31A:
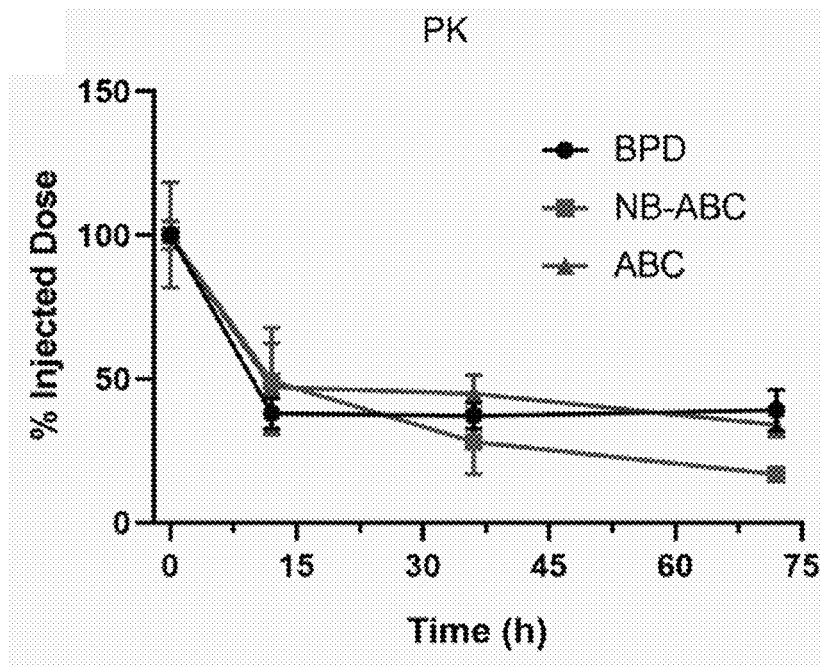

FIG. 31A shows PK of BPD, ctrl-ABC and ABC. The pharmacokinetics of the ABCs, BPD and control ABCs were measured to access the circulation half-life of these materials. In order to monitor these materials in vivo, the brush polymer was labeled by a higher amount of Cy5.5 fluorescent dye. The ABC, BPD and control ABC treatment groups contained the same amount of dye according to the same amount of polymer was injected into mice. The time dependent blood samples were collected and analyzed. ABC, BPD and control ABC showed similar PK.

Figure 31B:
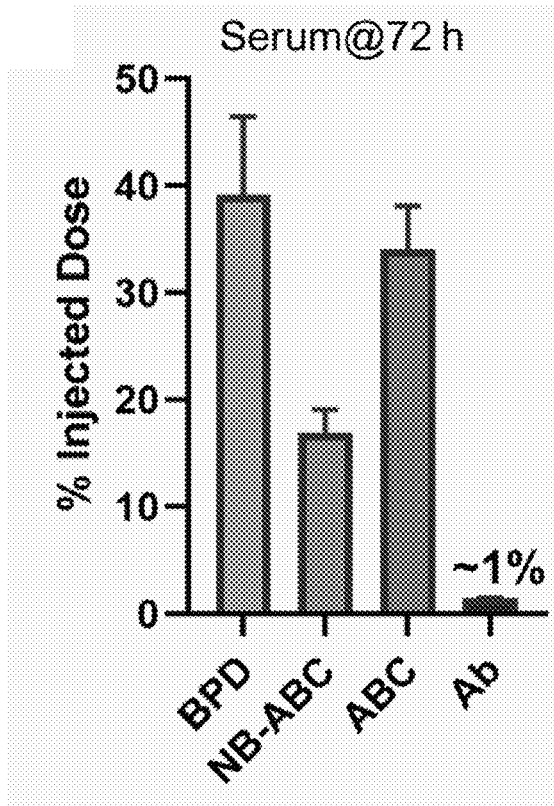

FIG. 31B shows blood remaining content after circulation for 72 h. More than 40% of polymers for ABC, BPD and Ctrl ABC was left inside the blood after 72 h. The dye labelled trastuzumab was also studied for the comparison of the PK. We tested the fluorescence of the Ab after 72 h injection and there is almost no signal for dye labelled Ab after 72 h.

Figure 31C:
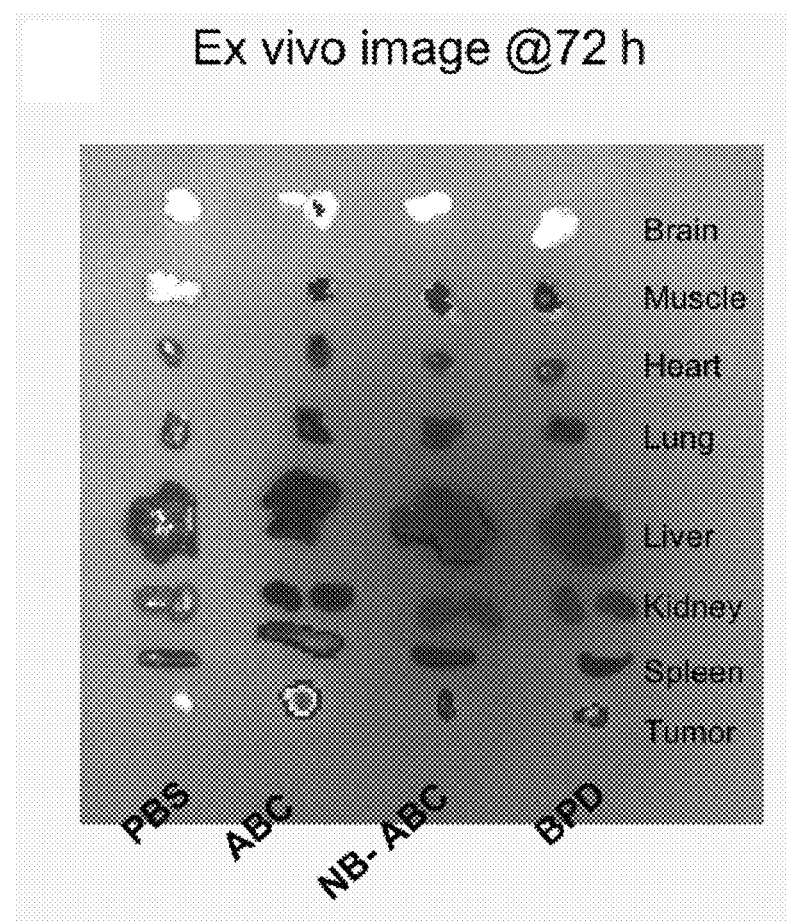

FIG. 31C shows ex vivo images of different organs after 72 h. The BT474 tumor bearing mice was i.v. injected by BPD, ctrl ABC and ABC with PBS as a control. At first, we harvested the organ and the time dependent ex vivo images were taken. After 12 h, ABC showed similar distribution in different tissues with BPD and control ABCs, where the majority of the ABCs was accumulated inside the liver. With the increase of the time to 36 h, ABCs were solely accumulated in tumor significantly without the other tissues. However, there is no accumulation in tumor for BPD and Ctrl ABC. Further, the accumulation in tumor for ABCs was further increased at 72 h. These results highlight the targeting efficiency of the ABCs over BPD and Ctrl ABCs.

Figure 31D:
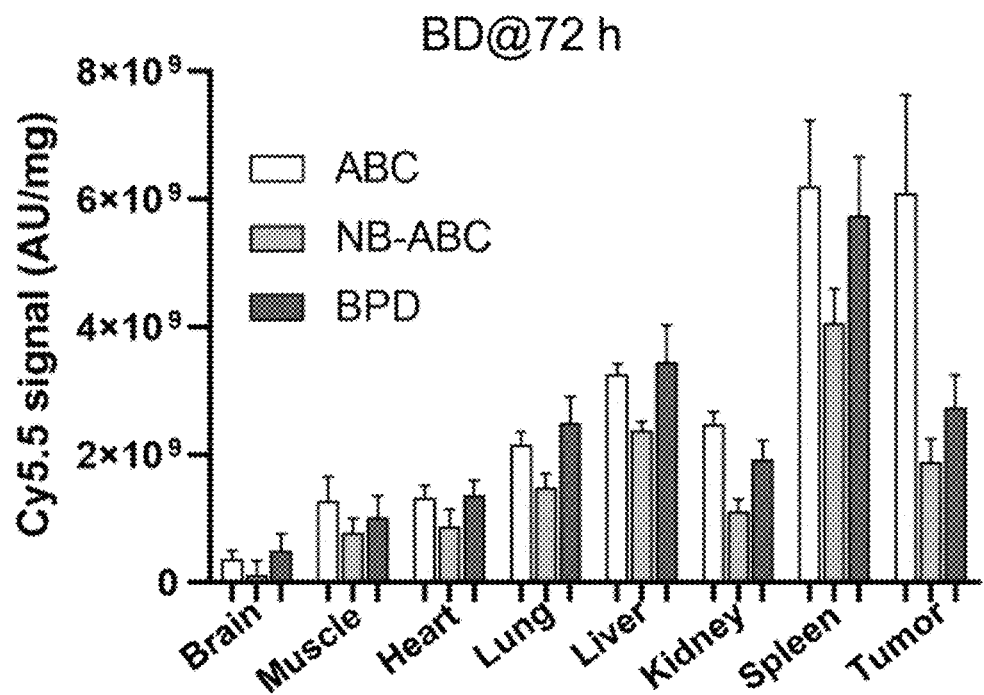

FIG. 31D shows biodistribution after 72 h. Time dependent biodistribution was evaluated. The other control groups were used to determination the targeting efficiency of the ABCs. The polymer itself without antibody conjugation ("BPD") and a control ABC with the targeting ability were also used for biodistribution study. The ABC was accumulated inside the BT474 tumor with time.

Figure 31E:
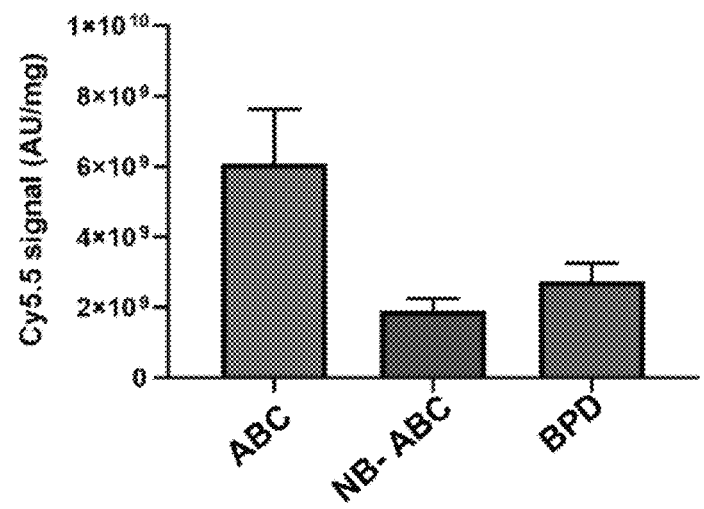

FIG. 31E shows tumor signal comparison after 72 h. We compared the BT474 tumor fluorescence signals with different treatment groups. ABC treatment groups showed significantly higher signal comparing to BPD and ctrl ABC treatment groups.

Figure 31F:
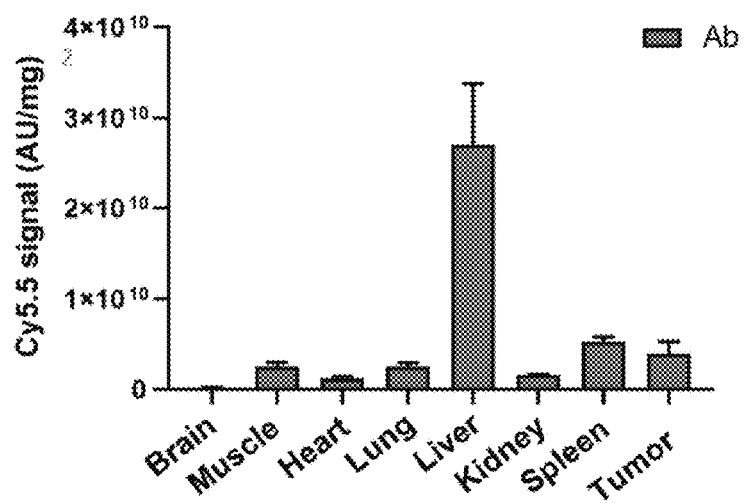

FIG. 31F shows biodistribution of dye labelled antibody after 72 h. We monitored the biodistribution of the ADC mimic, where the Ab were labelled by Cy5.5 dye directly. There is slight accumulation inside the BT474 tumor. However, significant amount of ADC mimics was accumulated in liver at 72 h. These results are consistent with the fact that less than 1% of ADCs accumulates in tumor tissue.

Figure 32A:
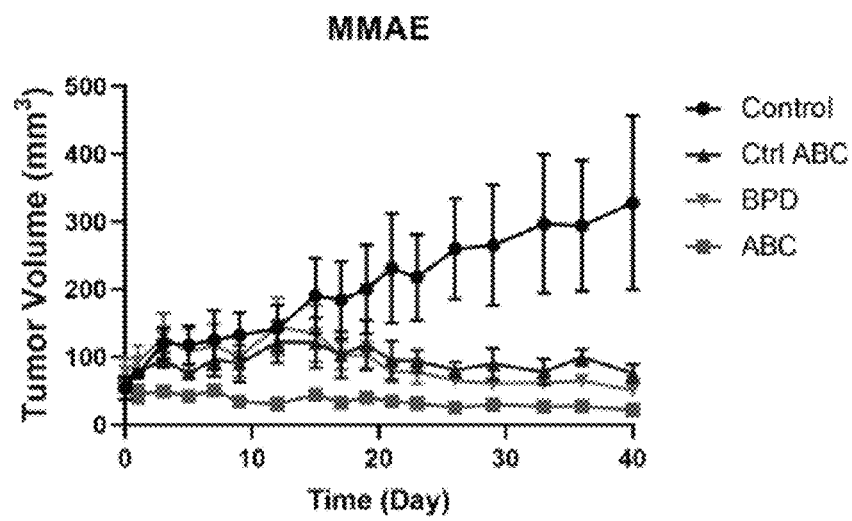

FIG. 32A shows tumor volume after treatment of PBS (Control), BPD, ctrl ABC and ABC with MMAE as the payload. We used the anti-HER2 antibody as the targeting moiety and the BT474 xenograft tumor model was used to evaluate the in vivo performance of MMAE loaded ABCs (with anti-HER2 MMAE). The antitumor efficacy was monitored thorough the measurement of tumor volume size. We dosed the mice with 1.7 mg/kg MMAE in the format of BPD, Ctrl ABC (with IgG1 MMAE), and ABC (with anti-HER2 MMAE) once the tumors reach an average size of ~50-100 $mm^3$ with the frequency of once a week and total 4 doses. The tumor sizes of the control group were continuous increasing during the study. The ABC treatment group significantly decreased the tumor size even after the first dose. There is no tumor after 40 days with four doses of ABCs treatment. BPD and Ctrl ABC also showed anticancer effects after 4 doses treatment, but the antitumor efficacy was not achieved after the initial 3 doses, which was worse than the ABCs. Due to the high potency of MMAE, the non-targeted BPD and Ctrl-ABC reached good therapeutic efficacy after 4 doses treatment.

Figure 32B:
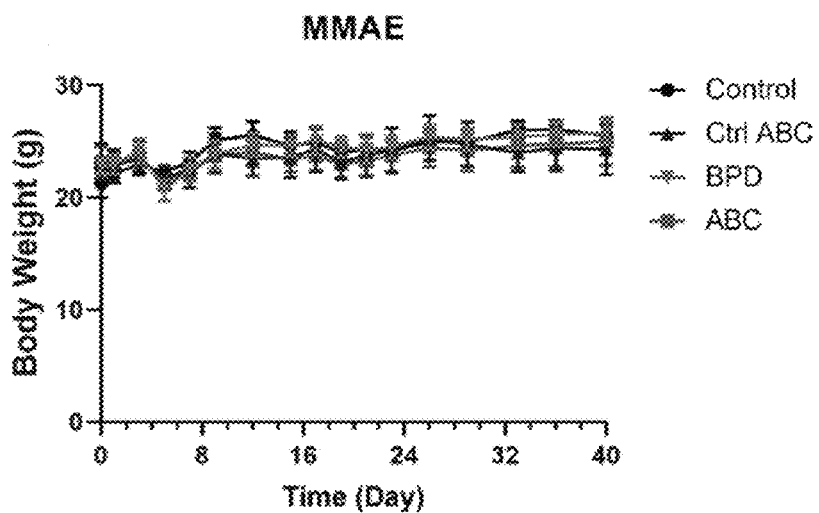

FIG. 32B shows body weight measurements for different treatment groups with MMAE as the payload. There is no toxicity after the injections as demonstrated by no significant body weight decrease. All the treatment groups showed almost the same body weight evolution as the control group.

Figure 32C:
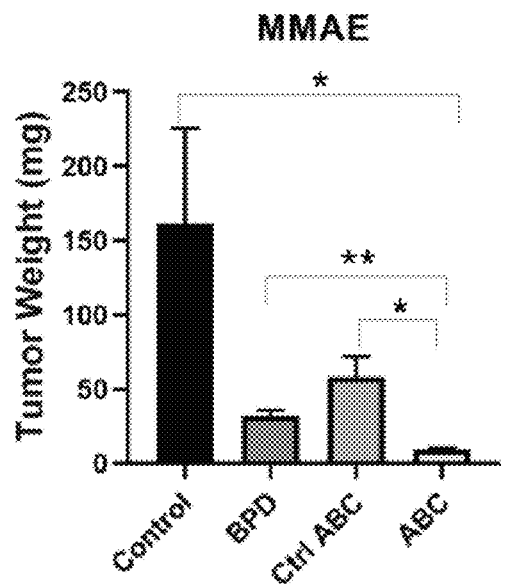

FIG. 32C shows BT474 tumor weight measurements for different treatment groups with MMAE as the payload. The mice were sacrificed, and the tumor was harvested after the treatments. Tumor weight was measured after 40 days. The results showed the superior anticancer activities of the ABC treatment, which is consistent with the tumor volume measurement.

Figure 32D:
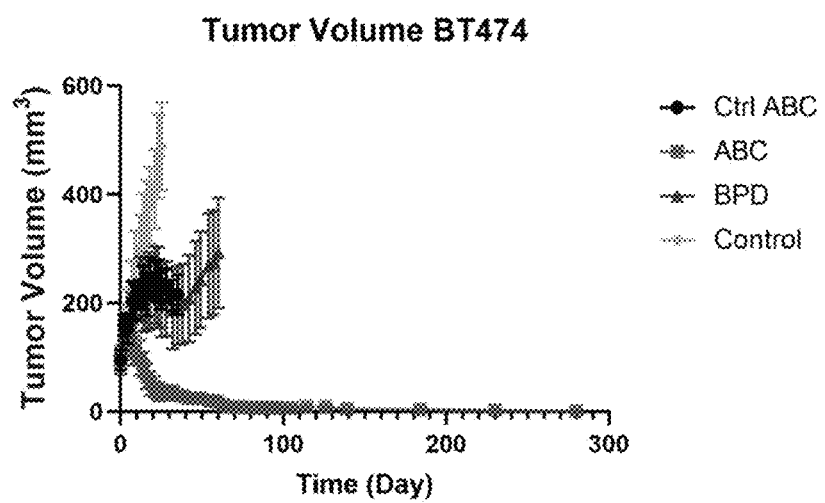

FIG. 32D shows BT474 tumor volume after treatment of PBS, BPD, ctrl ABC, or ABC with SN38 as the payload. Our results showed the continuous decrease of the tumor size after injection of the ABC, while the control group without treatment showed significant increase of the tumor size. For the BPD and Ctrl ABC groups, the tumor size was still increasing but much slower than the control group. After 7 doses of injection, the tumor totally disappeared for the ABC treatment even when the drug administration was stopped. The tumors for BPD and ctrl group continued to grow once the drug administration was stopped.

Figure 32E:
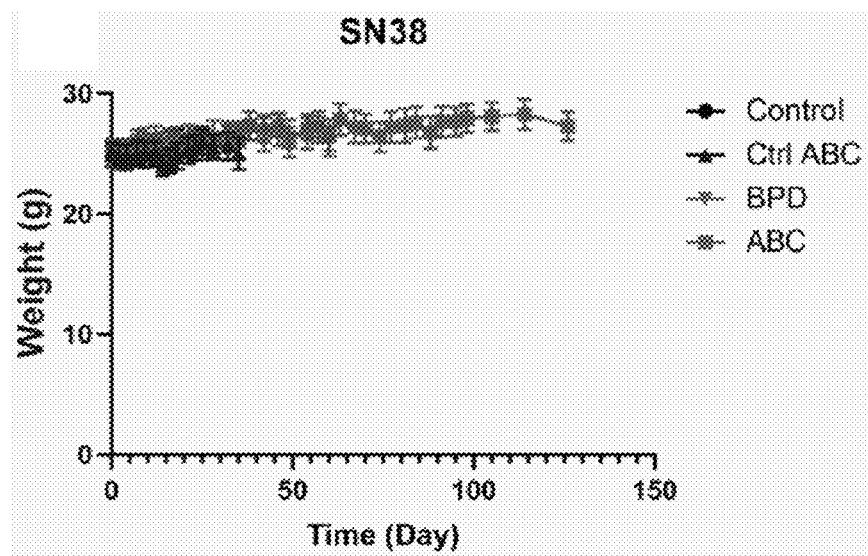

FIG. 32E shows body weight measurements for different treatment groups with SN38 as the payload. The injected drugs didn't show any toxicity for the treatment groups as there was no significant weight loss for all the treatment groups.

Figure 32F:
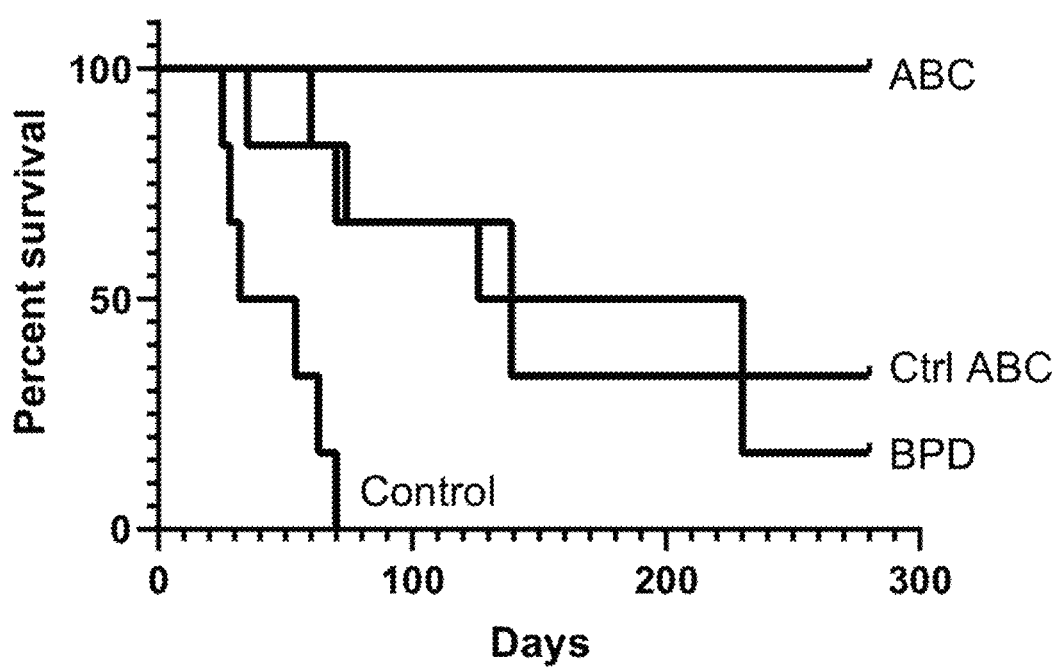

FIG. 32F shows survival curves for different treatment groups with SN38 as the payload. The survival study was also performed for these different treatment groups. All the mice for control group were dead after 70 days with a half-life of ~30 days. The BPD and Ctrl ABC still had some anti-cancer efficiency. During this period of study, there were 1 in 6 mice survived for BPD and 2 in 6 mice survived for ctrl ABC treatment groups. For the ABC treatment group, all the mice survived without tumor after 280 days period study. These results highlight the superior anticancer efficacy of the ABC strategy with SN38 drug.

Figure 32G:
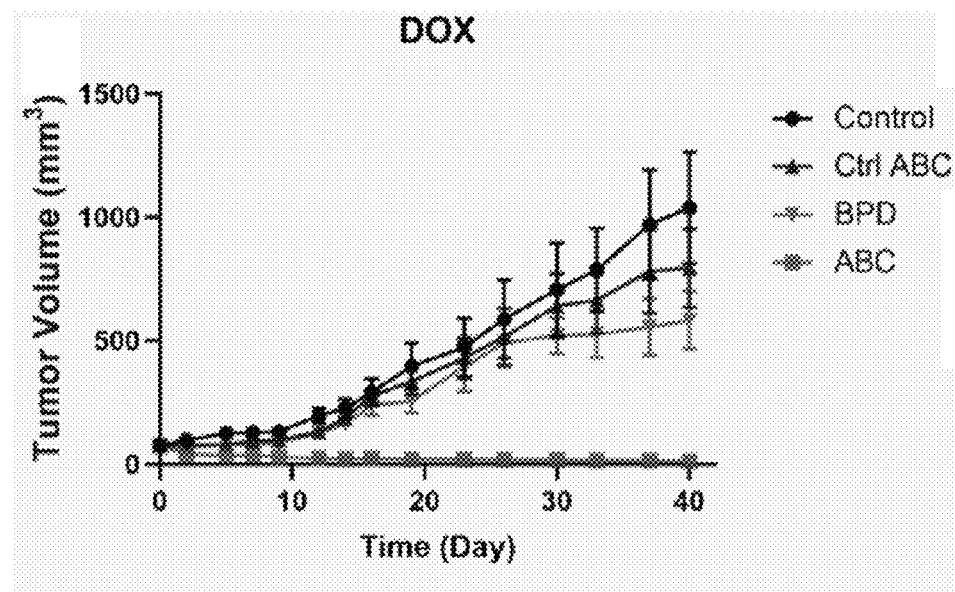

FIG. 32G shows BT474 tumor volume after treatment of PBS, BPD, ctrl ABC, or ABC with DOX as the payload. With the promising results from MMAE and SN38 for the ABC strategy, we then applied the ABC strategy to an less potent drug, DOX, for in vivo anticancer study, where DOX was previously failed for the ADCs development due to its low potency. As the ABC strategy can achieve very high DAR and high PK with long circulation time, we hypothesize that our ABC platform is applicable to DOX to reveal anticancer efficiency. To test that, we also used the BT474 xenograft mouse model to study the anticancer efficiency of ABCs with anti-HER2 DOX. Different prodrug platforms such as ABCs, BPD, and a control ABC with a nontargeting antibody were used for anti-cancer study. The ABCs showed superior anticancer efficacy after 4 doses treatment as the significant decrease of the tumor size over time. There was totally no tumor after the treatment till 40 days. However, the BPD and Ctrl ABC showed no therapeutic effects after 4 doses comparing to the control group.

Figure 32H:
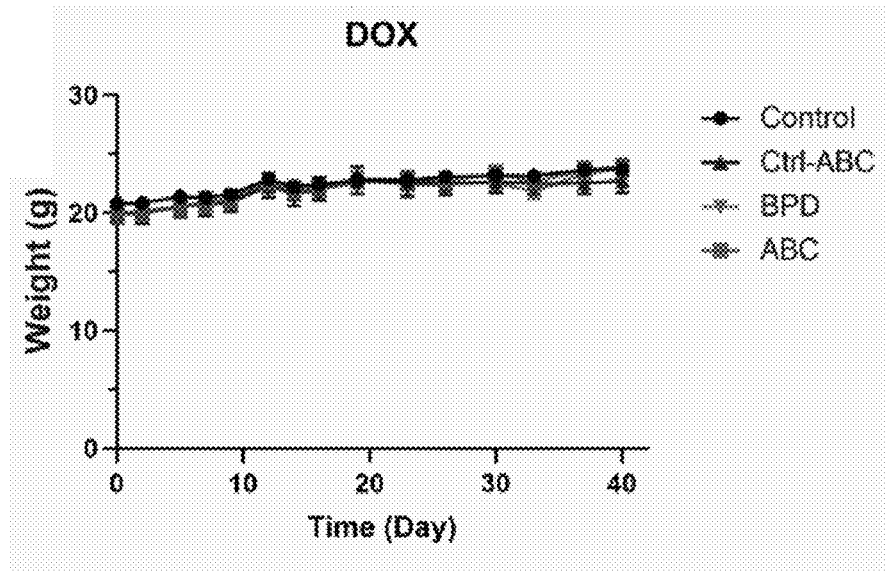

FIG. 32H shows body weight measurements for different treatment groups with DOX as the payload. The injected drugs didn't show any toxicity for the treatment groups as there is no significant weight loss for all the treatment groups.

Figure 32I:
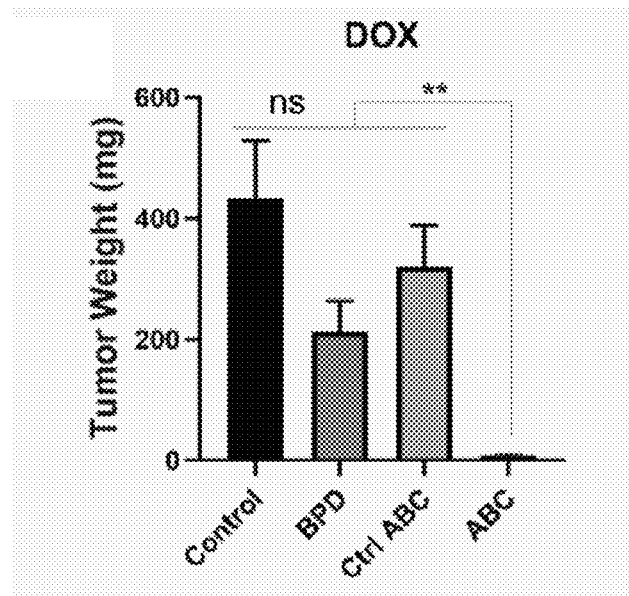

FIG. 32I shows BT474 tumor weight measurements for different treatment groups with DOX as the payload. The tumor was harvested after 40 days study. The tumor size showed significant difference between the ABC treatment group and the other groups. There was almost no tumor for the ABC treatment group with superior anticancer efficacy, while there was no difference between the BPD, ctrl ABC treatment groups, and the control group without any treatment. Further, the tumor weight correlated well with the tumor size and volume measurement.

Figure 33A:
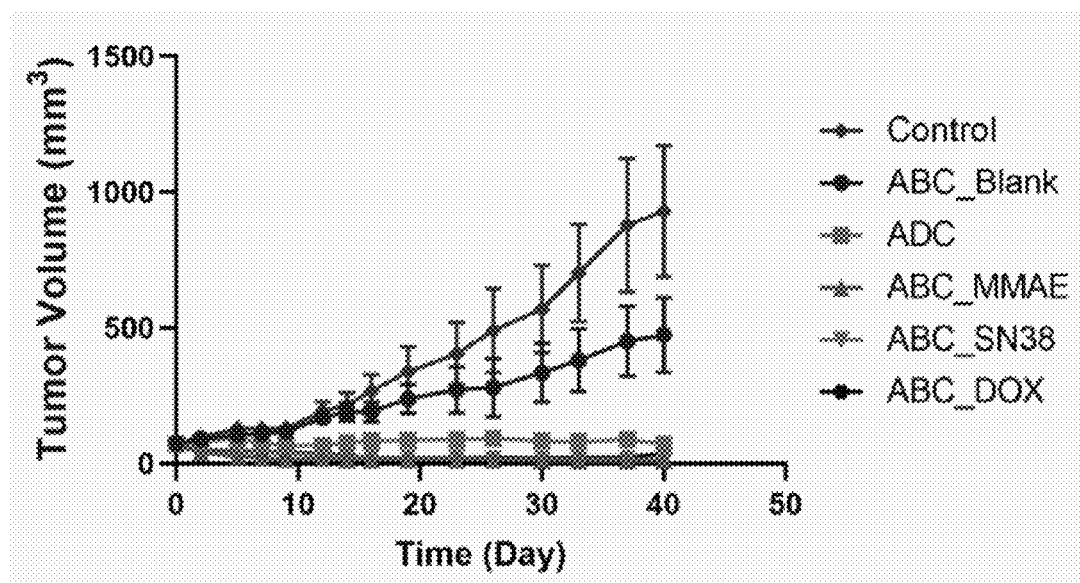

FIG. 33A shows comparison of BT474 tumor volume measurements after different treatments with one dose injection. We performed the antitumor efficacy study to compare the ABC platform to the benchmark commercially available Kadcyla (T-DM1, "ADC") targeting HER2+ tumors. In this study, different groups of materials (Control, ABC_Blank, 3 ABCs (ABC_MMAE, ABC_SN38, ABC_DOX), ADC) were injected to mice to evaluate their efficacy. In this case, we used the ABC platform with different payloads for study. We also further pursued a one-dose therapy. All the ADC and the ABCs showed good anticancer efficiency as comparing to the control group, and ABC_Blank, which was without any payload. ABCs with high potency MMAE payload and medium potency SN38 payload performed better anti-tumor effect than the ADC treatment. Even the low potency DOX loaded ABC showed better efficacy.

Figure 33B:
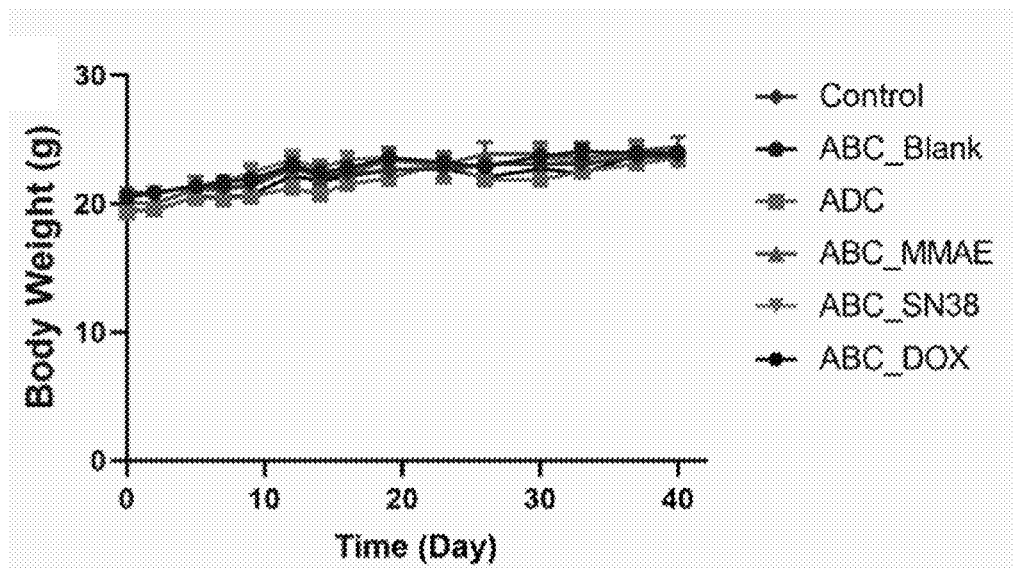

FIG. 33B shows body weight measurements for different treatment groups. There was no toxicity after the injections as demonstrated by no significant body weight decrease. All the treatment groups showed almost the same body weight evolution as the control group.

Figure 33C:
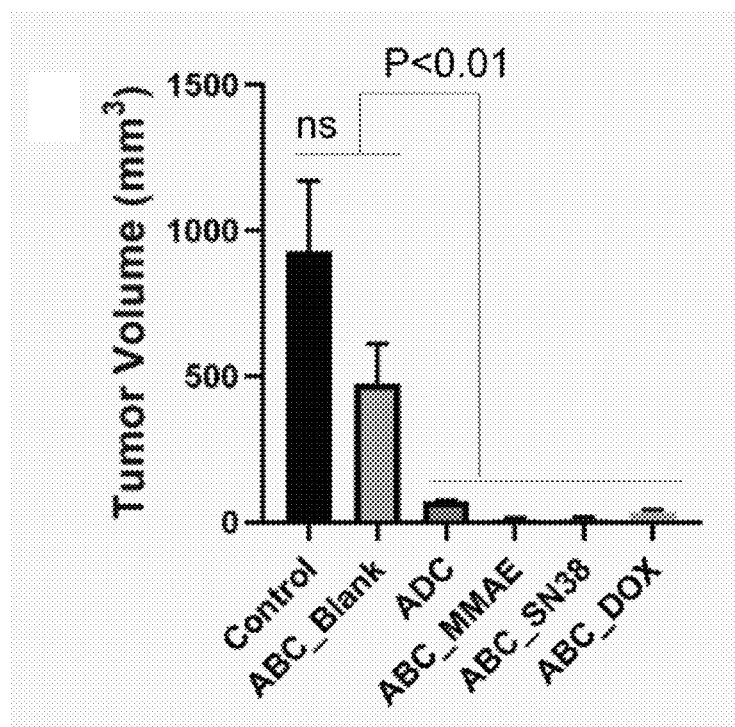

FIG. 33C shows tumor comparison of BT474 tumor volume measurements after 40 days. ABCs with high potency MMAE payload and medium potency SN38 payload performed better anti-tumor effect than the ADC treatment. Even the low potency DOX loaded ABC showed better efficacy.

Figure 33D:
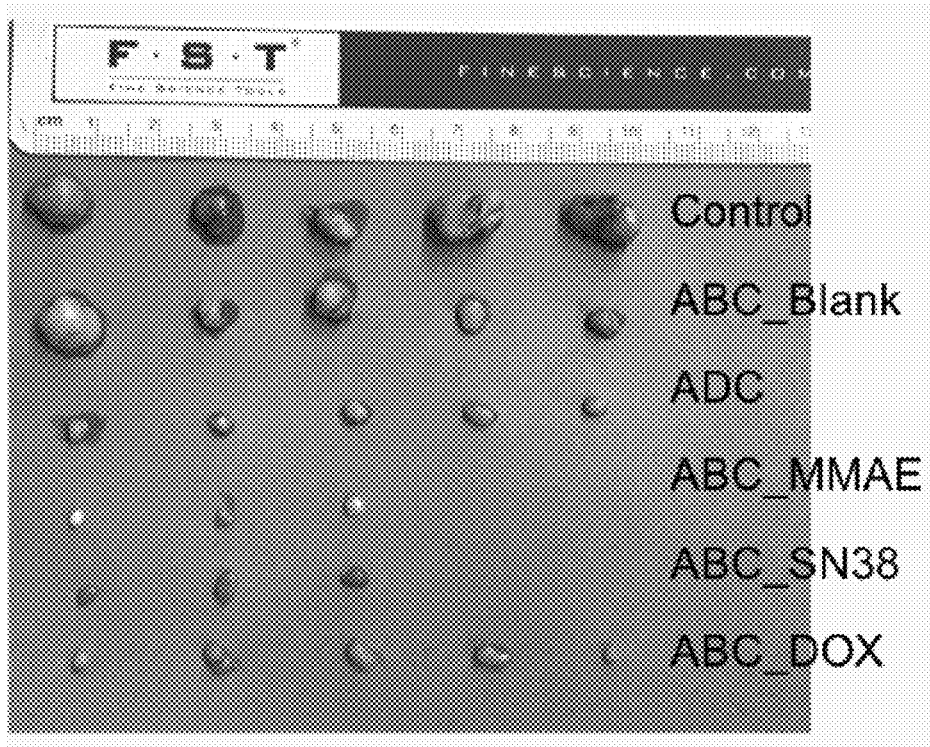

FIG. 33D shows BT474 tumor picture for different treatment groups. After 40 days, the mice were sacrificed, and the tumors were harvested. The results show that all ABCs with different payloads no matter the potency exhibited good anticancer efficacy similar to or better than Kadcyla ("ADC").

Figure 33E:
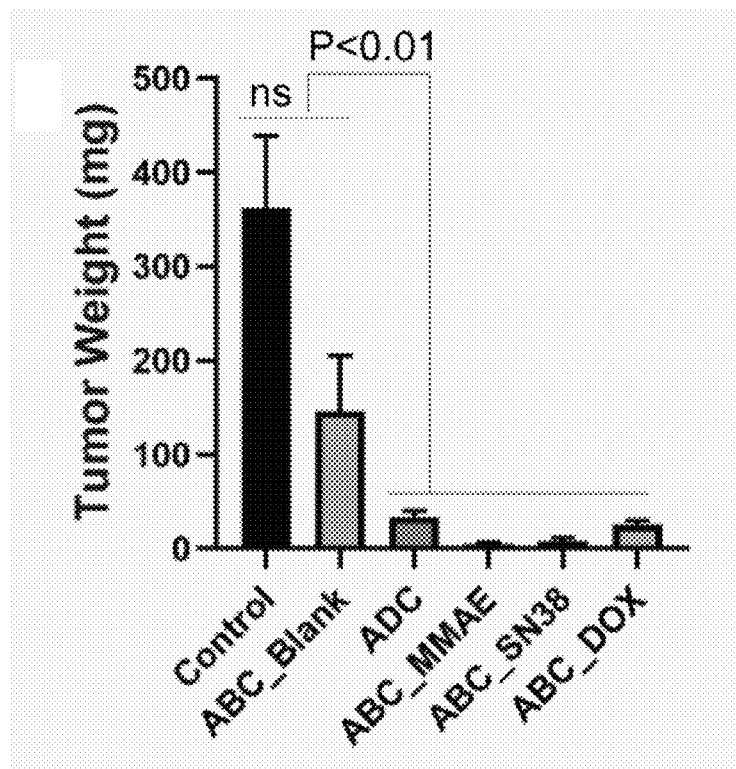

FIG. 33E shows BT474 tumor weight measurements for different treatment groups. After 40 days, the mice were sacrificed and the tumors were harvested. The results shown that all ABCs with different payloads no matter the potency exhibited good anticancer efficacy similar to or better than Kadcyla ("ADC").

Figure 34A:
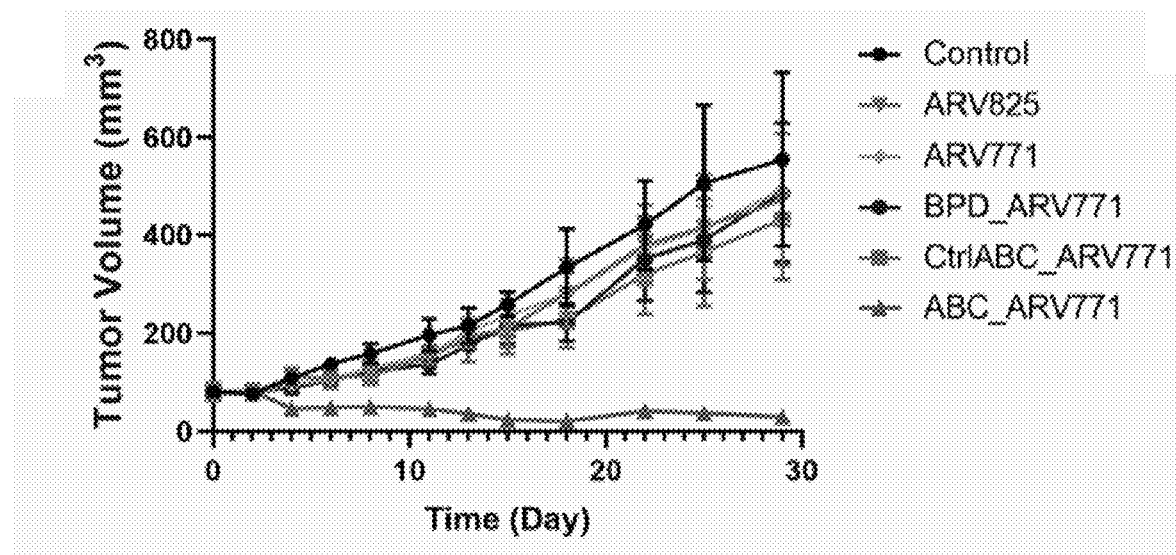

FIG. 34A shows tumor volume after treatment of PROTAC based ABCs and control groups. We used the ABC platform for antibody targeted delivery of PROTAC to tumors for cancer therapy. We chose ARV771 as the payload. We used PROTAC-ABC (ABC_ARV771) to perform in vivo anti-cancer study. The HER2 overexpressed BT474 xenograft mice model was also used for this study. 6 different treatments were performed on mice bearing ~50 mm³ volume tumor. 3 doses for treatment were performed once a week. BPD_ARV771, CtrlABC_ARV771, free ARV771, and free ARV825 showed little therapeutic effects, and the tumors continuously grew with almost the same trend as the control group. In contrast, PROTAC-ABC showed very good anticancer efficacy, and the tumor was almost disappeared after 3-doses treatment.

Figure 34B:
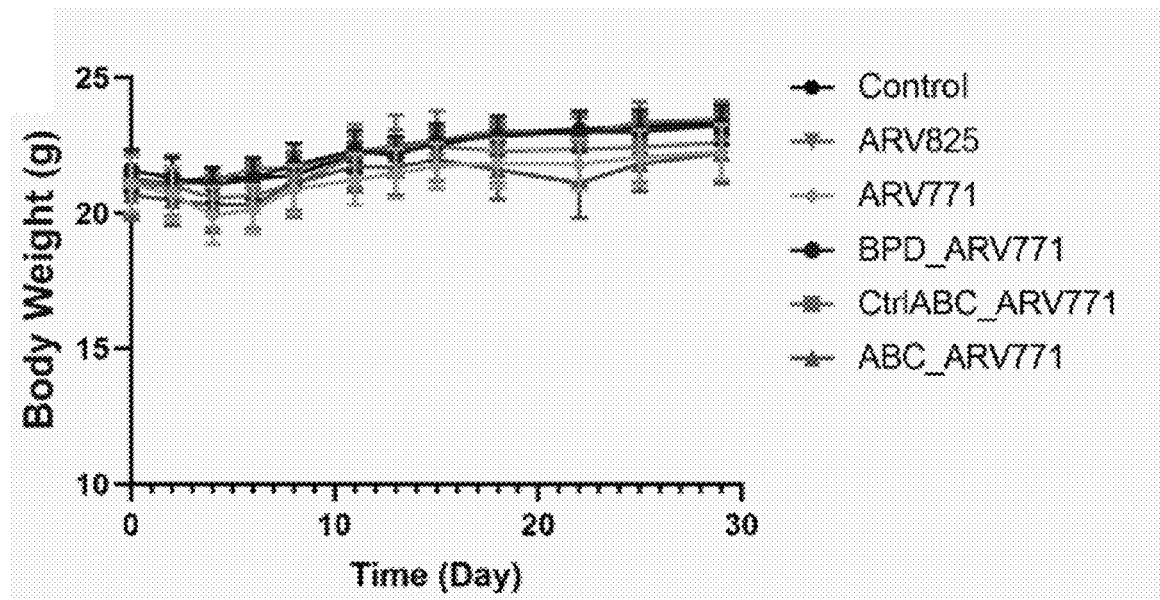

FIG. 34B shows body weight measurements after treatment of PROTAC-ABC (ABC_ARV771) and control groups. There was no toxicity after the injections as demonstrated by no significant body weight decrease. All the treatment groups showed almost the same body weight evolution as the control group.

Figure 34C:
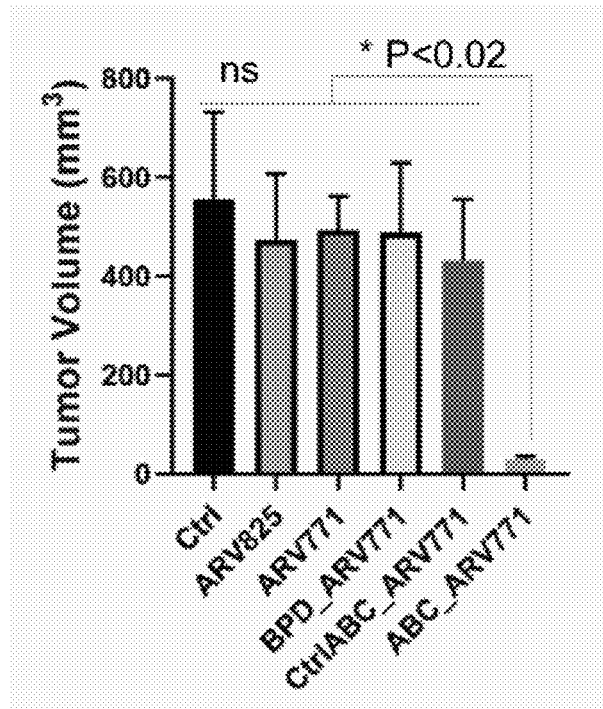

FIG. 34C shows BT474 tumor volume measurements after treatment of PROTAC-ABC (ABC_ARV771) and control groups at day 30. BPD_ARV771, CtrlABC_ARV771, free ARV771, and free ARV825 showed no therapeutic effects, as the tumor sizes were almost the same as the control group. In contrast, PROTAC-ABC showed very good anticancer efficacy, and the tumor was almost disappeared after 3-doses treatment.

Figure 34D:
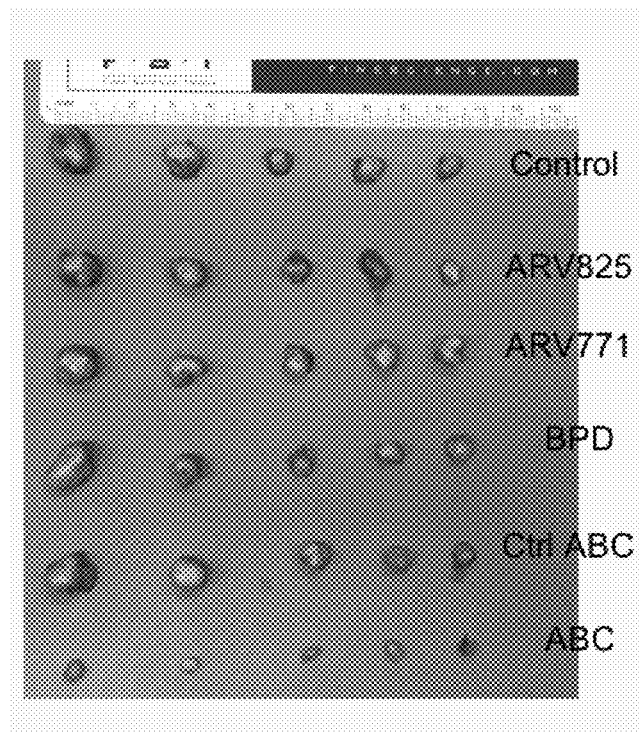

FIG. 34D shows BT474 tumor picture for different treatment groups with a PROTAC (ARV771) as payload. After 1-month study, the mice were sacrificed, and the tumor was collected. Except ABC treatment group, all the other groups showed similar tumor size comparing to the control group. The ABC treatment group showed excellent antitumor efficacy as almost totally disappearance of the tumor. ABC: ABC_ARV771. BPD: BPD_ARV771. Ctrl ABC: CtrlABC_ARV771.

Figure 34E:
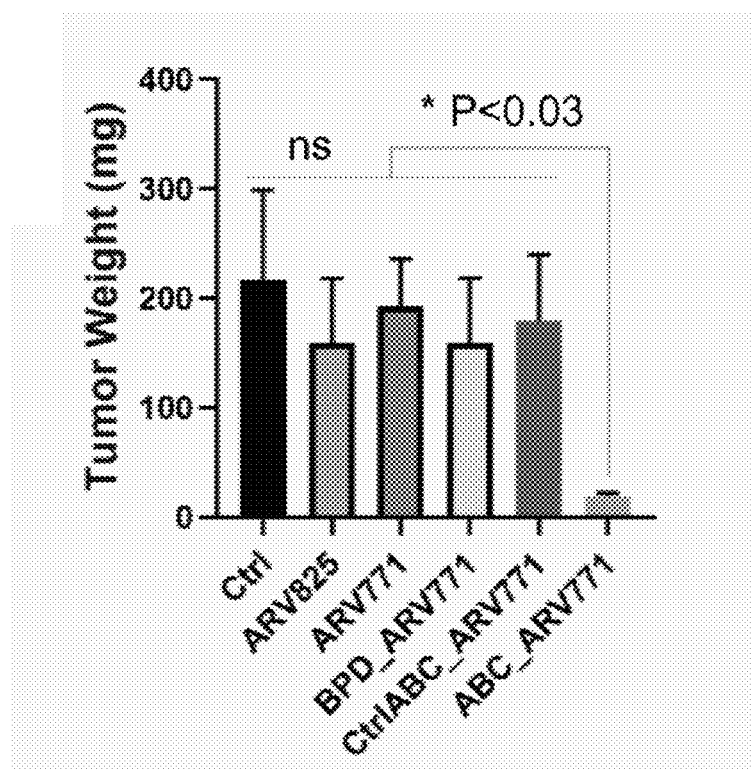

FIG. 34E shows BT474 tumor weight measurements after treatment of PROTAC-ABC (ABC_ARV771) and control groups. Except ABC treatment group, all the other groups showed very similar tumor weight comparing to the control group. The ABC treatment group showed excellent antitumor efficacy as almost totally disappearance of the tumor. Comparing to the literature results, the doses for our study is much lower with much less dosing frequency (once a week vs daily). Importantly, our targeted delivery platform can show superior anticancer efficacy.

Figure 35A:
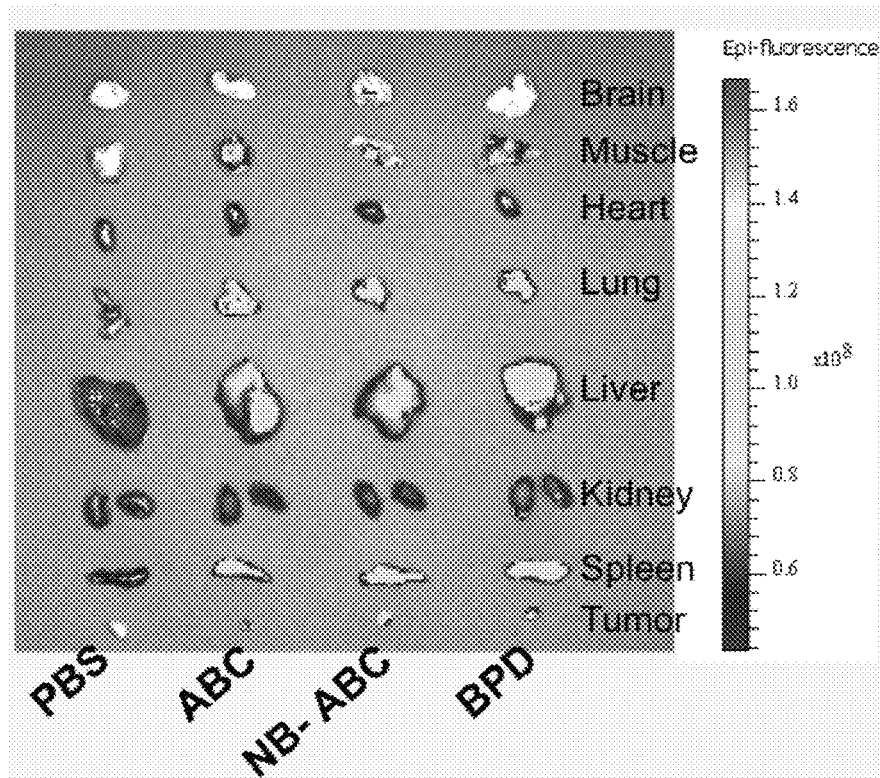

FIG. 35A shows ex vivo images of different organs with MUC1 model. MUC1 is an important surface expressed antigen for cancer therapy and has been ranked as the 2nd most promising antigen among 75 candidates by NCI. MUC1 is aberrantly overexpressed in different types of cancers such as ovarian cancer, lung cancer and breast cancer etc. CAOV3 cell line is an ovarian cancer cell line with high expression of MUC1 antigen on the surface. We also made the anti-MUC1 ABC using the same strategy as the anti-HER2 based ABCs. We performed in vivo study with a CAOV3 xenograft cancer model. Before anti-cancer study, we also evaluated the in vivo biodistribution study with ABC, BPD, and ctrl-ABC groups by ex vivo image. The ABC was efficiently accumulated inside the tumor tissue.

Figure 35B:
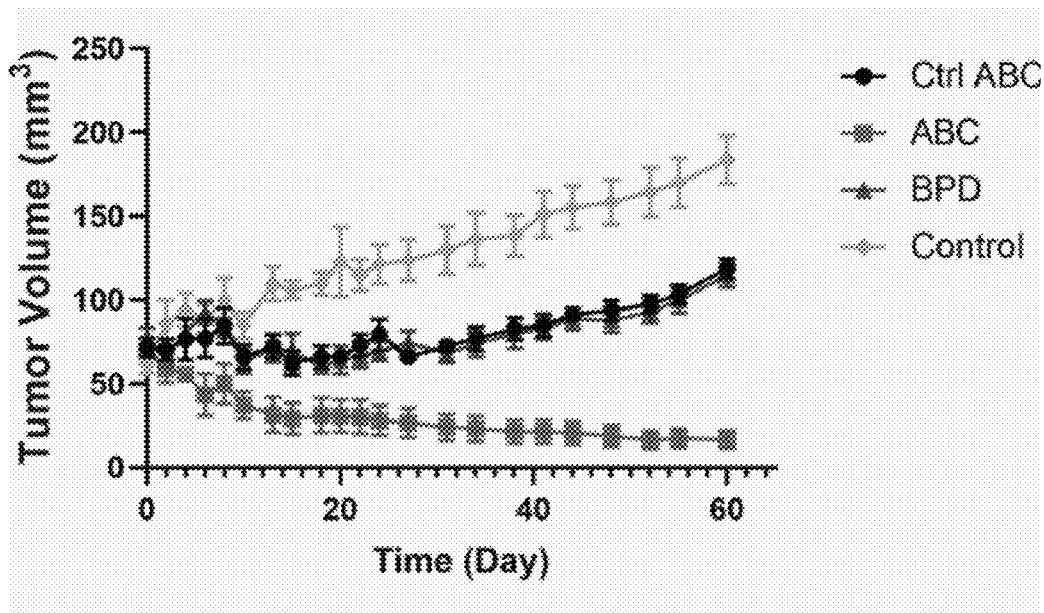

FIG. 35B shows CAOV3 tumor volume after treatment of PBS, BPD, ctrl ABC, or ABC with MMAE as the payload and anti-MUC1 as the targeting antibody. The anticancer study was performed by the anti-MUC1 ABCs with MMAE as the payload. BPD and Ctrl ABC showed very similar anti-cancer efficacy comparing to the control group. ABC efficiently shrank the tumor volume, and there was totally out of tumor after four doses of injections.

Figure 35C:
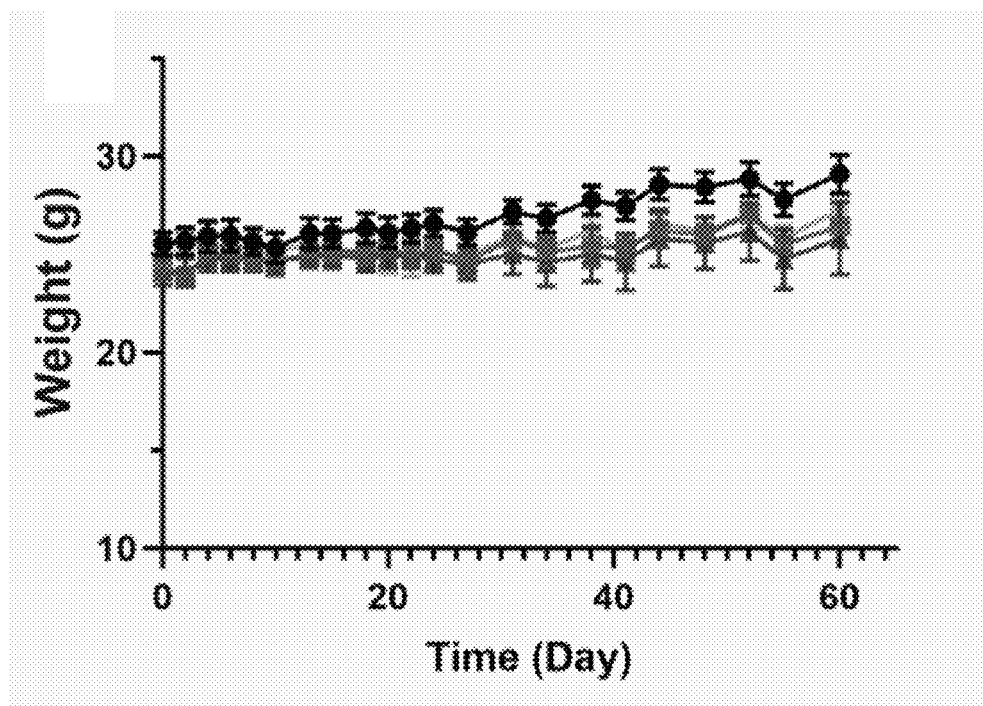

FIG. 35C shows body weight measurements after treatment of PBS, BPD, ctrl ABC, or ABC with MMAE as the payload and anti-MUC1 as the targeting antibody. There is no toxicity after the injections as demonstrated by no significant body weight decrease. All the treatment groups showed almost the same body weight evolution as the control group.

Figure 35D:
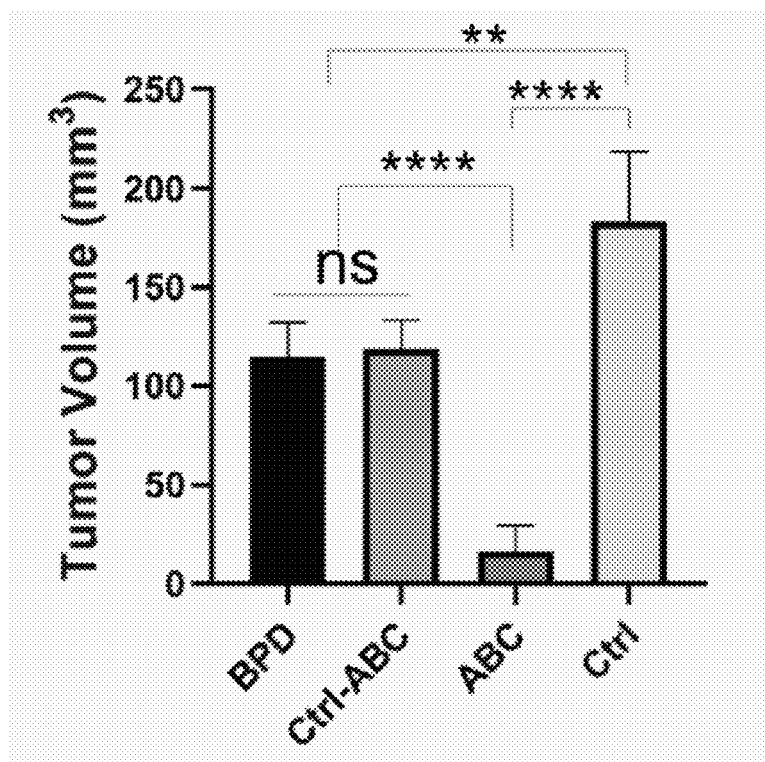

FIG. 35D shows CAOV3 tumor volume at day 60 after treatment of PBS, BPD, ctrl ABC, or ABC with MMAE as the payload and anti-MUC1 as the targeting antibody. ABC showed outstanding anti-tumor efficacy comparing to the other treatment groups.

Figure 35E:
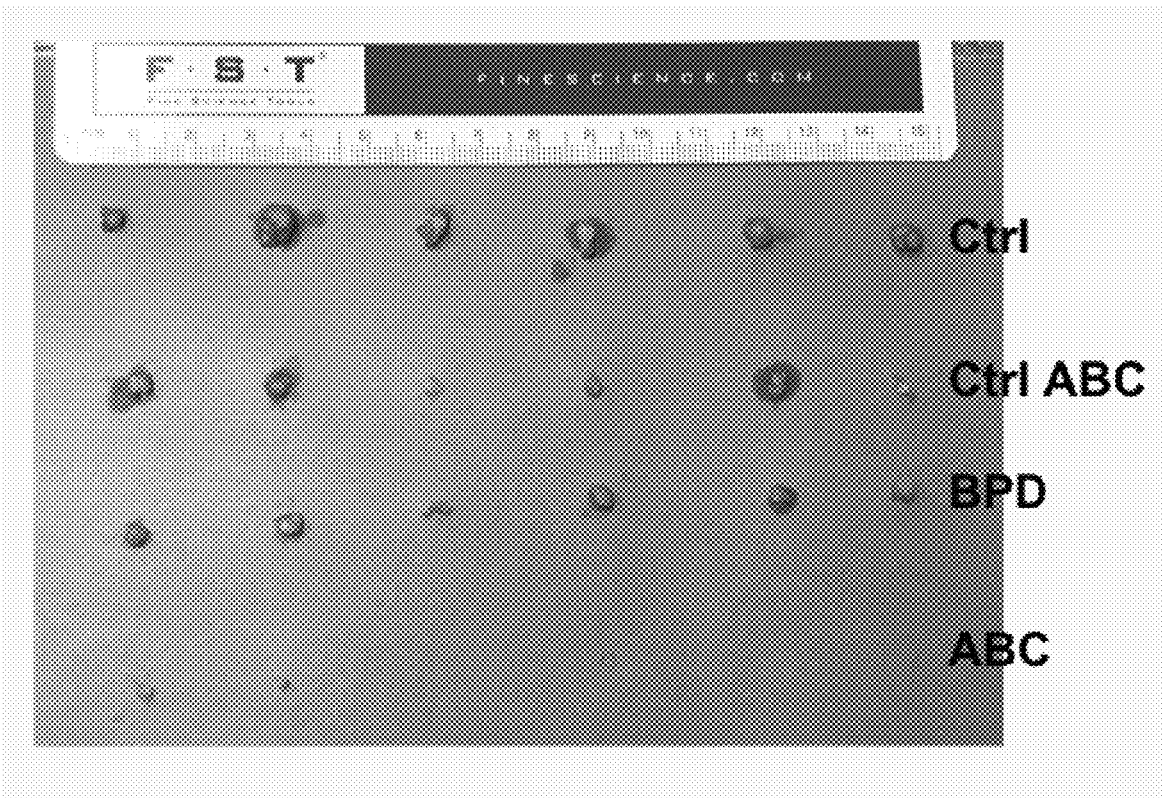

FIG. 35E shows CAOV3 tumor picture for different treatment groups with MMAE as the payload and anti-MUC1 as the targeting antibody. We harvested the tumors after 60 days study. Overall, ABC showed outstanding anti-tumor efficacy.

Figure 35F:
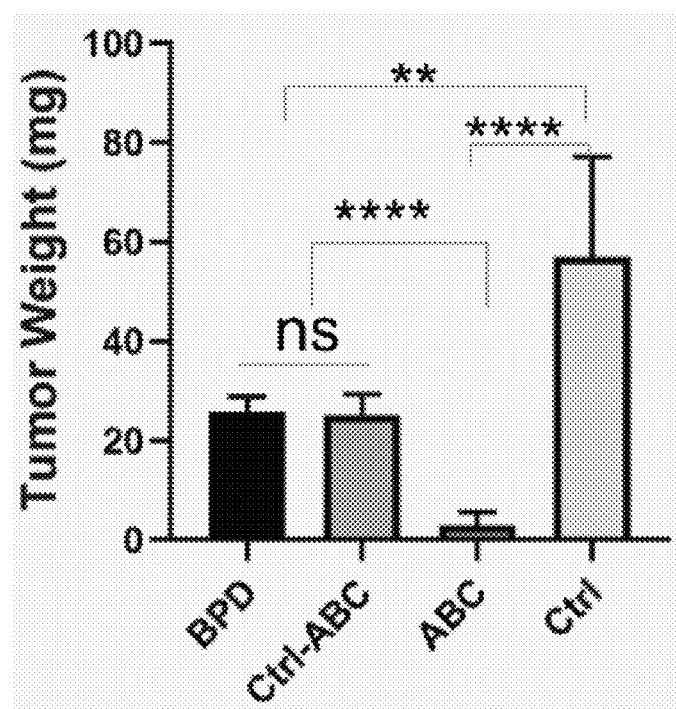

FIG. 35F shows CAOV3 tumor weight measurements after treatments with MMAE as the payload and anti-MUC1 as the targeting antibody. We harvested the tumors after 60 days study. The tumor weights were measured. Overall, ABC showed outstanding anti-tumor efficacy. Together, our strategy highlights the modularity of different drugs and also different antibodies for targeted cancer therapy.

Figure 36:
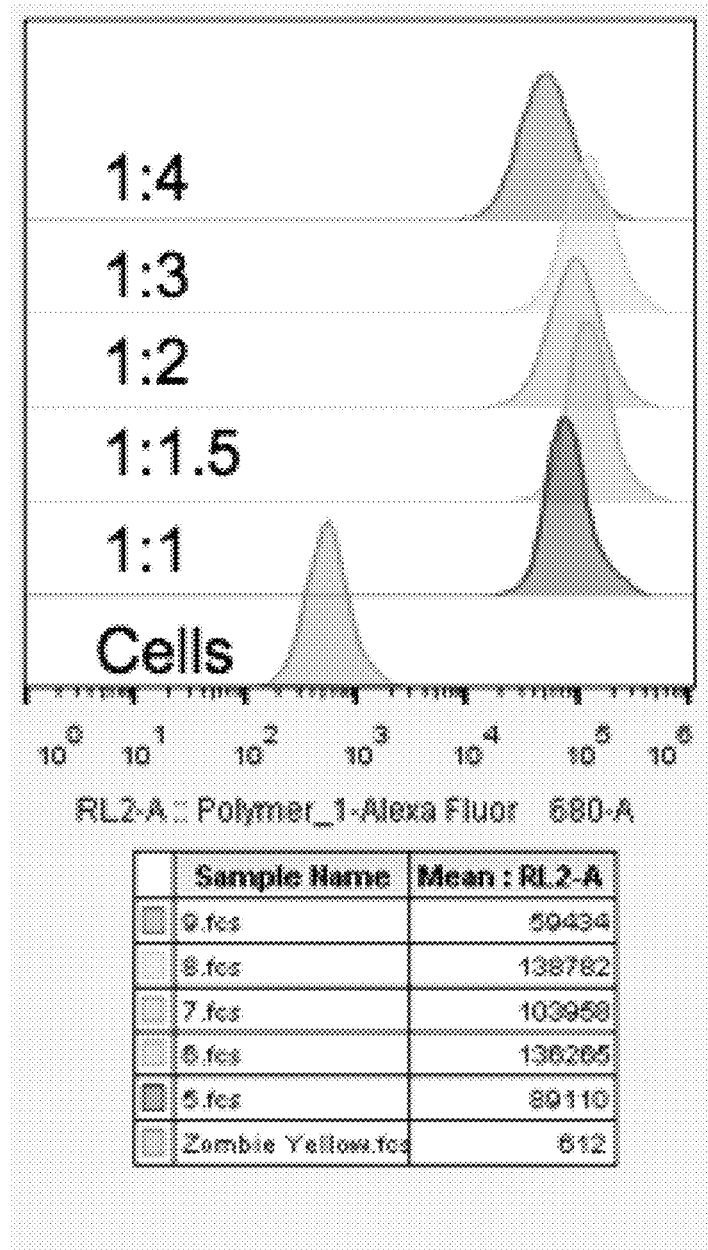

FIG. 36 shows cell uptake with different reaction ratios (feed ratios) between antibody and brush polymer. We studied the targeting efficiency of these conjugates with different polymer chains on each antibody. We did two experiments to explore the targeting efficiency. At first, we incubated the cells with the same amount of fluorophore for targeting evaluation. The cell uptake is similar when the chains on each antibody between 1-3 (e.g., n1 being 1, 2, or 3) with feed ratio less than 3:1 brush polymer:antibody. Further, when the chain number was increased to 4 (e.g., n1 being 4), the targeting efficiency was decreased. Secondly, we fed the same amount of antibody for cell uptake. The more conjugation chain will result in more payloads in each ABC. The highest targeting efficiency was the ABCs with average of 3 chains on each of the Ab (e.g., n1 being 3). Similarly, when the feed ratio was increased to 4:1 brush polymer:antibody (e.g., n1 being 4), the cell uptake was decreased.

Figure 37:
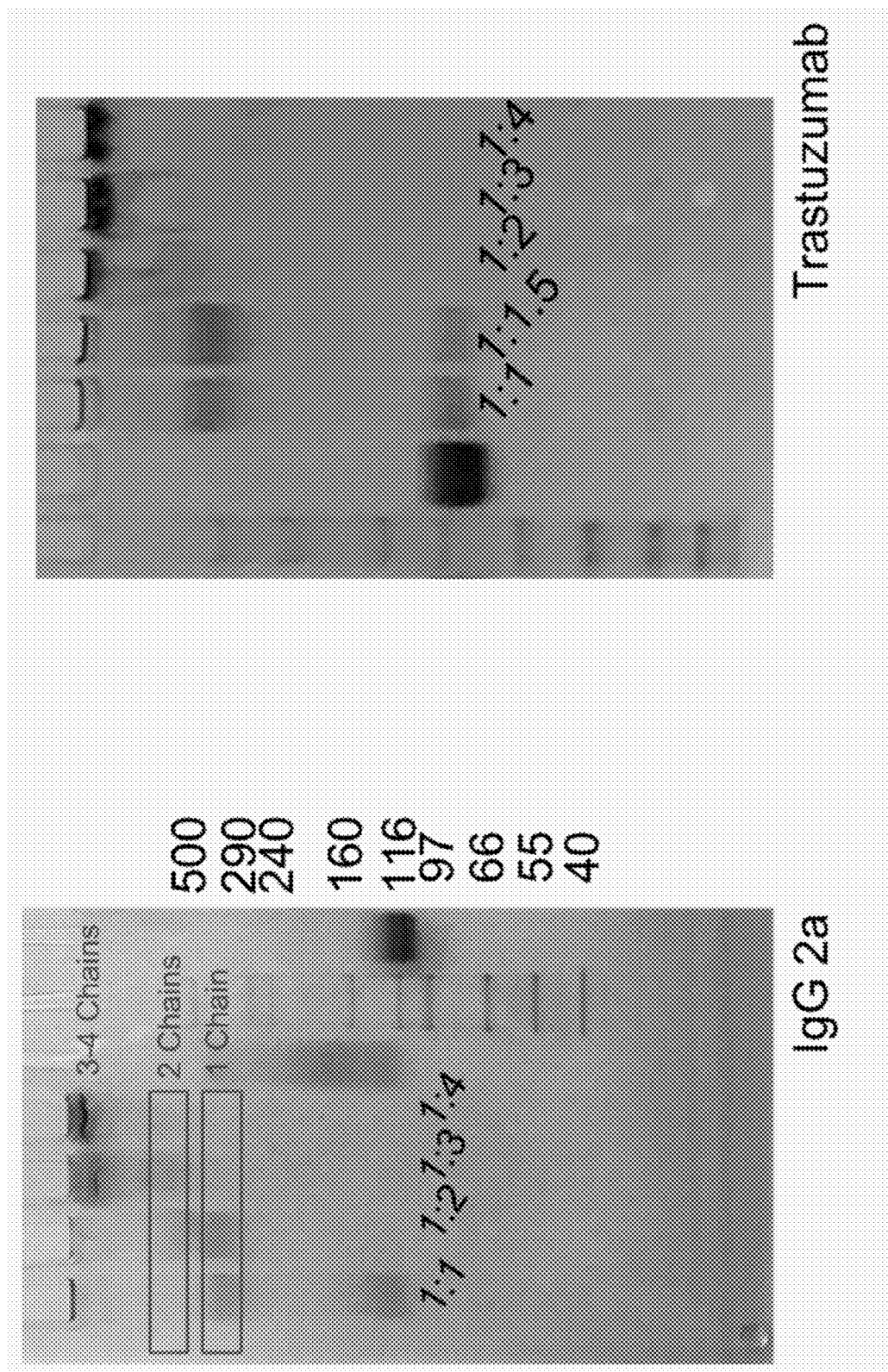

FIG. 37 shows SDS PAGE gels with different feed ratios between antibodies and brush polymers. The conjugation process was controlled by different feed ratio between Ab-TCO and BP-Tz to achieve different brush polymers on each antibody. We changed the reaction ratio between the BP-Tz and Ab-TCO from 1:1 to 4:1. The reaction was monitored by SDS-PAGE gel. With the increase of the feed ratio of the brush polymer, the conjugation amount of the BP chain on each of the conjugates can be increased. This process was monitored by SDS-PAGE gel. Two different antibodies (IgG2a and anti-HER2) were used for the conjugation. When 1 eq. of brush polymer was mixed with Ab-TCO, most of the antibody were consumed to form the conjugates with 1 brush polymer on each of the antibody. There were also some conjugates with more than one brush polymer on each antibody. Free antibody wasn't totally consumed in the reaction. When the ratio between the brush polymer and antibody was further increased to 2, the main product was conjugates with 2 brush polymers on each antibody, with small amount of one brush polymer on one antibody and small amount of more than 3 brush polymers on each antibody. But there is no free antibody left. Further increase of the eq. of the brush polymer resulted in more brush polymers conjugated on one antibody on average. This reaction was more homogeneous than the traditional conjugation between antibody and small molecules, which typically results in ~40% of free antibody with an average DAR value of ~4.

Figure 38:
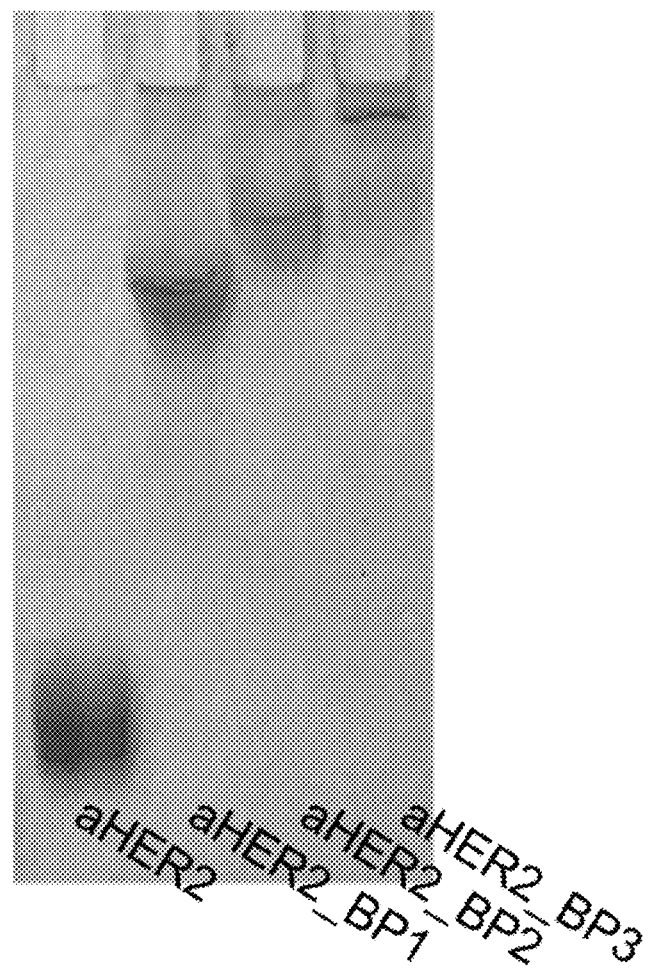

FIG. 38 shows the separation of ABCs with one brush polymer on one antibody and two brush polymers on one antibody. After the conjugation, we purified these conjugates by FPLC through a cationic exchange column. In this process, we easily purified the conjugates with different brush polymer:antibody ratios. In the gel, we clear showed that ABCs with one brush polymer per antibody (aHER2_BP1), two brush polymers per antibody (aHER2_BP2), and three brush polymers per antibody (aHER2_BP3) were separated.

Figure 39:
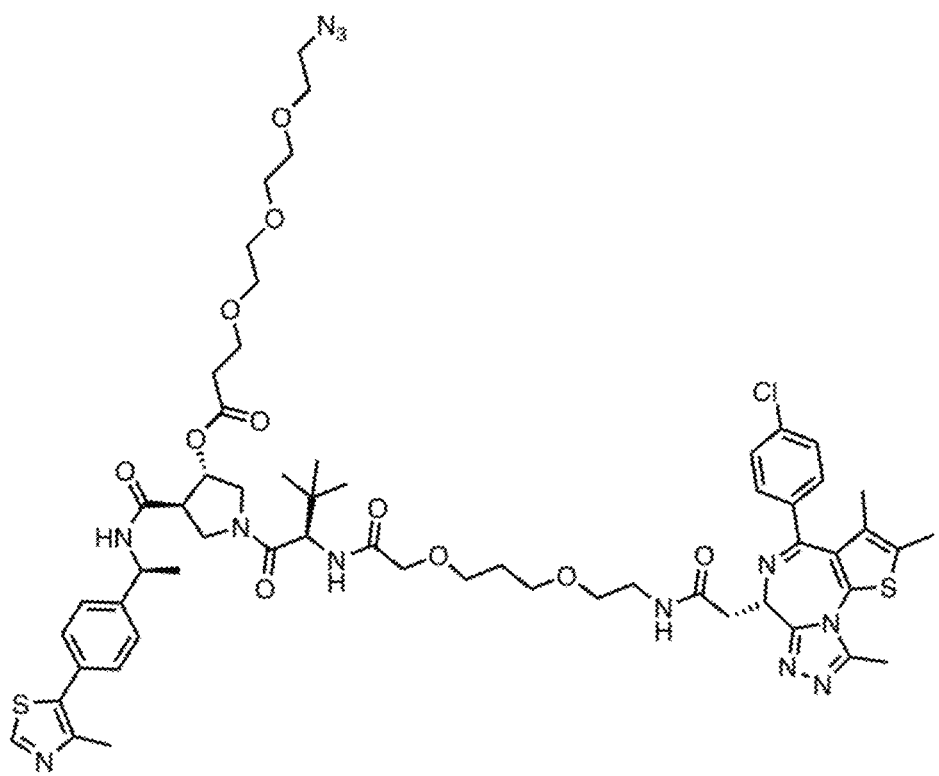
Figure 39:
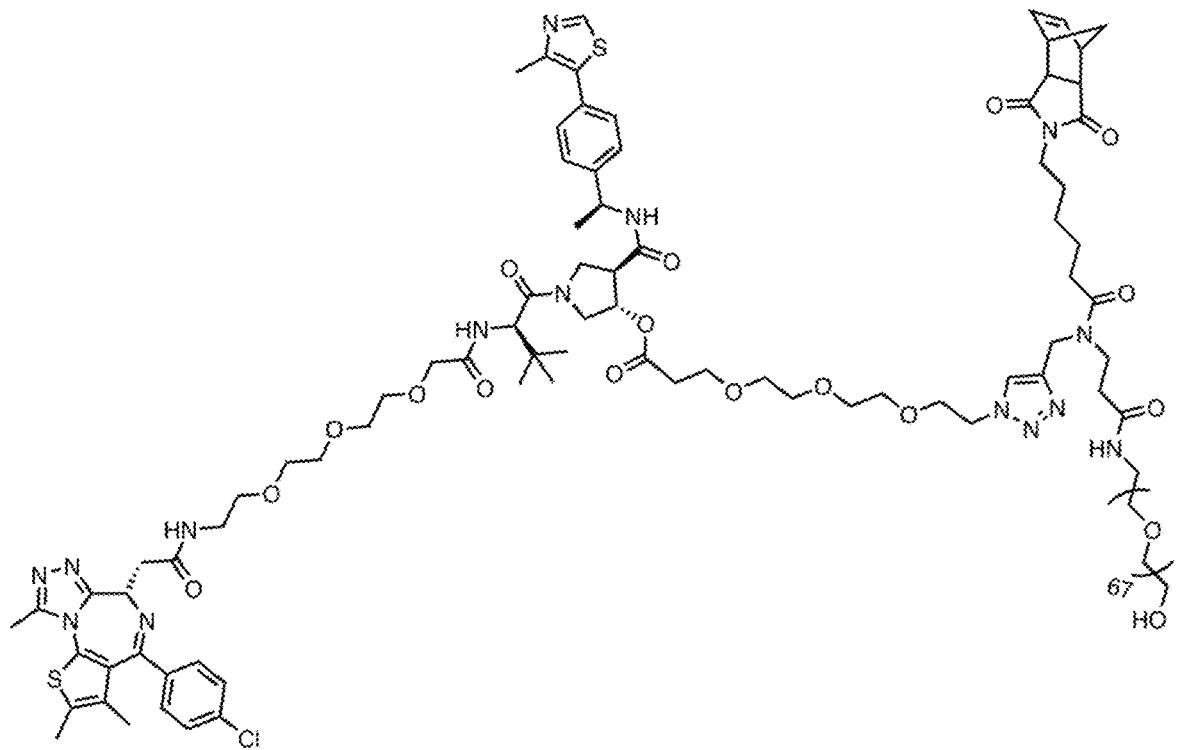

FIG. 39 shows the chemical structure of PROTAC-azide and PROTAC-MM.

DETAILED DESCRIPTION OF CERTAIN EMBODIMENTS OF THE DISCLOSURE

Enynes, End-Functionalized Polymers, Conjugates, and Methods of Preparation

In one aspect, the present disclosure provides an enyne of Formula (I):

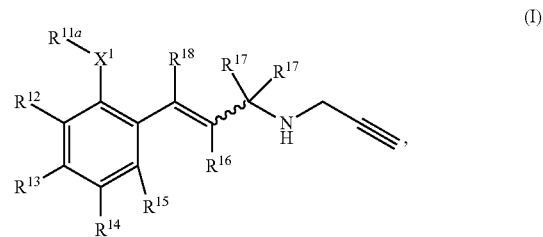

or a tautomer, isotopically labeled compound, salt, solvate, polymorph, or co-crystal thereof, wherein:

$X^1$ is S, O, Se, or a single bond;

$R^{11a}$ is substituted or unsubstituted, $C_{1-18}$ alkyl;

each of $R^{12}$, $R^{13}$, $R^{14}$, and $R^{15}$ is independently H, halogen, substituted or unsubstituted, $C_{1-6}$ alkyl, —O-(substituted or unsubstituted, $C_{1-6}$ alkyl), substituted or unsubstituted carbocyclyl, or substituted or unsubstituted aryl;

$R^{16}$ is H or substituted or unsubstituted, $C_{1-6}$ alkyl;

$R^{18}$ is H or substituted or unsubstituted, $C_{1-6}$ alkyl;

each instance of $R^{17}$ is independently H or substituted or unsubstituted, $C_{1-6}$ alkyl;

or $R^{16}$ and one instance of $R^{17}$ are joined with their intervening atoms to form substituted or unsubstituted carbocyclyl or substituted or unsubstituted heterocyclyl; and provided that —$X^1$—$R^{11a}$ is not —S-n-$C_{12}H_{25}$.

In certain embodiments, the present disclosure provides the enyne of Formula (I), or a tautomer, isotopically labeled compound, or salt thereof (e.g., a tautomer or salt thereof).

In certain embodiments, $R^{11a}$ is substituted or unsubstituted, $C_{1-6}$ alkyl. In certain embodiments, $R^{11a}$ is unsubstituted $C_{1-6}$ alkyl. In certain embodiments, $R^{11a}$ is unsubstituted n-$C_{3-6}$ alkyl, e.g., n-$C_4H_9$. In certain embodiments, $R^{11a}$ is substituted or unsubstituted, $C_{7-9}$ alkyl. In certain embodiments, $R^{11a}$ is substituted or unsubstituted, $C_{10-11}$ alkyl. In certain embodiments, $R^{11a}$ is substituted or unsubstituted, $C_{12}$ alkyl. In certain embodiments, $R^{11a}$ is unsubstituted n-dodecyl. In certain embodiments, $R^{11a}$ is not unsubstituted n-dodecyl. In certain embodiments, $R^{11a}$ is substituted or unsubstituted, $C_{13-15}$ alkyl. In certain embodiments, $R^{11a}$ is substituted or unsubstituted, $C_{16-18}$ alkyl. In certain embodiments, $R^{11a}$ is unsubstituted $C_{1-18}$ alkyl. In certain embodiments, $R^{11a}$ is unsubstituted $C_{1-11}$ alkyl. In certain embodiments, $R^{11a}$ is unsubstituted n-$C_{7-16}$ alkyl. In certain embodiments, the optional substituents included in $R^{11a}$ are independently halogen (e.g., F), —O-(unsubstituted $C_{1-6}$ alkyl), or —O—($C_{1-6}$ alkyl substituted with one or more halogen (e.g., F)).

In certain embodiments, the present disclosure provides an enyne of Formula (I-1):

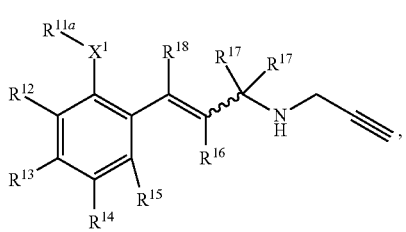

(I-1)

or a salt thereof, wherein:

$X^1$ is S;
$R^{11a}$ is unsubstituted $C_{1-18}$ alkyl;
each of $R^{12}$, $R^{13}$; $R^{14}$; and $R^{15}$ are H;
$R^{16}$ is H or unsubstituted $C_1$ alkyl;
$R^{18}$ is H or unsubstituted $C_1$ alkyl;
each instance of $R^{17}$ is independently H or unsubstituted $C_1$ alkyl;
provided that —$X^1$—$R^{11a}$ is not —S-n-$C_{12}H_{25}$.

In certain embodiments, $R^{11a}$ is unsubstituted $C_{1-ii}$ alkyl. In certain embodiments, $R^{11a}$ is unsubstituted $C_{1-9}$ alkyl. In certain embodiments, $R^{11a}$ is unsubstituted $C_{13-18}$ alkyl. In certain embodiments, $R^{11a}$ is unsubstituted $C_{14-18}$ alkyl.

In certain embodiments, Formula (I) is:

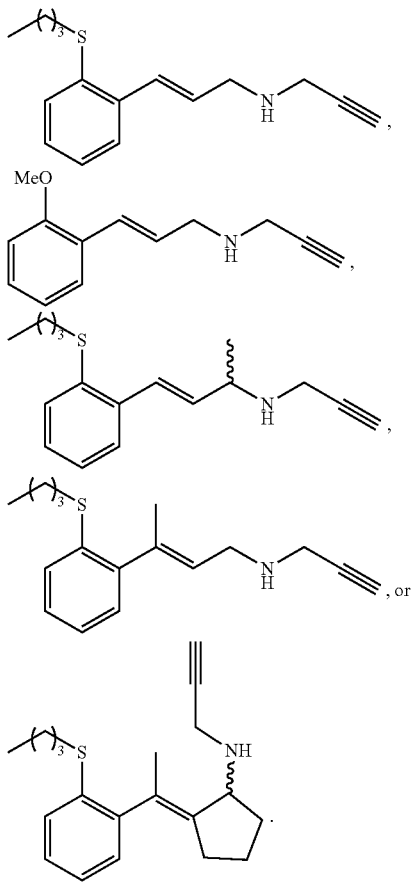

In another aspect, the present disclosure provides an enyne of Formula (II):

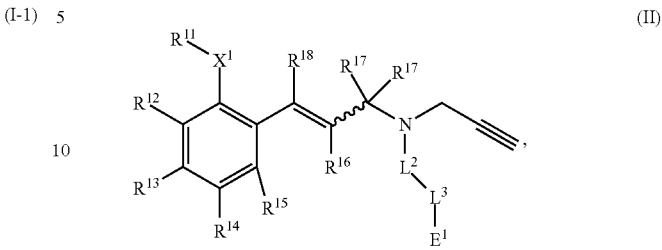

(II)

or a tautomer, isotopically labeled compound, salt, solvate, polymorph, or co-crystal thereof, wherein:

$X^1$ is S, O, Se, or a single bond;
$R^{11}$ is substituted or unsubstituted, $C_{1-18}$ alkyl;
each of $R^{12}$, $R^{13}$, $R^{14}$, and $R^{15}$ is independently H, halogen, substituted or unsubstituted, $C_{1-6}$ alkyl, —O-(substituted or unsubstituted, $C_{1-6}$ alkyl), substituted or unsubstituted carbocyclyl, or substituted or unsubstituted aryl;
$R^{16}$ is H or substituted or unsubstituted, $C_{1-6}$ alkyl;
$R^{18}$ is H or substituted or unsubstituted, $C_{1-6}$ alkyl;
each instance of $R^{17}$ is independently H or substituted or unsubstituted, $C_{1-6}$ alkyl;
or $R^{16}$ and one instance of $R^{17}$ are joined with their intervening atoms to form substituted or unsubstituted carbocyclyl or substituted or unsubstituted heterocyclyl;
$L^2$ is —C(=O)—, —S(=O)$_2$—, —S(=O)—, or a single bond;
$L^3$ is substituted or unsubstituted, $C_{1-1000}$ alkylene, substituted or unsubstituted, $C_{2-1000}$ alkenylene, substituted or unsubstituted, $C_{2-1000}$ alkynylene, substituted or unsubstituted, $C_{1-1000}$ heteroalkylene, substituted or unsubstituted, $C_{2-1000}$ heteroalkenylene, substituted or unsubstituted, $C_{2-1000}$ heteroalkynylene, or a single bond;
optionally wherein one or more backbone carbon atoms of the $C_{1-1000}$ alkylene, $C_{2-1000}$ alkenylene, $C_{2-1000}$ alkynylene, $C_{1-1000}$ heteroalkylene, $C_{2-1000}$ heteroalkenylene, or $C_{2-1000}$ heteroalkynylene are independently replaced with substituted or unsubstituted carbocyclylene, substituted or unsubstituted heterocyclylene, substituted or unsubstituted arylene, or substituted or unsubstituted heteroarylene, as valency permits;
at least one of $L^2$ and $L^3$ is not a single bond;
$E^1$ is a thiophile, a first click-chemistry handle, a nucleophile, an electrophile, or a leaving group, H, halogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=O)R$^a$, —C(=O)OR$^a$, —C(=O)N(R$^a$)$_2$, —C(=NR$^a$)R$^a$, —C(=NR$^a$)OR$^a$, —C(=NR$^a$)N(R$^a$)$_2$, —NO$_2$, —N$_3$, —NR$^a$C(=O)R$^a$, —NR$^a$C(=O)OR$^a$, —NR$^a$C(=O)N(R$^a$)$_2$, —NR$^a$C(=NR$^a$)R$^a$, —NR$^a$C(=NR$^a$)OR$^a$, —NR$^a$C(=NR$^a$)N(R$^a$)$_2$, —OC(=O)R$^a$, —OC(=O)OR$^a$, —OC(=O)N(R$^a$)$_2$, —OC(=NR$^a$)R$^a$, —OC(=NR$^a$)OR$^a$, —OC(=NR$^a$)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OS(=O)R$^a$, —OS(=O)OR$^a$, —OS(=O)N(R$^a$)$_2$, —S(=O)R$^a$, —S(=O)OR$^a$, —S(=O)N(R$^a$)$_2$, —OS(=O)$_2$R$^a$, —OS(=O)$_2$OR$^a$, —OS(=O)$_2$N(R$^a$)$_2$, —S(=O)$_2$R$^a$, —S(=O)$_2$OR$^a$, —S(=O)$_2$N(R$^a$)$_2$, or —P(=O)(R$^a$)$_2$; and each instance of $R^a$ is independently H, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ attached to a nitrogen atom are joined with the nitrogen atom to form substituted or unsubstituted heterocyclyl or substituted or unsubstituted heteroaryl.

In certain embodiments,

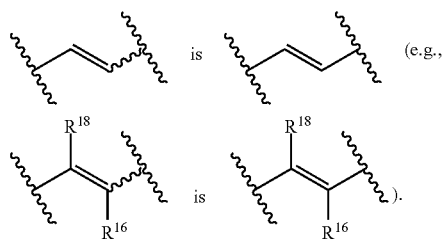

In certain embodiments,

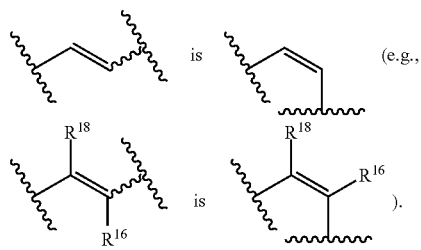

In certain embodiments, $X^1$ is S. In certain embodiments, $X^1$ is O. In certain embodiments, $X^1$ is a single bond.

In certain embodiments, $R^{11}$ is substituted or unsubstituted, $C_{1-6}$ alkyl. In certain embodiments, $R^{11}$ is unsubstituted $C_{1-6}$ alkyl. In certain embodiments, $R^{11}$ is unsubstituted n-$C_{3-6}$ alkyl, e.g., n-$C_4H_9$. In certain embodiments, $R^{11}$ is substituted or unsubstituted, $C_{7-9}$ alkyl. In certain embodiments, $R^{11}$ is substituted or unsubstituted, $C_{10-11}$ alkyl. In certain embodiments, $R^{11}$ is substituted or unsubstituted, $C_{12}$ alkyl. In certain embodiments, $R^{11}$ is unsubstituted n-dodecyl. In certain embodiments, $R^{11}$ is not unsubstituted n-dodecyl. In certain embodiments, $R^{11}$ is substituted or unsubstituted, $C_{13-15}$ alkyl. In certain embodiments, $R^{11}$ is substituted or unsubstituted, $C_{16-18}$ alkyl. In certain embodiments, $R^{11}$ is unsubstituted $C_{1-18}$ alkyl. In certain embodiments, $R^{11}$ is unsubstituted $C_{1-11}$ alkyl. In certain embodiments, $R^{11}$ is unsubstituted n-$C_{7-16}$ alkyl. In certain embodiments, the optional substituents included in $R^u$ are independently halogen (e.g., F), —O-(unsubstituted $C_{1-6}$ alkyl), or —O—($C_{1-6}$ alkyl substituted with one or more halogen (e.g., F)).

In certain embodiments, $R^{12}$ is H. In certain embodiments, $R^{12}$ is halogen (e.g., F, Cl). In certain embodiments, $R^{12}$ is unsubstituted $C_{1-6}$ alkyl (e.g., —$CH_3$, —$C_2H_5$). In certain embodiments, $R^{12}$ is substituted $C_{1-6}$ alkyl (e.g., $C_{1-6}$ alkyl substituted with one or more halogen (e.g., F)). In certain embodiments, $R^{12}$ is —$CF_3$. In certain embodiments, $R^{12}$ is —O-(unsubstituted $C_{1-6}$ alkyl) (e.g., —$OCH_3$, —$OC_2H_5$). In certain embodiments, $R^{12}$ is unsubstituted carbocyclyl (e.g., unsubstituted cyclopropyl). In certain embodiments, $R^{12}$ is unsubstituted aryl (e.g., unsubstituted phenyl). In certain embodiments, $R^{12}$ is aryl (e.g., phenyl) substituted with one or more halogen, unsubstituted $C_{1-6}$ alkyl, $C_{1-6}$ alkyl substituted with one or more halogen, or —O-(unsubstituted $C_{1-6}$ alkyl).

In certain embodiments, $R^{13}$ is H. In certain embodiments, $R^{13}$ is halogen (e.g., F, Cl). In certain embodiments, $R^{13}$ is unsubstituted $C_{1-6}$ alkyl (e.g., —$CH_3$, —$C_2H_5$). In certain embodiments, $R^{13}$ is substituted $C_{1-6}$ alkyl (e.g., $C_{1-6}$ alkyl substituted with one or more halogen (e.g., F)). In certain embodiments, $R^{13}$ is —$CF_3$. In certain embodiments, $R^{13}$ is —O-(unsubstituted $C_{1-6}$ alkyl) (e.g., —$OCH_3$, —$OC_2H_5$). In certain embodiments, $R^{13}$ is unsubstituted carbocyclyl (e.g., unsubstituted cyclopropyl). In certain embodiments, $R^{13}$ is unsubstituted aryl (e.g., unsubstituted phenyl). In certain embodiments, $R^{13}$ is aryl (e.g., phenyl) substituted with one or more halogen, unsubstituted $C_{1-6}$ alkyl, $C_{1-6}$ alkyl substituted with one or more halogen, or —O-(unsubstituted $C_{1-6}$ alkyl).

In certain embodiments, $R^{14}$ is H. In certain embodiments, $R^{14}$ is halogen (e.g., F, Cl). In certain embodiments, $R^{14}$ is unsubstituted $C_{1-6}$ alkyl (e.g., —$CH_3$, —$C_2H_5$). In certain embodiments, $R^{14}$ is substituted $C_{1-6}$ alkyl (e.g., $C_{1-6}$ alkyl substituted with one or more halogen (e.g., F)). In certain embodiments, $R^{14}$ is —$CF_3$. In certain embodiments, $R^{14}$ is —O-(unsubstituted $C_{1-6}$ alkyl) (e.g., —$OCH_3$, —$OC_2H_5$). In certain embodiments, $R^{14}$ is unsubstituted carbocyclyl (e.g., unsubstituted cyclopropyl). In certain embodiments, $R^{14}$ is unsubstituted aryl (e.g., unsubstituted phenyl). In certain embodiments, $R^{14}$ is aryl (e.g., phenyl) substituted with one or more halogen, unsubstituted $C_{1-6}$ alkyl, $C_{1-6}$ alkyl substituted with one or more halogen, or —O-(unsubstituted $C_{1-6}$ alkyl).

In certain embodiments, $R^{15}$ is H. In certain embodiments, $R^{15}$ is halogen (e.g., F, Cl). In certain embodiments, $R^{15}$ is unsubstituted $C_{1-6}$ alkyl (e.g., —$CH_3$, —$C_2H_5$). In certain embodiments, $R^{15}$ is substituted $C_{1-6}$ alkyl (e.g., $C_{1-6}$ alkyl substituted with one or more halogen (e.g., F)). In certain embodiments, $R^{15}$ is —$CF_3$. In certain embodiments, $R^{15}$ is —O-(unsubstituted $C_{1-6}$ alkyl) (e.g., —$OCH_3$, —$OC_2H_5$). In certain embodiments, $R^{15}$ is unsubstituted carbocyclyl (e.g., unsubstituted cyclopropyl). In certain embodiments, $R^{15}$ is unsubstituted aryl (e.g., unsubstituted phenyl). In certain embodiments, $R^{15}$ is aryl (e.g., phenyl) substituted with one or more halogen, unsubstituted $C_{1-6}$ alkyl, $C_{1-6}$ alkyl substituted with one or more halogen, or —O-(unsubstituted $C_{1-6}$ alkyl). In certain embodiments, each of $R^{12}$, $R^{13}$, $R^{14}$, and $R^{15}$ is independently H, halogen, unsubstituted $C_{1-3}$ alkyl, or —O-(unsubstituted $C_{1-3}$ alkyl). In certain embodiments, each of $R^{12}$, $R^{13}$, $R^{14}$, and $R^{15}$ is H.

In certain embodiments, $R^{16}$ is H. In certain embodiments, $R^{16}$ is unsubstituted $C_{1-6}$ alkyl, e.g., —$C_2H_5$. In certain embodiments, $R^{16}$ is unsubstituted $C_{1-3}$ alkyl, e.g., —$CH_3$. In certain embodiments, $R^{16}$ is substituted $C_{1-6}$ alkyl (e.g., $C_{1-6}$ alkyl substituted with one or more halogen (e.g., F)). In certain embodiments, $R^{16}$ is —$CF_3$.

In certain embodiments, $R^{18}$ is H. In certain embodiments, $R^{18}$ is unsubstituted $C_{1-6}$ alkyl, e.g., —$C_2H_5$. In certain embodiments, $R^{18}$ is unsubstituted $C_{1-3}$ alkyl, e.g., —$CH_3$. In certain embodiments, $R^{18}$ is substituted $C_{1-6}$ alkyl (e.g., $C_{1-6}$ alkyl substituted with one or more halogen (e.g., F)). In certain embodiments, $R^{18}$ is —$CF_3$.

In certain embodiments, each instance of $R^{17}$ is H. In certain embodiments, $R^{17}$ is one instance of $R^{17}$ is H, and the other instance of unsubstituted $C_{1-6}$ alkyl, e.g., —$C_2H_5$. In certain embodiments, one instance of $R^{17}$ is H, and the other instance of $R^{17}$ is unsubstituted $C_{1-3}$ alkyl, e.g., —$CH_3$. In certain embodiments, one instance of $R^{17}$ is H, and the other instance of $R^{17}$ is substituted $C_{1-6}$ alkyl (e.g., $C_{1-6}$ alkyl substituted with one or more halogen (e.g., F)). In certain embodiments, one instance of $R^{17}$ is H, and the other instance of $R^{17}$ is —$CF_3$. In certain embodiments, each instance of $R^{17}$ is independently unsubstituted $C_{1-3}$ alkyl, e.g., —$CH_3$. In certain embodiments, the carbon atom to which two $R^{17}$ are attached is of the R configuration. In certain embodiments, the carbon atom to which two $R^{17}$ are attached is of the S configuration. In certain embodiments, $R^{16}$ and one instance of $R^{17}$ are joined with their intervening atoms to form substituted or unsubstituted carbocyclyl, e.g., unsubstituted cyclopropyl.

In certain embodiments, $L^2$ is —C(=O)—, —S(=O)$_2$—, or —S(=O)—. In certain embodiments, $L^2$ is —C(=O)—. In certain embodiments, $L^2$ is a single bond.

In certain embodiments, $L^3$ is substituted or unsubstituted, $C_{1-30}$ alkylene. In certain embodiments, $L^3$ is substituted or unsubstituted, $C_{30-100}$ alkylene. In certain embodiments, $L^3$ is substituted or unsubstituted, $C_{100-300}$ alkylene. In certain embodiments, $L^3$ is substituted or unsubstituted, $C_{300-1000}$ alkylene.

In certain embodiments, $L^3$ is substituted or unsubstituted, $C_{1-30}$ heteroalkylene. In certain embodiments, $L^3$ is substituted or unsubstituted, $C_{30-100}$ heteroalkylene. In certain embodiments, $L^3$ is substituted or unsubstituted, $C_{100-300}$ heteroalkylene. In certain embodiments, $L^3$ is substituted or unsubstituted, $C_{300-1000}$ heteroalkylene.

In certain embodiments, optionally wherein one, two, three, four, or five backbone carbon atoms of the $C_{1-1000}$ alkylene, $C_{2-1000}$ alkenylene, $C_{2-1000}$ alkynylene, $C_{1-1000}$ heteroalkylene, $C_{2-1000}$ heteroalkenylene, or $C_{2-1000}$ heteroalkynylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, $L^3$ is substituted or unsubstituted, $C_{1-30}$ alkylene, optionally wherein one, two, or three backbone carbon atoms of the $C_{1-30}$ alkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, $L^3$ is substituted or unsubstituted, $C_{30-100}$ alkylene, optionally wherein one, two, or three backbone carbon atoms of the $C_{30-100}$ alkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, $L^3$ is substituted or unsubstituted, $C_{100-300}$ alkylene, optionally wherein one, two, or three backbone carbon atoms of the $C_{100-300}$ alkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, $L^3$ is substituted or unsubstituted, $C_{300-1000}$ alkylene, optionally wherein one, two, or three backbone carbon atoms of the $C_{300-1000}$ alkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, $L^3$ is substituted or unsubstituted, $C_{1-30}$ heteroalkylene, optionally wherein one, two, or three backbone carbon atoms of the $C_{1-30}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, $L^3$ is substituted or unsubstituted, $C_{30-100}$ heteroalkylene, optionally wherein one, two, or three backbone carbon atoms of the $C_{30-100}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, $L^3$ is substituted or unsubstituted, $C_{100-300}$ heteroalkylene, optionally wherein one, two, or three backbone carbon atoms of the $C_{100-300}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, $L^3$ is substituted or unsubstituted, $C_{300-1000}$ heteroalkylene, optionally wherein one, two, or three backbone carbon atoms of the $C_{300-1000}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, $L^3$ is substituted or unsubstituted, $C_{1-1000}$ alkylene or substituted or unsubstituted, $C_{1-1000}$ heteroalkylene, optionally wherein one, two, or three backbone carbon atoms of the $C_{1-1000}$ alkylene or $C_{1-1000}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, $L^3$ is substituted or unsubstituted, $C_{3-400}$ alkylene or substituted or unsubstituted, $C_{2-400}$ heteroalkylene, optionally wherein one, two, or three backbone carbon atoms of the $C_{3-400}$ alkylene or $C_{2-400}$ heteroalkylene are independently replaced with substituted or unsubstituted, monocyclic, 3- to 10-membered carbocyclylene, substituted or unsubstituted, monocyclic, 3- to 10-membered heterocyclylene, substituted or unsubstituted phenyl, or substituted or unsubstituted, monocyclic, 5- to 6-membered heteroarylene, as valency permits.

In certain embodiments, the optional substituents included in $L^3$ are independently halogen (e.g., F), unsubstituted $C_{1-6}$ alkyl, $C_{1-6}$ alkyl substituted with one or more halogen (e.g., F), —O-(unsubstituted $C_{1-6}$ alkyl), —O—($C_{1-6}$ alkyl substituted with one or more halogen (e.g., F)), or oxo.

In certain embodiments, the carbocyclylene or heterocyclylene included in $L^3$ is monocyclic and 3- to 10-membered. In certain embodiments, the arylene included in $L^3$ is phenylene. In certain embodiments, the heteroarylene included in $L^3$ is monocyclic and 5- to 6-membered.

In certain embodiments, $L^3$ is unsubstituted $C_{1-10}$ alkylene, unsubstituted para-phenylene,

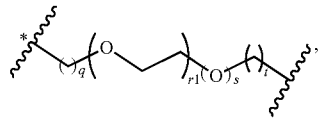

-continued

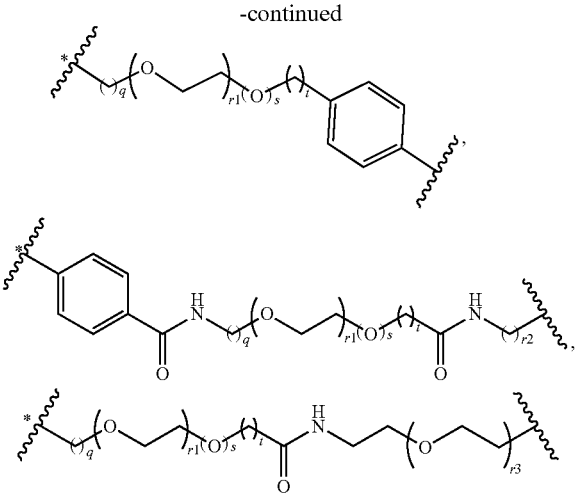

wherein:
each instance of q is independently an integer from 1 to 10, inclusive;
each instance of r1 is independently an integer from 2 to 40, inclusive;
each instance of s is independently 0 or 1;
each instance of t is independently an integer from 0 to 10, inclusive;
each instance of r2 is independently an integer from 0 to 10, inclusive;
each instance of r3 is independently an integer from 0 to 40, inclusive;
each instance of r4 is independently 0 or 1;
each instance of r5 is independently an integer from 0 to 10, inclusive; and
the attachment point marked with "*" is attached to $L^2$.

In certain embodiments, Formula (II) is:

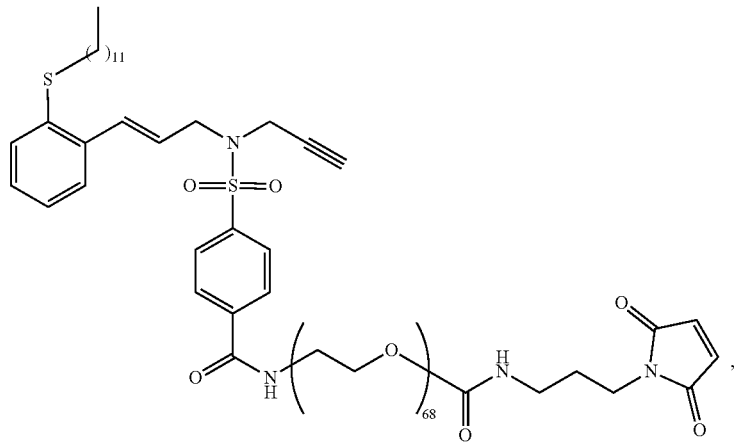

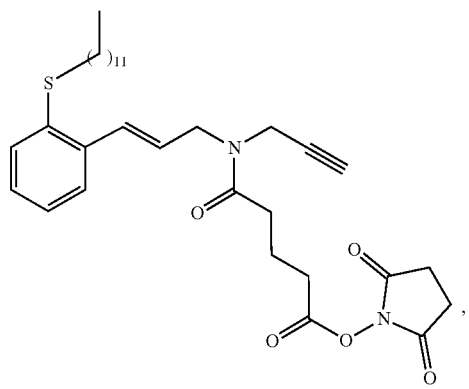

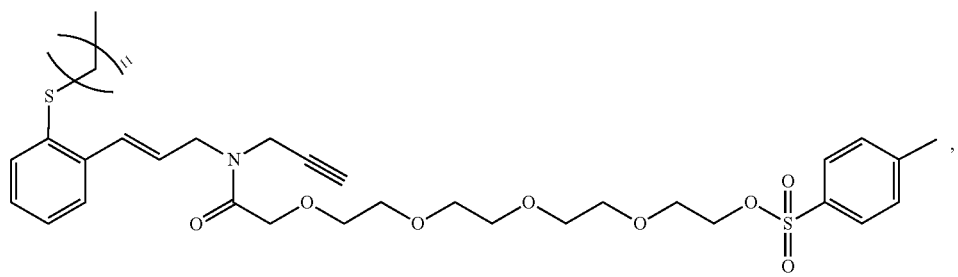

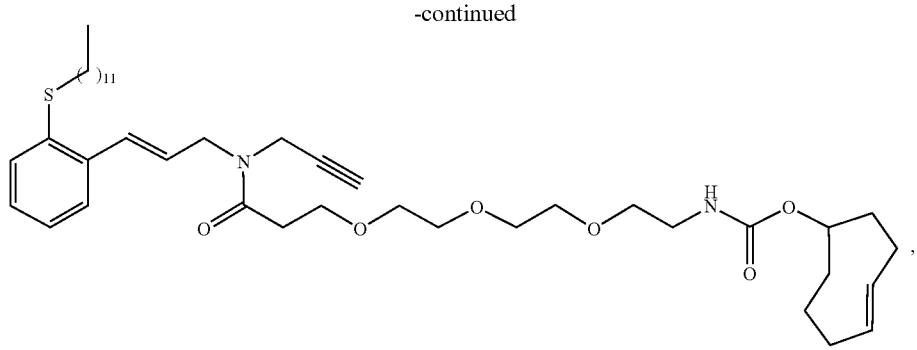
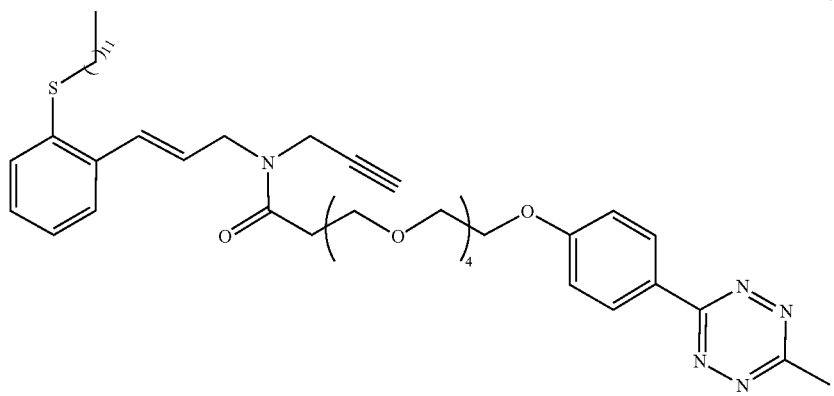
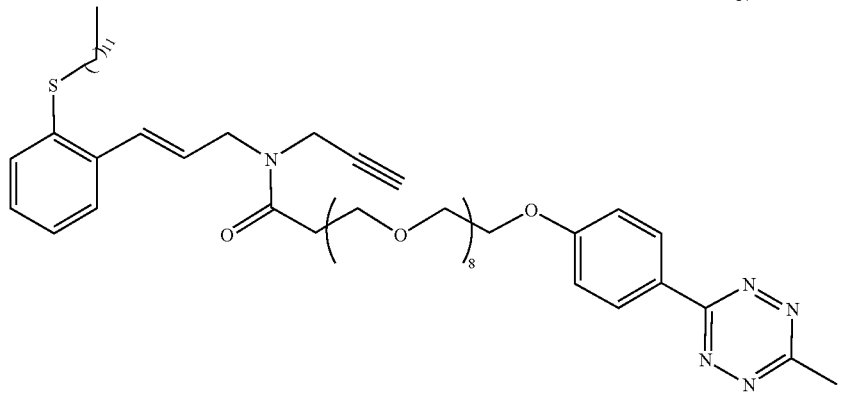
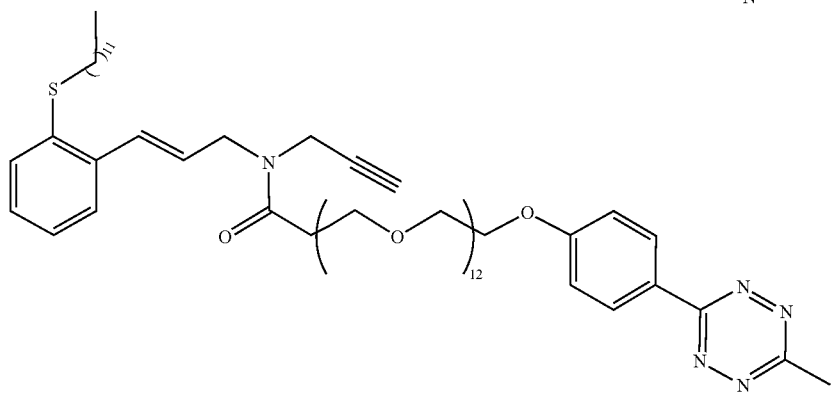
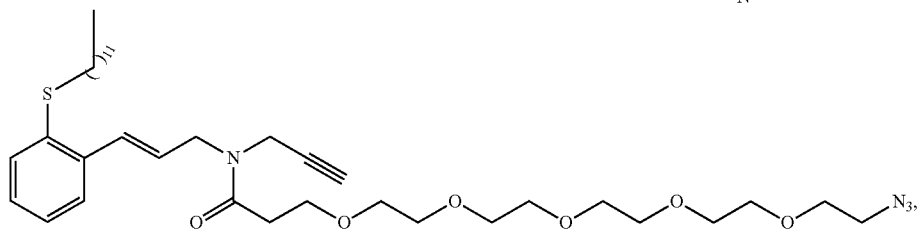

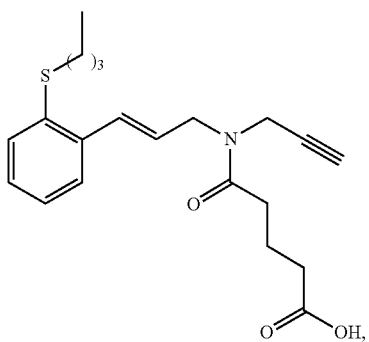
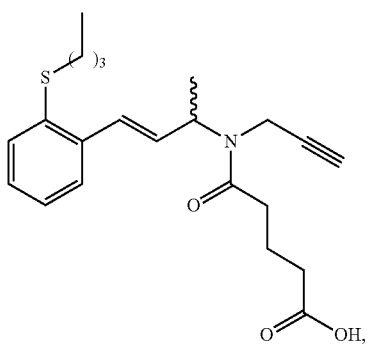
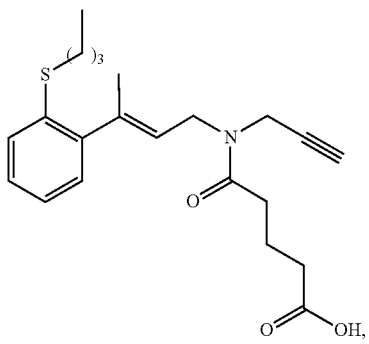
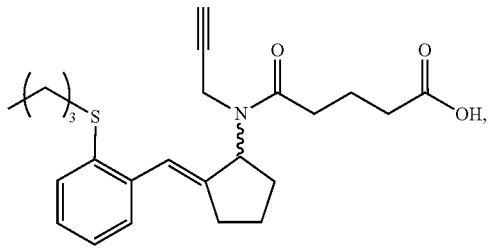
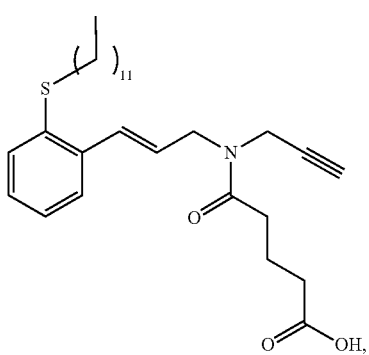

-continued
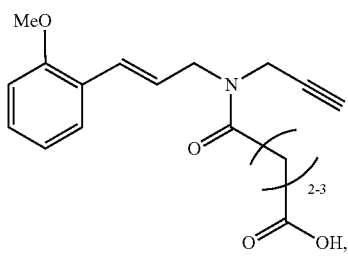
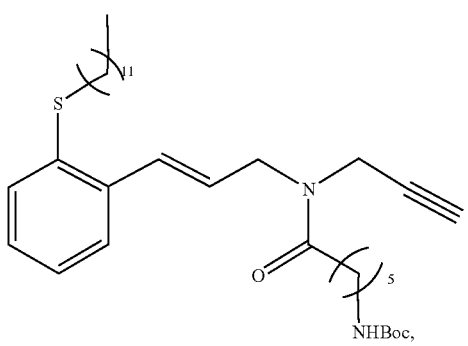
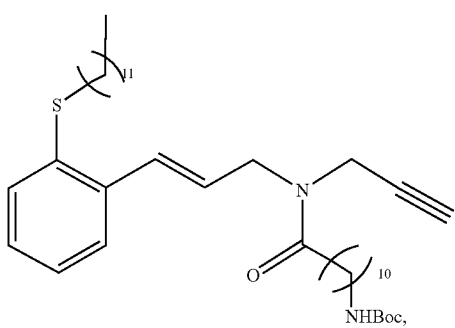
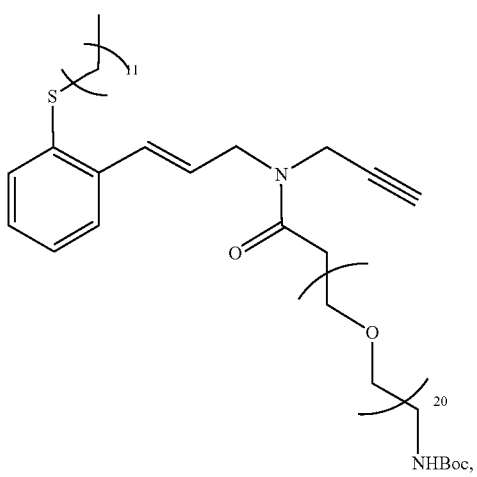
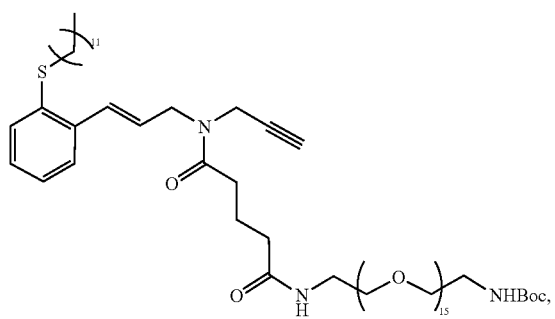

-continued

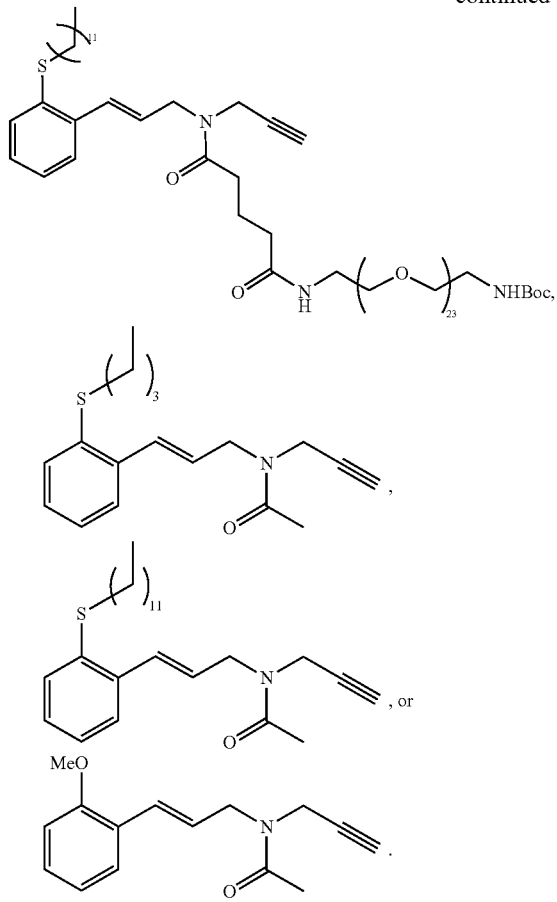

In another aspect, the present disclosure provides an end-functionalized polymer of Formula (III):

(III)

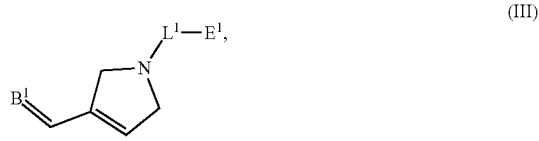

or a tautomer, isotopically labeled polymer, or salt thereof, wherein:

B$^1$ is a polymer, wherein the polymer comprises one or more pharmaceutical agents;

L$^1$ is substituted or unsubstituted, C$_{1-1000}$ alkylene, substituted or unsubstituted, C$_{2-1000}$ alkenylene, substituted or unsubstituted, C$_{2-1000}$ alkynylene, substituted or unsubstituted, C$_{1-1000}$ heteroalkylene, substituted or unsubstituted, C$_{2-1000}$ heteroalkenylene, or substituted or unsubstituted, C$_{2-1000}$ heteroalkynylene;

optionally wherein one or more backbone carbon atoms of the C$_{1-1000}$ alkylene, C$_2$-1000 alkenylene, C$_{2-1000}$ alkynylene, C$_{1-1000}$ heteroalkylene, C$_{2-1000}$ heteroalkenylene, or C$_2$-1000 heteroalkynylene are independently replaced with substituted or unsubstituted carbocyclylene, substituted or unsubstituted heterocyclylene, substituted or unsubstituted arylene, or substituted or unsubstituted heteroarylene, as valency permits;

E$^1$ is a thiophile, a first click-chemistry handle, a nucleophile, an electrophile, or a leaving group, H, halogen, substituted or unsubstituted, C$_{1-6}$ alkyl, substituted or unsubstituted, C$_{2-6}$ alkenyl, substituted or unsubstituted, C$_{2-6}$ alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=O)R$^a$, —C(=O)OR$^a$, —C(=O)N(R$^a$)$_2$, —C(=NR$^a$)R$^a$, —C(=NR$^a$)OR$^a$, —C(=NR$^a$)N(R$^a$)$_2$, —NO$_2$, —N$_3$, —NR$^a$C(=O)R$^a$, —NR$^a$C(=O)OR$^a$, —NR$^a$C(=O)N(R$^a$)$_2$, —NR$^a$C(=NR$^a$)R$^a$, —NR$^a$C(=NR$^a$)OR$^a$, —NR$^a$C(=NR$^a$)N(R$^a$)$_2$, —OC(=O)R$^a$, —OC(=O)OR$^a$, —OC(=O)N(R$^a$)$_2$, —OC(=NR$^a$)R$^a$, —OC(=NR$^a$)OR$^a$, —OC(=NR$^a$)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OS(=O)R$^a$, —OS(=O)OR$^a$, —OS(=O)N(R$^a$)$_2$, —S(=O)R$^a$, —S(=O)OR$^a$, —S(=O)N(R$^a$)$_2$, —OS(=O)$_2$R$^a$, —OS(=O)$_2$OR$^a$, —OS(=O)$_2$N(R$^a$)$_2$, —S(=O)$_2$R$^a$, —S(=O)$_2$OR$^a$, —S(=O)$_2$N(R$^a$)$_2$, or —P(=O)(R$^a$)$_2$; and each instance of R$^a$ is independently H, substituted or unsubstituted, C$_{1-6}$ alkyl, substituted or unsubstituted, C$_{2-6}$ alkenyl, substituted or unsubstituted, C$_{2-6}$ alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ attached to a nitrogen atom are joined with the nitrogen atom to form substituted or unsubstituted heterocyclyl or substituted or unsubstituted heteroaryl.

In certain embodiments, $B^1$ is a brush polymer or star polymer. In certain embodiments, $B^1$ is a brush polymer. In certain embodiments, $B^1$ is a condensation polymer. In certain embodiments, $B^1$ is a polyamide, polyester, polyacetal, polycarbonate, polyurethane, polyepoxide, or polysiloxane. In certain embodiments, $B^1$ is an addition polymer. In certain embodiments, $B^1$ is a polyethylene, polypropylene, polystyrene, polyvinyl chloride, polytetrafluoroethylene, polyvinylidene dichloride, polyacrylonitrile, polyvinyl acetate, polyvinyl alcohol, polymethyl methacrylate, polyisoprene, polybutadiene, or polychloroprene. In certain embodiments, the number average molecular weight of $B^1$ as determined by gel permeation chromatography is between 1,000 and 3,000, between 3,000 and 10,000, between 10,000 and 30,000, between 30,000 and 100,000, between 100,000 and 300,000, or between 300,000 and 1,000,000, g/mol, inclusive. In certain embodiments, the number average degree of polymerization of $B^1$ as determined by gel permeation chromatography is between 2 and 4, between 4 and 6, or between 7 and 9, inclusive. In certain embodiments, the number average degree of polymerization of $B^1$ as determined by gel permeation chromatography is between 10 and 20, between 20 and 40, between 40 and 60, between 60 and 80, between 80 and 100, between 100 and 300, or between 300 and 1,000, inclusive. In certain embodiments, the dispersity of $B^1$ is between 1.0 and 1.2, between 1.2 and 1.5, between 1.5 and 2.0, between 2.0 and 2.5, or between 2.5 and 3.0, inclusive. In certain embodiments, the crosslinking degree of $B^1$ is between 0% and 1%, inclusive. In certain embodiments, the crosslinking degree of $B^1$ is between 1% and 10%, between 10% and 20%, between 20% and 30%, between 30% and 40%, between 40% and 50%, or between 50% and 60%, inclusive.

In certain embodiments, $B^1$ is prepared by a method comprising polymerizing one or more types of monomers in the presence of a metathesis catalyst. In certain embodiments, $B^1$ is prepared by a method comprising polymerizing one or more types of monomers through ring-opening metathesis polymerization. In certain embodiments, $B^1$ is prepared by a method comprising polymerizing one or more types of monomers through radical polymerization, cationic polymerization, or anionic polymerization. In certain embodiments, $B^1$ is prepared by a method comprising polymerizing one or more types of monomers of Formula (A), or a tautomer, isotopically labeled compound, salt, solvate, polymorph, or co-crystal thereof, in the presence of a metathesis catalyst. In certain embodiments, at least one type of the monomers is a macromonomer.

In certain embodiments, the end-functionalized polymer, or a tautomer, isotopically labeled polymer, or salt thereof, is prepared by a method comprising:

(a) metathesis polymerizing one or more types of monomers in the presence of a metathesis catalyst to form a living polymer of Formula (B):

(B)

wherein each instance of the monomers comprises one or more non-aromatic alkenyl and/or one or more alkynyl; and (b) reacting the living polymer with an enyne, or a tautomer, isotopically labeled compound, salt, solvate, polymorph, or co-crystal thereof.

In another aspect, the present disclosure provides a method of preparing an end-functionalized polymer of Formula (III), or a tautomer, isotopically labeled polymer, or salt thereof, the method comprising reacting a living polymer of Formula (B):

with the enyne, or a tautomer, isotopically labeled compound, salt, solvate, polymorph, or co-crystal thereof.

In certain embodiments, the method further comprises metathesis polymerizing one or more types of monomers in the presence of a metathesis catalyst to form the living polymer, wherein each instance of the monomers comprises one or more non-aromatic alkenyl and/or one or more alkynyl.

In certain embodiments, the step of metathesis polymerizing comprises ring-opening metathesis polymerization (ROMP) (see, e.g., Liu et al. *J. Am. Chem. Soc.* 2012, 134, 16337; Liu, J.; Gao, A. X.; Johnson, J. A. *J Vis Exp* 2013, e50874). In certain embodiments, the metathesis catalyst is a ROMP catalyst. ROMP catalysts useful in the synthetic methods described herein include catalysts as depicted below, and as described in Grubbs et al., *Acc. Chem. Res.* 1995, 28, 446-452; U.S. Pat. No. 5,811,515; Schrock et al., *Organometallics* (1982) 1 1645; Gallivan et al., *Tetrahedron Letters* (2005) 46:2577-2580; Furstner et al., *J. Am. Chem. Soc.* (1999) 121:9453; and *Chem. Eur. J.* (2001) 7:5299; the entire contents of each of which are incorporated herein by reference. In certain embodiments, the metathesis catalyst is a transition metal metathesis catalyst. In certain embodiments, the metathesis catalyst is a tungsten (W), molybdenum (Mo), or ruthenium (Ru) catalyst. In certain embodiments, the metathesis catalyst is a Grubbs catalyst. In certain embodiments, the metathesis catalyst is of the formula:

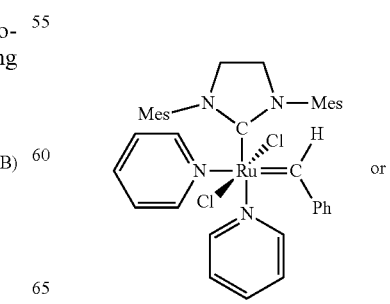 or

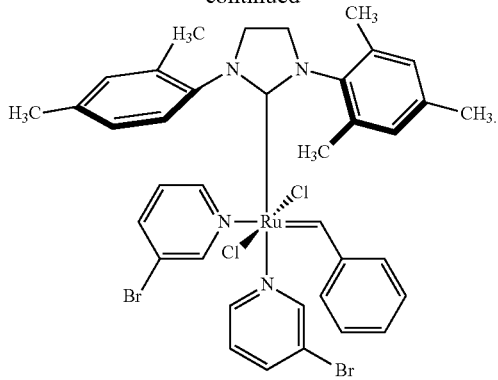

In certain embodiments, the Grubbs catalyst is:

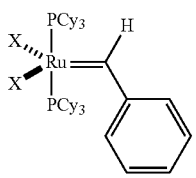

X = Cl; Br; I
Cy = cyclohexyl benzylidenebis-(tricyclohexylphosphine)-dichlororuthenium (X=Cl);
benzylidenebis-(tricyclohexylphosphine)-dibromoruthenium (X=Br);
benzylidenebis-(tricyclohexylphosphine)-diiodoruthenium (X=I);

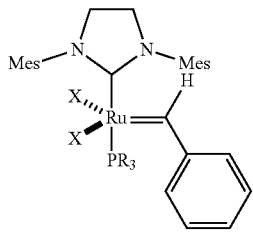

X = Cl; Br; I
R = cyclohexyl (Cy); phenyl (Ph); benzyl (Bn)

1,3-(bis(mesityl)-2-imidazolidinylidene)dichloro-(phenylmethylene) (tricyclohexyl-phosphine)ruthenium (X=Cl; R=cyclohexyl);
1,3-(bis(mesityl)-2-imidazolidinylidene)dibromo-(phenylmethylene) (tricyclohexyl-phosphine)ruthenium (X=Br; R=cyclohexyl);
1,3-(bis(mesityl)-2-imidazolidinylidene)diiodo-(phenylmethylene) (tricyclohexyl-phosphine)ruthenium (X=I; R=cyclohexyl);
1,3-(bis(mesityl)-2-imidazolidinylidene)dichloro-(phenylmethylene) (triphenylphosphine)ruthenium (X=Cl; R=phenyl);
1,3-(bis(mesityl)-2-imidazolidinylidene)dichloro-(phenylmethylene) (tribenzylphosphine)ruthenium (X=Cl; R=benzyl);

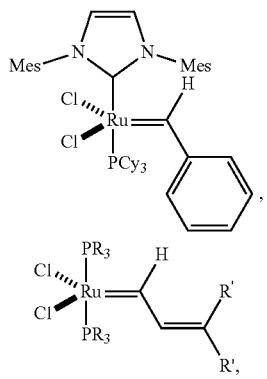

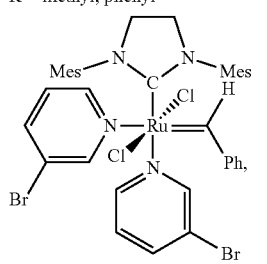

R = cyclohexyl (Cy); phenyl (Ph)
R' = methyl; phenyl

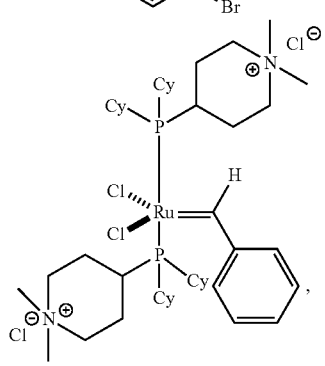

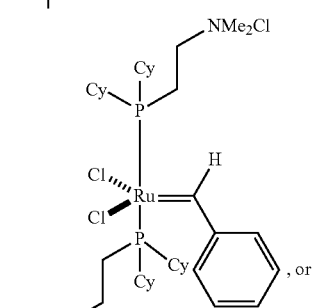

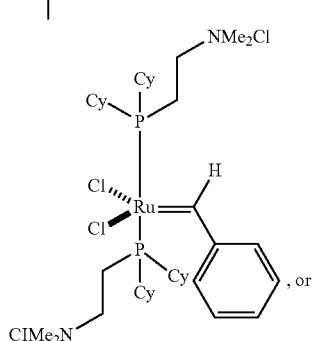

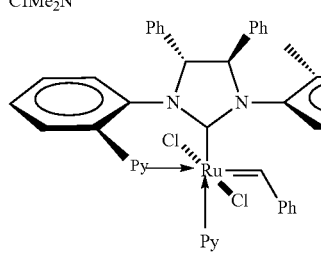

Py = pyridine
Ph = phenyl

In certain embodiments, the metathesis catalyst is a Grubbs-Hoveyda catalyst. In certain embodiments, the Grubbs-Hoveyda catalyst is of the formula:

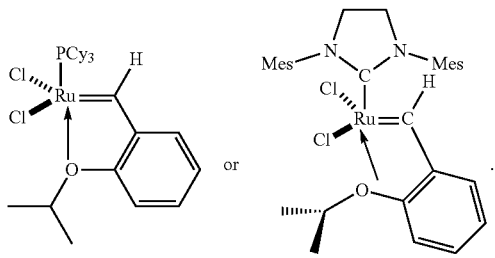

In certain embodiments, the metathesis catalyst is of the formula:

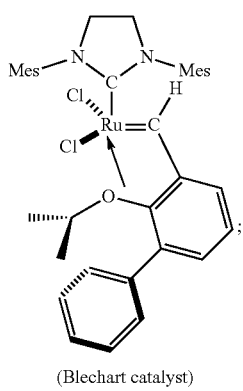

(Blechart catalyst)

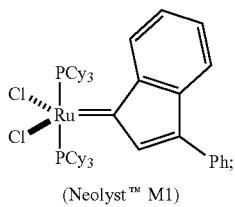

(Neolyst™ M1)

Or

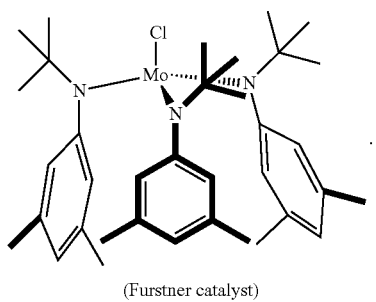

(Furstner catalyst)

In certain embodiments, the metathesis catalyst is of the formula:

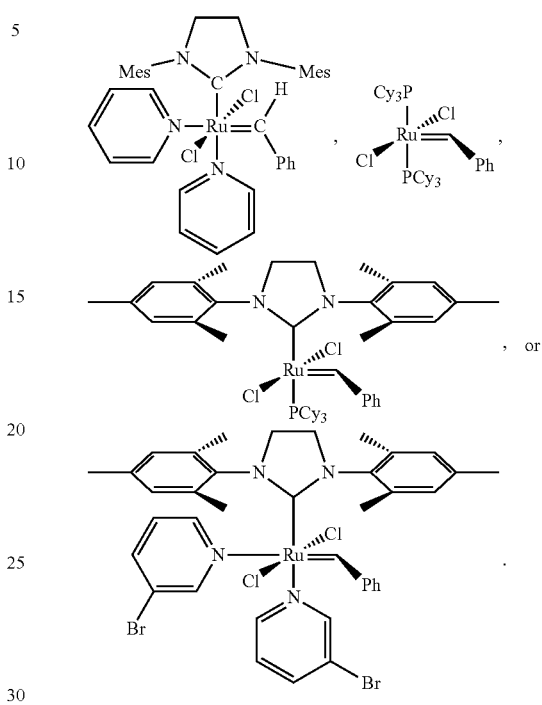

, or

In certain embodiments, the molar ratio of the metathesis catalyst to the monomers is between 1:10 and 1:30, between 1:30 and 1:100, between 1:100 and 1:300, between 1:300 and 1:1,000, inclusive. In certain embodiments, the molar ratio of the metathesis catalyst to the monomers is between 1:20 and 1:200, inclusive.

The step of metathesis polymerizing can be conducted in one or more aprotic solvents. The term "aprotic solvent" means a non-nucleophilic solvent having a boiling point range above ambient temperature, preferably from about 25° C. to about 190° C. at atmospheric pressure. In certain embodiments, the aprotic solvent has a boiling point from about 80° C. to about 160° C. at atmospheric pressure. In certain embodiments, the aprotic solvent has a boiling point from about 80° C. to about 150° C. at atmospheric pressure. Examples of such solvents are methylene chloride, acetonitrile, toluene, DMF, diglyme, THF, and DMSO.

Step (b) may be performed according to the methods described in Fu et al., *J. Am. Chem. Soc.*, 2018, 140, 12181-12188; and/or Zhang et al., *Macromolecules*, 2018, 51, 6497-6503, each of which is incorporated by reference in its entirety.

In certain embodiments, at least one instance of the monomers is of Formula (A):

(A)

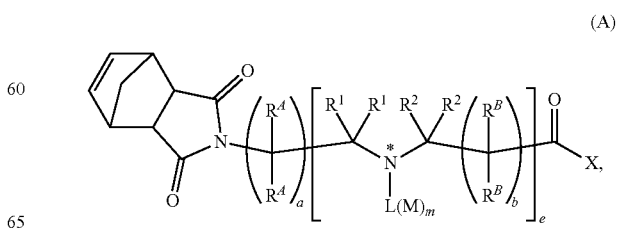

or a tautomer, isotopically labeled compound, salt, solvate, polymorph, or co-crystal thereof, wherein:

each instance of $R^A$ is independently H, halogen, or substituted or unsubstituted, $C_{1-6}$ alkyl;

each instance of a is independently an integer from 0 to 20, inclusive;

each instance of $R^1$ is independently H, halogen, or substituted or unsubstituted, $C_{1-6}$ alkyl, or two $R^1$ attached to the same carbon atom are taken together to form oxo;

each instance of $R^2$ is independently H, halogen, or substituted or unsubstituted, $C_{1-6}$ alkyl, or two $R^2$ attached to the same carbon atom are taken together to form oxo;

each instance of L is substituted or unsubstituted, $C_{1-1000}$ alkylene, substituted or unsubstituted, $C_{2-1000}$ alkenylene, substituted or unsubstituted, $C_{2-1000}$ alkynylene, substituted or unsubstituted, $C_{1-1000}$ heteroalkylene, substituted or unsubstituted, $C_{2-1000}$ heteroalkenylene, or substituted or unsubstituted, $C_{2-1000}$ heteroalkynylene;

optionally wherein one or more backbone carbon atoms of the $C_{1-1000}$ alkylene, $C_2$-1000 alkenylene, $C_{2-1000}$ alkynylene, $C_{1-1000}$ heteroalkylene, $C_{2-1000}$ heteroalkenylene, or $C_{2-1000}$ heteroalkynylene are independently replaced with substituted or unsubstituted carbocyclylene, substituted or unsubstituted heterocyclylene, substituted or unsubstituted arylene, or substituted or unsubstituted heteroarylene, as valency permits;

each instance of M is independently a pharmaceutical agent;

each instance of m is independently an integer from 1 to 10, inclusive;

each instance of $R^B$ is independently H, halogen, or substituted or unsubstituted, $C_{1-6}$ alkyl;

each instance of b is independently an integer from 0 to 20, inclusive;

each instance of e is independently an integer from 1 to 10, inclusive;

each instance of X is $-OR^c$ or $-N(R^D)_2$;

each instance of $R^c$ is independently H, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, an oxygen protecting group, or a leaving group; and each instance of $R^D$ is independently H, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, or a nitrogen protecting group, or two $R^D$ attached to the same nitrogen atom are taken together with the nitrogen atom to form substituted or unsubstituted heterocyclyl or substituted or unsubstituted heteroaryl.

In certain embodiments, $B^1$ is of Formula (B-1):

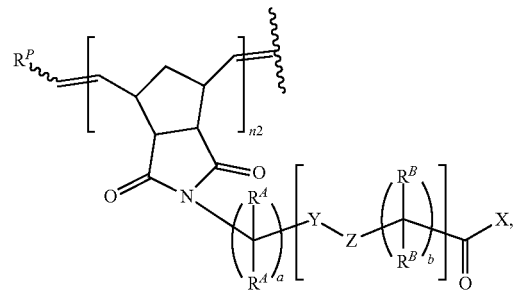

(B-1)

or a salt thereof, wherein:

each instance of $R^A$ is independently hydrogen, halogen, or substituted or unsubstituted, $C_{1-6}$ alkyl;

a is an integer from 1 to 20, inclusive;

each instance of —Y—Z— is independently

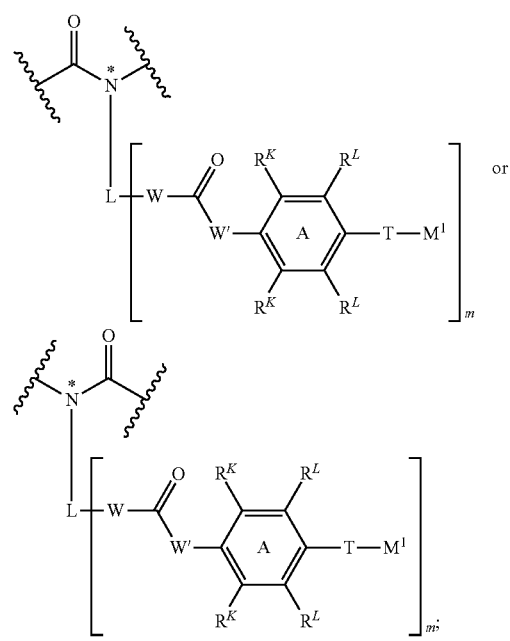

each instance of $M^1$ is independently hydrogen or a pharmaceutical agent;

each instance of m is independently an integer from 1 to 10, inclusive;

each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or $C_{2-200}$ heteroalkynylene, wherein:

optionally one or more carbons in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

provided that when each instance of $M^1$ is hydrogen, at least one instance of -L($M^1$)$_m$ comprises a click-chemistry handle;

each instance of W is independently a single bond, —O—, —S—, or —NR$^E$—;

each instance of $R^E$ is independently hydrogen, substituted or unsubstituted $C_{1-6}$ alkyl, or a nitrogen protecting group;

each instance of W' is independently —O—, —S—, or —NR$^J$—;

each instance of $R^J$ is independently hydrogen, substituted or unsubstituted $C_{1-6}$ alkyl, or a nitrogen protecting group;

each instance of $R^K$ and $R^L$ is independently hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of $R^a$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, an oxygen protecting group when attached to an oxygen atom, a sulfur protecting group when attached to a sulfur atom, or a nitrogen protecting group when attached to a nitrogen atom; or two instances of R$^a$ attached to the same nitrogen atom are joined to form substituted or unsubstituted, 3- to 7-membered, monocyclic heterocyclyl, or substituted or unsubstituted, 5- or 6-membered, monocyclic heteroaryl;

each instance of T is independently a single bond, substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{2-20}$ heteroalkylene, substituted or unsubstituted, $C_{2-20}$ heteroalkenylene, or $C_{2-20}$ heteroalkynylene, wherein:

optionally one or more carbons in each instance of the substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{2-20}$ heteroalkylene, substituted or unsubstituted, $C_{2-20}$ heteroalkenylene, and $C_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more heteroatoms in each instance of the substituted or unsubstituted, $C_{2-20}$ heteroalkylene, substituted or unsubstituted, $C_{2-20}$ heteroalkenylene, and substituted or unsubstituted, $C_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene;

each instance of $R^B$ is independently hydrogen, halogen, or substituted or unsubstituted, $C_{1-6}$ alkyl;

each instance of b is independently an integer from 1 to 20, inclusive;

e is an integer from 1 to 10, inclusive; and n2 is an integer from 5 to 300, inclusive;

X is OR$^c$ or N(R$^D$)$_2$, wherein:

$R^C$ is hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, an oxygen protecting group, or a leaving group;

each instance of $R^D$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, or a nitrogen protecting group; and $R^F$ is hydrogen, substituted or unsubstituted $C_{1-6}$ alkyl, or substituted or unsubstituted phenyl.

In certain embodiments, each instance of $R^A$ is independently hydrogen, halogen, or substituted or unsubstituted, $C_{1-6}$ alkyl;

a is an integer from 1 to 20, inclusive;

each instance of —Y—Z— is independently

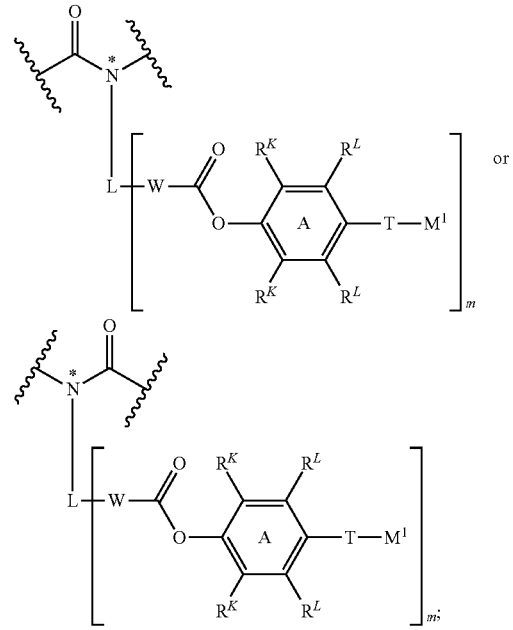

each instance of $M^1$ is independently hydrogen or a pharmaceutical agent;

each instance of m is independently an integer from 1 to 10, inclusive;

each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or $C_{2-200}$ heteroalkynylene, wherein:

optionally one or more carbons in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

provided that when each instance of $M^1$ is hydrogen, at least one instance of -L($M^1$)$_m$ comprises a click-chemistry handle;

each instance of W is independently a single bond or —O—;

each instance of $R^K$ and $R^L$ is independently hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, —OR$^a$, —N(R$^a$)$_2$, —SR$^a$, —CN, —SCN, —C(=NR$^a$)R$^a$, —C(=NR$^a$)OR$^a$, —C(=NR$^a$)N(R$^a$)$_2$, —C(=O)R$^a$, —C(=O)OR$^a$, —C(=O)N(R$^a$)$_2$, —NO$_2$, —NR$^a$C(=O)R$^a$, —NR$^a$C(=O)OR$^a$, —NR$^a$C(=O)N(R$^a$)$_2$, —OC(=O)R$^a$, —OC(=O)OR$^a$, or —OC(=O)N(R$^a$)$_2$;

each instance of R$^a$ is independently hydrogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, 3- to 7-membered, monocyclic carbocyclyl, substituted or unsubstituted, 3- to 7-membered, monocyclic heterocyclyl, substituted or unsubstituted phenyl, substituted or unsubstituted, 5- or 6-membered, monocyclic heteroaryl, an oxygen protecting group when attached to an oxygen atom, a sulfur protecting group when attached to a sulfur atom, or a nitrogen protecting group when attached to a nitrogen atom; or two instances of R$^a$ attached to the same nitrogen atom are joined to form substituted or unsubstituted, 3- to 7-membered, monocyclic heterocyclyl, or substituted or unsubstituted, 5- or 6-membered, monocyclic heteroaryl;

each instance of T is independently a single bond, substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{2-20}$ heteroalkylene, substituted or unsubstituted, $C_{2-20}$ heteroalkenylene, or $C_{2-20}$ heteroalkynylene, wherein:

optionally one or more carbons in each instance of the substituted or unsubstituted, $C_{1-20}$ alkylene, substituted or unsubstituted, $C_{2-20}$ alkenylene, substituted or unsubstituted, $C_{2-20}$ alkynylene, substituted or unsubstituted, $C_{2-20}$ heteroalkylene, substituted or unsubstituted, $C_{2-20}$ heteroalkenylene, and $C_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more heteroatoms in each instance of the substituted or unsubstituted, $C_{2-20}$ heteroalkylene, substituted or unsubstituted, $C_{2-20}$ heteroalkenylene, and substituted or unsubstituted, $C_{2-20}$ heteroalkynylene are independently replaced with substituted or unsubstituted carbocyclylene, substituted or unsubstituted heterocyclylene, substituted or unsubstituted arylene, or substituted or unsubstituted heteroarylene;

each instance of $R^B$ is independently hydrogen, halogen, or substituted or unsubstituted, $C_{1-6}$ alkyl;

each instance of b is independently an integer from 1 to 20, inclusive;

e is an integer from 1 to 10, inclusive; and

X is OR$^C$ or N(R$^D$)$_2$, wherein:

R$^C$ is hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_2$-1000 heteroalkynyl, an oxygen protecting group, or a leaving group; and each instance of R$^D$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, or a nitrogen protecting group.

In certain embodiments, $B^1$ is of Formula (B-1-a):

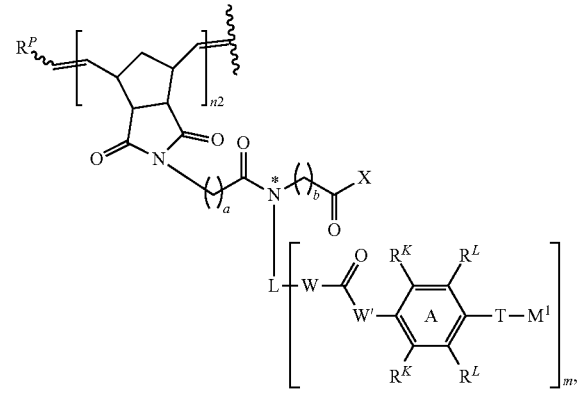

(B-1-a)

or a salt thereof.

In certain embodiments, $B^1$ is of Formula (B-1-b):

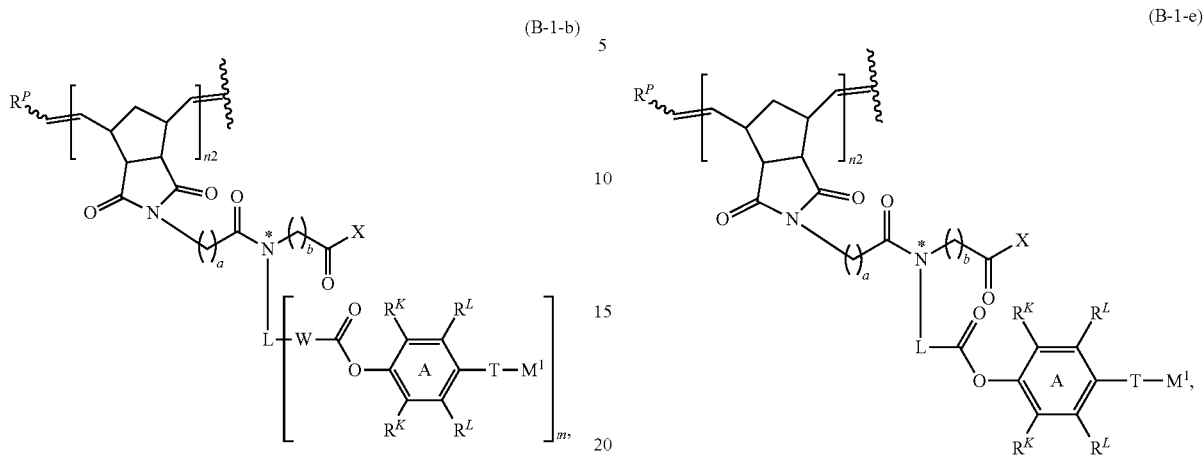

(B-1-b)

or a salt thereof.

In certain embodiments, $B^1$ is of Formula (B-1-c):

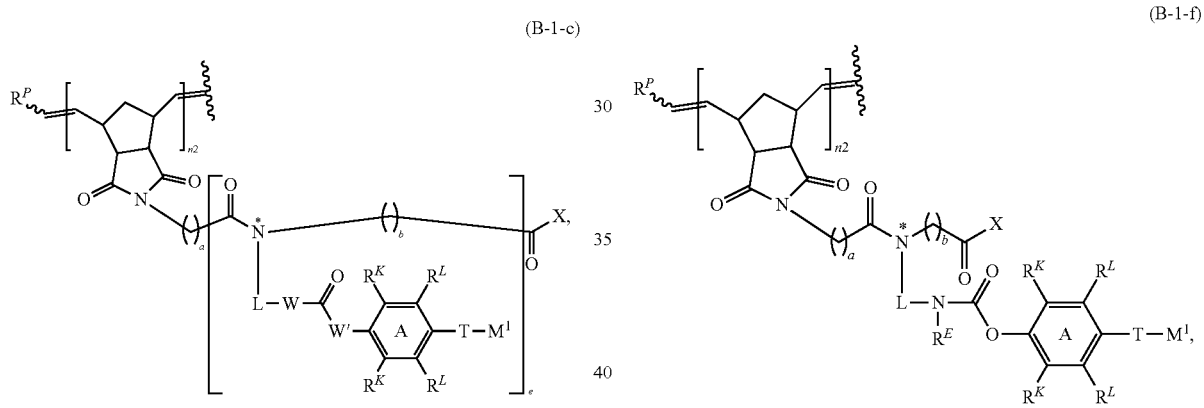

(B-1-c)

or a salt thereof.

In certain embodiments, $B^1$ is of Formula (B-1-d):

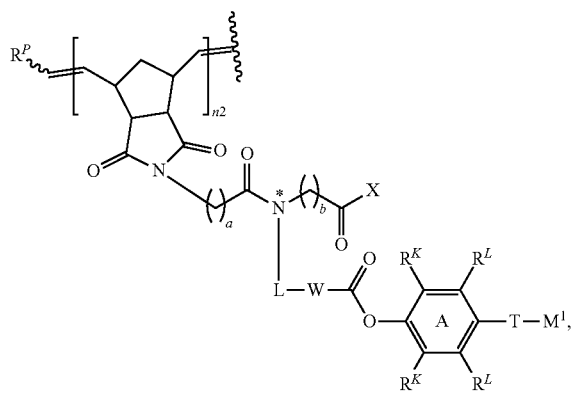

(B-1-d)

or a salt thereof.

In certain embodiments, $B^1$ is of Formula (B-1-e):

(B-1-e)

or a salt thereof.

In certain embodiments, $B^1$ is of Formula (B-1-f):

(B-1-f)

or a salt thereof.

In certain embodiments, each instance of $R^A$ is hydrogen.

In certain embodiments, a is an integer from 2 to 20, inclusive.

In certain embodiments, at least one instance of L is substituted or unsubstituted, $C_{2-200}$ alkynylene. In certain embodiments, at least one instance of L is substituted or unsubstituted, $C_{2-200}$ heteroalkynylene. In certain embodiments, at least one instance of L is substituted or unsubstituted, $C_{2-200}$ heteroalkylene, wherein one or more carbons and/or one or more heteroatoms, of the substituted or unsubstituted, $C_{2-200}$ heteroalkylene, are independently replaced with substituted or unsubstituted heteroarylene. In certain embodiments, at least one instance of L is substituted or unsubstituted, $C_{3-30}$ heteroalkylene, wherein one or two carbons and/or one or two heteroatoms, of the substituted or unsubstituted, $C_{3-30}$ heteroalkylene are independently replaced with substituted or unsubstituted phenylene or substituted or unsubstituted, monocyclic, 5- or 6-membered heteroarylene. In certain embodiments, at least one instance of L is substituted or unsubstituted, $C_{2-200}$ heteroalkylene, wherein one or more carbons and/or one or more heteroatoms, of the substituted or unsubstituted, $C_{2-200}$ heteroalkylene, are independently replaced with

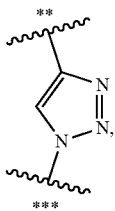

wherein the nitrogen atom labeled with "*" is closer to the attachment point labeled with "" than the attachment point labeled with "*".

In certain embodiments, one carbon or one heteroatom, of the substituted or unsubstituted, $C_{2-200}$ heteroalkylene, is replaced with

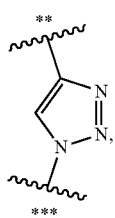

wherein the nitrogen atom labeled with "*" is closer to the attachment point labeled with "" than the attachment point labeled with "*".

In certain embodiments, at least one instance of L comprises

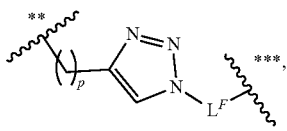

wherein:
each instance of p is independently an integer from 1 to 10, inclusive;
each instance of $L^F$ is independently substituted or unsubstituted, $C_{2-180}$ heteroalkylene; and
the nitrogen atom labeled with "*" is closer to the attachment point labeled with "" than the attachment point labeled with "*".

In certain embodiments, at least one instance of L is

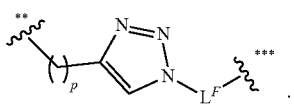

In certain embodiments, at least one instance of $L^F$ comprises —S—S—. In certain embodiments, at least one instance of $L^F$ comprises a peptide comprising between 1 and 20, inclusive, amino acid residues.

In certain embodiments, at least one instance of L comprises

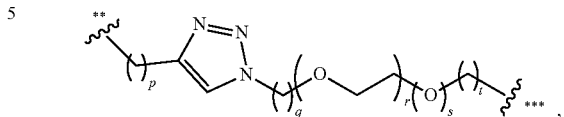

wherein:
each instance of p is independently an integer from 1 to 10, inclusive;
each instance of q is independently an integer from 1 to 10, inclusive;
each instance of r is independently an integer from 0 to 10, inclusive;
each instance of s is independently 0 or 1;
each instance of t is independently an integer from 0 to 10, inclusive; and
the nitrogen atom labeled with "*" is closer to the attachment point labeled with "" than the attachment point labeled with "*".

In certain embodiments, at least one instance of L is

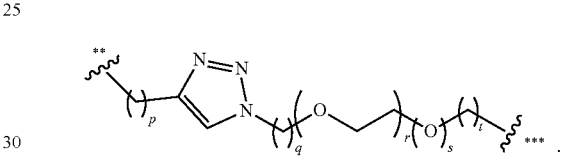

In certain embodiments, at least one instance of L is

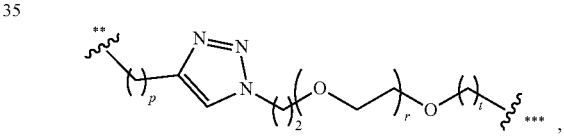

wherein r is 1, 2, or 3; and t is 1 or 2.

In certain embodiments, at least one instance of L comprises

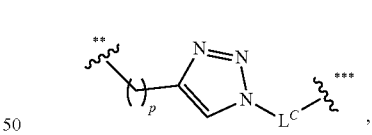

wherein:
each instance of p is independently an integer from 1 to 10, inclusive;
each instance of $L^C$ is independently substituted or unsubstituted, $C_{1-180}$ alkylene; and the nitrogen atom labeled with "*" is closer to the attachment point labeled with "" than the attachment point labeled with "*".

In certain embodiments, at least one instance of L is

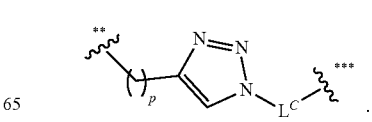

In certain embodiments, $R^P$ is hydrogen. In certain embodiments, $R^P$ is substituted or unsubstituted $C_{1-6}$ alkyl. In certain embodiments, $R^P$ is substituted or unsubstituted phenyl. In certain embodiments, $R^P$ is unsubstituted phenyl.

In certain embodiments, n2 is an integer from 5 to 100, inclusive. In certain embodiments, n2 is an integer from 5 to 60, inclusive. In certain embodiments, n2 is an integer from 5 to 40, inclusive. In certain embodiments, n2 is an integer from 5 to 20, inclusive. In certain embodiments, n2 is an integer from 5 to 10, inclusive. In certain embodiments, n2 is an integer from 10 to 60, inclusive. In certain embodiments, n2 is an integer from 10 to 40, inclusive. In certain embodiments, n2 is an integer from 10 to 20, inclusive. In certain embodiments, n2 is an integer from 20 to 60, inclusive. In certain embodiments, n2 is an integer from 20 to 40, inclusive.

In certain embodiments, $B^1$ is of Formula (B-2):

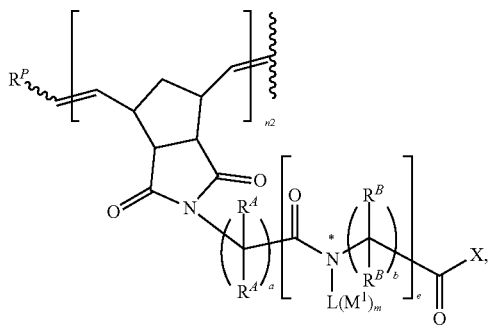

(B-2)

or a salt thereof, wherein:

each instance of $R^A$ is independently hydrogen, halogen, or substituted or unsubstituted, $C_{1-6}$ alkyl;

a is an integer from 1 to 20, inclusive;

each instance of $M^1$ is independently hydrogen or a pharmaceutical agent;

each instance of m is independently an integer from 1 to 10, inclusive;

each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or substituted or unsubstituted, $C_{2-200}$ heteroalkynylene, wherein:

optionally one or more carbons in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

provided that when each instance of $M^1$ is hydrogen, at least one instance of $-L(M^1)_m$ comprises a click-chemistry handle;

each instance of $R^B$ is independently hydrogen, halogen, or substituted or unsubstituted, $C_{1-6}$ alkyl;

each instance of b is independently an integer from 1 to 20, inclusive;

e is an integer from 1 to 10, inclusive;

n2 is an integer from 5 to 300, inclusive; and

X is $OR^C$ or $N(R^D)_2$, wherein:

$R^C$ is hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_2$-1000 heteroalkynyl, an oxygen protecting group, or a leaving group;

each instance of $R^D$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, or a nitrogen protecting group, or two $R^D$ are taken together to form a substituted or unsubstituted heterocyclyl or substituted or unsubstituted heteroaryl moiety; and $R^P$ is hydrogen, substituted or unsubstituted $C_{1-6}$ alkyl, or substituted or unsubstituted phenyl.

In certain embodiments, $R^P$ is hydrogen. In certain embodiments, $R^P$ is substituted or unsubstituted $C_{1-6}$ alkyl. In certain embodiments, $R^P$ is substituted or unsubstituted phenyl. In certain embodiments, $R^P$ is unsubstituted phenyl.

In certain embodiments, n2 is an integer from 5 to 100, inclusive. In certain embodiments, n2 is an integer from 5 to 60, inclusive. In certain embodiments, n2 is an integer from 5 to 40, inclusive. In certain embodiments, n2 is an integer from 5 to 20, inclusive. In certain embodiments, n2 is an integer from 5 to 10, inclusive. In certain embodiments, n2 is an integer from 10 to 60, inclusive. In certain embodiments, n2 is an integer from 10 to 40, inclusive. In certain embodiments, n2 is an integer from 10 to 20, inclusive. In certain embodiments, n2 is an integer from 20 to 60, inclusive. In certain embodiments, n2 is an integer from 20 to 40, inclusive.

In certain embodiments, $B^1$ is of Formula (B-3):

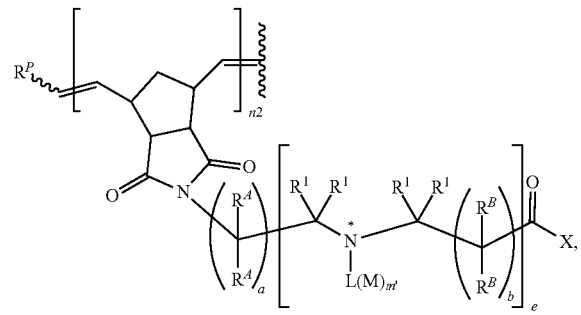

(B-3)

or a salt thereof, wherein:

each instance of $R^A$ is independently hydrogen, halogen, or substituted or unsubstituted, $C_{1-6}$ alkyl;

a is an integer from 1 to 20, inclusive;

each instance of M is independently a pharmaceutical agent;

each instance of m' is independently an integer from 2 to 10, inclusive;

each instance of L is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or substituted or unsubstituted, $C_{2-200}$ heteroalkynylene, wherein:

optionally one or more carbons in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene; and optionally one or more heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclylene, substituted or unsubstituted heterocyclylene, substituted or unsubstituted arylene, or substituted or unsubstituted heteroarylene;

each instance of $R^B$ is independently hydrogen, halogen, or substituted or unsubstituted, $C_{1-6}$ alkyl;

each instance of b is independently an integer from 1 to 20, inclusive;

e is an integer from 1 to 10, inclusive;

n2 is an integer from 5 to 300, inclusive; and

X is $OR^C$ or $N(R^D)_2$, wherein:

$R^C$ is hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_2$-1000 heteroalkynyl, an oxygen protecting group, or a leaving group; and each instance of $R^D$ is independently hydrogen, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, or a nitrogen protecting group, or two $R^D$ are taken together to form a substituted or unsubstituted heterocyclyl or substituted or unsubstituted heteroaryl moiety;

each instance of $R^1$ is independently hydrogen, halogen, or substituted or unsubstituted, $C_{1-6}$ alkyl, or each instance of

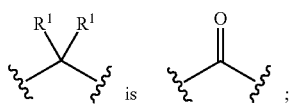

and $R^P$ is hydrogen, substituted or unsubstituted $C_{1-6}$ alkyl, or substituted or unsubstituted phenyl.

In certain embodiments, $R^P$ is hydrogen. In certain embodiments, $R^P$ is substituted or unsubstituted $C_{1-6}$ alkyl. In certain embodiments, $R^P$ is substituted or unsubstituted phenyl. In certain embodiments, $R^P$ is unsubstituted phenyl.

In certain embodiments, n2 is an integer from 5 to 100, inclusive. In certain embodiments, n2 is an integer from 5 to 60, inclusive. In certain embodiments, n2 is an integer from 5 to 40, inclusive. In certain embodiments, n2 is an integer from 5 to 20, inclusive. In certain embodiments, n2 is an integer from 5 to 10, inclusive. In certain embodiments, n2 is an integer from 10 to 60, inclusive. In certain embodiments, n2 is an integer from 10 to 40, inclusive. In certain embodiments, n2 is an integer from 10 to 20, inclusive. In certain embodiments, n2 is an integer from 20 to 60, inclusive. In certain embodiments, n2 is an integer from 20 to 40, inclusive.

In certain embodiments, $B^1$ is of Formula (B-4):

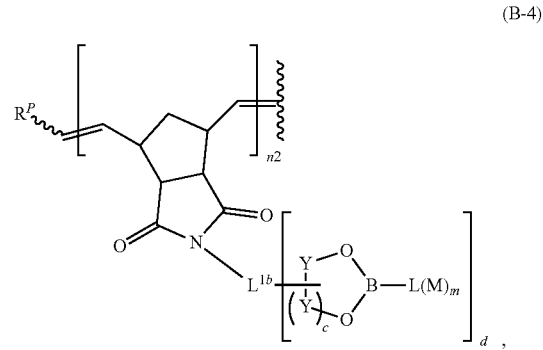

(B-4)

or a salt thereof, wherein:

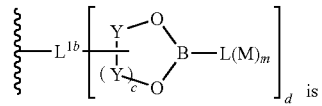
is

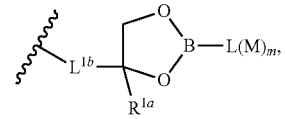

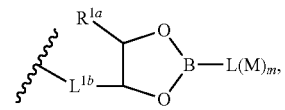

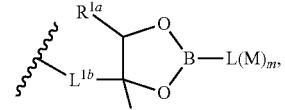

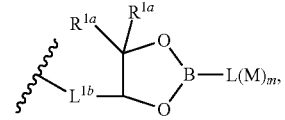

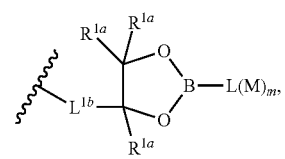

-continued

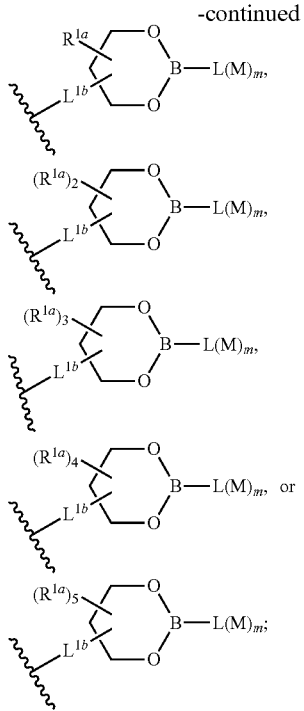

In certain embodiments, $L^{1b}$ is of the formula:

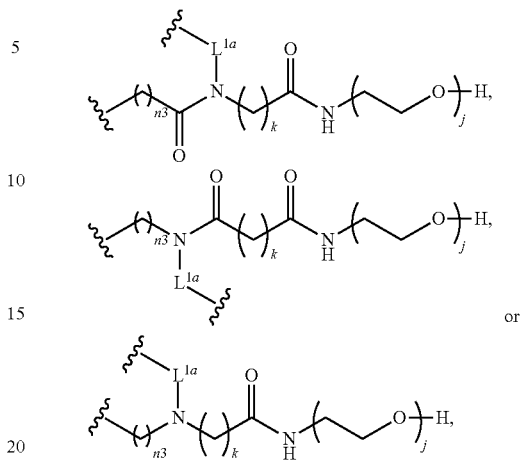

wherein:
n3 is an integer between 0 and 12 inclusive;
k is an integer between 1 and 12 inclusive;
j is an integer between 10 and 200 inclusive; and
$L^{1a}$ is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or $C_2$-200 heteroalkynylene, wherein:
optionally one or more backbone carbon atoms in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and $C_{2-200}$ heteroalkynylene are independently replaced with substituted or unsubstituted carbocyclene, substituted or unsubstituted heterocyclene, substituted or unsubstituted arylene, or substituted or unsubstituted heteroarylene;
optionally one or more backbone heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclene, substituted or unsubstituted heterocyclene, substituted or unsubstituted arylene, or substituted or unsubstituted heteroarylene.

$L^{1b}$ is a substituted or unsubstituted linker, wherein the backbone of $L^{1b}$ comprises two or more atoms;
each instance of $R^{1a}$ is independently halogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$, or two instances of $R^{1a}$ are joined to form substituted or unsubstituted carbocyclyl or substituted or unsubstituted heterocyclyl;
each instance of $R^a$ is independently hydrogen, halogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ on a nitrogen atom are joined with the nitrogen atom to form substituted or unsubstituted heterocyclyl or substituted or unsubstituted heteroaryl;
$R^P$ is hydrogen, substituted or unsubstituted $C_{1-6}$ alkyl, or substituted or unsubstituted phenyl;
each instance of L is independently a bond or a substituted or unsubstituted linker;
each instance of M is independently a pharmaceutical agent;
each instance of m is independently an integer between 1 and 10, inclusive;
n2 is an integer from 5 to 300, inclusive; and
d is an integer between 1 and 10, inclusive.

In certain embodiments, $R^P$ is hydrogen. In certain embodiments, $R^P$ is substituted or unsubstituted $C_{1-6}$ alkyl. In certain embodiments, $R^P$ is substituted or unsubstituted phenyl. In certain embodiments, $R^P$ is unsubstituted phenyl.

In certain embodiments, n2 is an integer from 5 to 100, inclusive. In certain embodiments, n2 is an integer from 5 to 60, inclusive. In certain embodiments, n2 is an integer from 5 to 40, inclusive. In certain embodiments, n2 is an integer from 5 to 20, inclusive. In certain embodiments, n2 is an integer from 5 to 10, inclusive. In certain embodiments, n2 is an integer from 10 to 60, inclusive. In certain embodiments, n2 is an integer from 10 to 40, inclusive. In certain embodiments, n2 is an integer from 10 to 20, inclusive. In certain embodiments, n2 is an integer from 20 to 60, inclusive. In certain embodiments, n2 is an integer from 20 to 40, inclusive.

In certain embodiments, $B^1$ is of Formula (B-4-a):

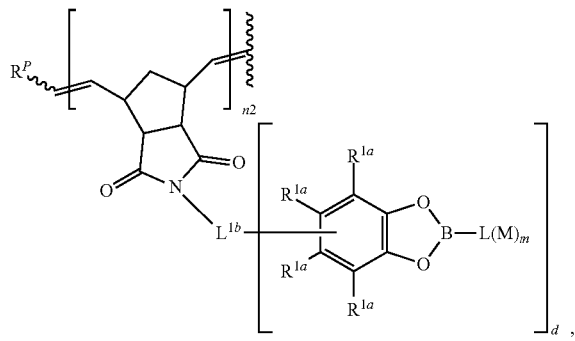

(B-4-a)

or a salt thereof, wherein:

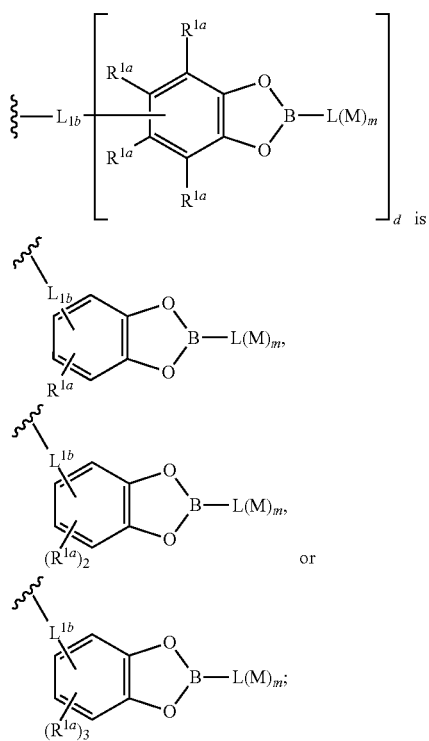

$L^{1b}$ is a substituted or unsubstituted linker, wherein the backbone of $L^{1b}$ comprises two or more atoms;

each instance of $R^{1a}$ is independently halogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=$NR^a$)$R^a$, —C(=$NR^a$)$OR^a$, —C(=$NR^a$)N($R^a$)$_2$, —C(=O)$R^a$, —C(=O)$OR^a$, —C(=O)N($R^a$)$_2$, —$NO_2$, —$NR^a$C(=O)$R^a$, —$NR^a$C(=O)$OR^a$, —$NR^a$C(=O)N($R^a$)$_2$, —OC(=O)$R^a$, —OC(=O)$OR^a$, or —OC(=O)N($R^a$)$_2$, or two instances of $R^{1a}$ are joined to form substituted or unsubstituted carbocyclyl or substituted or unsubstituted heterocyclyl;

each instance of $R^a$ is independently hydrogen, halogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ on a nitrogen atom are joined with the nitrogen atom to form substituted or unsubstituted heterocyclyl or substituted or unsubstituted heteroaryl;

$R^P$ is hydrogen, substituted or unsubstituted $C_{1-6}$ alkyl, or substituted or unsubstituted phenyl;

each instance of L is independently a bond or a substituted or unsubstituted linker;

each instance of M is independently a pharmaceutical agent;

each instance of m is independently an integer between 1 and 10, inclusive;

n2 is an integer from 5 to 300, inclusive; and d is an integer between 1 and 10, inclusive.

In certain embodiments, $L^{1b}$ is of the formula:

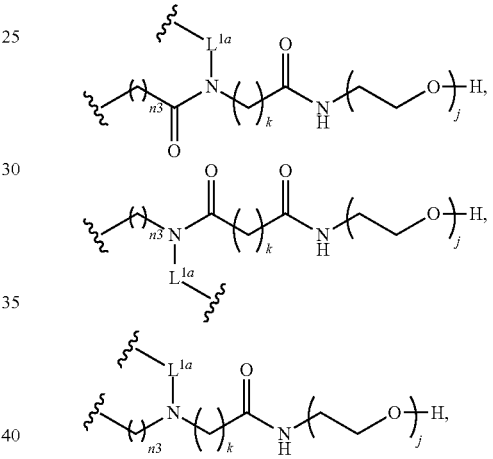

wherein:

n3 is an integer between 0 and 12 inclusive;

k is an integer between 1 and 12 inclusive;

j is an integer between 10 and 200 inclusive; and $L^{1a}$ is independently substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, or $C_{2-200}$ heteroalkynylene, wherein:

optionally one or more backbone carbon atoms in each instance of the substituted or unsubstituted, $C_{1-200}$ alkylene, substituted or unsubstituted, $C_{2-200}$ alkenylene, substituted or unsubstituted, $C_{2-200}$ alkynylene, substituted or unsubstituted, $C_{2-200}$ heteroalkylene, substituted or unsubstituted, $C_{2-200}$ heteroalkenylene, and $C_{2-200}$ heteroalkynylene are independently replaced with substituted or unsubstituted carbocyclene, substituted or unsubstituted heterocyclene, substituted or unsubstituted arylene, or substituted or unsubstituted heteroarylene;

optionally one or more backbone heteroatoms in each instance of the substituted or unsubstituted, $C_{2-200}$ heteroalkylene, substituted or unsubstituted, $C_{2-200}$ heteroalkenylene, and substituted or unsubstituted, $C_{2-200}$ heteroalkynylene are independently replaced with substituted or unsubstituted carbocyclene, substituted or unsubstituted heterocyclene, substituted or unsubstituted arylene, or substituted or unsubstituted heteroarylene.

In certain embodiments, $R^P$ is hydrogen. In certain embodiments, $R^P$ is substituted or unsubstituted $C_{1-6}$ alkyl. In certain embodiments, $R^P$ is substituted or unsubstituted phenyl. In certain embodiments, $R^P$ is unsubstituted phenyl.

In certain embodiments, n2 is an integer from 5 to 100, inclusive. In certain embodiments, n2 is an integer from 5 to 60, inclusive. In certain embodiments, n2 is an integer from 5 to 40, inclusive. In certain embodiments, n2 is an integer from 5 to 20, inclusive. In certain embodiments, n2 is an integer from 5 to 10, inclusive. In certain embodiments, n2 is an integer from 10 to 60, inclusive. In certain embodiments, n2 is an integer from 10 to 40, inclusive. In certain embodiments, n2 is an integer from 10 to 20, inclusive. In certain embodiments, n2 is an integer from 20 to 60, inclusive. In certain embodiments, n2 is an integer from 20 to 40, inclusive.

In certain embodiments, at least one instance (e.g., each instance) of the monomers is a monomer or macromonomer described in U.S. Patent Application Publication No. 2014-0308234, 2017-0348431, 2018-0094099, 2020-0123297, 2019-0038751, 2020-0369685, 2021-0220391, or 2021-0113701, or in International PCT Application Publication No. 2019/200367, each of which is incorporated by reference in its entirety.

In certain embodiments, each instance of $R^4$ is independently H, F, Cl, or —$CH_3$. In certain embodiments, each instance of $R^4$ is H.

In certain embodiments, each instance of a is independently 2, 3, 4, 5, 6, or 7. In certain embodiments, each instance of a is 2, 3, 4, 5, 6, or 7.

In certain embodiments, each two $R^1$ attached to the same carbon atom are taken together to form oxo. In certain embodiments, each $R^1$ is H.

In certain embodiments, each two $R^2$ attached to the same carbon atom are taken together to form oxo. In certain embodiments, each $R^2$ is H.

In certain embodiments, each two $R^1$ attached to the same carbon atom are taken together to form oxo; and each $R^2$ is H. In certain embodiments, each $R^1$ is H, and each two $R^2$ attached to the same carbon atom are taken together to form oxo.

In certain embodiments, each instance of L is independently substituted or unsubstituted, $C_{1-30}$ alkylene. In certain embodiments, each instance of L is independently substituted or unsubstituted, $C_{30-100}$ alkylene. In certain embodiments, each instance of L is independently substituted or unsubstituted, $C_{100-300}$ alkylene. In certain embodiments, each instance of L is independently substituted or unsubstituted, $C_{300-1000}$ alkylene.

In certain embodiments, each instance of L is independently substituted or unsubstituted, $C_{1-30}$ heteroalkylene. In certain embodiments, each instance of L is independently substituted or unsubstituted, $C_{30-100}$ heteroalkylene. In certain embodiments, each instance of L is independently substituted or unsubstituted, $C_{100-300}$ heteroalkylene. In certain embodiments, each instance of L is independently substituted or unsubstituted, $C_{300-1000}$ heteroalkylene.

In certain embodiments, optionally wherein one, two, three, four, or five backbone carbon atoms of the $C_{1-1000}$ alkylene, $C_{2-1000}$ alkenylene, $C_{2-1000}$ alkynylene, $C_{1-1000}$ heteroalkylene, $C_{2-1000}$ heteroalkenylene, or $C_{2-1000}$ heteroalkynylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, each instance of L is independently substituted or unsubstituted, $C_{1-30}$ alkylene, optionally wherein one, two, or three backbone carbon atoms of the $C_{1-30}$ alkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, each instance of L is independently substituted or unsubstituted, $C_{30-100}$ alkylene, optionally wherein one, two, or three backbone carbon atoms of the $C_{30-100}$ alkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, each instance of L is independently substituted or unsubstituted, $C_{100-300}$ alkylene, optionally wherein one, two, or three backbone carbon atoms of the $C_{100-300}$ alkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, each instance of L is independently substituted or unsubstituted, $C_{300-1000}$ alkylene, optionally wherein one, two, or three backbone carbon atoms of the $C_{300-1000}$ alkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, each instance of L is independently substituted or unsubstituted, $C_{1-30}$ heteroalkylene, optionally wherein one, two, or three backbone carbon atoms of the $C_{1-30}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, each instance of L is independently substituted or unsubstituted, $C_{30-100}$ heteroalkylene, optionally wherein one, two, or three backbone carbon atoms of the $C_{30-100}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, each instance of L is independently substituted or unsubstituted, $C_{100-300}$ heteroalkylene, optionally wherein one, two, or three backbone carbon atoms of the $C_{100-300}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, each instance of L is independently substituted or unsubstituted, $C_{300-1000}$ heteroalkylene, optionally wherein one, two, or three backbone carbon atoms of the $C_{300-1000}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, each instance of L is independently substituted or unsubstituted, $C_{1-1000}$ alkylene or substituted or unsubstituted, $C_{1-1000}$ heteroalkylene, optionally wherein one, two, or three backbone carbon atoms of the $C_{1-1000}$ alkylene or $C_{1-1000}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, each instance of L is independently substituted or unsubstituted, $C_{3-400}$ alkylene or substituted or unsubstituted, $C_{2-400}$ heteroalkylene, optionally wherein one, two, or three backbone carbon atoms of the $C_{3-400}$ alkylene or $C_{2-400}$ heteroalkylene are independently replaced with substituted or unsubstituted, monocyclic, 3- to 10-membered carbocyclylene, substituted or unsubstituted, monocyclic, 3- to 10-membered heterocyclylene, substituted or unsubstituted phenyl, or substituted or unsubstituted, monocyclic, 5- to 6-membered heteroarylene, as valency permits.

In certain embodiments, the optional substituents included in each instance of L are independently halogen (e.g., F), unsubstituted $C_{1-6}$ alkyl, $C_{1-6}$ alkyl substituted with one or more halogen (e.g., F), —O—(unsubstituted $C_{1-6}$ alkyl), —O—($C_{1-6}$ alkyl substituted with one or more halogen (e.g., F)), or oxo.

In certain embodiments, each instance of L comprises at least one instance of —O—C(=O)— or —C(=O)—O—.

In certain embodiments, the carbocyclylene or heterocyclylene included in each instance of L is independently monocyclic and 3- to 7-membered. In certain embodiments, the arylene included in each instance of L is phenylene. In certain embodiments, the heteroarylene included in each instance of L is independently monocyclic and 5- to 6-membered.

In certain embodiments, at least one instance (e.g., each instance) of L is independently substituted or unsubstituted, $C_{2-400}$ heteroalkylene, wherein:

one or two backbone carbon atoms of the $C_{2-400}$ heteroalkylene are replaced with

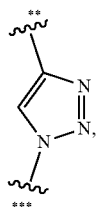

wherein the nitrogen atom labeled with "*" is closer to the attachment point labeled with "" than the attachment point labeled with "*"; and optionally wherein one or two backbone carbon atoms of the $C_{2-400}$ heteroalkylene is replaced with substituted or unsubstituted phenylene.

In certain embodiments, at least one instance of L is independently substituted or unsubstituted, $C_{2-200}$ heteroalkylene, wherein one carbon or one heteroatom, of the substituted or unsubstituted, $C_{2-200}$ heteroalkylene, is independently replaced with

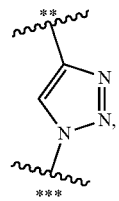 [SMILES: *c1cn(*)nn1]

wherein the nitrogen atom labeled with "*" is closer to the attachment point labeled with "" than the attachment point labeled with "*". In certain embodiments, at least one instance of L comprises

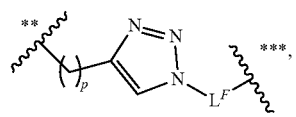

wherein:
each instance of p is independently an integer from 1 to 10, inclusive;
each instance of $L^F$ is independently substituted or unsubstituted, $C_{2-180}$ heteroalkylene; and
the nitrogen atom labeled with "*" is closer to the attachment point labeled with "" than the attachment point labeled with "*". In certain embodiments, at least one instance of L is independently

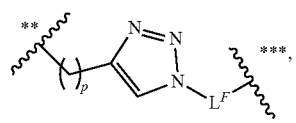

In certain embodiments, at least one instance of L comprises

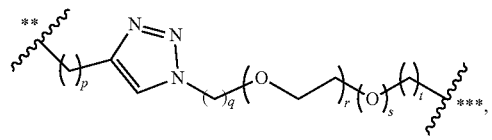

wherein:
each instance of p is independently an integer from 1 to 10, inclusive;
each instance of q is independently an integer from 1 to 10, inclusive;
each instance of r is independently an integer from 0 to 10, inclusive;
each instance of s is independently 0 or 1;
each instance of t is independently an integer from 0 to 10, inclusive; and the nitrogen atom labeled with "*" is closer to the attachment point labeled with "" than the attachment point labeled with "*".

In certain embodiments, at least one instance of $L^F$ is independently substituted or unsubstituted, $C_{3-30}$ heteroalkylene. In certain embodiments, at least one instance of $L^F$ comprises —S—S—. In certain embodiments, at least one instance of $L^F$ is independently substituted or unsubstituted, $C_{3-30}$ heteroalkylene comprising one —S—S— and no other heteroatoms in the backbone. In certain embodiments, at least one instance of $L^F$ comprises a peptide comprising between 1 and 20 (e.g., between 1 and 4), inclusive, amino acid residues.

In certain embodiments, at least one instance of L is independently

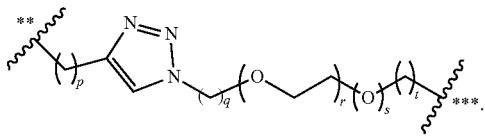

In certain embodiments, at least one instance of L is independently

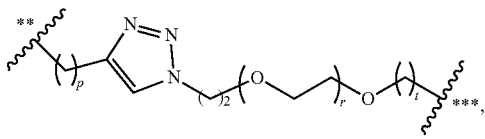

wherein r is independently 1, 2, or 3; and t is independently 1 or 2. In certain embodiments, at least one instance of L comprises

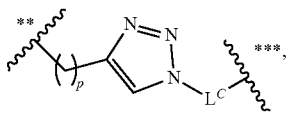

wherein:
each instance of p is independently an integer from 1 to 10, inclusive;
each instance of $L^C$ is independently substituted or unsubstituted, $C_{1-180}$ alkylene; and
the nitrogen atom labeled with "*" is closer to the attachment point labeled with "" than the attachment point labeled with "*". In certain embodiments, at least one instance of L is independently

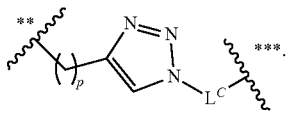

In certain embodiments, at least one instance of $L^C$ is independently substituted or unsubstituted $C_{1-12}$ alkylene. In certain embodiments, at least one instance of $L^C$ is independently unsubstituted $C_{1-12}$ alkylene. In certain embodiments, each instance of $L^C$ is independently $C_{1-180}$ alkylene substituted with one or more instances of: substituted or unsubstituted phenyl and/or substituted or unsubstituted, $C_{1-6}$ alkyl. In certain embodiments, at least one instance of L comprises a polymer. In certain embodiments, at least one instance of the polymer is independently substituted or unsubstituted polyethylene (e.g., unsubstituted polystyrene). In certain embodiments, the weight-average molecular weight of at least one instance of the polymer is independently between 300 and 10,000, between 300 and 3,000, between 300 and 1,000, between 1,000 and 10,000, between 1,000 and 3,000, or between 3,000 and 10,000, inclusive, g/mol. In certain embodiments, at least one instance of L comprises an amino acid or a peptide. In certain embodiments, at least one instance the peptide consists of between 3 and 60, between 3 and 30, between 3 and 10, between 10 and 60, between 10 and 30, or between 30 and 60, inclusive, amino acids. In certain embodiments, each instance of the amino acid is independently a natural amino acid. In certain embodiments, at least one instance of the amino acid is independently an unnatural amino acid.

A cleavable linker is "cleaved" or "degraded" when one or more bonds of the cleavable linker are broken, e.g., resulting in release of an agent, e.g., from the Brush prodrug or particle. Linker cleavage or agent release need not be 100%, e.g., a cleavage or release of at least 10%, 20%, 30%, 40%, 50%, 60%, 70%, 80%, 90%, 95% or higher, e.g., over a period of seconds, minutes, hours (e.g., 6 hours, 12 hours, or 24 hours), days (e.g., 2 days or 7 days), weeks, or months is encompassed by this term. In certain embodiments, at least 50% of all instances of the L that is cleavable is cleaved after about 10 minutes, about 1 hour, about 6 hours, about 12 hours, about 1 day, about 2 days, about 3 days, about 5 days, or about 7 days of the ultraviolet irradiation, hydrolysis, reduction, oxidation, or contact with the enzyme. In some embodiments, the cleavable linker is cleavable by or is sensitive to an enzyme (e.g., an esterase or a protease), pH (e.g., acidic pH, basic pH), light (e.g., ultraviolet light), a nucleophile, reduction, or oxidation. In some embodiments, the cleavable linker is cleavable by or is sensitive to an enzyme (e.g., an esterase or a protease) or pH (e.g., acidic pH, basic pH). In some embodiments, the cleavable linker is not cleavable by light (e.g., ultraviolet light). In certain embodiments, at least one instance of L is cleavable by ultraviolet irradiation. In certain embodiments, at least one instance of L is cleavable by hydrolysis, reduction, or oxidation. In certain embodiments, at least one instance of L is cleavable by contacting with an enzyme.

The cleavable linker may include an atom or a part of a moiety that is derived in part from the agent (e.g., a therapeutic agent).

In some embodiments, the cleavable linker is cleaved or degraded, e.g., preferentially cleaved or degraded, upon exposure to a first set of conditions relative to a second set of conditions. For example, the cleavable linker can be "preferentially cleaved" or "preferentially degraded" in a first set of conditions relative to a second set of conditions if at least 10%, 20%, 30%, 40%, 50%, 60%, 70%, 80%, 90%, 95% or more of a bond or bonds of the cleavable linker are broken, or the agent is released, in the first set of conditions relative to the second set of conditions.

In some embodiments, the cleavable linker is degraded or hydrolyzed at physiological conditions. In some embodiments, the linker is pH sensitive or cleaved at a certain pH. In some embodiments, the linker is degraded or hydrolyzed through the action of an enzyme (e.g., a protease or esterase). For example, in some embodiments, the cleavable linker is preferentially cleaved in a tissue microenvironment, e.g., a tumor microenvironment, which is referred to herein as a "tissue microenvironment cleavable linker." In embodiments, the tissue (e.g., tumor) microenvironment cleavable linker is preferentially cleaved or degraded upon exposure to a first desired tissue or tumor microenvironment relative to a second tissue or non-tumor tissue. A tissue (e.g., tumor) microenvironment cleavable linker can be preferentially cleaved if at least 10%, 20%, 30%, 40%, 50%, 60%, 70%, 80%, 90%, 95% or more of a bond or bonds of the linker are broken, or the agent is released, in a desired tissue or tumor microenvironment relative to another tissue or non-tumor tissue. In one embodiment, the tissue (e.g., tumor) microenvironment cleavable linker is preferentially cleaved or degraded if one or more of the bonds of the linker are broken, or the agent is released, at least 2, 5, 10, 20, 30, 40, 50, 60, 70, 80, or 100 times faster upon exposure to a first desired tissue or tumor microenvironment relative to a second tissue or non-tumor tissue. The tissue (e.g., tumor) microenvironment can have a particular set of conditions, e.g., pH, enzymes, that cause the cleavage or degradation of the linker.

In certain embodiments, at least two instances of L are different from each other. In all instances of L are the same.

In one embodiment, the tissue (e.g., tumor) microenvironment cleavable linker is cleavable by an enzyme. In some embodiments, the enzyme comprises an esterase or a protease. Exemplary proteases include MMP-1, MMP-2, MMP-3, MMP-8, MMP-9, MMP-14, plasmin, PSA, PSMA, CATHEPSIN D, CATHEPSIN K, CATHEPSIN S, ADAM10, ADAM12, ADAMTS, Caspase-1, Caspase-2, Caspase-3, Caspase-4, Caspase-5, Caspase-6, Caspase-7, Caspase-8, Caspase-9, Caspase-10, Caspase-11, Caspase-12, Caspase-13, Caspase-14, or TACE.

In other embodiments, the tissue microenvironment cleavable linker is cleavable at a particular pH. In some embodiments, the tissue microenvironment cleavable linker is cleavable at a pH between about 5.0 and about 7.4, between 5.0 and 7.0, between 5.0 and 6.5, between 5.0 and 5.5, or between 5.9 and 6.2. In one embodiment, the tissue microenvironment cleavable linker is cleavable at a pH between about 6.0 and about 7.0, between about 6.2 and about 6.9, between about 6.5 and about 6.8, or between about 6.5 and about 6.7. In one embodiment, the tissue microenvironment cleavable linker is cleavable at a pH between about 5.5 and about 6.5, e.g., between 5.9 and 6.2. In one embodiment, the tissue microenvironment cleavable linker is cleavable at a hypoxic pH, e.g., a pH about 6.7 to 6.9, e.g., compared to a physiological pH of about 7.4.

In some embodiments, the tissue microenvironment cleavable linker is cleavable is cleaved at a pH of no more than 7.4, no more than 7.0, no more than 6.9, no more than 6.8, no more than 6.7, no more than 6.6, no more than 6.5, no more than 6.4, no more than 6.3, no more than 6.2, no more than 6.1, no more than 6.0, no more than 5.5 or lower.

In one embodiment, the tissue microenvironment cleavable linker is preferentially cleaved or degraded upon exposure to a first pH relative to a second pH. In one embodiment, the tissue microenvironment cleavable linker is cleaved or degraded at least 2, 5, 10, 20, 30, 40, 50, 60, 70, 80, or 100 times faster upon exposure to a first pH relative to a second pH. In other embodiments, the tissue microenvironment cleavable linker shows a greater release or degradation rate at a first acidic pH (e.g., pH=6.7) relative to a second more basic pH (e.g., pH=7.4). In one embodiment, ratio of release or degradation rate of the tissue microenvironment cleavable linker at pH=6.7 relative to pH=7.4 is greater than 1, 1.2, 1.4, 1.6, 1.8, 2, 2.2, 2.4, 2.6, 2.8, 3 or higher. In one embodiment, ratio of release or degradation rate of the tissue microenvironment cleavable linker at pH=6.7 relative to pH=7.4 is greater than 2.

In one embodiment, the tissue microenvironment cleavable linker shows increased pH-sensitivity in a hypoxic microenvironment, e.g., in a tumor, or fibrotic tissue.

In some embodiments, the tissue microenvironment cleavable linker exhibits an increased release rate or increased release yield of the agent at a desired site (e.g., a tumor), e.g., relative to the release rate or release yield at another site. In one embodiment, the tissue microenvironment cleavable linker comprises an electron withdrawing group (e.g., an electron withdrawing group that enhances the cleavage rate or yield, e.g., upon exposure to a first set of conditions relative to a second set of conditions).

In certain embodiments, at least one instance of $M^1$ is M. In certain embodiments, at least one instance of the pharmaceutical agents is M. In certain embodiments, each instance of M is independently a pharmaceutical agent. The pharmaceutical agents include chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; antibodies and antigen binding fragments thereof; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the pharmaceutical agent is a small molecule. In some embodiments, the pharmaceutical agent is a peptide or protein. Exemplary pharmaceutical agents include, but are not limited to, those found in *Harrison's Principles of Internal Medicine,* 13th Edition, Eds. T. R. Harrison et al. McGraw-Hill N.Y., NY; Physicians' Desk Reference, 50th Edition, 1997, Oradell New Jersey, Medical Economics Co.; Pharmacological Basis of Therapeutics, 8th Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete contents of all of which are incorporated herein by reference.

In certain embodiments, each instance of M is independently a therapeutic agent or a diagnostic agent. In certain embodiments, at least one instance of M is a therapeutic agent. In certain embodiments, each instance of M is a therapeutic agent. In some embodiments, exemplary therapeutic agents include, but are not limited to, one or more of the agents listed in Paragraph 0148 of U.S. Pat. No. 9,381, 253, incorporated by reference herein. In other embodiments, exemplary therapeutic agents include, but are not limited to, one or more of the therapeutic agents listed in WO 2013/169739, including the anti-hypertensive and/or a collagen modifying agents ("AHCM") disclosed, e.g., in Paragraphs 40-49, 283, 286-295; the microenviroment modulators disclosed, e.g., in Paragraphs 113-121, of WO 2013/169739, incorporated herein by reference. Examples of therapeutic agents also include, but are not limited to, antimicrobial agents, analgesics, antinflammatory agents, counterirritants, coagulation modifying agents, diuretics, sympathomimetics, anorexics, antacids and other gastrointestinal agents; antiparasitics, antidepressants, antihypertensives, anticholinergics, stimulants, antihormones, central and respiratory stimulants, drug antagonists, lipid-regulating agents, uricosurics, cardiac glycosides, electrolytes, ergot and derivatives thereof, expectorants, hypnotics and sedatives, antidiabetic agents, dopaminergic agents, antiemetics, muscle relaxants, para-sympathomimetics, anticonvulsants, antihistamines, beta-blockers, purgatives, antiarrhythmics, contrast materials, radiopharmaceuticals, antiallergic agents, tranquilizers, vasodilators, antiviral agents, and antineoplastic or cytostatic agents or other agents with anticancer properties, or a combination thereof. Other suitable therapeutic agents include contraceptives and vitamins as well as micro- and macronutrients. Still other examples include antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrleals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

In certain embodiments, at least one instance of M is an anti-cancer agent. In some embodiments, the anti-cancer agent is selected from the group consisting of abiraterone acetate, ABVD, AB VE, ABVE-PC, AC, AC-T, ADE, adotrastuzumab emtansine, afatinib dimaleate, aldesleukin, alemtuzumab, anastrozole, arsenic trioxide, asparaginase *Erwinia chrysanthemi*, axitinib, azacitidine, BEACOPP, belinostat, bendamustine hydrochloride, BEP, bevacizumab, bicalutamide, bleomycin, blinatumomab, bortezomib, bosutinib, brentuximab vedotin, busulfan, cabazitaxel, cabozantinib-s-malate, CAF, capecitabine, CAPDX, carboplatin, carboplatin-taxol, carfilzomibcarmustine, carmustine implant, ceritinib, cetuximab, chlorambucil, chlorambucil-prednisone, CHOP, cisplatin, clofarabine, CMF, COPP, COPP-ABV, crizotinib, CVP, cyclophosphamide, cytarabine, dabrafenib, dacarbazine, dactinomycin, dasatinib, daunorubicin hydrochloride, decitabine, degarelix, denileukin diftitox, denosumab, Dinutuximab, docetaxel, doxorubicin hydrochloride, doxorubicin hydrochloride liposome, enzalutamide, epirubicin hydrochloride, EPOCH, erlotinib hydrochloride, etoposide, etoposide phosphate, everolimus, exemestane, FEC, fludarabine phosphate, fluorouracil, FOLFIRI, FOLFIRI-BEVACIZUMAB, FOLFIRI-CETUXIMAB, FOLFIRINOX, FOLFOX, FU-LV, fulvestrant, gefitinib, gemcitabine hydrochloride, gemcitabine-cisplatin, gemcitabine-oxaliplatin, goserelin acetate, Hyper-CVAD, ibritumomab tiuxetan, ibrutinib, ICE, idelalisib, ifosfamide, imatinib mesylate, imiquimod, ipilimumab, irinotecan hydrochloride, ixabepilone, lanreotide acetate, lapatinib ditosylate, lenalidomide, lenvatinib, letrozole, leucovorin calcium, leuprolide acetate, liposomal cytarabine, lomustine, mechlorethamine hydrochloride, megestrol acetate, mercaptopurine, methotrexate, mitomycin c, mitoxantrone hydrochloride, MOPP, nelarabine, nilotinib, nivolumab, obinutuzumab, OEPA, ofatumumab, OFF, olaparib, omacetaxine mepesuccinate, OPPA, oxaliplatin, paclitaxel, paclitaxel albumin-stabilized nanoparticle formulation, PAD, palbociclib, pamidronate disodium, panitumumab, panobinostat, pazopanib hydrochloride, pegaspargase, peginterferon alfa-2b, peginterferon alfa-2b, pembrolizumab, pemetrexed disodium, pertuzumab, plerixafor, pomalidomide, ponatinib hydrochloride, pralatrexate, prednisone, procarbazine hydrochloride, radium 223 dichloride, raloxifene hydrochloride, ramucirumab, R-CHOP, recombinant HPV bivalent vaccine, recombinant human papillomavirus, nonavalent vaccine, recombinant human papillomavirus, quadrivalent vaccine, recombinant interferon alfa-2b, regorafenib, rituximab, romidepsin, ruxolitinib phosphate, siltuximab, sipuleucel-t, sorafenib tosylate, STANFORD V, sunitinib malate, TAC, tamoxifen citrate, temozolomide, temsirolimus, thalidomide, thiotepa, topotecan hydrochloride, toremifene, tositumomab and iodine I 131, tositumomab, TPF, trametinib, trastuzumab, VAMP, vandetanib, VEIP, vemurafenib, vinblastine sulfate, vincristine sulfate, vincristine sulfate liposome, vinorelbine tartrate, vismodegib, vorinostat, XELIRI, XELOX, ziv-aflibercept, and zoledronic acid. Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g., HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g., tamoxifen, raloxifene, and megestrol), LHRH agonists (e.g., goscrelin and leuprolide), anti-androgens (e.g., flutamide and bicalutamide), photodynamic therapies (e.g., vertoporfin (BPD-MA), phthalocyanine, photosensitizer Pc4, and demethoxy-hypocrellin A (2BA-2-DMHA)), nitrogen mustards (e.g., cyclophosphamide, ifosfamide, trofosfamide, chlorambucil, estramustine, and melphalan), nitrosoureas (e.g., carmustine (BCNU) and lomustine (CCNU)), alkylsulphonates (e.g., busulfan and treosulfan), triazenes (e.g., dacarbazine, temozolomide), platinum containing compounds (e.g., cisplatin, carboplatin, oxaliplatin), vinca alkaloids (e.g., vincristine, vinblastine, vindesine, and vinorelbine), taxoids (e.g., paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g., etoposide, etoposide phosphate, teniposide, topotecan, 9-aminocamptothecin, camptoirinotecan, irinotecan, crisnatol, mytomycin C), anti-metabolites, DHFR inhibitors (e.g., methotrexate, dichloromethotrexate, trimetrexate, edatrexate), IMP dehydrogenase inhibitors (e.g., mycophenolic acid, tiazofurin, ribavirin, and EICAR), ribonuclotide reductase inhibitors (e.g., hydroxyurea and deferoxamine), uracil analogs (e.g., 5-fluorouracil (5-FU), floxuridine, doxifluridine, ratitrexed, tegafur-uracil, capecitabine), cytosine analogs (e.g., cytarabine (ara C), cytosine arabinoside, and fludarabine), purine analogs (e.g., mercaptopurine and Thioguanine), Vitamin D3 analogs (e.g., EB 1089, CB 1093, and KH 1060), isoprenylation inhibitors (e.g., lovastatin), dopaminergic neurotoxins (e.g., 1-methyl-4-phenylpyridinium ion), cell cycle inhibitors (e.g., staurosporine), actinomycin (e.g., actinomycin D, dactinomycin), bleomycin (e.g., bleomycin A2, bleomycin B2, peplomycin), anthracycline (e.g., daunorubicin, doxorubicin, pegylated liposomal doxorubicin, idarubicin, epirubicin, pirarubicin, zorubicin, mitoxantrone), MDR inhibitors (e.g., verapamil), Ca2+ ATPase inhibitors (e.g., thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TAR- CEVA®), gefitinib (IRESSAC)), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLA-DIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUXC)), panitumumab (VECTIBIXC)), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

In certain embodiments, the anti-cancer agent is abiraterone acetate (e.g., ZYTIGA), ABVD, ABVE, ABVE-PC, AC, AC-T, ADE, ado-trastuzumab emtansine (e.g., KADCYLA), afatinib dimaleate (e.g., GILOTRIF), aldesleukin (e.g., PROLEUKIN), alemtuzumab (e.g., CAMPATH), anastrozole (e.g., ARIMIDEX), arsenic trioxide (e.g., TRISENOX), asparaginase *Erwinia chrysanthemi* (e.g., ERWINAZE), axitinib (e.g., INLYTA), azacitidine (e.g., MYLOSAR, VIDAZA), BEACOPP, belinostat (e.g., BELEODAQ), bendamustine hydrochloride (e.g., TREANDA), BEP, bevacizumab (e.g., AVASTIN), bicalutamide (e.g., CASODEX), bleomycin (e.g., BLENOXANE), blinatumomab (e.g., BLINCYTO), bortezomib (e.g., VELCADE), bosutinib (e.g., BOSULIF), brentuximab vedotin (e.g., ADCETRIS), busulfan (e.g., BUSULFEX, MYLERAN), cabazitaxel (e.g., JEVTANA), cabozantinib-s-malate (e.g., COMETRIQ), CAF, capecitabine (e.g., XELODA), CAPDX, carboplatin (e.g., PARAPLAT, PARAPLATIN), carboplatin-taxol, carfilzomib (e.g., KYPROLIS), carmustine (e.g., BECENUM, BICNU, CARMUBRIS), carmustine implant (e.g., GLIADEL WAFER, GLIADEL), ceritinib (e.g., ZYKADIA), cetuximab (e.g., ERBITUX), chlorambucil (e.g., AMB OCHLORIN, AMB OCLORIN, LEUKERAN, LINFOLIZIN), chlorambucil-prednisone, CHOP, cisplatin (e.g., PLATINOL, PLATINOL-AQ), clofarabine (e.g., CLOFAREX, CLOLAR), CMF, COPP, COPP-ABV, crizotinib (e.g., XALKORI), CVP, cyclophosphamide (e.g., CLAFEN, CYTOXAN, NEOSAR), cytarabine (e.g., CYTOSAR-U, TARABINE PFS), dabrafenib (e.g., TAFINLAR), dacarbazine (e.g., DTIC-DOME), dactinomycin (e.g., COSMEGEN), dasatinib (e.g., SPRYCEL), daunorubicin hydrochloride (e.g., CERUBIDINE), decitabine (e.g., DACOGEN), degarelix, denileukin diftitox (e.g., ONTAK), denosumab (e.g., PROLIA, XGEVA), Dinutuximab (e.g., UNITUXIN), docetaxel (e.g., TAXOTERE), doxorubicin hydrochloride (e.g., ADRIAMYCIN PFS, ADRIAMYCIN RDF), doxorubicin hydrochloride liposome (e.g., DOXIL, DOX-SL, EVACET, LIPODOX), enzalutamide (e.g., XTANDI), epirubicin hydrochloride (e.g., ELLENCE), EPOCH, erlotinib hydrochloride (e.g., TARCEVA), etoposide (e.g., TOPOSAR, VEPESID), etoposide phosphate (e.g., ETOPOPHOS), everolimus (e.g., AFINITOR DISPERZ, AFINITOR), exemestane (e.g., AROMASIN), FEC, fludarabine phosphate (e.g., FLUDARA), fluorouracil (e.g., ADRUCIL, EFUDEX, FLUOROPLEX), FOLFIRI, FOLFIRI-BEVACIZUMAB, FOLFIRI-CETUXIMAB, FOLFIRINOX, FOLFOX, FU-LV, fulvestrant (e.g., FASLODEX), gefitinib (e.g., IRESSA), gemcitabine hydrochloride (e.g., GEMZAR), gemcitabine-cisplatin, gemcitabine-oxaliplatin, goserelin acetate (e.g., ZOLADEX), Hyper-CVAD, ibritumomab tiuxetan (e.g., ZEVALIN), ibrutinib (e.g., IMBRUVICA), ICE, idelalisib (e.g., ZYDELIG), ifosfamide (e.g., CYFOS, IFEX, IFOSFAMIDUM), imatinib mesylate (e.g., GLEEVEC), imiquimod (e.g., ALDARA), ipilimumab (e.g., YERVOY), irinotecan hydrochloride (e.g., CAMPTOSAR), ixabepilone (e.g., IXEMPRA), lanreotide acetate (e.g., SOMATULINE DEPOT), lapatinib ditosylate (e.g., TYKERB), lenalidomide (e.g., REVLIMID), lenvatinib (e.g., LENVIMA), letrozole (e.g., FEMARA), leucovorin calcium (e.g., WELLCOVORIN), leuprolide acetate (e.g., LUPRON DEPOT, LUPRON DEPOT-3 MONTH, LUPRON DEPOT-4 MONTH, LUPRON DEPOT-PED, LUPRON, VIADUR), liposomal cytarabine (e.g., DEPOCYT), lomustine (e.g., CEENU), mechlorethamine hydrochloride (e.g., MUSTARGEN), megestrol acetate (e.g., MEGACE), mercaptopurine (e.g., PURINETHOL, PURIXAN), methotrexate (e.g., ABITREXATE, FOLEX PFS, FOLEX, METHOTREXATE LPF, MEXATE, MEXATE-AQ), mitomycin c (e.g., MITOZYTREX, MUTAMYCIN), mitoxantrone hydrochloride, MOPP, nelarabine (e.g., ARRANON), nilotinib (e.g., TASIGNA), nivolumab (e.g., OPDIVO), obinutuzumab (e.g., GAZYVA), OEPA, ofatumumab (e.g., ARZERRA), OFF, olaparib (e.g., LYNPARZA), omacetaxine mepesuccinate (e.g., SYNRIBO), OPPA, OTX-015, oxaliplatin (e.g., ELOXATIN), paclitaxel (e.g., TAXOL), paclitaxel albumin-stabilized nanoparticle formulation (e.g., ABRAXANE), PAD, palbociclib (e.g., IBRANCE), pamidronate disodium (e.g., AREDIA), panitumumab (e.g., VECTIBIX), panobinostat (e.g., FARYDAK), pazopanib hydrochloride (e.g., VOTRIENT), pegaspargase (e.g., ONCASPAR), peginterferon alfa-2b (e.g., PEG-INTRON), peginterferon alfa-2b (e.g., SYLATRON), pembrolizumab (e.g., KEYTRUDA), pemetrexed disodium (e.g., ALIMTA), pertuzumab (e.g., PERJETA), plerixafor (e.g., MOZOBIL), pomalidomide (e.g., POMALYST), ponatinib hydrochloride (e.g., ICLUSIG), pralatrexate (e.g., FOLOTYN), prednisone, procarbazine hydrochloride (e.g., MATULANE), radium 223 dichloride (e.g., XOFIGO), raloxifene hydrochloride (e.g., EVISTA, KEOXIFENE), ramucirumab (e.g., CYRAMZA), R-CHOP, recombinant HPV bivalent vaccine (e.g., CERVARIX), recombinant human papillomavirus (e.g., HPV) nonavalent vaccine (e.g., GARDASIL 9), recombinant human papillomavirus (e.g., HPV) quadrivalent vaccine (e.g., GARDASIL), recombinant interferon alfa-2b (e.g., INTRON A), regorafenib (e.g., STIVARGA), rituximab (e.g., RITUXAN), romidepsin (e.g., ISTODAX), ruxolitinib phosphate (e.g., JAKAFI), siltuximab (e.g., SYLVANT), sipuleucel-t (e.g., PROVENGE), sorafenib tosylate (e.g., NEXAVAR), STANFORD V, sunitinib malate (e.g., SUTENT), TAC, tamoxifen citrate (e.g., NOLVADEX, NOVALDEX), temozolomide (e.g., METHAZOLAS- TONE, TEMODAR), temsirolimus (e.g., TORISEL), thalidomide (e.g., SYNOVIR, THALOMID), thiotepa, topotecan hydrochloride (e.g., HYCAMTIN), toremifene (e.g., FARES TON), tositumomab and iodine I 131 tositumomab (e.g., BEXXAR), TPF, trametinib (e.g., MEKINIST), trastuzumab (e.g., HERCEPTIN), VAMP, vandetanib (e.g., CAPRELS A), VEIP, vemurafenib (e.g., ZELBORAF), vinblastine sulfate (e.g., VELBAN, VELSAR), vincristine sulfate (e.g., VINCASAR PFS), vincristine sulfate liposome (e.g., MARQIBO), vinorelbine tartrate (e.g., NAVELBINE), vismodegib (e.g., ERIVEDGE), vorinostat (e.g., ZOLINZA), XELIRI, XELOX, ziv-aflibercept (e.g., ZALTRAP), or zoledronic acid (e.g., ZOMETA), or a pharmaceutically acceptable salt thereof. In certain embodiments, at least one instance of the therapeutic agent is a bromodomain inhibitor. In certain embodiments, at least one instance of the therapeutic agent is a bromo and extra terminal protein (BET) inhibitor. In certain embodiments, at least one instance of the therapeutic agent is a bromodomain-containing protein 2 (BRD2) inhibitor, bromodomain-containing protein 3 (BRD3) inhibitor, bromodomain-containing protein 4 (BRD4) inhibitor, TBP (TATA box binding protein)-associated factor protein (TAF) (e.g., TAF1 or TAF1L) inhibitor, CREB-binding protein (CBP) inhibitor, or E1A binding protein p300 (EP300) inhibitor. In certain embodiments, at least one instance of M is a PARP inhibitor, ALK inhibitor, or STING ligand. In certain embodiments, at least one instance of the therapeutic agent is MMAE. In certain embodiments, at least one instance of the therapeutic agent is PTX. In certain embodiments, at least one instance of the therapeutic agent is DOX. In certain embodiments, at least one instance of the therapeutic agent is SN-38.

In certain embodiments, at least one instance of the therapeutic agent is a proteolysis-targeting chimera (PROTAC). In certain embodiments, at least one instance of the PROTAC is ARV771, ARV825, ARV766, ARV110, ARV471, AC682, CC-94676, DT2216, FHD-609, KT-474, KT-413, KT-333, NX-2127, NX-5948, CFT8634, CFT8919, or CG001419, or a pharmaceutically acceptable salt thereof.

In certain embodiments, at least one instance of M is a prophylactic agent. In certain embodiments, each instance of M is a prophylactic agent. Prophylactic agents that can be included in the conjugates of the invention include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Prophylactic agents may be combined with interleukins, interferon, cytokines, and adjuvants such as cholera toxin, alum, Freund's adjuvant.

In certain embodiments, at least one instance of M is a diagnostic agent. In certain embodiments, each instance of M is a diagnostic agent. Exemplary diagnostic agents include, but are not limited to, fluorescent molecules; gases; metals; imaging agents, such as commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in MRI include gadolinium chelates, as well as iron, magnesium, manganese, copper, and chromium. Examples of materials useful for CAT and x-ray imaging include iodine-based materials. In certain embodiments, the diagnostic agent is used in magnetic resonance imaging (MRI), such as iron oxide particles or gadolinium complexes. Gadolinium complexes that have been approved for clinical use include gadolinium chelates with DTPA, DTPA-BMA, DOTA and HP-DO3A which are reviewed in Aime, et al. (Chemical Society Reviews (1998), 27:19-29), the entire teachings of which are incorporated herein by reference.

In certain embodiments, the diagnostic agent is a metal, inorganic compound, organometallic compound, organic compound, or salt thereof. In certain embodiments, the imaging agent contains a metal selected from the group consisting of scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, mercury, rutherfordium, dubnium, seaborgium, bohrium, hassium, meitnerium, gadolinium, gallium, thallium, and barium. In certain embodiments, the diagnostic agent is an organic compound. In certain embodiments, the diagnostic agent is metal-free. In certain embodiments, the diagnostic agent is a metal-free organic compound.

In certain embodiments, the imaging agent is a magnetic resonance imaging (MRI) agent. In certain embodiments, the MRI agent is gadolinium. In certain embodiments, the MRI agent is a nitroxide radical-containing compound.

In certain embodiments, the imaging agent is a nuclear medicine imaging agent. In certain embodiments, the nuclear medicine imaging agent is selected from the group consisting of $^{64}$Cu diacetyl-bis(N$^4$-methylthiosemicarbazone) ($^{64}$Cu-ASTM), $^{18}$F-fluorodeoxyglucose (FDG), $^{18}$F-fluoride, 3'-deoxy-3'-[$^{18}$F]fluorothymidine (FLT), $^{18}$F-fluoromisonidazole (FMISO), gallium, technetium-99m, and thallium.

In certain embodiments, the imaging agent is radiographic imaging agent. In certain embodiments, the radiographic imaging agent is selected from the group consisting of barium, gastrografin, and iodine contrast agent.

In certain embodiments, the imaging agent the diagnostic agent is a radical-containing compound. In certain embodiments, the imaging agent is a nitroxide radical-containing compound. In certain embodiments, the imaging agent the diagnostic agent is of the formula:

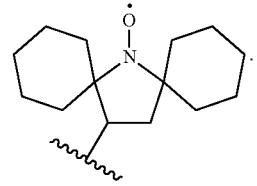

In certain embodiments, the imaging agent the diagnostic agent is an organic compound. In certain embodiments, the imaging agent is a salt of an organic compound. In certain embodiments, the imaging agent the diagnostic agent is of the formula:

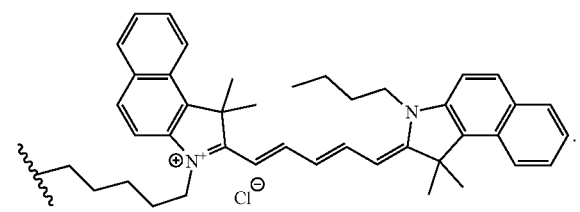

In certain embodiments, the diagnostic agent may comprise a fluorescent molecule, a metal chelate, a contrast agent, a radionuclide, or a positron emission tomography (PET) imaging agent, an infrared imaging agent, a near-IR imaging agent, a computer assisted tomography (CAT) imaging agent, a photon emission computerized tomography imaging agent, an X-ray imaging agent, or a magnetic resonance imaging (MRI) agent.

In some embodiments, the diagnostic agent is a fluorescent molecule. In some embodiments, the fluorescent molecule comprises an acridine dye, a cyanine dye, a rhodamine dye, a BODIPY dye, a fluorescein dye, a dansyl dye, an Alexa dye, an atto dye, a quantum dot, or a fluorescent protein. In some embodiments, the fluorescent molecule is a cyanine dye (e.g., Cy3, Cy 3.5, Cy5, Cy5.5, Cy7, or Cy7.5).

In some embodiments, the diagnostic agent is an MRI agent (e.g., a contrast agent). Examples of suitable materials for use as MRI agents (e.g., contrast agents) include gadolinium chelates, as well as iron, magnesium, manganese, copper, and chromium.

In some embodiments, the diagnostic agent is a CAT imaging agent or an X-ray imaging agent. Examples of materials useful for CAT and X-ray imaging include iodine-based materials.

In some embodiments, the diagnostic agent is a PET imaging agent. Examples of suitable PET imaging agents include compounds and compositions comprising the positron emitting radioisotopoes $^{18}$F, $^{15}$O, $^{13}$N, $^{11}$C, $^{82}$Rb, $^{64}$Cu, and $^{68}$Ga, e.g., fludeoxyglucose ($^{18}$F-FDG), $^{68}$Ga-DOTA-psuedopeptides (e.g., $^{68}$Ga-DOTA-TOC), $^{11}$C-metomidate, $^{11}$C-acetate, $^{11}$C-methionine, $^{11}$C-choline, $^{18}$F-fluciclovine, $^{18}$F-fluorocholine, $^{18}$F-fluorodeoxysorbitol, $^{18}$F-3'-fluoro-3'-deoxythymidine, $^{11}$C-raclopride, and $^{18}$F-desmethoxyfallypride.

In some embodiments, the diagnostic agent is a near-IR imaging agent. Examples of near-IR imaging agents include Pz 247, DyLight 750, DyLight 800, cyanine dyes (e.g., Cy5, Cy5.5, Cy7), AlexaFluor 680, AlexaFluor 750, IRDye 680, IRDye 800CW, and Kodak X-SIGHT dyes.

In some embodiments, the agent can be a radionuclide, e.g., for use as a therapeutic, diagnostic, or prognostic agents. Among the radionuclides used, gamma-emitters, positron-emitters, and X-ray emitters are suitable for diagnostic and/or therapy, while beta emitters and alpha-emitters may also be used for therapy. Suitable radionuclides for forming use with various embodiments of the present invention include, but are not limited to, $^{123}$I, $^{125}$I, $^{130}$I, $^{131}$I, $^{133}$I, $^{135}$I, $^{47}$Sc, $^{72}$As, $^{72}$Sc, $^{90}$Y, $^{88}$Y, $^{97}$Ru, $^{100}$Pd, $^{101m}$Ru, $^{119}$Sb, $^{128}$Ba, $^{197}$Hg, $^{211}$At, $^{212}$Bi, $^{212}$Pb, $^{109}$Pd, $^{111}$In, $^{67}$Ga, $^{68}$Ga, $^{67}$Cu, $^{75}$Br, $^{77}$Br, $^{99m}$Tc, $^{14}$C, $^{13}$N, $^{15}$O, $^{32}$P, $^{33}$P, or $^{18}$F.

In certain embodiments, at least one instance of the diagnostic agent is a contrast agent. In certain embodiments, at least one instance of the contrast agent is a magnetic-resonance signal enhancing agent, X-ray attenuating agent, ultrasound scattering agent, or ultrasound frequency shifting agent.

In certain embodiments, M being a pharmaceutical agent refers to M being a monovalent radical of the pharmaceutical agent. In certain embodiments, the monovalent radical of the pharmaceutical agent is formed by removing a hydrogen atom from the moiety HV of the pharmaceutical agent. In certain embodiments, V is a carbon atom. In certain embodiments, V is a heteroatom. In certain embodiments, V is an oxygen atom. In certain embodiments, V is a sulfur atom. In certain embodiments, V is a nitrogen atom. In certain embodiments, the monovalent radical of the pharmaceutical agent is formed further by changing the atom V of the pharmaceutical agent to substituted or unsubstituted U, wherein each of V and U is a heteroatom, and V and U are different from each other.

In certain embodiments, at least two instances of M of at least one instance of the monomers, or a tautomer, isotopically labeled compound, salt, solvate, polymorph, or co-crystal thereof, are different from each other. In certain embodiments, at least one instance of M of a first instance of the monomers, or a tautomer, isotopically labeled compound, salt, solvate, polymorph, or co-crystal thereof, is different from at least one instance of M of a second instance of the monomers, or a tautomer, isotopically labeled compound, salt, solvate, polymorph, or co-crystal thereof. In certain embodiments, all instances of M are the same.

In certain embodiments, each instance of m is 1. In certain embodiments, at least one instance of m is 1. In certain embodiments, each instance of m is 1. In certain embodiments, at least one instance of m is an integer from 2 to 10, inclusive. In certain embodiments, at least one instance of m is 2, 3, 4, or 5. In certain embodiments, the end-functionalized polymer comprises between 10 and 1,000 (e.g., between 10 and 30, between 30 and 100, between 100 and 300, or between 300 and 1,000), inclusive, instances of M.

In certain embodiments, each instance of $R^B$ is independently H, F, Cl, or —CH$_3$. In certain embodiments, each instance of $R^B$ is H.

In certain embodiments, each instance of b is independently 0, 1, 2, 3, or 4. In certain embodiments, each instance of b is independently 1, 2, 3, or 4. In certain embodiments, each instance of b is 2.

In certain embodiments, each instance of e is independently 1, 2, 3, or 4. In certain embodiments, each instance of e is 1. In certain embodiments, each instance of e is independently 2, 3, or 4.

In certain embodiments, at least one instance of X is OR$^C$. In certain embodiments, each instance of X is OR$^C$. In certain embodiments, at least one instance of X is N(R$^D$)$_2$. In certain embodiments, each instance of X is N(R$^D$)$_2$. In certain embodiments, each instance of R$^C$ is independently hydrogen, substituted or unsubstituted, C$_{1-6}$ alkyl, an oxygen protecting group, or a leaving group; and at least one instance of R$^D$ is hydrogen, substituted or unsubstituted, C$_{1-6}$ alkyl, or a nitrogen protecting group. In certain embodiments, each instance of X is —OR$^C$, wherein R$^C$ is an oxygen protecting group or a leaving group. In certain embodiments, each instance of X is —OH. In certain embodiments, at least one instance of X is

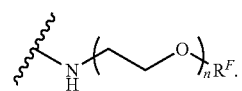

In certain embodiments, each instance of X is

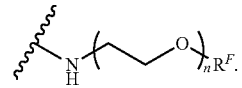

In certain embodiments, each instance of X is

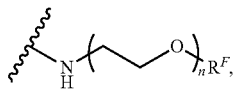

wherein each instance of n is independently an integer from 40 to 100, inclusive; and each instance of $R^F$ is independently hydrogen or unsubstituted $C_{1-6}$ alkyl.

In certain embodiments, each instance of $R^c$ or at least one instance of $R^D$ is substituted or unsubstituted, $C_{50-1000}$ heteroalkyl. In certain embodiments, each instance of $R^C$ or at least one instance of $R^D$ is

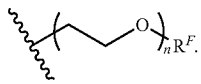

wherein:
each instance of n is independently an integer from 1 to 300, inclusive; and
each instance of $R^F$ is independently hydrogen, substituted or unsubstituted, $C_{1-6}$ alkyl, or an oxygen protecting group.

In certain embodiments, at least one instance of n is an integer from 10 to 30, from 30 to 100, from 100 to 300, or from 300 to 1,000, inclusive. In certain embodiments, at least one instance of n is an integer from 40 to 100, inclusive. In certain embodiments, at least one instance of n is an integer from 50 to 80, inclusive.

In certain embodiments, each instance of $R^c$ or at least one instance of $R^D$ is

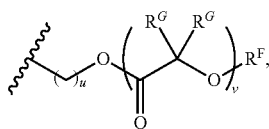

wherein:
each instance of u is independently 1, 2, 3, 4, 5, or 6;
each instance of $R^G$ is independently hydrogen, halogen, or substituted or unsubstituted, $C_{1-6}$ alkyl;
each instance of v is independently an integer from 1 to 300, inclusive; and
each instance of $R^F$ is independently hydrogen, substituted or unsubstituted, $C_{1-6}$ alkyl, or an oxygen protecting group.

In certain embodiments, at least one instance of $R^D$ is substituted or unsubstituted, $C_{1-1000}$ heteroalkyl, e.g., unsubstituted, $C_{40-400}$ heteroalkyl. In certain embodiments, at least one instance of $R^D$ is —$(CH_2CH_2O)_{30-200}$—H or —$(CH_2CH_2O)_{30-200}$-(substituted or unsubstituted, $C_{1-6}$ alkyl). In certain embodiments, at least one instance of $R^D$ is —$(CH_2CH_2O)_{10-30}$—H, —$(CH_2CH_2O)_{10-30}$-(substituted or unsubstituted, $C_{1-6}$ alkyl), —$(CH_2CH_2O)_{30-100}$—H, —$(CH_2CH_2O)_{30-100}$-(substituted or unsubstituted, $C_{1-6}$ alkyl), —$(CH_2CH_2O)_{100-300}$—H, —$(CH_2CH_2O)_{100-300}$-(substituted or unsubstituted, $C_{1-6}$ alkyl), —$(CH_2CH_2O)_{300-1000}$—H, or —$(CH_2CH_2O)_{300-1000}$-(substituted or unsubstituted, $C_{1-6}$ alkyl).

In certain embodiments,

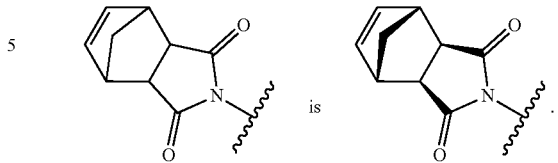

The monomers may be described by a number of properties, including molecular weight and hydrodynamic diameter. In some embodiments, the molecular weight of the monomer is between about 1 kDa and about 10 kDa, e.g., between about 2 kDa and about 8 kDa or about 3 kDa and about 6 kDa, e.g., as detected by mass spectrometry. In some embodiments, the molecular weight of the monomer is between about 3 kDa and about 6 kDa. In some embodiments, the molecular weight of the monomer is about 2 kDa, about 3 kDa, about 4 kDa, about 5 kDa, or about 6 kDa. In some embodiments, the hydrodynamic diameter of the monomer is between about 0.5 nm and about 3 nm, e.g., about 1 nm and about 2 nm, e.g., as detected by dynamic light scattering.

In another aspect, the present disclosure provides a conjugate of Formula (IV'):

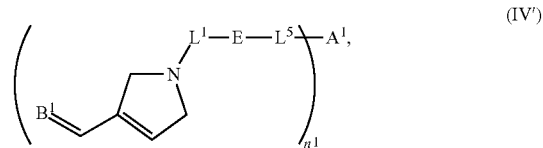

or a tautomer, isotopically labeled conjugate, or salt thereof, wherein:
each instance of $B^1$ is a polymer, wherein each instance of the polymer comprises independently one or more pharmaceutical agents;
each instance of $L^1$ is independently substituted or unsubstituted, $C_{1-1000}$ alkylene, substituted or unsubstituted, $C_{2-1000}$ alkenylene, substituted or unsubstituted, $C_{2-1000}$ alkynylene, substituted or unsubstituted, $C_{1-1000}$ heteroalkylene, substituted or unsubstituted, $C_{2-1000}$ heteroalkenylene, or substituted or unsubstituted, $C_{2-1000}$ heteroalkynylene;
optionally wherein one or more backbone carbon atoms of the $C_{1-1000}$ alkylene, $C_{2-1000}$ alkenylene, $C_{2-1000}$ alkynylene, $C_{1-1000}$ heteroalkylene, $C_{2-1000}$ heteroalkenylene, or $C_{2-1000}$ heteroalkynylene are independently replaced with substituted or unsubstituted carbocyclylene, substituted or unsubstituted heterocyclylene, substituted or unsubstituted arylene, or substituted or unsubstituted heteroarylene, as valency permits;
each instance of E is independently a moiety formed by reacting under suitable conditions an instance of $E^1$ with an instance of $E^2$;
each instance of $E^1$ is independently a thiophile, a first click-chemistry handle, a nucleophile, an electrophile, or a leaving group, H, halogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted carbocyclyl, substituted or unsubstituted heterocyclyl, substituted or unsubstituted aryl, substituted or unsubstituted heteroaryl, —$OR^a$, —$N(R^a)_2$, —$SR^a$, —CN, —SCN, —C(=O)$R^a$, —C(=O)$OR^a$, —C(=O)N($R^a$)$_2$, —C(=N$R^a$)$R^a$, —C(=N$R^a$)$OR^a$, —C(=N$R^a$)N($R^a$)$_2$, —NO$_2$, —N$_3$, —NR$^a$C(=O)R$^a$, —NR$^a$C(=O)OR$^a$, —NR$^a$C(=O)N(R$^a$)$_2$, —NR$^a$C(=NR$^a$)R$^a$, —NR$^a$C(=NR$^a$)OR$^a$, —NR$^a$C(=NR$^a$)N(R$^a$)$_2$, —OC(=O)R$^a$, —OC(=O)OR$^a$, —OC(=O)N(R$^a$)$_2$, —OC(=NR$^a$)R$^a$, —OC(=NR$^a$)OR$^a$, —OC(=NR$^a$)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OS(=O)R$^a$, —OS(=O)OR$^a$, —OS(=O)N(R$^a$)$_2$, —S(=O)R$^a$, —S(=O)OR$^a$, —S(=O)N(R$^a$)$_2$, —OS(=O)$_2$R$^a$, —OS(=O)$_2$OR$^a$, —OS(=O)$_2$N(R$^a$)$_2$, —S(=O)$_2$R$^a$, —S(=O)$_2$OR$^a$, —S(=O)$_2$N(R$^a$)$_2$, or —P(=O)(R$^a$)$_2$;

each instance of E$^2$ is independently —SH, a second click-chemistry handle, an electrophile, a nucleophile, or a leaving group, H, halogen, substituted or unsubstituted, C$_{1-6}$ alkyl, substituted or unsubstituted, C$_{2-6}$ alkenyl, substituted or unsubstituted, C$_{2-6}$ alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=O)R$^a$, —C(=O)OR$^a$, —C(=O)N(R$^a$)$_2$, —C(=NR$^a$)R$^a$, —C(=NR$^a$)OR$^a$, —C(=NR$^a$)N(R$^a$)$_2$, —NO$_2$, —N$_3$, —NR$^a$C(=O)R$^a$, —NR$^a$C(=O)OR$^a$, —NR$^a$C(=O)N(R$^a$)$_2$, —NR$^a$C(=NR$^a$)R$^a$, —NR$^a$C(=NR$^a$)OR$^a$, —NR$^a$C(=NR$^a$)N(R$^a$)$_2$, —OC(=O)R$^a$, —OC(=O)OR$^a$, —OC(=O)N(R$^a$)$_2$, —OC(=NR$^a$)R$^a$, —OC(=NR$^a$)OR$^a$, —OC(=NR$^a$)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OS(=O)R$^a$, —OS(=O)OR$^a$, —OS(=O)N(R$^a$)$_2$, —S(=O)R$^a$, —S(=O)OR$^a$, —S(=O)N(R$^a$)$_2$, —OS(=O)$_2$R$^a$, —OS(=O)$_2$OR$^a$, —OS(=O)$_2$N(R$^a$)$_2$, —S(=O)$_2$R$^a$, —S(=O)$_2$OR$^a$, —S(=O)$_2$N(R$^a$)$_2$, or —P(=O)(R$^a$)$_2$;

each instance of R$^a$ is independently H, substituted or unsubstituted, C$_{1-6}$ alkyl, substituted or unsubstituted, C$_{2-6}$ alkenyl, substituted or unsubstituted, C$_{2-6}$ alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of R$^a$ attached to a nitrogen atom are joined with the nitrogen atom to form substituted or unsubstituted heterocyclyl or substituted or unsubstituted heteroaryl;

n1 is an integer between 1 and 20, inclusive; and

A$^1$ is a peptide, protein, nucleoprotein, mucoprotein, lipoprotein, glycoprotein, or polynucleotide.

In certain embodiments, Formula (IV') is Formula (IV).

In certain embodiments, at least one instance of L$^1$ is substituted or unsubstituted, C$_{1-30}$ alkylene. In certain embodiments, at least one instance of L$^1$ is substituted or unsubstituted, C$_{30}$-100 alkylene. In certain embodiments, at least one instance of L$^1$ is substituted or unsubstituted, C$_{100-300}$ alkylene. In certain embodiments, at least one instance of L$^1$ is substituted or unsubstituted, C$_{300-1000}$ alkylene.

In certain embodiments, at least one instance of L$^1$ is substituted or unsubstituted, C$_{1-30}$ heteroalkylene. In certain embodiments, at least one instance of L$^1$ is substituted or unsubstituted, C$_{30-100}$ heteroalkylene. In certain embodiments, at least one instance of L$^1$ is substituted or unsubstituted, C$_{100-300}$ heteroalkylene. In certain embodiments, at least one instance of L$^1$ is substituted or unsubstituted, C$_{300-1000}$ heteroalkylene.

In certain embodiments, optionally wherein one, two, three, four, or five backbone carbon atoms of the C$_{1-1000}$ alkylene, C$_{2-1000}$ alkenylene, C$_{2-1000}$ alkynylene, C$_{1-1000}$ heteroalkylene, C$_{2-1000}$ heteroalkenylene, or C$_{2-1000}$ heteroalkynylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of L$^1$ is substituted or unsubstituted, C$_{1-30}$ alkylene, optionally wherein one, two, or three backbone carbon atoms of the C$_{1-30}$ alkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of L$^1$ is substituted or unsubstituted, C$_{30-100}$ alkylene, optionally wherein one, two, or three backbone carbon atoms of the C$_{30-100}$ alkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of L$^1$ is substituted or unsubstituted, C$_{100-300}$ alkylene, optionally wherein one, two, or three backbone carbon atoms of the C$_{100-300}$ alkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of L$^1$ is substituted or unsubstituted, C$_{300-1000}$ alkylene, optionally wherein one, two, or three backbone carbon atoms of the C$_{300-1000}$ alkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of L$^1$ is substituted or unsubstituted, C$_{1-30}$ heteroalkylene, optionally wherein one, two, or three backbone carbon atoms of the C$_{1-30}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of L$^1$ is substituted or unsubstituted, C$_{30-100}$ heteroalkylene, optionally wherein one, two, or three backbone carbon atoms of the C$_{30-100}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of L$^1$ is substituted or unsubstituted, C$_{100-300}$ heteroalkylene, optionally wherein one, two, or three backbone carbon atoms of the C$_{100-300}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of L$^1$ is substituted or unsubstituted, C$_{300}$-moo heteroalkylene, optionally wherein one, two, or three backbone carbon atoms of the C$_{300-1000}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of $L^1$ is substituted or unsubstituted, $C_{1-1000}$ alkylene or substituted or unsubstituted, $C_{1-1000}$ heteroalkylene, optionally wherein one, two, or three backbone carbon atoms of the $C_{1-1000}$ alkylene or $C_{1-1000}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of $L^1$ is substituted or unsubstituted, $C_{3-400}$ alkylene or substituted or unsubstituted, $C_{2-400}$ heteroalkylene, optionally wherein one, two, or three backbone carbon atoms of the $C_{3-400}$ alkylene or $C_{2-400}$ heteroalkylene are independently replaced with substituted or unsubstituted, monocyclic, 3- to 10-membered carbocyclylene, substituted or unsubstituted, monocyclic, 3- to 10-membered heterocyclylene, substituted or unsubstituted phenyl, or substituted or unsubstituted, monocyclic, 5- to 6-membered heteroarylene, as valency permits.

In certain embodiments, the optional substituents included in at least one instance of $L^1$ are independently halogen (e.g., F), unsubstituted $C_{1-6}$ alkyl, $C_{1-6}$ alkyl substituted with one or more halogen (e.g., F), —O-(unsubstituted $C_{1-6}$ alkyl), —O—($C_{1-6}$ alkyl substituted with one or more halogen (e.g., F)), or oxo.

In certain embodiments, the carbocyclylene or heterocyclylene included in at least one instance of $L^1$ is monocyclic and 3- to 10-membered. In certain embodiments, the arylene included in at least one instance of $L^1$ is phenylene. In certain embodiments, the heteroarylene included in at least one instance of $L^1$ is monocyclic and 5- to 6-membered.

In certain embodiments, at least one instance of $L^1$ is independently

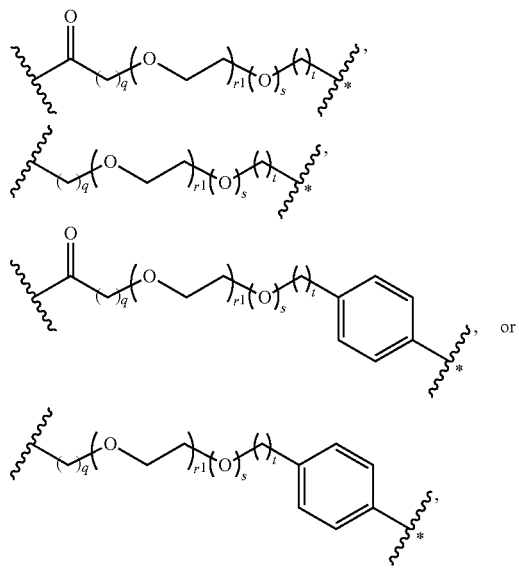

wherein:
each instance of q is independently an integer from 1 to 10, inclusive;
each instance of r1 is independently an integer from 2 to 40, inclusive;
each instance of s is independently 0 or 1;
each instance of t is independently an integer from 0 to 10, inclusive; and
the attachment point marked with "*" is attached to $E^1$ or E.

In certain embodiments, at least one instance of $L^5$ is substituted or unsubstituted, $C_{1-30}$ alkylene. In certain embodiments, at least one instance of $L^5$ is substituted or unsubstituted, $C_{30-100}$ alkylene. In certain embodiments, at least one instance of $L^5$ is substituted or unsubstituted, $C_{100-300}$ alkylene. In certain embodiments, at least one instance of $L^5$ is substituted or unsubstituted, $C_{300-1000}$ alkylene.

In certain embodiments, at least one instance of $L^5$ is substituted or unsubstituted, $C_{1-30}$ heteroalkylene. In certain embodiments, at least one instance of $L^5$ is substituted or unsubstituted, $C_{30-100}$ heteroalkylene. In certain embodiments, at least one instance of $L^5$ is substituted or unsubstituted, $C_{100-300}$ heteroalkylene. In certain embodiments, at least one instance of $L^5$ is substituted or unsubstituted, $C_{300-1000}$ heteroalkylene.

In certain embodiments, optionally wherein one, two, three, four, or five backbone carbon atoms of the $C_{1-1000}$ alkylene, $C_{2-1000}$ alkenylene, $C_{2-1000}$ alkynylene, $C_{1-1000}$ heteroalkylene, $C_{2-1000}$ heteroalkenylene, or $C_{2-1000}$ heteroalkynylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of $L^5$ is substituted or unsubstituted, $C_{1-30}$ alkylene, optionally wherein one, two, or three backbone carbon atoms of the $C_{1-30}$ alkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of $L^5$ is substituted or unsubstituted, $C_{30-100}$ alkylene, optionally wherein one, two, or three backbone carbon atoms of the $C_{30-100}$ alkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of $L^5$ is substituted or unsubstituted, $C_{100-300}$ alkylene, optionally wherein one, two, or three backbone carbon atoms of the $C_{100-300}$ alkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of $L^5$ is substituted or unsubstituted, $C_{300-1000}$ alkylene, optionally wherein one, two, or three backbone carbon atoms of the $C_{300-1000}$ alkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of $L^5$ is substituted or unsubstituted, $C_{1-30}$ heteroalkylene, optionally wherein one, two, or three backbone carbon atoms of the $C_{1-30}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of $L^5$ is substituted or unsubstituted, $C_{30-100}$ heteroalkylene, optionally wherein one, two, or three backbone carbon atoms of the $C_{30-100}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of $L^5$ is substituted or unsubstituted, $C_{100-300}$ heteroalkylene, optionally wherein one, two, or three backbone carbon atoms of the $C_{100-300}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of $L^5$ is substituted or unsubstituted, $C_{300-1000}$ heteroalkylene, optionally wherein one, two, or three backbone carbon atoms of the $C_{300-1000}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of $L^5$ is substituted or unsubstituted, $C_{1-1000}$ alkylene or substituted or unsubstituted, $C_{1-1000}$ heteroalkylene, optionally wherein one, two, or three backbone carbon atoms of the $C_{1-1000}$ alkylene or $C_{1-1000}$ heteroalkylene are independently replaced with substituted or unsubstituted carbocyclylene, substituted or unsubstituted heterocyclylene, substituted or unsubstituted arylene, or substituted or unsubstituted heteroarylene, as valency permits.

In certain embodiments, at least one instance of $L^5$ is substituted or unsubstituted, $C_{3-400}$ alkylene or substituted or unsubstituted, $C_{2-400}$ heteroalkylene, optionally wherein one, two, or three backbone carbon atoms of the $C_{3-400}$ alkylene or $C_{2-400}$ heteroalkylene are independently replaced with substituted or unsubstituted, monocyclic, 3- to 10-membered carbocyclylene, substituted or unsubstituted, monocyclic, 3- to 10-membered heterocyclylene, substituted or unsubstituted phenyl, or substituted or unsubstituted, monocyclic, 5- to 6-membered heteroarylene, as valency permits.

In certain embodiments, the optional substituents included in at least one instance of $L^5$ are independently halogen (e.g., F), unsubstituted $C_{1-6}$ alkyl, $C_{1-6}$ alkyl substituted with one or more halogen (e.g., F), —O—(unsubstituted $C_{1-6}$ alkyl), —O—($C_{1-6}$ alkyl substituted with one or more halogen (e.g., F)), or oxo.

In certain embodiments, the carbocyclylene or heterocyclylene included in at least one instance of $L^5$ is monocyclic and 3- to 10-membered. In certain embodiments, the arylene included in at least one instance of $L^5$ is phenylene. In certain embodiments, the heteroarylene included in at least one instance of $L^5$ is monocyclic and 5- to 6-membered.

In certain embodiments, at least one instance of $L^5$ is independently

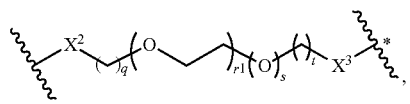

wherein:
each instance of $X^2$ is independently —O—, —S—, —S—S—, —NH—, —C(=O)—, —C(=O)—O—, —C(=O)—NH—, —O—C(=O)—, —NH—C(=O)—, —O—C(=O)—O—, —O—C(=O)—NH—, —NH—C(=O)—O—, or —NH—C(=O)—NH—;

each instance of $X^3$ is independently —O—, —S—, —S—S—, —NH—, —C(=O)—, —C(=O)—O—, —C(=O)—NH—, —O—C(=O)—, —NH—C(=O)—, —O—C(=O)—O—, —O—C(=O)—NH—, —NH—C(=O)—O—, or —NH—C(=O)—NH—;

each instance of q is independently an integer from 1 to 10, inclusive;

each instance of r1 is independently an integer from 2 to 40, inclusive;

each instance of s is independently 0 or 1;

each instance of t is independently an integer from 0 to 10, inclusive; and the attachment point marked with "*" is attached to $E^2$ or E.

In certain embodiments, n1 is an integer between 1 and 10, inclusive. In certain embodiments, n1 is 1, 2, 3, 4, 5, or 6. In certain embodiments, n1 is 1, 2, or 3. In certain embodiments, n1 is 1 or 2. In certain embodiments, n1 is 1. In certain embodiments, n1 is 2. In certain embodiments, n1 is 3. In certain embodiments, the conjugate is a mixture of at least a conjugate where n1 is 1 and a conjugate where n1 is 2. In certain embodiments, the conjugate is a mixture of at least two of: a conjugate where n1 is 1, a conjugate where n1 is 2, and a conjugate where n1 is 3. In certain embodiments, the conjugate is purified so that between 50% and 70%, between 70% and 90%, between 90% and 95%, between 95% and 99%, or between 99% and 99.9% of all instances of n1 are the same. In certain embodiments, the conjugate is purified so that between 50% and 70%, between 70% and 90%, between 90% and 95%, between 95% and 99%, or between 99% and 99.9% of all instances of n1 are 1. In certain embodiments, the conjugate is purified so that between 50% and 70%, between 70% and 90%, between 90% and 95%, between 95% and 99%, or between 99% and 99.9% of all instances of n1 are 2. In certain embodiments, the conjugate is purified so that between 50% and 70%, between 70% and 90%, between 90% and 95%, between 95% and 99%, or between 99% and 99.9% of all instances of n1 are 3.

In certain embodiments, $A^1$ is an antibody. In certain embodiments, $A^1$ is an immunoglobulin G (IgG). In certain embodiments, $A^1$ is an IgG1, IgG2, IgG3, or IgG4. In certain embodiments, $A^1$ is an immunoglobulin A (IgA), immunoglobulin D (IgD), immunoglobulin E (IgE), or immunoglobulin M (IgM). In certain embodiments, $A^1$ is IgA1 or IgA2, In certain embodiments, $A^1$ is an anti-HER2 antibody (e.g., trastuzumab) or anti-MUC1 antibody. In certain embodiments, $A^1$ is an anti-oncoprotein antibody, and the oncoprotein is an oncoprotein of the cancer described herein. In certain embodiments, the antibody is a monoclonal antibody. In certain embodiments, the antibody is a polyclonal antibody. In certain embodiments, the antibody is a humanized antibody. In certain embodiments, $A^1$ is a peptide or protein. In certain embodiments, $A^1$ is a peptide or protein and comprises between 3 and 10, between 10 and 30, between 30 and 100, between 100 and 300, between 300 and 1,000, between 1,000 and 3,000, or between 3,000 and 10,000, inclusive, amino acids.

In certain embodiments, E¹ is a thiophile. In certain embodiments, E¹ is

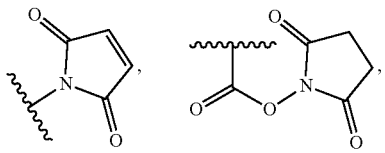 [SMILES: *N1C(=O)C=CC1=O ; *C(=O)ON1C(=O)CCC1=O]

or —OS(=O)₂(substituted or unsubstituted phenyl or substituted or unsubstituted, $C_{1-6}$ alkyl). In certain embodiments, E¹ is —C(=O)OH. In certain embodiments, E¹ is a first click-chemistry handle. In certain embodiments, E¹ is —N₃. In certain embodiments, E¹ is substituted or unsubstituted nitrone. In certain embodiments, E¹ is trans-cyclooctenyl, e.g.,

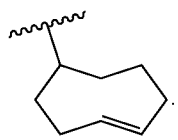 [SMILES: *C1CC/C=C/CCC1]

In certain embodiments, E¹ is substituted or unsubstituted 1,2,4,5-tetrazinyl. In certain embodiments, E¹ is

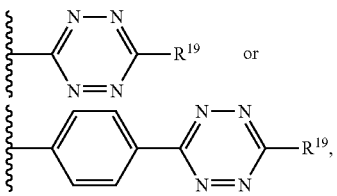

wherein $R^{19}$ is H, halogen, unsubstituted $C_{1-6}$ alkyl, or —O-(unsubstituted $C_{1-6}$ alkyl). In certain embodiments, E¹ is substituted or unsubstituted tetrazolyl. In certain embodiments, E¹ is an electrophile. In certain embodiments, E¹ is a leaving group. In certain embodiments, E¹ is H. In certain embodiments, E¹ is a polymerization handle. In certain embodiments, E¹ is an addition polymerization handle or condensation polymerization handle. In certain embodiments, E¹ is a metathesis polymerization handle. In certain embodiments, E¹ is substituted or unsubstituted $C_{2-6}$ alkenyl or substituted or unsubstituted $C_{2-6}$ alkynyl. In certain embodiments, E¹ is —OH, —NH₂, —C(=O)OH, or —C(=O)H. In certain embodiments, E¹ is a nucleophile, an electrophile, a leaving group, substituted or unsubstituted $C_{2-6}$ alkenyl, substituted or unsubstituted $C_{2-6}$ alkynyl, —OH, —SH, —NHR$^a$, —N₃, —C(=O)OH, —C(=O)N(R$^a$)₂, —C(=NR$^a$)OH, —S(=O)OH, —S(=O)₂OH, —C(=O)-(a leaving group), —C(=NR$^a$)-(a leaving group), —S(=O)-(a leaving group), or —S(=O)₂-(a leaving group). In certain embodiments, E¹ is —N₃, substituted or unsubstituted 1,2,4,5-tetrazinyl, or substituted or unsubstituted tetrazolyl.

In certain embodiments, E² is —SH. In certain embodiments, E² is a click-chemistry handle. In certain embodiments, E² is CC. In certain embodiments, E² is —C≡CH. In certain embodiments, E² is substituted or unsubstituted, monocyclic, bicyclic, or tricyclic cycloalkynyl. In certain embodiments, E² is substituted or unsubstituted, cyclooctynyl or azacyclooctynyl. In certain embodiments, E² is substituted or unsubstituted, dibenzocyclooctynyl or dibenzo-5-azacyclooctynyl. In certain embodiments, E² is

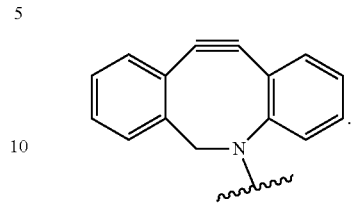

In certain embodiments, E² is

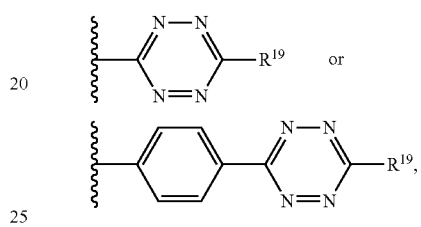

wherein $R^{19}$ is H, halogen, unsubstituted $C_{1-6}$ alkyl, or —O-(unsubstituted $C_{1-6}$ alkyl). In certain embodiments, $R^{19}$ is —CH₃. In certain embodiments, E² is non-aromatic C=C. In certain embodiments, E² is substituted or unsubstituted, monocyclic, bicyclic, or tricyclic, trans-cycloalkenyl. In certain embodiments, E² is trans-cyclooctenyl, e.g.,

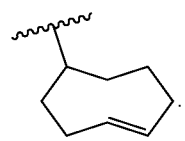 [SMILES: *C1CC/C=C/CCC1]

In certain embodiments, E² is substituted or unsubstituted, norbornenyl, 7-oxanorbornenyl, or 7-azanorbornenyl. In certain embodiments, E² is substituted or unsubstituted, norbornadienyl, 7-oxanorbornadienyl, or 7-azanorbornadienyl. In certain embodiments, E² is a nucleophile, an electrophile, a leaving group, substituted or unsubstituted $C_{2-6}$ alkenyl, substituted or unsubstituted $C_{2-6}$ alkynyl, —OH, —SH, —NHR$^a$, —N₃, —C(=O)OH, —C(=O)N(R$^a$)₂, —C(=NR$^a$)OH, —S(=O)OH, —S(=O)₂OH, —C(=O)-(a leaving group), —C(=NR$^a$)-(a leaving group), —S(=O)-(a leaving group), or —S(=O)₂-(a leaving group). In certain embodiments, E² is CC or non-aromatic C=C.

In certain embodiments, E¹ is —N₃, and E² is

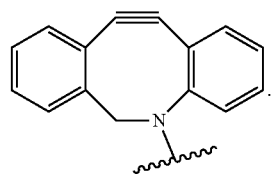 [SMILES: *N1Cc2ccccc2C#Cc2ccccc21]

In certain embodiments, E¹ is trans-cyclooctenyl, e.g.,

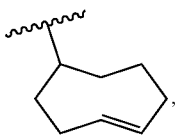

and E² is

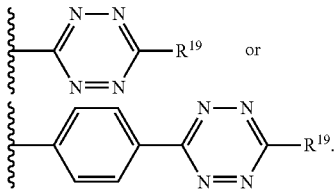

In certain embodiments, E¹ is

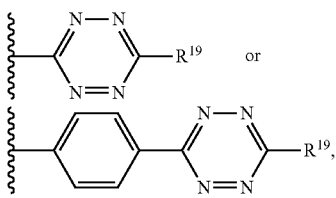

and E² is trans-cyclooctenyl, e.g., 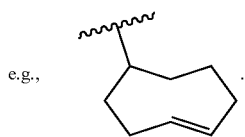 [SMILES: *C1CC/C=C/CCC1]

In certain embodiments, E¹ is —N₃, substituted or unsubstituted 1,2,4,5-tetrazinyl, or substituted or unsubstituted tetrazolyl, and E² is CC or non-aromatic C=C.

In certain embodiments, E is

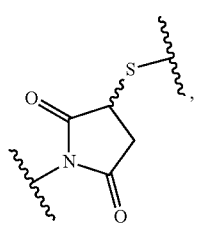

wherein the S is attached to A¹. In certain embodiments, E is a moiety formed by reacting two click-chemistry handles (e.g., two orthogonal click-chemistry handles). In certain embodiments, E is a single bond, —O—, —S—, —NR$^a$—, —C(=O)O—, —C(=NR$^a$)O—, —S(=O)O—, —S(=O)₂O—, —C(=O)NR$^a$—, —C(=NR$^a$)NR$^a$—, —S(=O)NR$^a$—, —S(=O)₂NR$^a$—, —OC(=O)—, —OC(=NR$^a$)—, —OS(=O)—, —OS(=O)₂—, —NR$^a$C(=O)—, —NR$^a$C(=NR$^a$)—, —NR$^a$S(=O)—, —NR$^a$S(=O)₂—, —OC(=O)O—, —OC(=NR$^a$)O—, —OS(=O)O—, —OS(=O)₂O—, —NR$^a$C(=O)O—, —NR$^a$C(=NR$^a$)O—, —NR$^a$S(=O)O—, —NR$^a$S(=O)₂O—, —OC(=O)NR$^a$—, —OC(=NR$^a$)NR$^a$—, —OS(=O)NR$^a$—, —OS(=O)₂NR$^a$—, —NR$^a$C(=O)NR$^a$—, —NR$^a$C(=NR$^a$)NR$^a$—, —NR$^a$S(=O)NR$^a$—, —NR$^a$S(=O)₂NR$^a$—, —C(=O)—, —C(=NR$^a$)—, —S(=O)—, or —S(=O)₂—. In certain embodiments, E is

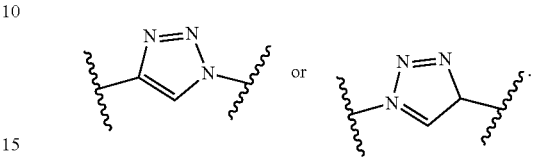

In another aspect, the present disclosure provides a method of preparing a conjugate of Formula (IV'), or a tautomer, isotopically labeled conjugate, or salt thereof, the method comprising reacting the end-functionalized polymer with a biomolecule of Formula (C'):

$$(E^2-L^5)_{n1}A^1 \qquad (C'),$$

wherein:
each instance of E² is independently —SH, a second click-chemistry handle, an electrophile, a nucleophile, or a leaving group, H, halogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)₂, —SR$^a$, —CN, —SCN, —C(=O)R$^a$, —C(=O)OR$^a$, —C(=O)N(R$^a$)₂, —C(=NR$^a$)R$^a$, —C(=NR$^a$)OR$^a$, —C(=NR$^a$)N(R$^a$)₂, —NO₂, —N₃, —NR$^a$C(=O)R$^a$, —NR$^a$C(=O)OR$^a$, —NR$^a$C(=O)N(R$^a$)₂, —NR$^a$C(=NR$^a$)R$^a$, —NR$^a$C(=NR$^a$)OR$^a$, —NR$^a$C(=NR$^a$)N(R$^a$)₂, —OC(=O)R$^a$, —OC(=O)OR$^a$, —OC(=O)N(R$^a$)₂, —OC(=NR$^a$)R$^a$, —OC(=NR$^a$)OR$^a$, —OC(=NR$^a$)N(R$^a$)₂, —NR$^a$S(=O)₂R$^a$, —NR$^a$S(=O)₂OR$^a$, —NR$^a$S(=O)₂N(R$^a$)₂, —OS(=O)R$^a$, —OS(=O)OR$^a$, —OS(=O)N(R$^a$)₂, —S(=O)R$^a$, —S(=O)OR$^a$, —S(=O)N(R$^a$)₂, —OS(=O)₂R$^a$, —OS(=O)₂OR$^a$, —OS(=O)₂N(R$^a$)₂, —S(=O)₂R$^a$, —S(=O)₂OR$^a$, —S(=O)₂N(R$^a$)₂, or —P(=O)(R$^a$)₂;
n1 is an integer between 1 and 20, inclusive;
A¹ is a peptide, protein, nucleoprotein, mucoprotein, lipoprotein, glycoprotein, or polynucleotide; and
each instance of E is independently a moiety formed by reacting under suitable conditions an instance of E¹ with an instance of E².

In certain embodiments, Formula (C') is Formula (C):

$$(E^2)_{n1}-A^1 \qquad (C).$$

In certain embodiments, the suitable conditions are physiological conditions.

Compositions, Kits, and Methods of Use

In another aspect, the present disclosure provides a composition comprising the enyne, or a tautomer, isotopically labeled compound, salt, solvate, polymorph, or co-crystal thereof, and optionally an excipient. In certain embodiments, the composition comprises an effective amount of the enyne, or a tautomer, isotopically labeled compound, salt, solvate, polymorph, or co-crystal thereof.

In another aspect, the present disclosure provides a composition comprising the end-functionalized polymer, or a tautomer, isotopically labeled polymer, or salt thereof, and optionally an excipient. In certain embodiments, the composition comprises an effective amount of the end-functionalized polymer, or a tautomer, isotopically labeled polymer, or salt thereof.

In another aspect, the present disclosure provides a composition comprising the conjugate, or a tautomer, isotopically labeled conjugate, or salt thereof, and optionally an excipient. In certain embodiments, the composition comprises an effective amount of the conjugate, or a tautomer, isotopically labeled conjugate, or salt thereof.

In certain embodiments, the composition is a pharmaceutical composition, wherein the excipient is a pharmaceutically acceptable excipient.

In certain embodiments, the compositions are useful for delivering an agent (e.g., to a subject in need thereof or cell). In certain embodiments, the compositions are useful for treating a disease in a subject in need thereof. In certain embodiments, the compositions are useful for preventing a disease in a subject in need thereof. In certain embodiments, the compositions are useful for diagnosing a disease in a subject in need thereof.

In certain embodiments, the subject is an animal. In certain embodiments, the subject is a mammal. In certain embodiments, the subject is a human. In certain embodiments, the subject is a human two-years and older. In certain embodiments, the subject is a human eighteen-years and older.

In certain embodiments, the cell is in vitro. In certain embodiments, the cell is in vivo.

Pharmaceutical compositions described herein can be prepared by any method known in the art of pharmacology. In general, such preparatory methods include bringing the conjugate described herein (which may includes a therapeutic agent (the "active ingredient")) into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredient, the pharmaceutically acceptable excipient, and/or any additional ingredients in a pharmaceutical composition described herein will vary, depending upon the identity, size, and/or condition of the subject treated and further depending upon the route by which the composition is to be administered. The composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween® 20), polyoxyethylene sorbitan monostearate (Tween® 60), polyoxyethylene sorbitan monooleate (Tween® 80), sorbitan monopalmitate (Span® 40), sorbitan monostearate (Span® 60), sorbitan tristearate (Span® 65), glyceryl monooleate, sorbitan monooleate (Span® 80), polyoxyethylene esters (e.g., polyoxyethylene monostearate (Myrj® 45), polyoxyethylene hydrogenated castor oil, polyethoxylated castor oil, polyoxymethylene stearate, and Solutol®), sucrose fatty acid esters, polyethylene glycol fatty acid esters (e.g., Cremophor®), polyoxyethylene ethers, (e.g., polyoxyethylene lauryl ether (Brij® 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic® F-68, poloxamer P-188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, antiprotozoan preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant® Plus, Phenonip®, methylparaben, Germall® 115, Germaben® II, Neolone®, Kathon®, and Euxyl®.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates described herein are mixed with solubilizing agents such as Cremophor®, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P., and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form may be accomplished by dissolving or suspending the drug in an oil vehicle.

Compositions for rectal or vaginal administration are typically suppositories which can be prepared by mixing the conjugates described herein with suitable non-irritating excipients or carriers such as cocoa butter, polyethylene glycol, or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of encapsulating agents which can be used include polymeric substances and waxes.

Dosage forms for topical and/or transdermal administration of a conjugate described herein may include ointments, pastes, creams, lotions, gels, powders, solutions, sprays, inhalants, and/or patches. Generally, the active ingredient is admixed under sterile conditions with a pharmaceutically acceptable carrier or excipient and/or any needed preservatives and/or buffers as can be required. Additionally, the present disclosure contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices. Intradermal compositions can be administered by devices which limit the effective penetration length of a needle into the skin. Alternatively or additionally, conventional syringes can be used in the classical mantoux method of intradermal administration. Jet injection devices which deliver liquid formulations to the dermis via a liquid jet injector and/or via a needle which pierces the stratum corneum and produces a jet which reaches the dermis are suitable. Ballistic powder/particle delivery devices which use compressed gas to accelerate the conjugate in powder form through the outer layers of the skin to the dermis are suitable.

Formulations suitable for topical administration include liquid and/or semi-liquid preparations such as liniments, lotions, oil-in-water and/or water-in-oil emulsions such as creams, ointments, and/or pastes, and/or solutions and/or suspensions. Topically administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition described herein can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers, or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions described herein formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition described herein. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition described herein can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition described herein can be prepared, packaged, and/or sold in a formulation for ophthalmic administration. Such formulations may, for example, be in the form of eye drops including, for example, a 0.1-1.0% (w/w) solution and/or suspension of the active ingredient in an aqueous or oily liquid carrier or excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are also contemplated as being within the scope of this disclosure.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Polymers provided herein are typically formulated in dosage unit form for ease of administration and uniformity of dosage. It will be understood, however, that the total daily usage of the compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

The conjugates and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In certain embodiments, the conjugate or pharmaceutical composition described herein is suitable for topical administration to the eye of a subject.

The exact amount of a conjugate required to achieve an effective amount will vary from subject to subject, depending, for example, on species, age, and general condition of a subject, severity of the side effects or disorder, identity of the particular conjugate, mode of administration, and the like. An effective amount may be included in a single dose (e.g., single oral dose) or multiple doses (e.g., multiple oral doses). In certain embodiments, when multiple doses are administered to a subject or applied to a tissue or cell, any two doses of the multiple doses include different or substantially the same amounts of a conjugate described herein. In certain embodiments, when multiple doses are administered to a subject or applied to a tissue or cell, the frequency of administering the multiple doses to the subject or applying the multiple doses to the tissue or cell is three doses a day, two doses a day, one dose a day, one dose every other day, one dose every third day, one dose every week, one dose every two weeks, one dose every three weeks, or one dose every four weeks. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, the frequency of administering the multiple doses to the subject or applying the multiple doses to the tissue or cell is three doses per day. In certain embodiments, when multiple doses are administered to a subject or applied to a tissue or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, tissue, or cell. In certain embodiments, the duration between the first dose and last dose of the multiple doses is three months, six months, or one year. In certain embodiments, the duration between the first dose and last dose of the multiple doses is the lifetime of the subject, tissue, or cell. In certain embodiments, a dose (e.g., a single dose, or any dose of multiple doses) described herein includes independently between 0.1 μg and 1 μg, between 0.001 mg and 0.01 mg, between 0.01 mg and 0.1 mg, between 0.1 mg and 1 mg, between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of a conjugate described herein. In certain embodiments, a dose described herein includes independently between 1 mg and 3 mg, inclusive, of a conjugate described herein. In certain embodiments, a dose described herein includes independently between 3 mg and 10 mg, inclusive, of a conjugate described herein. In certain embodiments, a dose described herein includes independently between 10 mg and 30 mg, inclusive, of a conjugate described herein. In certain embodiments, a dose described herein includes independently between 30 mg and 100 mg, inclusive, of a conjugate described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult. In certain embodiments, a dose described herein is a dose to an adult human whose body weight is 70 kg.

The conjugate or composition can be administered in combination with one or more additional pharmaceutical agents (e.g., therapeutically and/or prophylactically active agents). The conjugate or composition can be administered in combination with additional pharmaceutical agents that improve their activity (e.g., activity (e.g., potency and/or efficacy) in treating a disease in a subject in need thereof, in preventing a disease in a subject in need thereof, in reducing the risk to develop a disease in a subject in need thereof, and/or in inhibiting the activity of a protein kinase in a subject or cell), improve bioavailability, improve safety, reduce drug resistance, reduce and/or modify metabolism, inhibit excretion, and/or modify distribution in a subject or cell. It will also be appreciated that the therapy employed may achieve a desired effect for the same disorder, and/or it may achieve different effects. In certain embodiments, a pharmaceutical composition described herein including a conjugate described herein and an additional pharmaceutical agent shows a synergistic effect that is absent in a pharmaceutical composition including one of the polymer/conjugate and the additional pharmaceutical agent, but not both.

The conjugate or composition can be administered concurrently with, prior to, or subsequent to one or more additional pharmaceutical agents, which are different from the conjugate or composition and may be useful as, e.g., combination therapies. Pharmaceutical agents include therapeutically active agents. Pharmaceutical agents also include prophylactically active agents. Pharmaceutical agents include small organic molecules such as drug compounds (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful for treating and/or preventing a disease (e.g., proliferative disease, hematological disease, neurological disease, painful condition, psychiatric disorder, or metabolic disorder). Each additional pharmaceutical agent may be administered at a dose and/or on a time schedule determined for that pharmaceutical agent. The additional pharmaceutical agents may also be administered together with each other and/or with the conjugate or composition described herein in a single dose or administered separately in different doses. The particular combination to employ in a regimen will take into account compatibility of the conjugate described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

The additional pharmaceutical agents include anti-proliferative agents, anti-cancer agents, cytotoxic agents, anti-angiogenesis agents, anti-inflammatory agents, immunosuppressants, anti-bacterial agents, anti-viral agents, cardiovascular agents, cholesterol-lowering agents, antidiabetic agents, anti-allergic agents, contraceptive agents, and pain-relieving agents. In certain embodiments, the additional pharmaceutical agent is an anti-proliferative agent. In certain embodiments, the additional pharmaceutical agent is an anti-cancer agent. In certain embodiments, the additional pharmaceutical agent is an anti-viral agent. In certain embodiments, the additional pharmaceutical agent is a binder or inhibitor of a protein kinase. In certain embodiments, the additional pharmaceutical agent is selected from the group consisting of epigenetic or transcriptional modulators (e.g., DNA methyltransferase inhibitors, histone deacetylase inhibitors (HDAC inhibitors), lysine methyltransferase inhibitors), antimitotic drugs (e.g., taxanes and vinca alkaloids), hormone receptor modulators (e.g., estrogen receptor modulators and androgen receptor modulators), cell signaling pathway inhibitors (e.g., tyrosine protein kinase inhibitors), modulators of protein stability (e.g., proteasome inhibitors), Hsp90 inhibitors, glucocorticoids, all-trans retinoic acids, and other agents that promote differentiation. In certain embodiments, the conjugate described herein or pharmaceutical composition can be administered in combination with an anti-cancer therapy including surgery, radiation therapy, transplantation (e.g., stem cell transplantation, bone marrow transplantation), immunotherapy, and chemotherapy.

In some embodiments, the percentage of the conjugates (e.g., in a particle) that comprise an agent is between about 1 and about 100% (e.g., about 1%, about 2%, about 3%, about 4%, about 5%, about 10%, about 15%, about 20%, about 30%, about 40%, about 50%, about 60%, about 70%, about 80%, about 90%, or about 100%). In some embodiments, the percentage of the conjugates that comprise an agent is less than about 50%, e.g., less than about 40%, less than about 35%, less than about 30%, less than about 25%, less than about 20%, less than about 15%, or less than about 10%. In some embodiments, the percentage of the conjugates (e.g., in a particle) that comprise an agent is between about 5% and about 50%, about 5% and about 40%, about 5% and about 30%, about 5% and about 25%, or about 5% and about 20%. In some embodiments, the percentage of the conjugates (e.g., in a particle) that comprise an agent is between about 5% and 90%. In some embodiments, the percentage of the conjugates (e.g., in a particle) that comprise an agent is between about 5% and about 75%. In the some embodiments, the the conjugates (e.g., in a particle) that comprise an agent is between about 5% and about 50%. In the some embodiments, the percentage of the conjugates (e.g., in a particle) that comprise an agent is between about 10% and about 25%.

In some embodiments, the total amount of the agent present in the Brush prodrug or particle is greater than about 5% (e.g., about 6%, about 7%, about 8%, about 9%, about 10%, about 12%, about 15%, about 20%, about 25%, about 30%, or more) of the total size or weight of the Brush prodrug or particle. In some embodiments, the total amount of the agent present in the Brush prodrug or particle is greater than about 10% (e.g., about 12%, about 15%, about 20%, about 25%, about 30%, or more) of the total size or weight of the Brush prodrug or particle.

Without being bound by theory, the conjugates or particles disclosed herein may improve the efficiency of an agent by one or more of increasing the localization and/or release (e.g., preferential release) of the agent to a target cell (e.g., a cancer or a fibrotic cell; a cell associated with a hypoxic environment), or increasing the half life of the agent, thus resulting in a significantly higher amount of a released agent at a target site (e.g., a tumor or liver (e.g., cirrhotic cell). According, the conjugates and particles disclosed herein can be more effective therapeutically than the free agent (e.g., due to enhanced drug uptake in the target tissue) and/or allow for a lower therapeutic dose of the agent, e.g., without substantially compromising the resulting drug concentration at a target tissue. In some embodiments, the conjugates and particles disclosed herein can reduce the adverse effect associated with systemic administration of an agent in free form (e.g., not coupled to a conjugate or particle described herein).

Without being bound by theory, due to the localized delivery of the compositions described herein (e.g., the agent-containing particles), a lower dose or amount of the agent in the particles can be administered (e.g., through local sustained delivery) compared to the agent in free form. In other embodiments, the agent-containing particles are administered at a dose or amount of the agent that is less than the dose or amount of said agent in free form to have a desired effect (e.g., a desired therapeutic effect).

In some embodiments, the agent is incorporated into a particle at a dose that is less than the dose or amount of said agent in free form to have a desired effect (e.g., a desired therapeutic effect), e.g., the standard of care dose for the intended use of the free agent. In one embodiment, the agent are incorporated into the particles at a dose or amount of the agent that is less than the standard of care dose of the agent for a desired therapy (e.g., a dose that is less than about 0.01, about 0.02, about 0.03, about 0.04, about 0.05, about 0.06, about 0.07, about 0.08, about 0.09, about 0.1, about 0.2, about 0.3, about 0.4, about 0.5, about 0.6, about 0.7, about 0.8, about 0.9, or about 0.95 that of the standard of care dose of the agent).

In some embodiments, the agent is incorporated into a particle at a dose equivalent to the dose or amount of said agent in free form to have a desired effect (e.g., a desired therapeutic effect), e.g., the standard of care dose for the intended use of the free agent. In these embodiments, the particle produces a greater therapeutic effect and/or a less adverse effect than the free agent. In certain embodiments, the particle increases the amount of the agent delivered to a tissue or cell in need thereof and reduces the amount of the agent exposed to a non-target tissue or cell, as compared to the free agent.

In some embodiments, the agent is incorporated into a particle at a dose higher than the dose or amount of said agent in free form to have a desired effect (e.g., a desired therapeutic effect), e.g., the standard of care dose for the intended use of the free agent. In some embodiments, the agent is incorporated into a particle at a dose higher than the dose or amount of said agent in free form that would produce an adverse effect by systemic administration (e.g., a reduction in blood pressure). In some embodiments, since the particle described herein releases the agent at a target site based on pH microenvironment, other non-target sites (e.g., blood vessels) with different pH would be less likely to be exposed to the agent.

In another aspect, the present disclosure provides a kit comprising:

the enyne, or a tautomer, isotopically labeled compound, salt, solvate, polymorph, or co-crystal thereof, or the composition; and instructions for using the enyne, tautomer, isotopically labeled compound, salt, solvate, polymorph, co-crystal, or composition.

In another aspect, the present disclosure provides a kit comprising:

the end-functionalized polymer, or a tautomer, isotopically labeled polymer, or salt thereof, or the composition; and instructions for using the end-functionalized polymer, tautomer, isotopically labeled polymer, salt, or composition.

In another aspect, the present disclosure provides a kit comprising:

the conjugate, or a tautomer, isotopically labeled conjugate, or salt thereof, or the composition; and instructions for using the conjugate, tautomer, isotopically labeled conjugate, salt, or composition.

In certain embodiments, the kit comprises a first container. In certain embodiments, the first container comprises the enyne, or a tautomer, isotopically labeled compound, salt, solvate, polymorph, or co-crystal thereof, or the composition. In certain embodiments, the first container comprises the end-functionalized polymer, or a tautomer, isotopically labeled polymer, or salt thereof, or the composition. In certain embodiments, the first container comprises the conjugate, or a tautomer, isotopically labeled conjugate, or salt thereof, or the composition. In some embodiments, the kit further comprises a second container. In certain embodiments, the second container comprises the instructions. In certain embodiments, the instructions comprise information required by a regulatory agency, such as the U.S. Food and Drug Administration (FDA) or European Medicines Agency (EMA). In certain embodiments, the instructions comprise prescribing information. In certain embodiments, the second container comprises the first container. In some embodiments, the kit further comprises a third container. In certain embodiments, the third container comprises the excipient. In certain embodiments, the third container comprises the additional pharmaceutical agent. In certain embodiments, the second container comprises the third container. In certain embodiments, each of the first, second, and third containers is independently a vial, ampule, bottle, syringe, dispenser package, tube, or box.

In another aspect, the present disclosure provides a method of delivering a pharmaceutical agent to a subject in need thereof comprising administering to the subject in need thereof: an effective amount of the conjugate, or a tautomer, isotopically labeled conjugate, or salt thereof; or the composition.

In another aspect, the present disclosure provides a method of delivering a pharmaceutical agent to a cell comprising contacting the cell with an effective amount of: the conjugate, or a tautomer, isotopically labeled conjugate, or salt thereof; or the composition.

In another aspect, the present disclosure provides a method of treating a disease in a subject in need thereof comprising administering to or implanting in the subject in need thereof an effective amount of:

the conjugate, or a tautomer, isotopically labeled conjugate, or salt thereof; or the composition;

wherein at least one pharmaceutical agent is a therapeutic agent.

In another aspect, the present disclosure provides a method of preventing a disease in a subject in need thereof comprising administering to or implanting in the subject in need thereof a prophylactically effective amount of:

the conjugate, or a tautomer, isotopically labeled conjugate, or salt thereof; or the composition;

wherein at least one pharmaceutical agent is a prophylactic agent.

In another aspect, the present disclosure provides a method of diagnosing a disease in a subject comprising administering to or implanting in the subject a diagnostically effective amount of:

the conjugate, or a tautomer, isotopically labeled conjugate, or salt thereof; or the composition;

wherein at least one pharmaceutical agent is a diagnostic agent.

In certain embodiments, the disease is cancer, benign neoplasm, pathologic angiogenesis, inflammatory disease, autoinflammatory disease, autoimmune disease, metabolic disease, neurological disease, painful condition, or psychiatric disease. In certain embodiments, the disease is cancer. In certain embodiments, the disease is a hematological malignancy. In certain embodiments, the disease is lymphoma or leukemia. In certain embodiments, the disease is a solid tumor. In certain embodiments, the disease is bladder cancer, breast cancer, colon cancer, esophageal cancer, glioma, lung cancer, melanoma, multiple myeloma, Kaposi's sarcoma, ovarian cancer, pancreatic cancer, prostate cancer, stomach cancer, soft tissue sarcoma, or thyroid cancer. In certain embodiments, the disease is breast cancer or ovarian cancer.

In certain embodiments, the method of treating a disease further comprises administering to or implanting in the subject in need thereof an effective amount of an additional therapeutic agent. In certain embodiments, the method of preventing a disease further comprises administering to or implanting in the subject in need thereof an effective amount of an additional prophylactic agent. In certain embodiments, the method of diagnosing a disease further comprises administering to or implanting in the subject in need thereof an effective amount of an additional diagnostic agent.

In certain embodiments, the additional therapeutic agent is an anti-cancer agent.

EXAMPLES

In order that the present disclosure may be more fully understood, the following examples are set forth. The synthetic and biological examples described in this application are offered to illustrate the compounds, pharmaceutical compositions, and methods provided herein and are not to be construed in any way as limiting their scope.

Unless expressly provided otherwise, BPD is a brush polymer without antibody conjugation; ctrl-ABC is an ABC with IgG1 antibody conjugation; the anti-HER2 antibody is trastuzumab; ABC_Blank is an ABC without pharmaceutical agent conjugation; the general method suggested in FIG. 17E was used to synthesize the anti-HER2 ABCs and the PROTAC-ABC; and MMAE-M was used to synthesize MMAE ABCs.

Example 1. Synthesis of Antibody-Brush Polymer Conjugations

Antibody-brush polymer conjugates (ABCs) were prepared via click reaction between a brush polymer and antibody (FIGS. 17A to 17E).

Synthesis of Tetrazine Terminated Brush Polymers

Figures 1, 2:
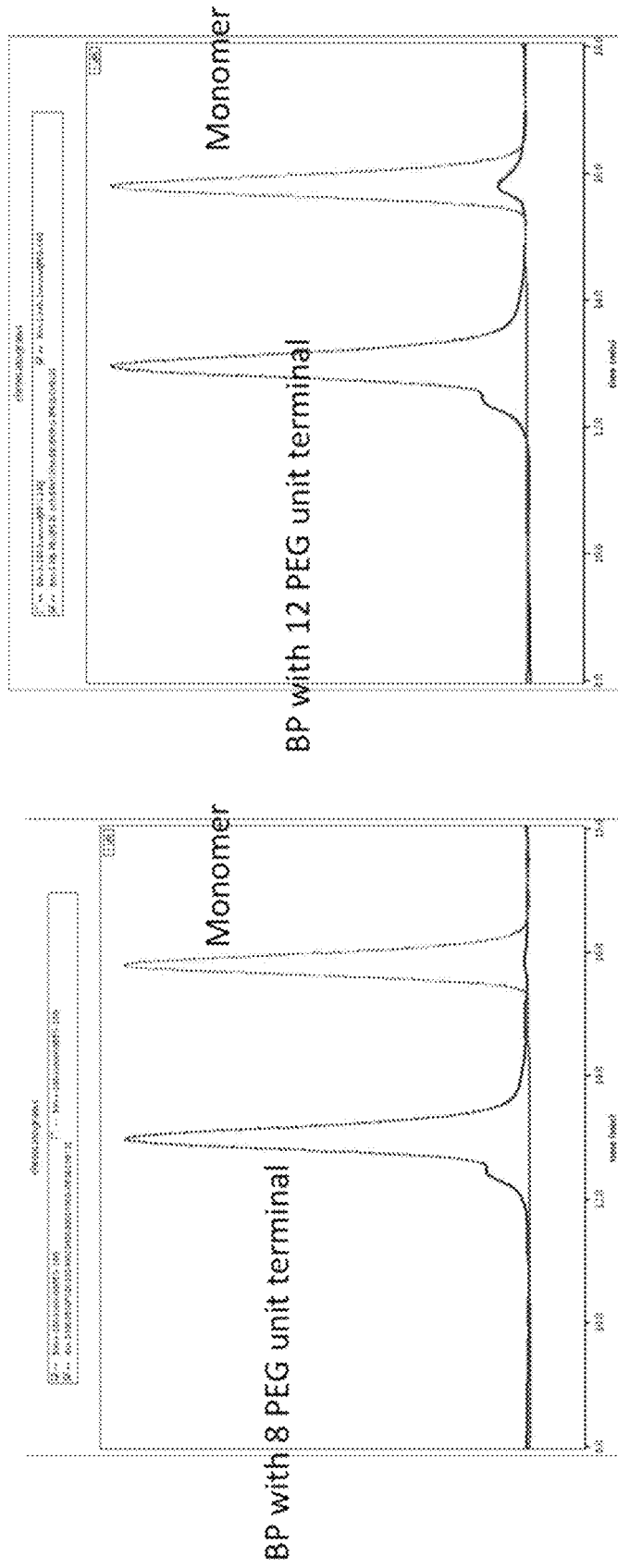
FIG. 1 shows GPC traces illustrating the successful polymerization of tetrazine-terminated brush polymers. BP: brush polymer.
FIG. 2 shows GPC traces illustrating the successful polymerization of tetrazine-terminated brush polymers.
Figure 17E:
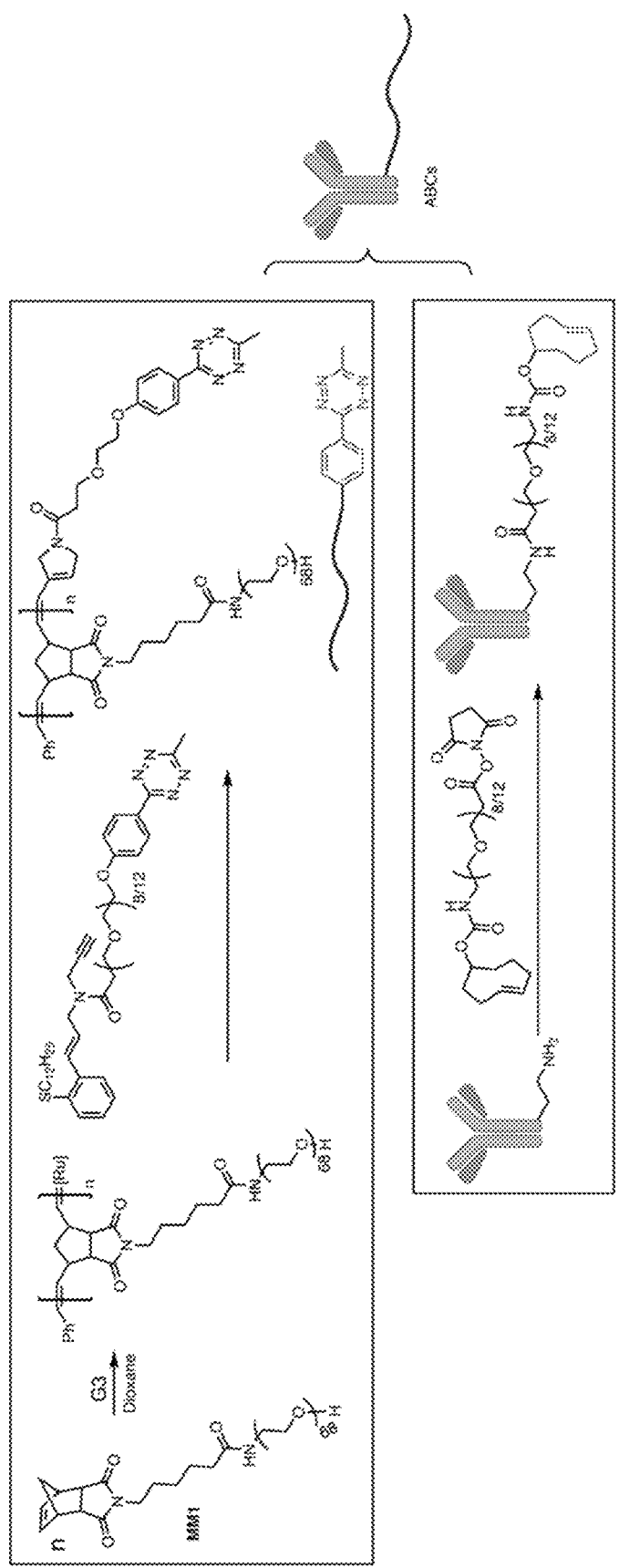

Tetrazine terminated brush polymers were synthesized using the reaction shown in FIG. 17E, top panel. GPC traces showed the successful polymerization of brush polymers (FIGS. 1 to 2).

Synthesis of Drug Loaded Brush Polymers

Drug loaded brush polymers were synthesized by polymerizing MMAE-S-MM (FIG. 26), MMAE-M-MM (FIG. 26), MMAE-F-MM (FIG. 26), PTX-MM (FIG. 27), DOX-MM (FIG. 27), or SN-38-MM (FIG. 27). MMAE: monomethyl auristatin E. PTX: paclitaxel. DOX: doxorubicin. SN-38: (4S)-4,11-diethyl-4,9-dihydroxy-1,4-dihydro-3H,14H-pyrano[3',4':6,7]indolizino[1,2-b]quinoline-3,14-dione.

Figures 3A, 3B:
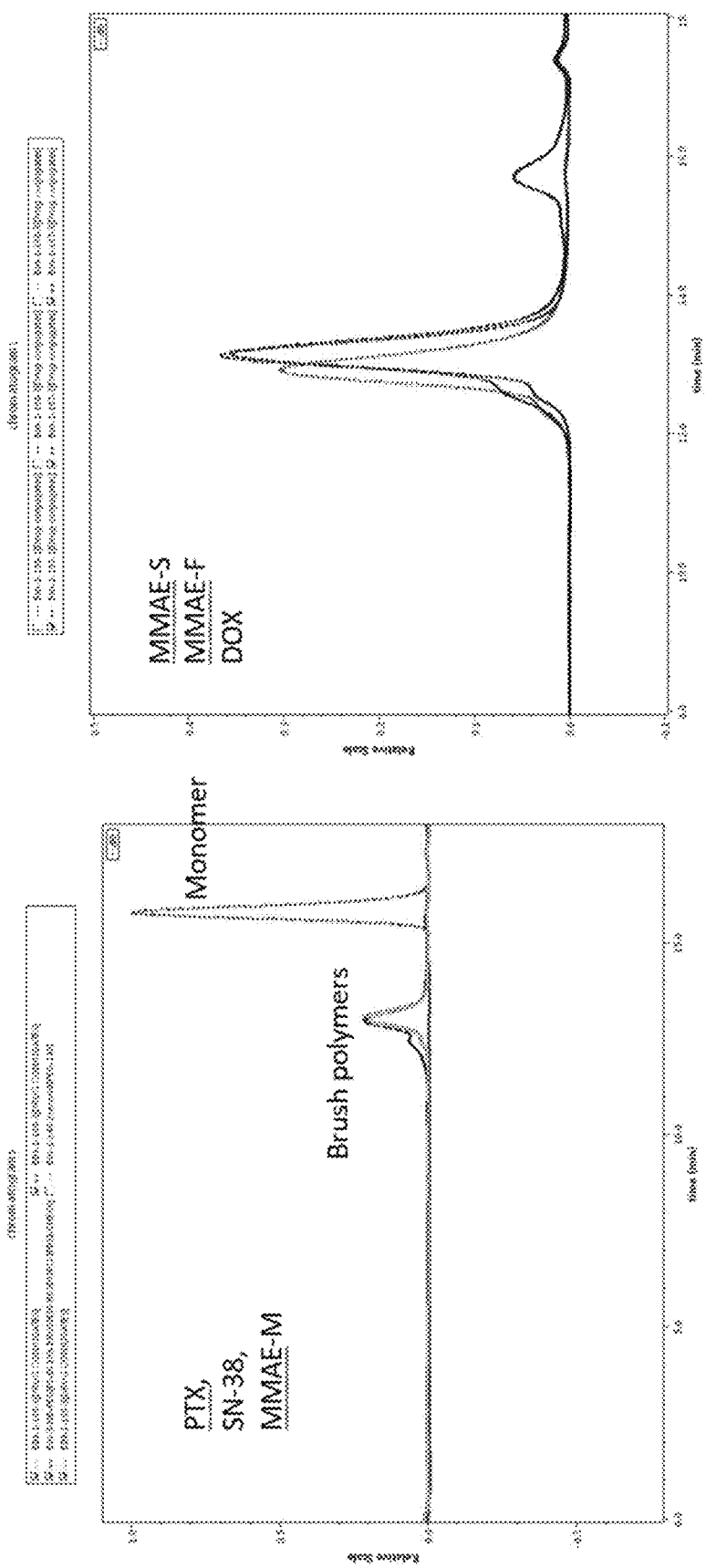
FIGS. 3A to 3B show GPC traces illustrating the successful polymerization of drug loaded brush polymers. For FIG. 3A, red color is MMAE-F; pink color is MMAE-S; blue color is DOX. For FIG. 3B, gray color is PTX; black color is SN38; green color is MMAE-M.

GPC traces showed the successful polymerization of drug conjugated brush polymers (FIGS. 3A to 3B).

Antibody Lysine Modification

Figure 4A:
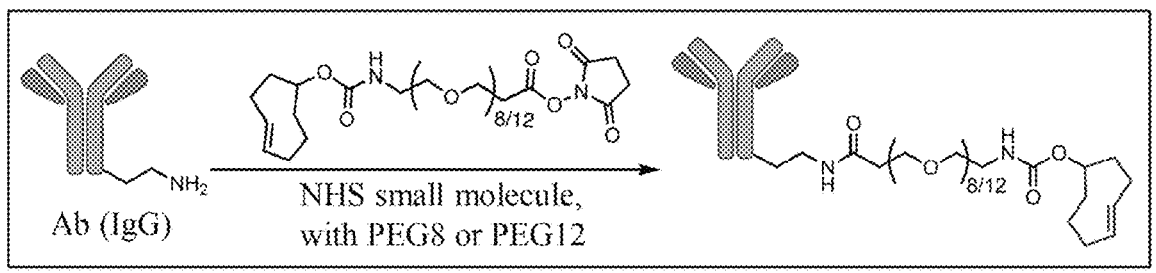
FIGS. 4A to 4D show results of antibody lysine modification.
Figure 4B:
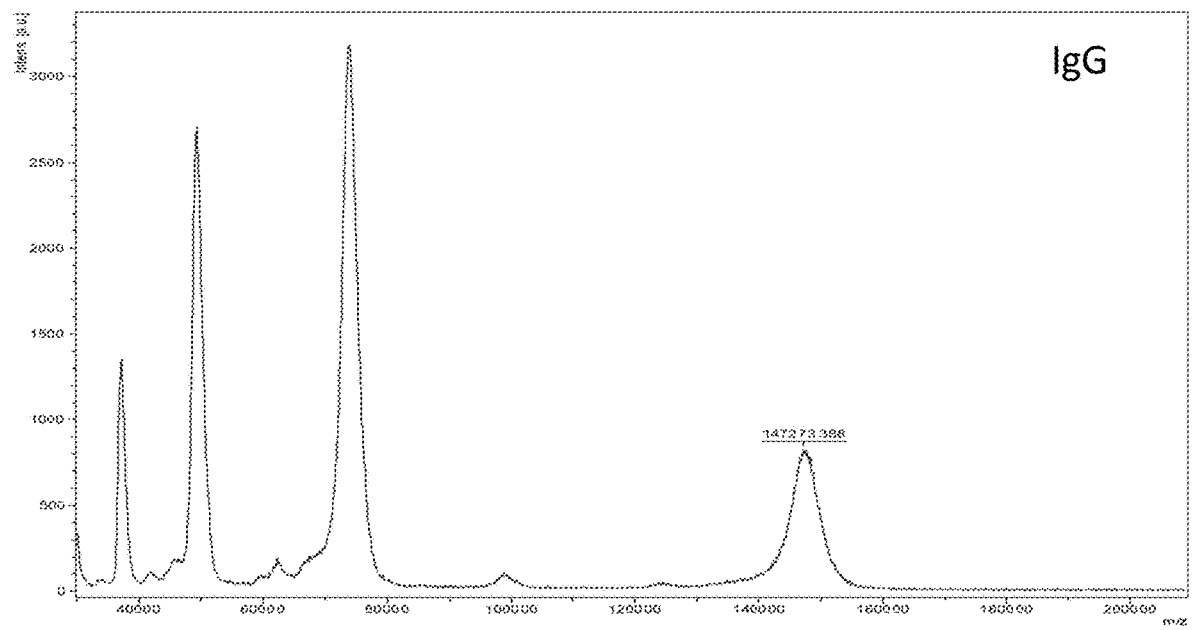
Figure 4C:
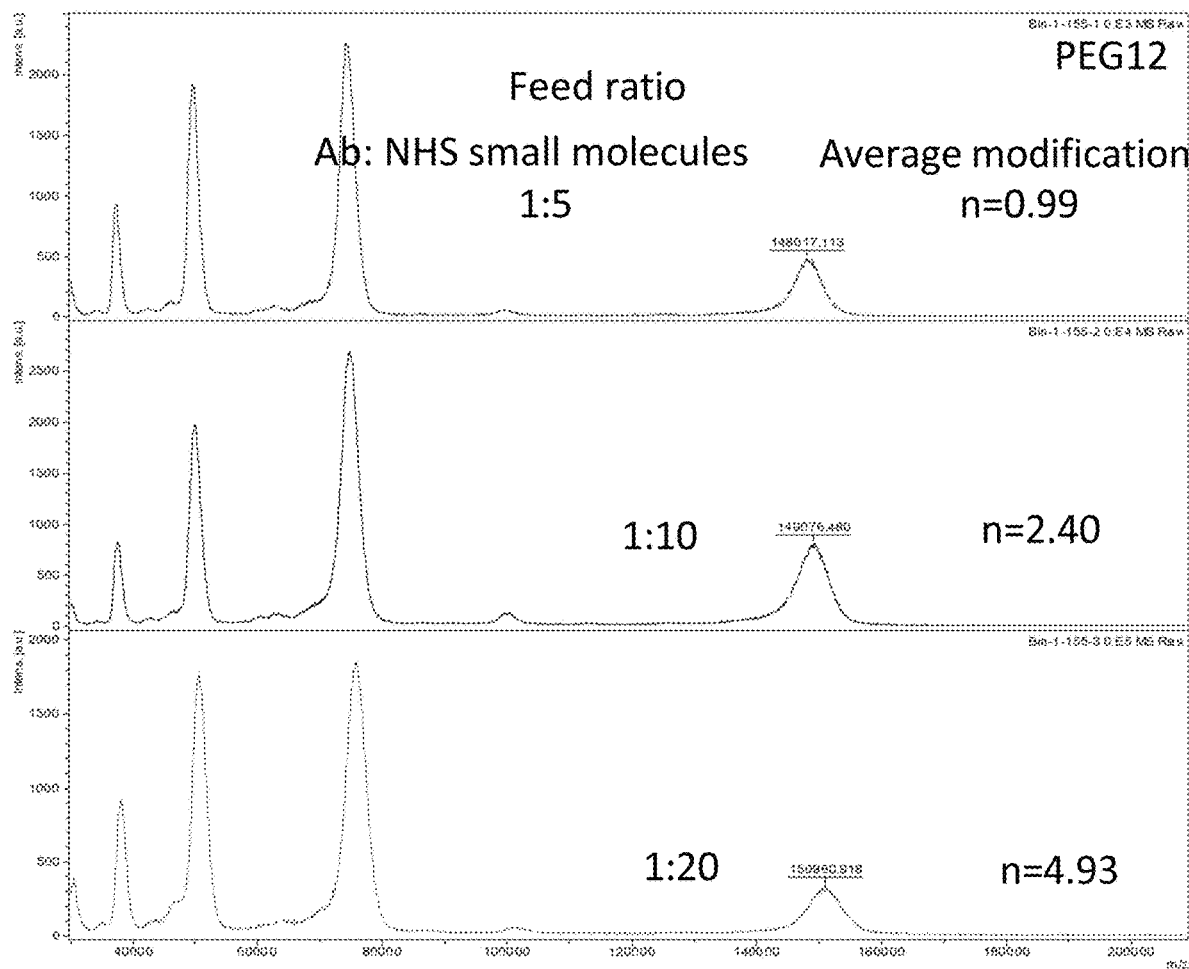
Figure 4D:
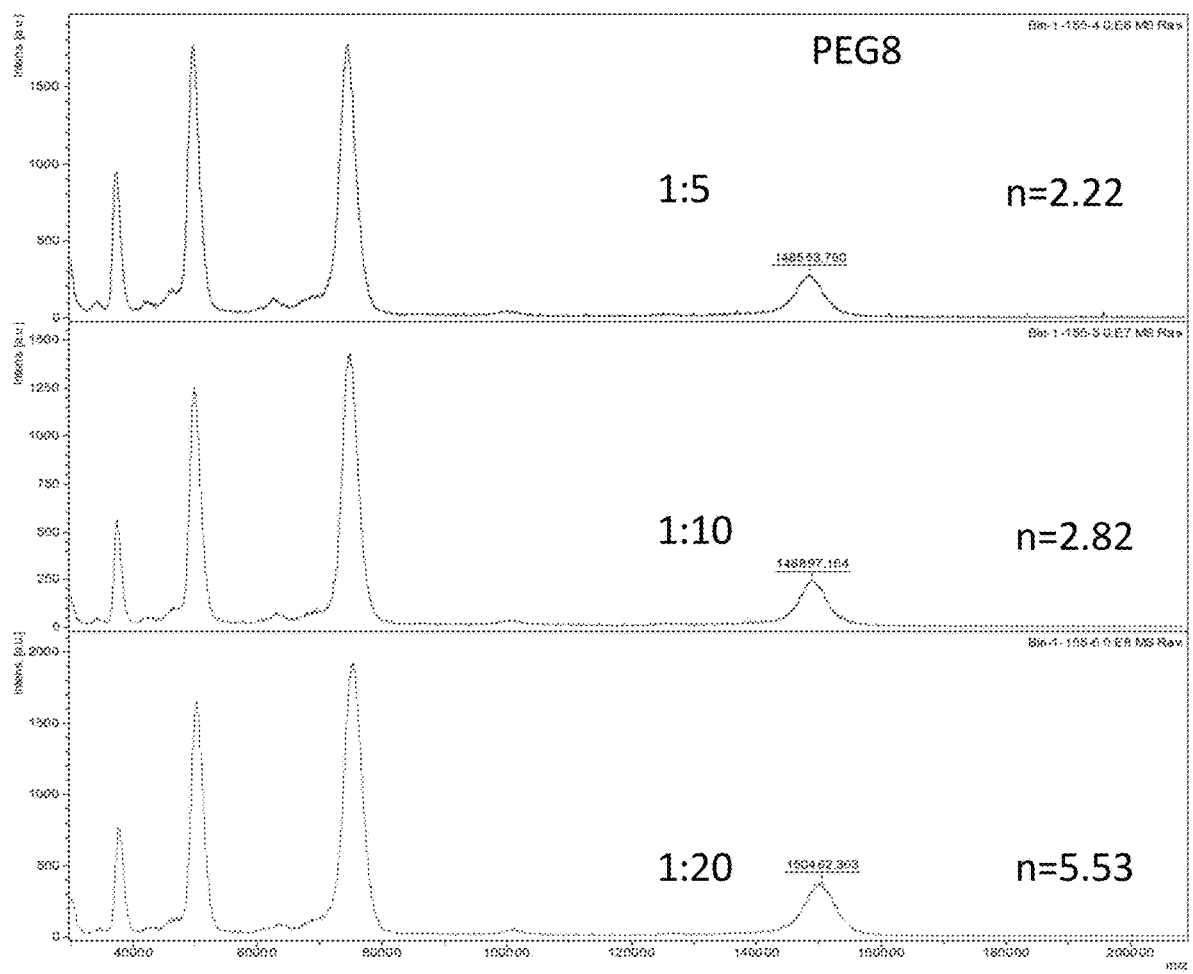

The surface of the antibody IgG was modified by transcyclooctene (TCO) moiety using the reaction shown in FIG. 4A. Mass spectrometry analysis was performed for IgG (FIG. 4B), NHS small molecule with PEG12 (PEG12) (FIG. 4C) and NHS small molecule with PEG8 (PEG8) (FIG. 4D).

Azide-DBCO Conjugation

Polymers P1, P2, P3 and *P4 (control) were conjugated with IgG1: 1:5 linker reaction (1 mg scale, 1 mL); IgG2: 1:10 linker reaction (1 mg scale, 1 mL); IgG3: 1:15 linker reaction (1 mg scale, 1 mL) using the azide-DBCO conjugation reaction shown in FIG. 17A. Results are shown in FIGS. 18A to 18E.

Additional conjugations were performed using the azide-DBCO conjugation reaction shown in FIGS. 17B and 17D. Results are shown in FIGS. 20A to 20D.

Tz-TCO Conjugation

An alternative strategy for Tz-TCO conjugation (FIGS. 17B and 17C) was used and GPC was performed (FIGS. 19A to 19B). Results are shown in FIGS. 20A to 20D. FPLC protein separation was performed (FIG. 21A to 21C). Dye labeled polymers for conjugation were synthesized (FIGS. 22A to 22C).

ROMP for Drug Conjugated MMs

FIGS. 23A to 23E show ROMP for drug conjugated MMs. FIGS. 24A to 24I show block or statistic polymerizations for ROMP of drug conjugated MMs. FIGS. 25A to 25B show anti-HER-2 ABCs.

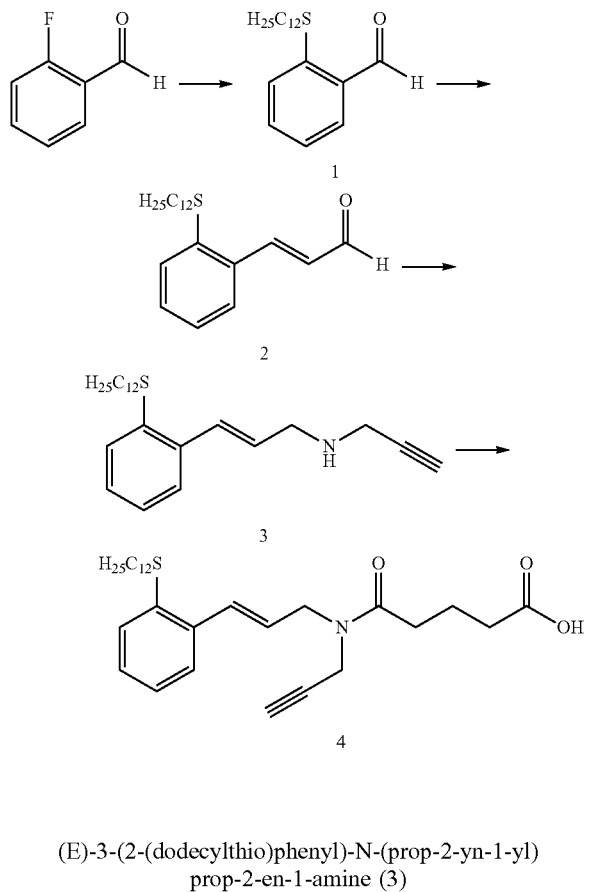

(E)-3-(2-(dodecylthio)phenyl)-N-(prop-2-yn-1-yl) prop-2-en-1-amine (3)

This compound was prepared according to the method disclosed in *J. Am. Chem. Soc.* 2018, 140, 38, 12181-12188.

(E)-5-((3-(2-(dodecylthio)phenyl)allyl)(prop-2-yn-1-yl)amino)-5-oxopentanoic acid (4)

3 (872 mg, 2.35 mmol, 1 eq.) was dissolved in 3 mL of dichloromethane. A small crystal of 4-(dimethyamino)pyridine was added. Glutaric anhydride (321 mg, 2.82 mmol, 1.2 eq.) was added, and the solution was stirred at room temperature. The reaction was monitored by TLC (5% MeOH/DCM). Upon complete consumption of 3, the solution was evaporated under reduced pressured. The residue was purified by silica gel chromatography (MeOH/DCM) to afford (E)-5-((3-(2-(dodecylthio)phenyl)allyl)(prop-2-yn-1-yl) amino)-5-oxopentanoic acid (4) (847 mg, 74% yield) as a waxy yellow solid. $^1$H NMR (400 MHz, CDCl$_3$) δ 7.47-7.37 (m, 1H), 7.33 (dt, J=7.9, 2.0 Hz, 1H), 7.27-7.12 (m, 3H), 7.04 (dd, J=15.7, 12.3 Hz, 1H), 6.03 (dt, J=15.7, 5.7 Hz, 1H), 4.37-3.98 (m, 4H), 2.85 (t, J=7.4 Hz, 2H), 2.61-2.44 (m, 4H), 2.33-2.20 (m, 1H), 2.03 (h, J=7.3 Hz, 2H), 1.61 (p, J=7.5 Hz, 2H), 1.40 (p, J=7.4 Hz, 2H), 1.25 (s, 16H), 0.88 (t, J=6.8 Hz, 3H).

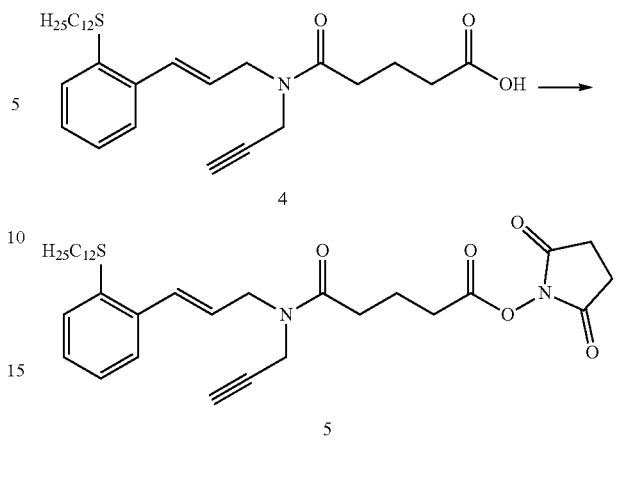

2,5-dioxopyrrolidin-1-yl (E)-5-((3-(2-(dodecylthio) phenyl)allyl)(prop-2-yn-1-yl)amino)-5-oxopentanoate (5)

4 (256 mg, 0.53 mmol, 1 eq.), N-hydroxysuccinimide (132 mg, 1.15 mmol, 2.2 eq), and a small crystal of DMAP were dissolved in 2 mL of anhydrous dichloromethane. The flask was then evacuated and back-filled with nitrogen 3×. In a separate vial, 1-(3-dimethylaminopropyl)-3-ethylcarbodiimide hydrochloride (204 mg, 1.06 mmol, 2 eq.) was suspended in 5 mL of anhydrous dichloromethane. The suspension was slowly injected into the reaction flask over 5 minutes with a syringe fitted with a thick needle. The reaction was monitored by thin layer silica gel chromatography (EtOAc/Hexanes). Upon complete consumption of 4, 10 mL of water was added to the reaction and stirred for 10 minutes. The heterogeneous mixture was transferred to a separatory funnel, and the aqueous layer discarded. The organics were washed with 2×10 mL water followed by 1×10 mL brine. The solution was dried with anhydrous Na$_2$SO$_4$, decanted, and evaporated. The residue was purified by silica gel column chromatography (EtOAc/Hexanes) to afford 2,5-dioxopyrrolidin-1-yl (E)-5-((3-(2-(dodecylthio) phenyl)allyl)(prop-2-yn-1-yl)amino)-5-oxopentanoate (5) (201 mg, 65% yield). $^1$H NMR (500 MHz, CDCl$_3$) δ 7.47-7.39 (m, 1H), 7.36-7.30 (m, 1H), 7.25-7.12 (m, 2H), 7.10-6.97 (m, 1H), 6.08-5.99 (m, 1H), 4.35-4.02 (m, 4H), 2.88-2.68 (m, 8H), 2.66-2.56 (m, 2H), 2.33-2.20 (m, 1H), 2.15 (h, J=6.9 Hz, 2H), 1.61 (p, J=7.2 Hz, 2H), 1.40 (p, J=7.1 Hz, 2H), 1.26 (s, 16H), 0.88 (t, J=7.2 Hz, 3H).

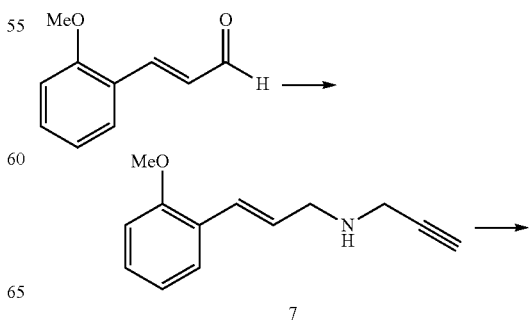

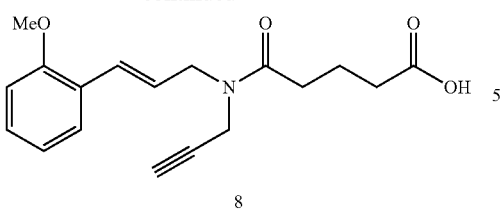

8

(E)-3-(2-methoxyphenyl)-N-(prop-2-yn-1-yl)prop-2-en-1-amine (7)

o-methoxycinnamaldehyde (9.93 g, 61.3 mmol, 1 eq.) was dissolved in 60 mL of methanol. Propargylamine (6.78 g, 123 mmol, 2 eq.) was added to the solution and stirred at 30° C. Upon complete consumption of o-methoxycinnamaldehyde by crude NMR, the solution was cooled to 0° C. with an ice bath. Then, NaBH$_4$ (4.65 g, 123 mmol, 2 eq.) was carefully added to the solution over 5 minutes. The reaction was allowed to come to room temperature and stirred overnight. The methanol was evaporated under reduced pressure, and the residue was dissolved in 50 mL of EtOAc. The solution was then washed with 2×30 mL water and 1×30 mL brine. The organic layer was then dried with anhydrous Na$_2$SO$_4$, decanted, and evaporated. The resulting crude product was purified by short-path vacuum distillation to afford (E)-3-(2-methoxyphenyl)-N-(prop-2-yn-1-yl)prop-2-en-1-amine (7) (5.75 g, 47% yield) as a yellow oil. $^1$H NMR (400 MHz, CDCl$_3$) δ 7.43 (dd, J=7.7, 1.6 Hz, 1H), 7.26-7.17 (m, 1H), 6.96-6.81 (m, 3H), 6.29 (dt, J=16.0, 6.4 Hz, 1H), 3.84 (s, 3H), 3.51 (dd, J=6.5, 1.5 Hz, 2H), 3.47 (d, J=2.4 Hz, 2H), 2.24 (t, J=2.4 Hz, 1H), 1.32 (s, 1H).

(E)-5-((3-(2-methoxyphenyl)allyl)(prop-2-yn-1-yl)amino)-5-oxopentanoic acid (8)

7 (911 mg, 4.53 mmol, 1 eq.) was dissolved in 9 mL of dichloromethane. A small crystal of 4-(dimethylamino)pyridine was added. Glutaric anhydride (573 mg, 4.98 mmol, 1.1 eq) was added, and the solution was stirred at room temperature. The reaction was monitored by thin layer silica gel chromatography (50% EtOAc/Hexanes). Upon complete consumption of 7, the solution was concentrated under reduced pressure. The residue was purified by silica gel chromatography (33%-66% EtOAc/Hexanes) to afford 1.22 g (85% yield) of (E)-5-((3-(2-methoxyphenyl)allyl)(prop-2-yn-1-yl)amino)-5-oxopentanoic acid (8) as a viscous yellow oil. $^1$H NMR (400 MHz, CDCl$_3$) δ 10.54 (s, 1H), 7.45-7.35 (m, 1H), 7.28-7.19 (m, 1H), 6.97-6.77 (m, 3H), 6.20-6.06 (m, 1H), 4.32-4.00 (m, 4H), 3.85 (s, 3H), 2.60-2.43 (m, 4H), 2.31-2.20 (m, 1H), 2.10-1.96 (m, 2H).

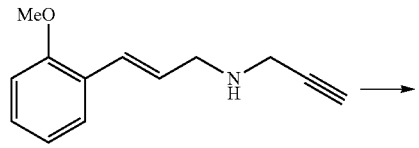

7

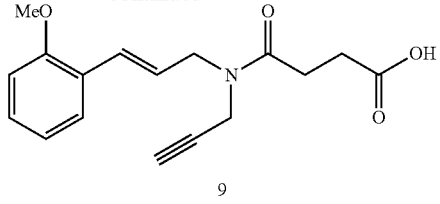

9

(E)-5-((3-(2-methoxyphenyl)allyl)(prop-2-yn-1-yl)amino)-5-oxobutanoic acid (9)

7 (948 mg, 4.72 mmol, 1 eq.) was dissolved in 9 mL of dichloromethane. A small crystal of 4-(dimethylamino)pyridine was added. Succinic anhydride (519 mg, 5.19 mmol, 1.1 eq) was added, and the solution was stirred at room temperature. The reaction was monitored by thin layer silica gel chromatography (4% MeOH/DCM). Upon complete consumption of 7, the reaction was transferred to a separatory funnel and washed with 2×5 mL 1M HCl and 1×5 mL brine. The organic layer was dried with anhydrous sodium sulfate, evaporated under reduced pressure, and purified by silica gel chromatography (MeOH/DCM) to afford 1.21 g (85% yield) of (E)-5-((3-(2-methoxyphenyl)allyl)(prop-2-yn-1-yl)amino)-5-oxobutanoic acid (9) as a viscous yellow oil. $^1$H NMR (400 MHz, CDCl$_3$) δ 11.04 (s, 1H), 7.45-7.36 (m, 1H), 7.29-7.19 (m, 1H), 6.97-6.79 (m, 3H), 6.23-6.06 (m, 1H), 4.33-4.04 (m, 4H), 3.85 (s, 3H), 2.86-2.70 (m, 4H), 2.33-2.22 (m, 1H).

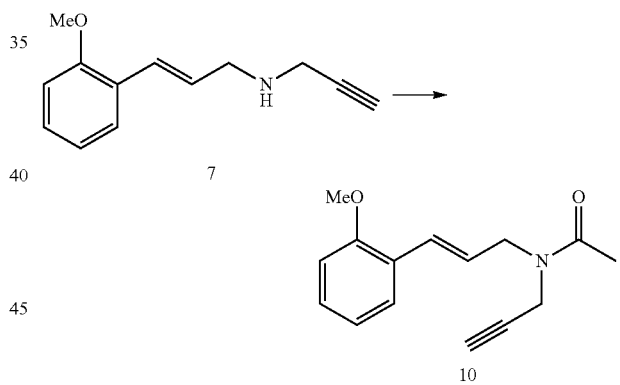

(E)-N-(3-(2-methoxyphenyl)allyl)-N-(prop-2-yn-1-yl)acetamide (10)

7 (559 mg, 2.78 mmol, 1 eq.) and triethylamine (0.47 mL, 3.34 mmol, 1.2 eq) were dissolved in 3 mL of dichloromethane. A small crystal of 4-(dimethylamino)pyridine was added, and the solution was cooled to 0° C. with an ice bath. Acetic anhydride (340 mg, 3.34 mmol, 1.2 eq.) was added to the stirred solution. The ice bath was removed after the addition. After 2 hours, the solution was evaporated under reduced pressure. The residue was purified by silica gel chromatography (50% EtOAc/Hexanes) to afford 587 mg (87% yield) of (E)-N-(3-(2-(butylthio)phenyl)allyl)-N-(prop-2-yn-1-yl)acetamide (10) as a yellow oil. $^1$H NMR (500 MHz, CDCl$_3$) δ 7.44-7.37 (m, 1H), 7.28-7.18 (m, 1H), 6.96-6.79 (m, 3H), 6.22-6.09 (m, 1H), 4.30-4.00 (m, 4H), 3.85 (s, 3H), 2.30-2.20 (m, 1H), 2.18 (s, 3H).

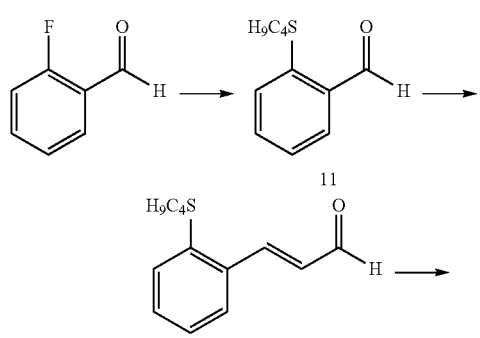

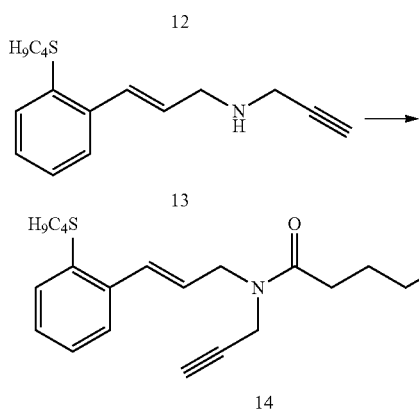

2-(butylthio)benzaldehyde (11)

1-Butanethiol (20.9 g, 232 mmol, 1 eq.) was dissolved in 25 mL of DMSO. 39 g (282 mmol, 1.2 eq.) of oven-dried $K_2CO_3$ was added to the flask and the resulting heterogeneous mixture was stirred and cooled to 0° C. with an ice bath. 43 g (347 mmol, 1.5 eq.) of 2-fluorobenzaldehye was slowly added to the stirred mixture over 2 minutes. The mixture was then heated to 60° C. and stirred overnight. Upon complete consumption of 1-butanethiol as monitored by crude NMR, the flask was fitted with a short-path vacuum distillation apparatus and fractionated under vacuum. 29.4 g (151 mmol, 65% yield) of 2-(butylthio)benzaldehyde (11) was isolated as a yellow oil. $^1$H NMR (400 MHz, CDCl$_3$) δ 10.39 (s, 1H), 7.83 (dd, J=7.7, 1.5 Hz, 1H), 7.51 (ddd, J=8.0, 7.2, 1.6 Hz, 1H), 7.42 (dd, J=8.0, 1.1 Hz, 1H), 7.29 (td, J=7.4, 1.1 Hz, 1H), 2.95 (d, J=7.4 Hz, 2H), 1.68 (p, J=7.5 Hz, 2H), 1.48 (h, J=7.7 Hz, 2H), 0.94 (t, J=7.3 Hz, 3H).

(E)-3-(2-(butylthio)phenyl)acrylaldehyde (12)

11 (29.4 g, 151 mmol, 1 eq.) was dissolved in 151 mL of absolute ethanol and cooled to 0° C. with an ice bath. 8.7 g (198 mmol, 1.3 eq.) of cold acetaldehyde was added to the solution. 68 mL of 1M aqueous NaOH solution (69 mmol, 0.45 eq) was added to the ethanolic solution. Shortly after the addition, the solution turns yellow and cloudy as the product begins to precipitate. The temperature was maintained at 0° C. and the reaction was monitored by crude NMR. Upon complete consumption of acetaldehyde, the precipitated product was allowed to settle to the bottom of the flask, and the supernatant was decanted. The precipitated product was washed by adding 50 mL of cold 1:1 v/v EtOH/H$_2$O to the flask, stirring for five minutes, and decanting off the supernatant. This was repeated once more for a total of two washes. Finally, the crude product was recrystallized from methanol to afford 13.3 g (60 mmol, 40% yield) of (E)-3-(2-(butylthio)phenyl)acrylaldehyde (12) as a yellow solid. $^1$H NMR (400 MHz, CDCl$_3$) δ 9.76 (d, J=7.8 Hz, 1H), 8.14 (d, J=15.9 Hz, 1H), 7.61 (dd, J=7.7, 1.5 Hz, 1H), 7.46 (dd, J=7.9, 1.3 Hz, 1H), 7.37 (td, J=7.6, 1.5 Hz, 1H), 7.32-7.20 (m, 1H), 6.67 (dd, J=15.9, 7.8 Hz, 1H), 2.91 (t, J=7.3 Hz, 2H), 1.63 (p, J=7.6 Hz, 2H), 1.46 (h, J=7.6 Hz, 2H), 0.92 (t, J=7.3 Hz, 3H).

(E)-3-(2-(butylthio)phenyl)-N-(prop-2-yn-1-yl)prop-2-en-1-amine (13)

12 (2.81 g, 12.8 mmol, 1 eq.) was dissolved in 26 mL of methanol. Propargylamine (1.06 g, 19.2 mmol, 1.5 eq.) was added to the solution and stirred at room temperature. Upon complete consumption of 12 by crude NMR, the solution was cooled to 0° C. with an ice bath. Then, NaBH$_4$ (0.97 g, 25.6 mmol, 2 eq.) was added to the solution and the reaction was stirred overnight. The solution was concentrated under reduced pressure, and the residue was dissolved in 30 mL of EtOAc. The solution was then washed with 2×30 mL water and 1×30 mL brine. The organic layer was dried with anhydrous Na$_2$SO$_4$, decanted, and evaporated. This crude product (13) was used without further purification for subsequent synthetic steps. Alternatively, the crude product can be purified by silica gel column chromatography (EtOAc/Hexanes) to afford an analytical sample of 13. $^1$H NMR (400 MHz, CDCl$_3$) δ 7.48-7.44 (m, 1H), 7.39-7.29 (m, 1H), 7.22-7.13 (m, 2H), 7.08 (dt, J=15.8, 1.6 Hz, 1H), 6.18 (dt, J=15.7, 6.4 Hz, 1H), 3.54 (dd, J=6.4, 1.5 Hz, 2H), 3.49 (d, J=2.4 Hz, 2H), 2.86 (t, J=7.3 Hz, 2H), 2.25 (t, J=2.4 Hz, 1H), 1.61 (p, J=7.5 Hz, 2H), 1.56 (s, 1H), 1.45 (h, J=7.7 Hz, 2H), 0.91 (t, J=7.3 Hz, 3H).

(E)-5-((3-(2-(butylthio)phenyl)allyl)(prop-2-yn-1-yl)amino)-5-oxopentanoic acid (14)

Crude 13 (1.78 g, 6.9 mmol, 1 eq.) was dissolved in 10 mL of dichloromethane. A small crystal of 4-(dimethylamino)pyridine was added, and the solution was cooled to 0° C. with an ice bath. Glutaric anhydride (0.91 g, 8.0 mmol, 1.2 eq.) was added, and the reaction was heated to 35° C. for 3 hours. The solution was allowed to cool to room temperature before diluting with 40 mL of diethyl ether. The organic layer was washed with 3×20 mL water, 1×20 mL brine, dried with anhydrous Na$_2$SO$_4$, decanted, and evaporated. Finally, the residue was purified by silica gel chromatography (40% EtOAc/Hexanes+1% AcOH) to afford 1.14 g (44% yield) of (E)-5-((3-(2-(butylthio)phenyl)allyl)(prop-2-yn-1-yl)amino)-5-oxopentanoic acid (14), a viscous yellow oil. $^1$H NMR (400 MHz, CDCl$_3$) δ 7.47-7.37 (m, 1H), 7.37-7.30 (m, 1H), 7.27-7.12 (m, 2H), 7.10-6.98 (m, 1H), 6.03 (dt, J=15.7, 6.0 Hz, 1H), 4.43-4.02 (m, 4H), 2.86 (t, J=7.1 Hz, 2H), 2.61-2.42 (m, 4H), 2.33-2.21 (m, 1H), 2.09-1.96 (m, 2H), 1.61 (p, J=7.4 Hz, 2H), 1.44 (h, J=7.5 Hz, 2H), 0.92 (t, J=7.3 Hz, 3H).

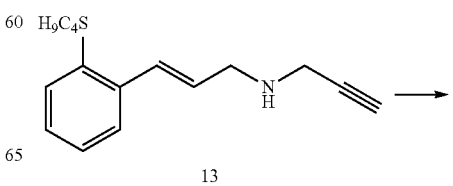

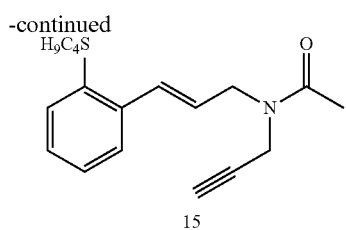

15

(E)-N-(3-(2-(butylthio)phenyl)allyl)-N-(prop-2-yn-1-yl)acetamide (15)

1.20 g (4.62 mmol, 1 eq.) of crude 13 was dissolved in 10 mL of dichloromethane. A small crystal of 4-(dimethylamino)pyridine was added, and the solution was cooled to 0° C. with an ice bath. Acetic anhydride (0.94 g, 9.24 mmol, 2 eq.) was added, and the solution was stirred and allowed to come to room temperature. After 2 hours, the solution was evaporated under reduced pressure. The residue was purified by silica gel chromatography (40% EtOAc/Hexanes) to afford 329 mg (24% yield) of (E)-N-(3-(2-(butylthio)phenyl)allyl)-N-(prop-2-yn-1-yl)acetamide (15) as a yellow oil. $^1$H NMR (400 MHz, CDCl$_3$) δ 7.47-7.38 (m, 1H), 7.35 (dd, J=7.6, 1.5 Hz, 1H), 7.27-7.12 (m, 2H), 7.10-7.01 (m, 1H), 6.10-5.98 (m, 1H), 4.35-4.00 (m, 4H), 2.86 (t, J=7.4 Hz, 2H), 2.32-2.21 (m, 1H), 2.25-2.17 (m, 3H), 1.60 (p, J=7.4 Hz, 2H), 1.44 (h, J=7.3 Hz, 2H), 0.91 (t, J=7.3 Hz, 3H).

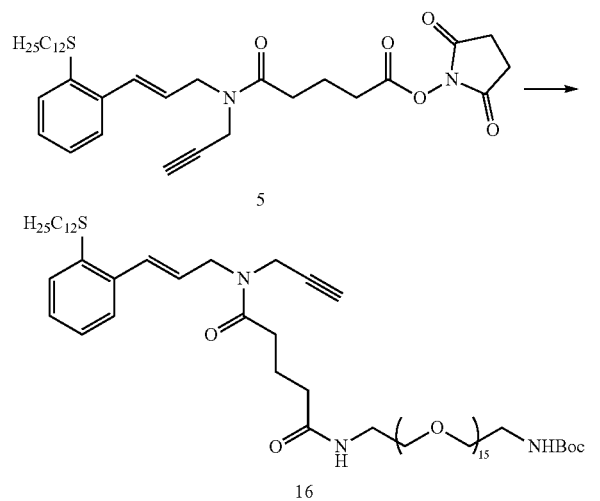

5 (53 mg, 0.092 mmol, 1.5 eq.) and diisopropylethylamine (32 μL, 0.184 mmol, 3 eq.) were dissolved in 1 mL of dichloromethane at room temperature. H$_2$N-PEG15-NHBoc (50 mg, 0.061 mmol, 1 eq.) was dissolved in a minimal amount of dichloromethane and was added to the stirred solution of 5 and diisopropylethylamine. The reaction was allowed to stir overnight at room temperature. The solution was then evaporated under reduced pressure, and the residue was purified by silica gel chromatography (MeOH/DCM) to afford 16 (57 mg, 72% yield) as a slightly yellow gummy solid.

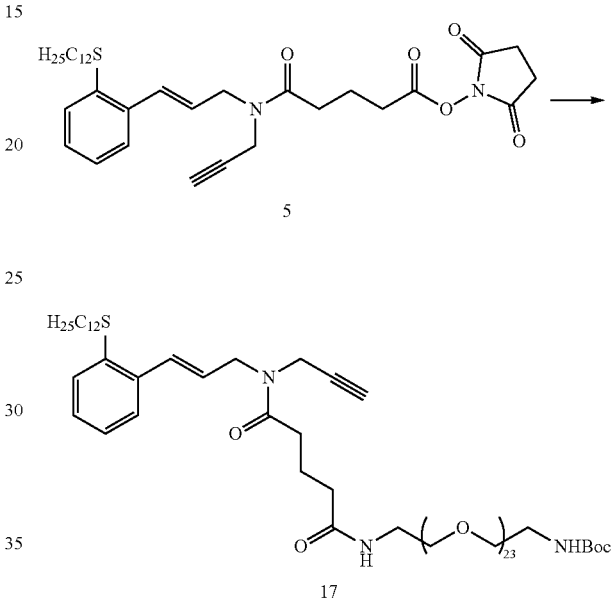

5 (43 mg, 0.074 mmol, 1.5 eq.) and diisopropylethylamine (26 μL, 0.148 mmol, 3 eq.) were dissolved in 1 mL of dichloromethane at room temperature. H$_2$N-PEG23-NHBoc (58 mg, 0.049 mmol, 1 eq.) was dissolved in a minimal amount of dichloromethane and was added to the stirred solution of 5 and diisopropylethylamine. The reaction was allowed to stir overnight at room temperature. The solution was then evaporated under reduced pressure, and the residue was purified by silica gel chromatography (MeOH/DCM) to afford 17 (51 mg, 64% yield) as a slightly yellow gummy solid.

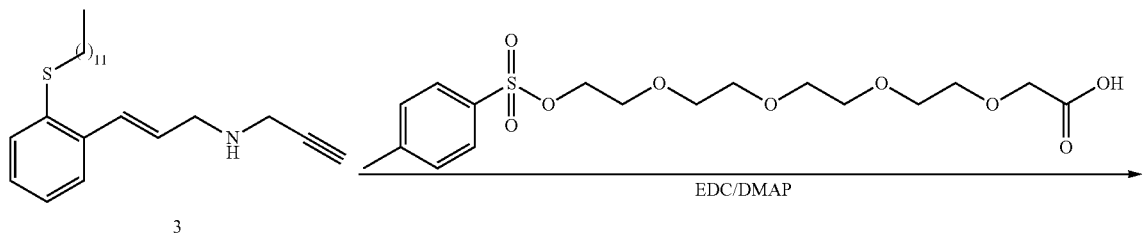

-continued

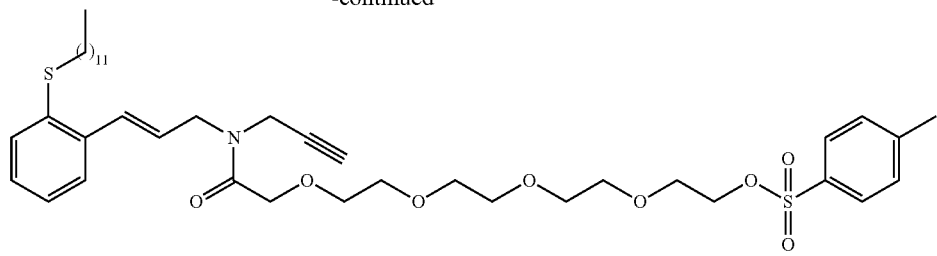

18

3 (100 mg, 0.27 mmol, 1 eq.) and Tos-PEG$_5$-CH$_2$COOH (120 mg, 0.297 mmol, 1.1 eq.) were dissolved in 2 mL of dichloromethane. 6.6 mg of 4-(dimethyamino)pyridine (0.2 eq.) was added. Then, EDC (62 mg, 1.2 eq.) was added, and the solution was stirred at room temperature. The reaction was monitored by TLC (5% MeOH/DCM). Upon complete consumption of 3, the solution was evaporated under reduced pressured. The residue was purified by silica gel chromatography (MeOH/DCM) to afford 18 (160 mg, 78% yield).

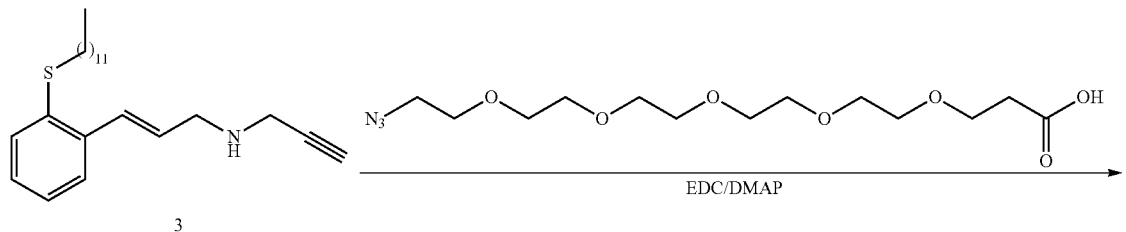

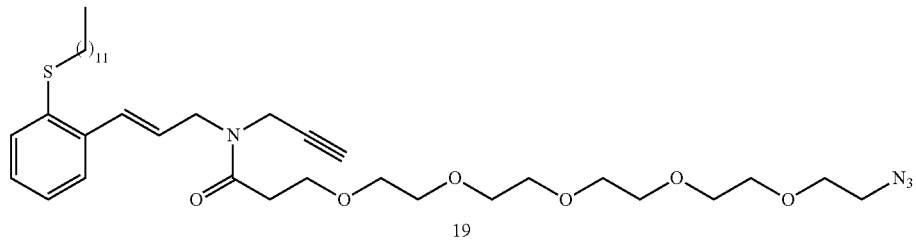

19

3 (166.2 mg, 0.448 mmol, 1 eq.) and Amino-PEG$_5$-acid (150 mg, 0.448 mmol, 1 eq.) were dissolved in 2 mL of dichloromethane. 11 mg of 4-(dimethyamino)pyridine (0.2 eq.) was added. Then, EDC (103 mg, 1.2 eq.) was added, and the solution was stirred at room temperature. The reaction was monitored by TLC (5% MeOH/DCM). Upon complete consumption of 3, the solution was evaporated under reduced pressured. The residue was purified by silica gel chromatography (MeOH/DCM) to afford 19 (277.6 mg, 90% yield).

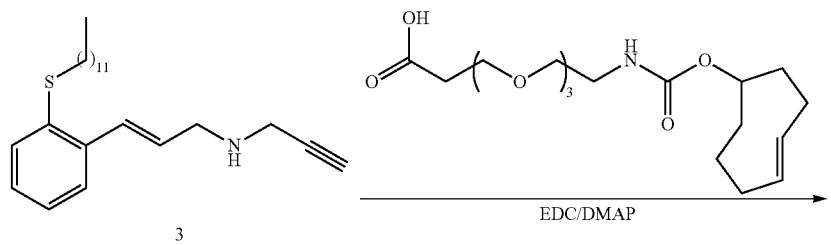

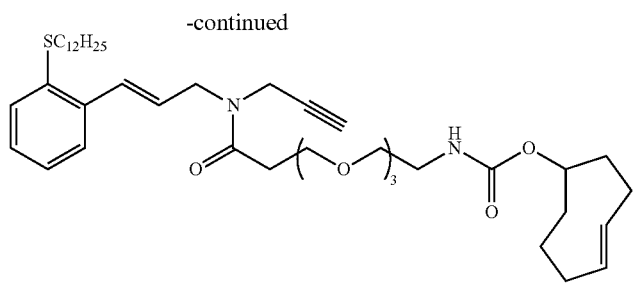

20

3 (33 mg, 0.087 mmol, 1.3 eq.) and TCO-PEG$_3$-acid (25 mg, 0.067 mmol, 1 eq.) were dissolved in 1 mL of dichloromethane. 1.64 mg of 4-(dimethyamino)pyridine (0.2 eq.) was added. Then, EDC (21 mg, 1.6 eq.) was added, and the solution was stirred at room temperature. The reaction was monitored by TLC (5% MeOH/DCM). Upon complete consumption of 3, the solution was evaporated under reduced pressured. The residue was purified by silica gel chromatography (MeOH/DCM) to afford 20 (48 mg, 99% yield).

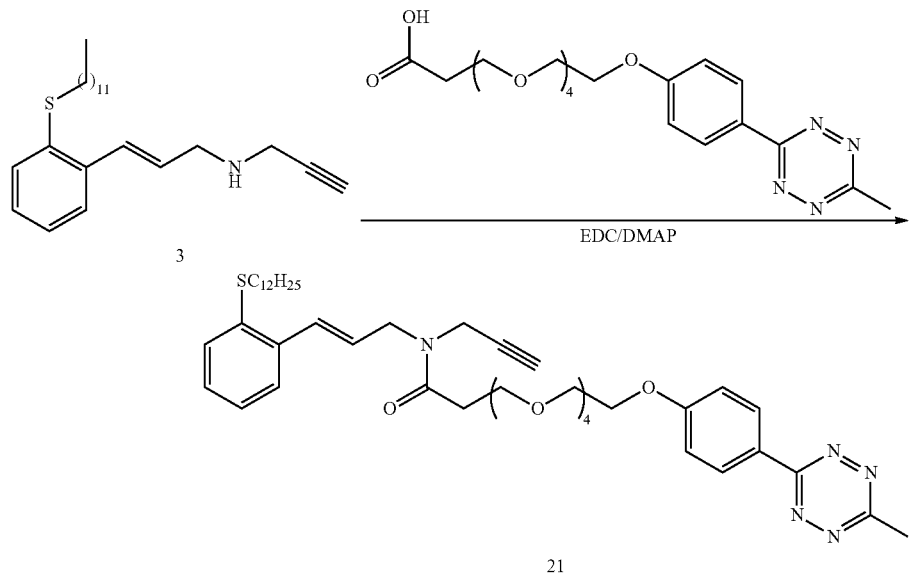

21

3 (43.4 mg, 0.087 mmol, 1.3 eq.) and Methyltetrazine-PEG$_4$-acid (50 mg, 0.115 mmol, 1 eq.) were dissolved in 1 mL of dichloromethane. 2.16 mg of 4-(dimethyamino)pyridine (0.2 eq.) was added. Then, EDC (27.6 mg, 1.6 eq.) was added, and the solution was stirred at room temperature. The reaction was monitored by TLC (5% MeOH/DCM). Upon complete consumption of 3, the solution was evaporated under reduced pressured. The residue was purified by silica gel chromatography (MeOH/DCM) to afford 21 (86.9 mg, 96% yield).

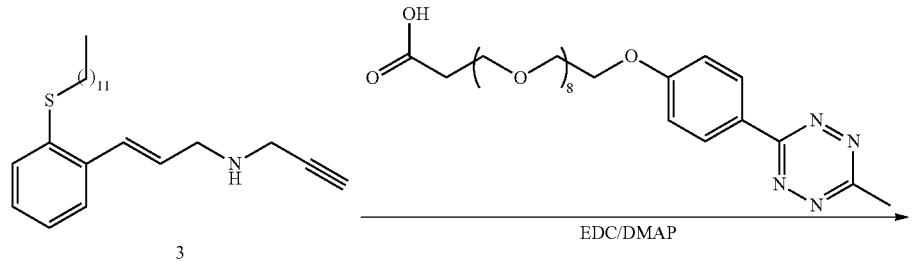

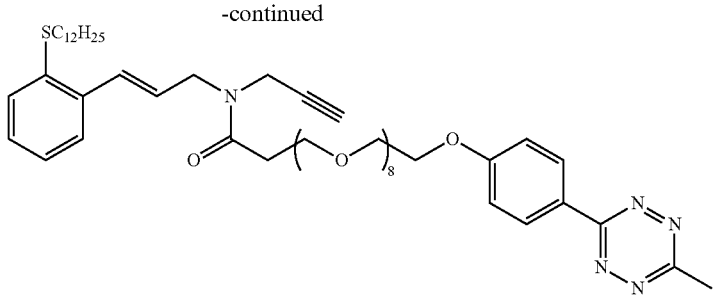

22

3 (39.4 mg, 0.106 mmol, 1.3 eq.) and Methyltetrazine-PEG$_8$-acid (50 mg, 0.0816 mmol, 1 eq.) were dissolved in 1 mL of dichloromethane. 2.02 mg of 4-(dimethyamino)pyridine (0.2 eq.) was added. Then, EDC (23.5 mg, 1.5 eq.) was added, and the solution was stirred at room temperature. The reaction was monitored by TLC (5% MeOH/DCM). Upon complete consumption of 3, the solution was evaporated under reduced pressured. The residue was purified by silica gel chromatography (MeOH/DCM) to afford 22 (79 mg, Quantitative yield).

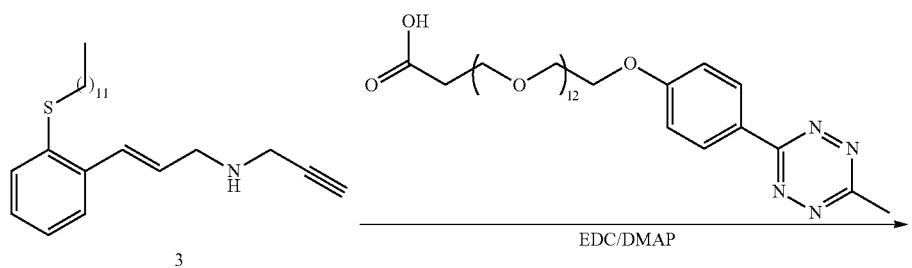

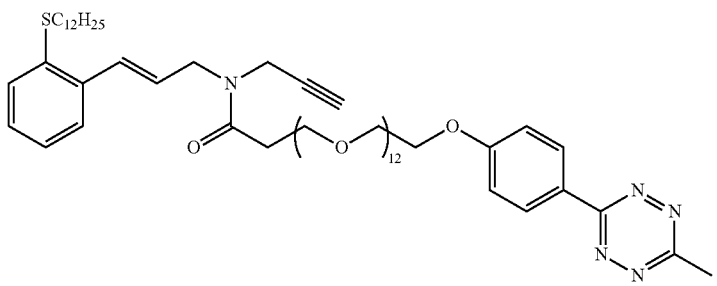

23

3 (15.5 mg, 0.0416 mmol, 1.3 eq.) and Methyltetrazine-PEG$_{12}$-acid (25 mg, 0.032 mmol, 1 eq.) were dissolved in 1 mL of dichloromethane. 0.8 mg of 4-(dimethyamino)pyridine (0.2 eq.) was added. Then, EDC (9.24 mg, 1.5 eq.) was added, and the solution was stirred at room temperature. The reaction was monitored by TLC (5% MeOH/DCM). Upon complete consumption of 3, the solution was evaporated under reduced pressured. The residue was purified by silica gel chromatography (MeOH/DCM) to afford 23 (34.9 mg, 96% yield).

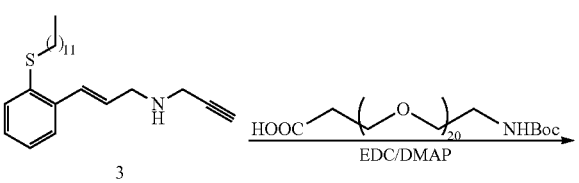

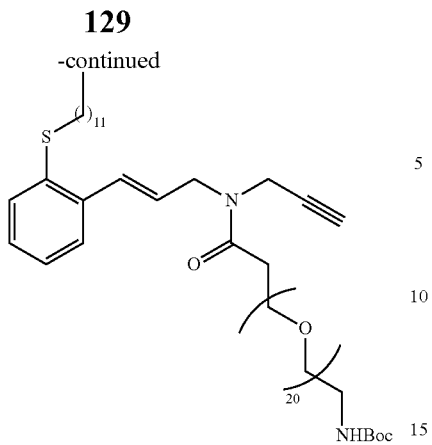

3 (45.3 mg, 0.12 mmol, 1.3 eq.) and t-Boc-N-amido-PEG$_{20}$-acid (100 mg, 0.093 mmol, 1 eq.) were dissolved in 1 mL of dichloromethane. 2.29 mg of 4-(dimethyamino) pyridine (0.2 eq.) was added. Then, EDC (26.6 mg, 1.5 eq.) was added, and the solution was stirred at room temperature. The reaction was monitored by TLC (5% MeOH/DCM). Upon complete consumption of 3, the solution was evaporated under reduced pressured. The residue was purified by silica gel chromatography (MeOH/DCM) to afford 24 (122.4 mg, 92% yield).

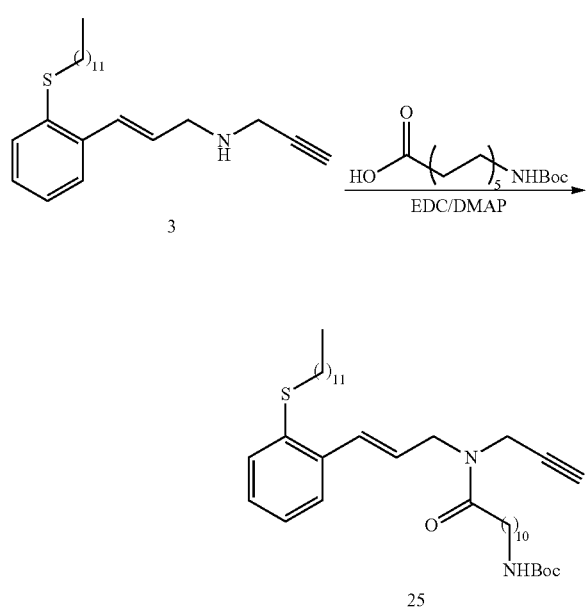

3 (150 mg, 0.404 mmol, 1 eq.) and BOC-11-AUN-OH (128 mg, 0.424 mmol, 1.05 eq.) were dissolved in 3 mL of dichloromethane. 9.9 mg of 4-(dimethyamino)pyridine (0.2 eq.) was added. Then, EDC (100.6 mg, 1.3 eq.) was added, and the solution was stirred at room temperature. The reaction was monitored by TLC (5% MeOH/DCM). Upon complete consumption of 3, the solution was evaporated under reduced pressured. The residue was purified by silica gel chromatography (MeOH/DCM) to afford 25 (264 mg, Quantitative yield).

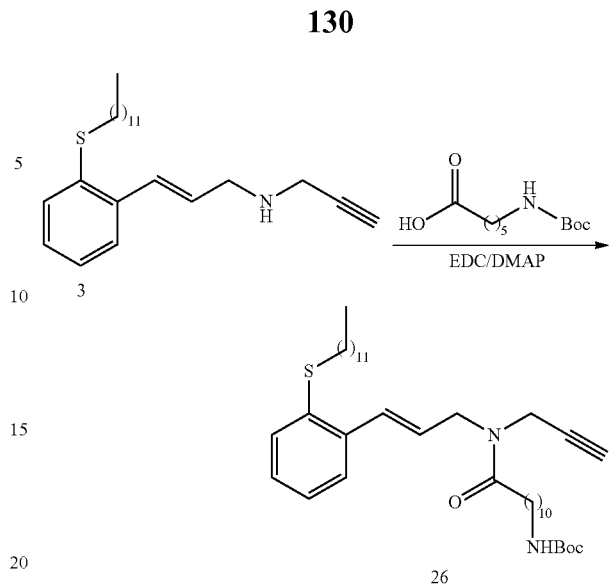

3 (150 mg, 0.404 mmol, 1 eq.) and BOC-6-AHX-OH (98.2 mg, 0.093 mmol, 1.05 eq.) were dissolved in 1 mL of dichloromethane. 9.9 mg of 4-(dimethyamino)pyridine (0.2 eq.) was added. Then, EDC (100.6 mg, 1.3 eq.) was added, and the solution was stirred at room temperature. The reaction was monitored by TLC (5% MeOH/DCM). Upon complete consumption of 3, the solution was evaporated under reduced pressured. The residue was purified by silica gel chromatography (MeOH/DCM) to afford 26 (236 mg, Quantitative yield).

Synthesis of Exemplary Brush Polymers

In a nitrogen filled glovebox, to a 4-mL scintillation vial charged with a stir bar and containing PEG based MM, dye labelled or drug conjugated MM (100 mg) was added anhydrous THF (400 µL). To this solution then was added Grubbs III catalyst solution in THF, all at once (0.376 mg) to give MM: Grubbs III ratio of 60:1. The polymerization reaction was stirred at room temperature for 60 min. Then, different enyne compounds were added for additional 1.5 h reaction to obtain different terminal functional groups. A 10-µL aliquot was taken out for size exclusion chromatography analysis of polymerization product. The remaining brush solution was precipitated in cold ethyl ether and washed with the cold ether for several times.

Antibody Brush Polymer Conjugation for ABCs

Antibody Surface Modification with TCO Functionality 1 mg of antibody was dissolved in 0.6 mL PBS. Then, 60 µL of 0.5 M NaHCO$_3$ buffer solution was added under stirring. To the above solution was added 60 µg of TCO-PEG$_{12}$-NHS

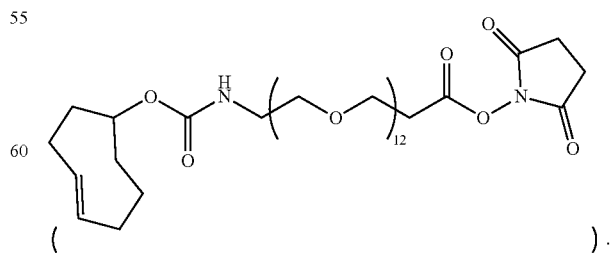

The reaction mixture was then stirred at room temperature for an additional 4 h, followed by filtration with a 220 µm filter and an ultrafiltration purification using Amicon Ultra Centrifugal Filters (MWCO=10,000). The final protein was dissolved in 200 μL of DI water (5 mg/mL) and stored at 4° C. The modification of the boronic acid linker was quantified by MADLI-MS.

In some experiments, TCO-PEG$_{n4}$-NHS was used, wherein n4 is an integer from 1 to 20, inclusive. In some experiments, TCO-PEG$_8$-NHS was used, Antibody-Brush Polymer Conjugation 30 μL of above TCO functionalized antibody was mixed with 60 μL tetrazine functionalized brush polymer

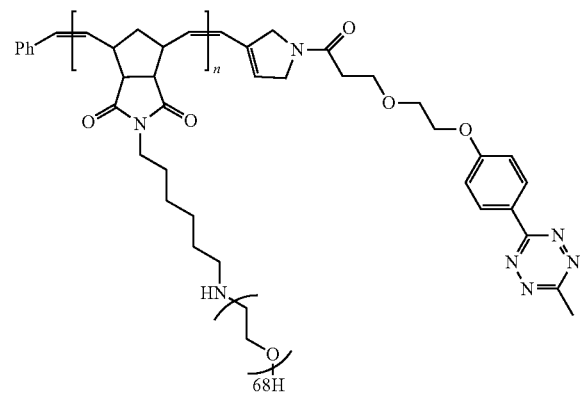

(which does not contain a pharmaceutical agent) or a derivative that contains a pharmaceutical agent, 10 mg/mL). The reaction solution was stirred at room temperature for 24 h.

Example 2. Anti-HER2 Targeted ABCs

Anti-HER2 Brush Polymers Conjugation

Figure 5A:
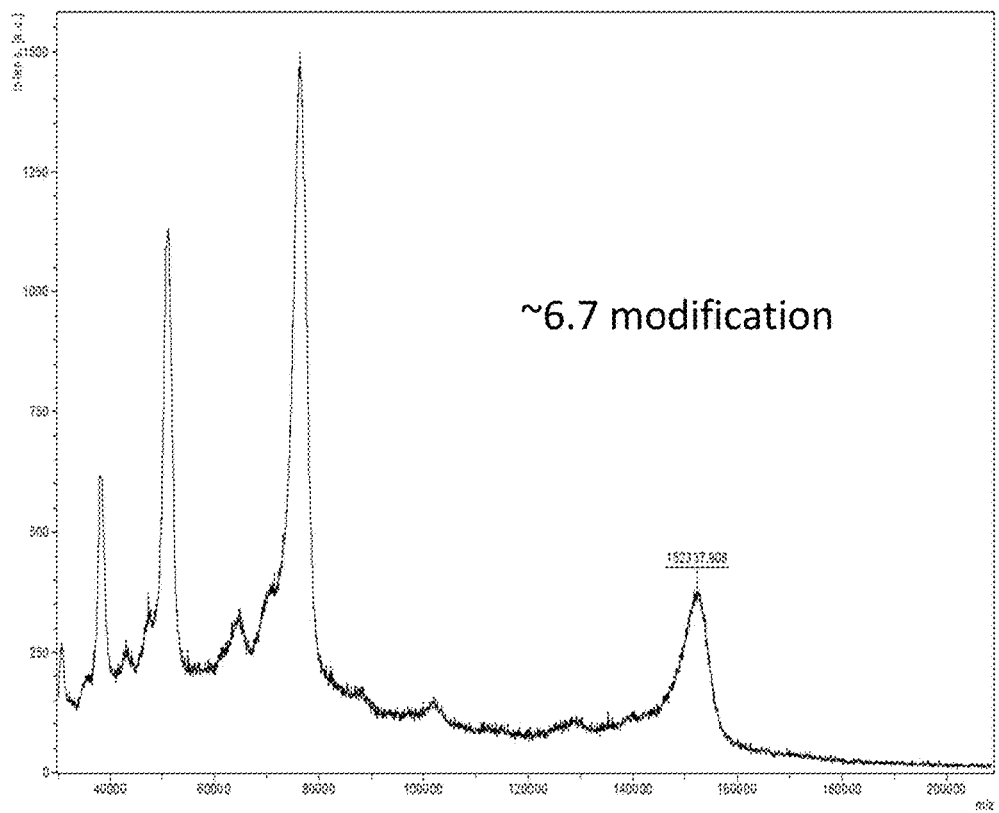
FIG. 5A shows a mass spectrum of an anti-HER2 brush polymer conjugate.
Figure 5B:
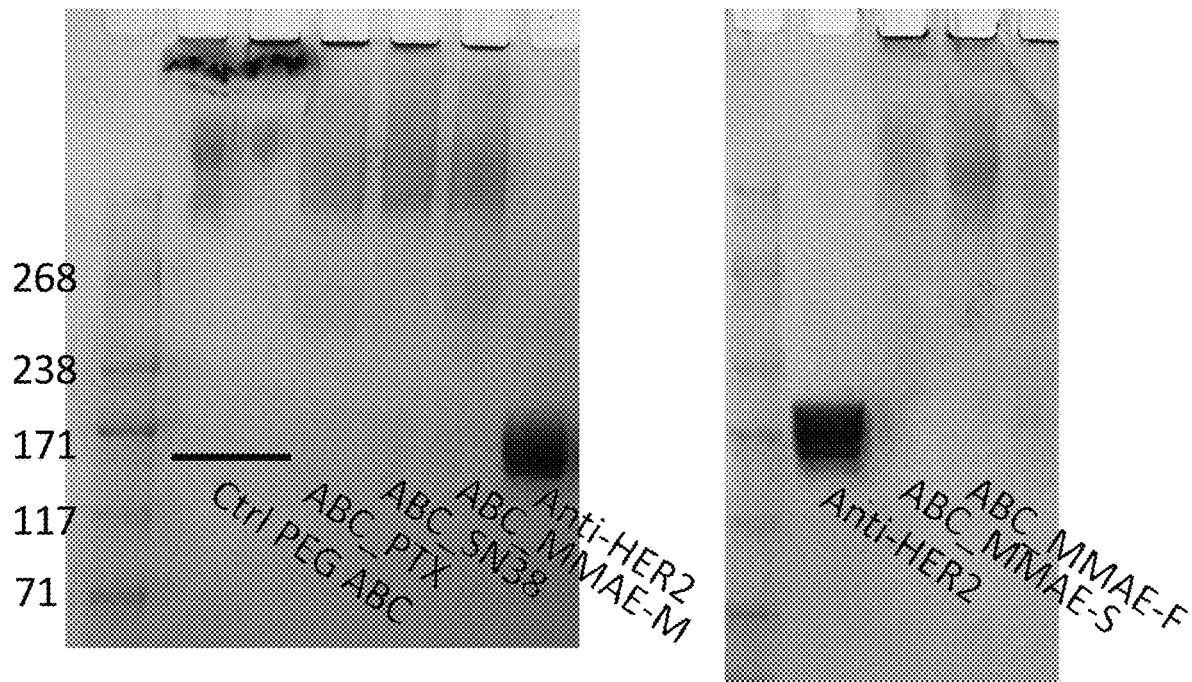
FIG. 5B are images of SDS-PAGE gels that showed successful anti-HER2 brush polymer conjugation due to the smear band in the higher molecular weight and disappearance of the free antibody band. "Ctrl" refers to control.

Mass spectrometry was performed (FIG. 5A). SDS-PAGE gels showed successful conjugation due to the smear band in the higher molecular weight and disappearance of the free antibody band (FIG. 5B).

Anti-HER2 ABCs for Cell Targeting

Figure 6A:
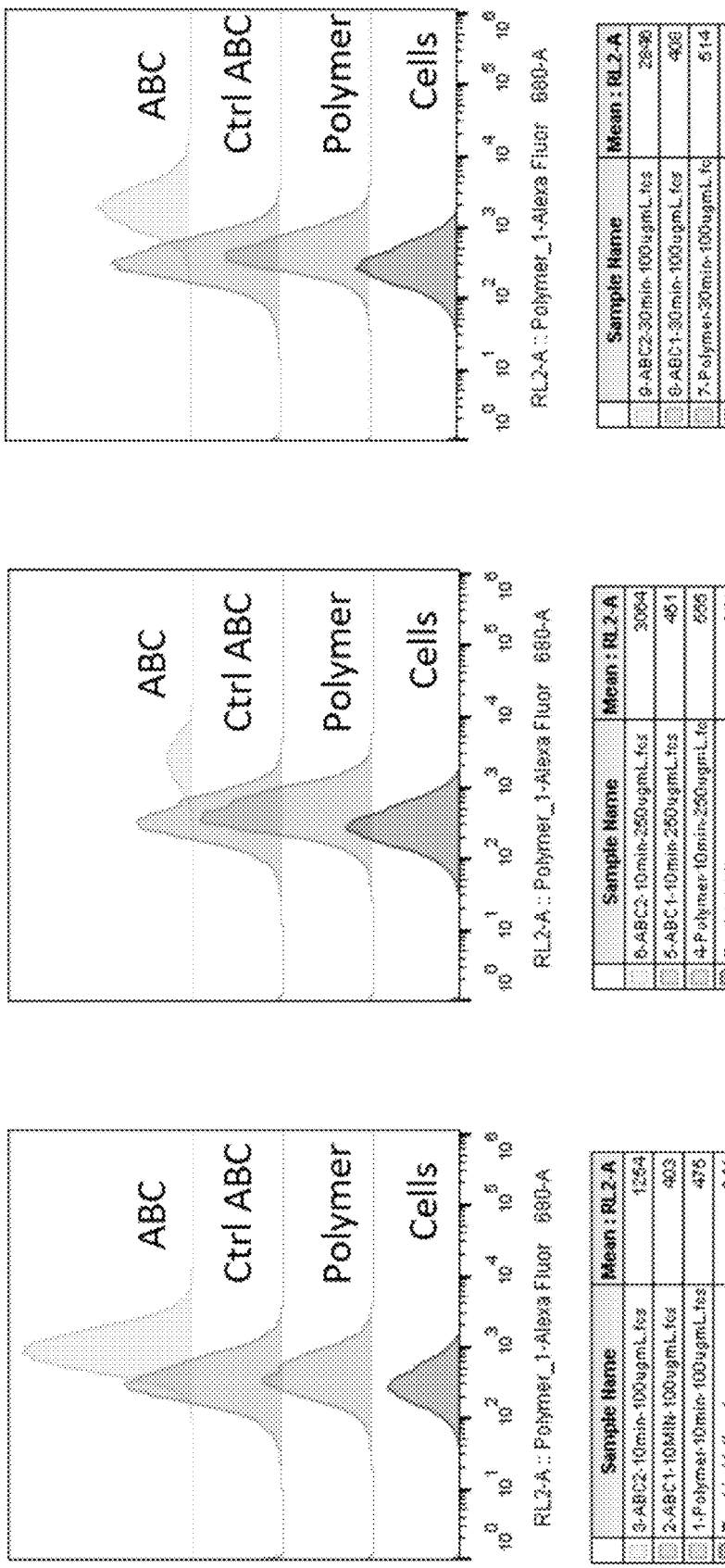
FIGS. 6A to 6B show anti-HER2 ABCs in the SKBR-3 cell line (HER2 high expression). Results show that ABCs can significantly enhance cell uptake toward HER2 high expression cell line.
Figure 6B:
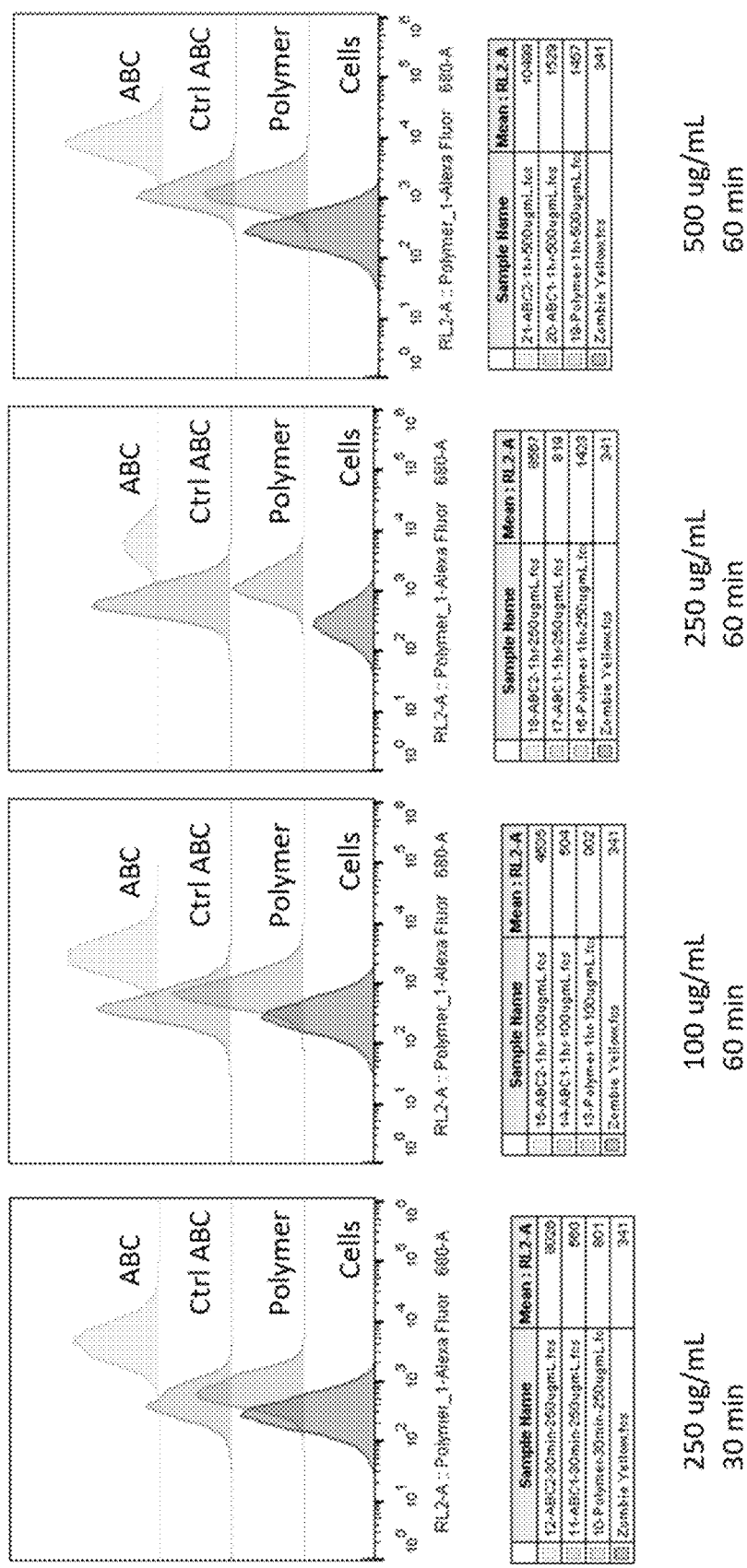
Figure 7A:
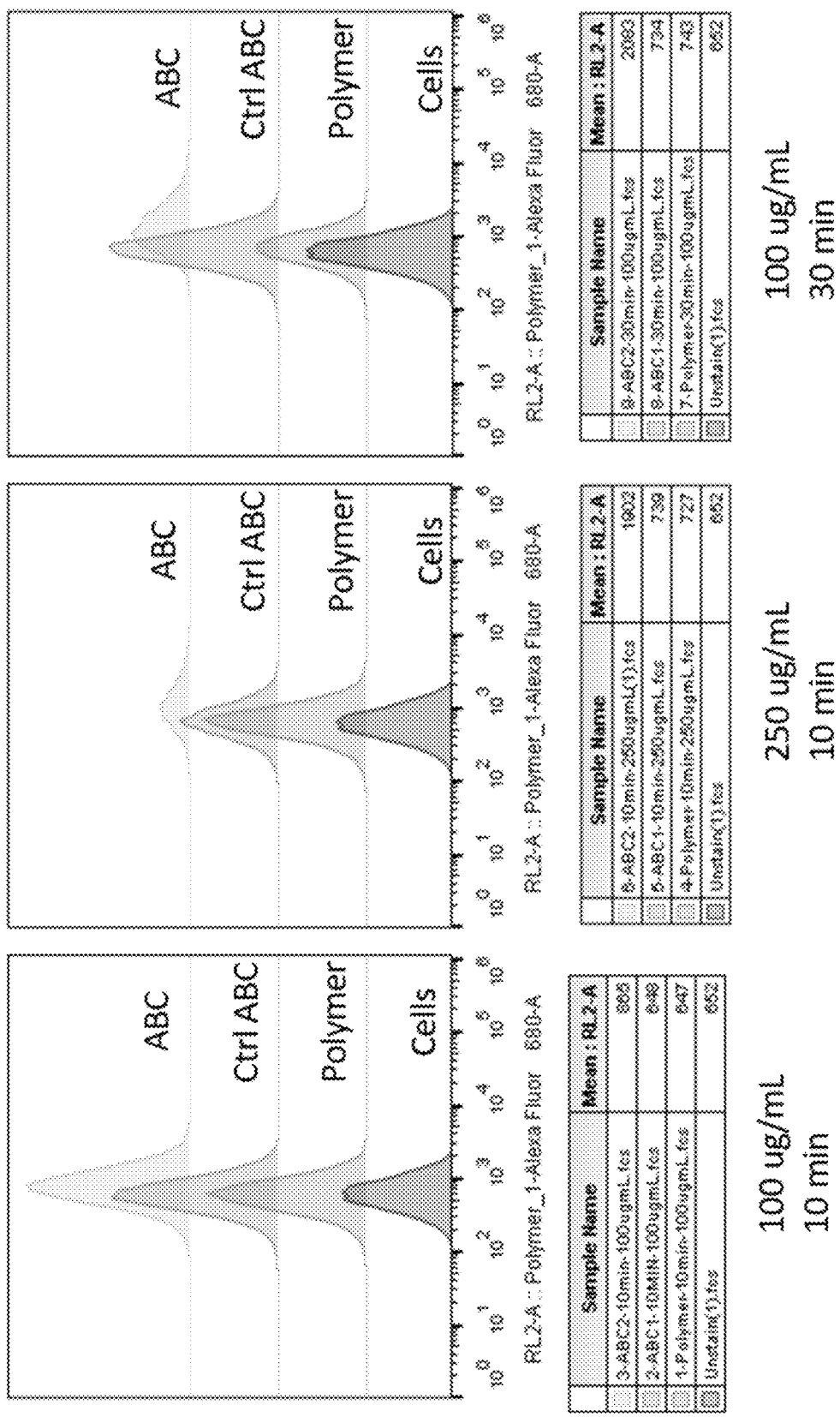
FIGS. 7A to 7B show anti-HER2 ABCs in the SKOV-3 cell line (HER2 medium expression). Results show that ABCs can significantly enhance cell uptake toward HER2 medium expression cell line.
Figure 7B:
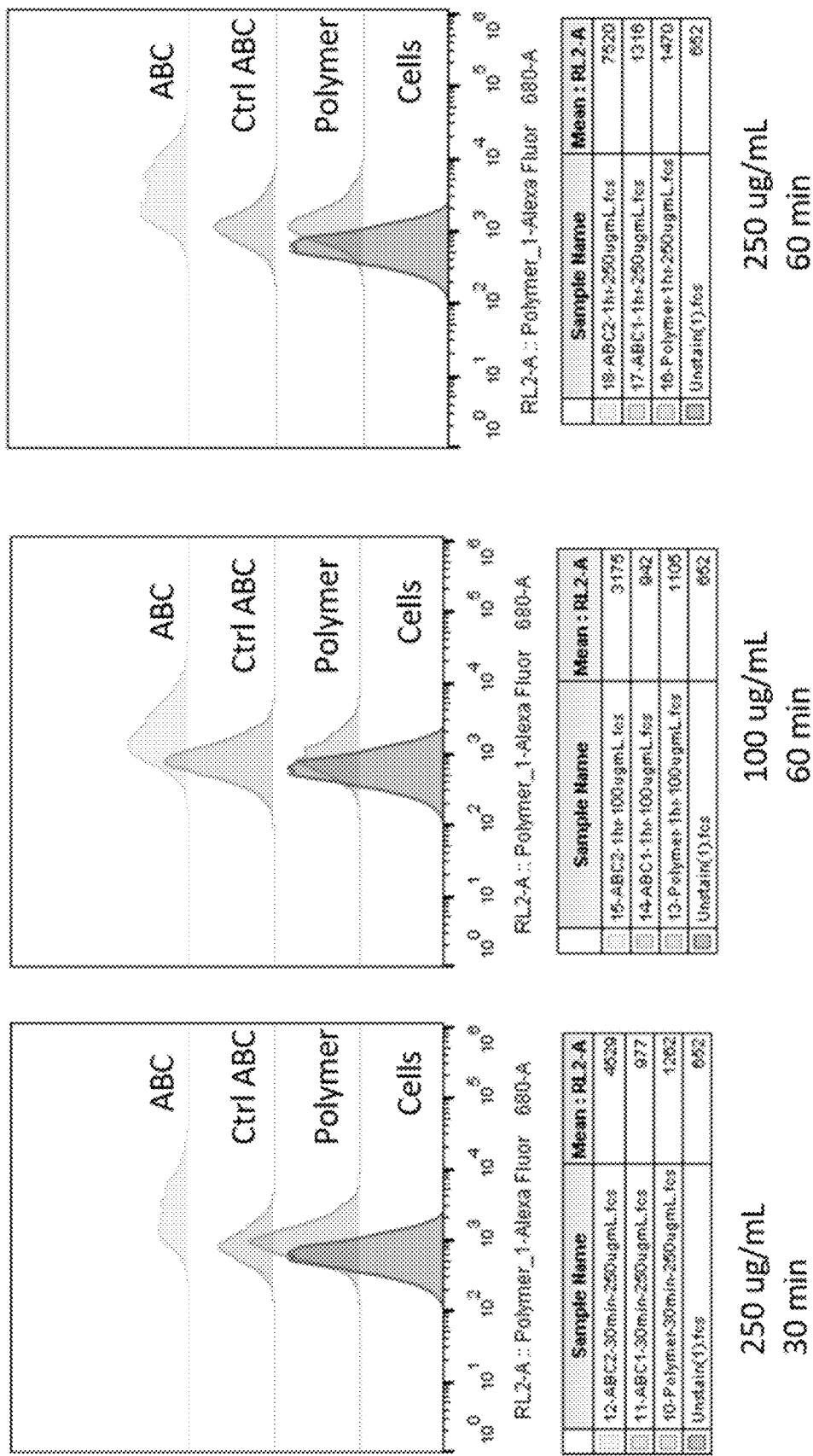
Figure 8A:
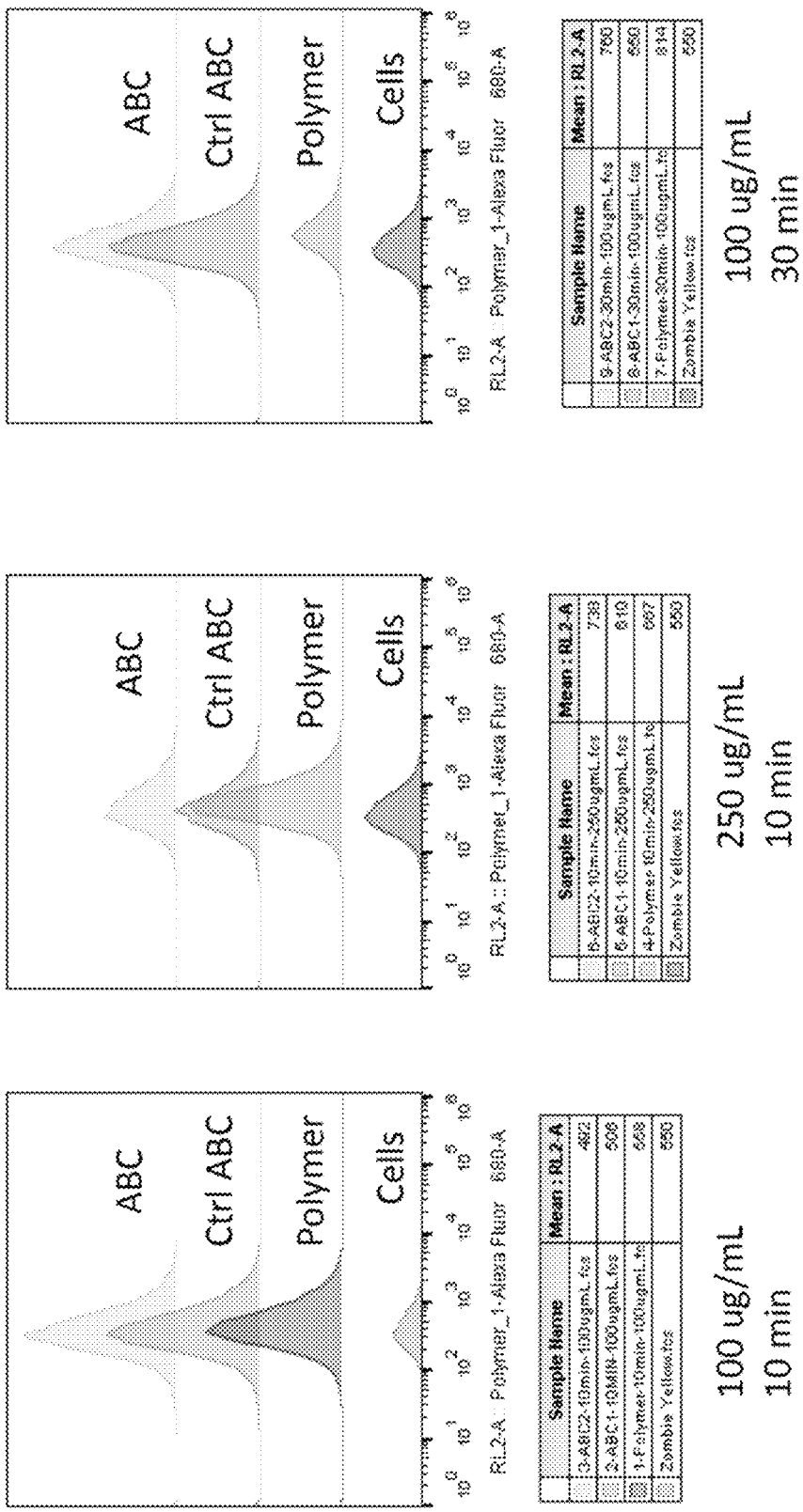
FIGS. 8A to 8B show anti-HER2 ABCs in the MCF-10A cell line (control cell line, no HER2 expression). Results show that ABCs cannot enhance cell uptake toward HER2 no expression cell line, demonstrating the specificity.
Figure 8B:
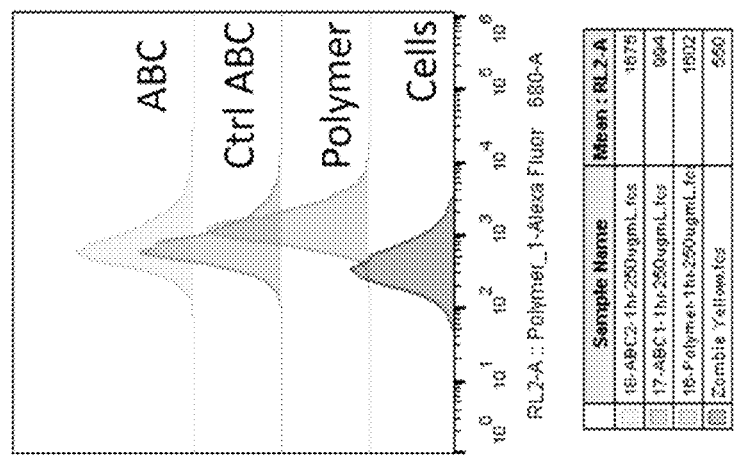
Figure 8B:
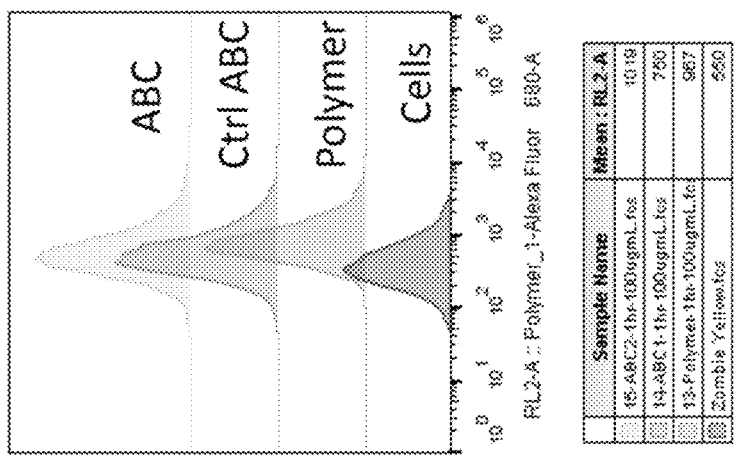
Figure 8B:
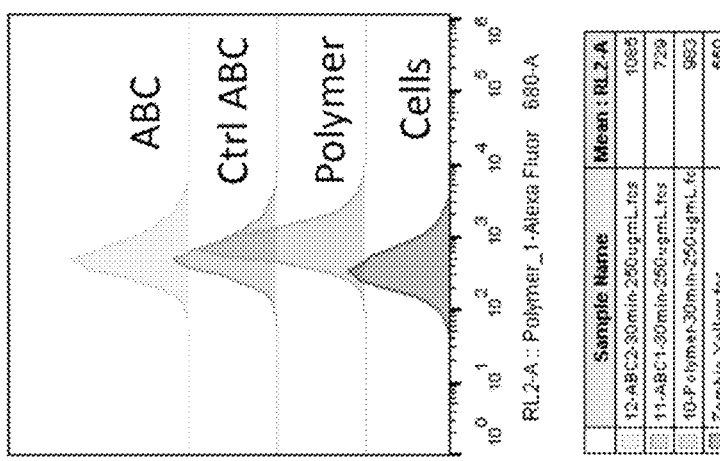

ABCs were tested in cell lines with high (SKBR-3), medium (SKOV-3), and no (MCF-10A) HER2 expression. Results showed that ABCs can significantly enhance cell uptake toward HER2 in high (FIGS. 6A to 6B) and medium (FIGS. 7A to 7B) expression cell lines. ABC could not enhance the cell uptake toward HER2 in the control (FIGS. 8A to 8B), demonstrating specificity. ABCs were also shown to significantly enhance cell uptake toward HCC-1954 (HER2 medium expression, FIG. 9A) and BT-474 cell lines (HER2 high expression, FIG. 9B).

Cell Toxicity Studies

Figure 10A:
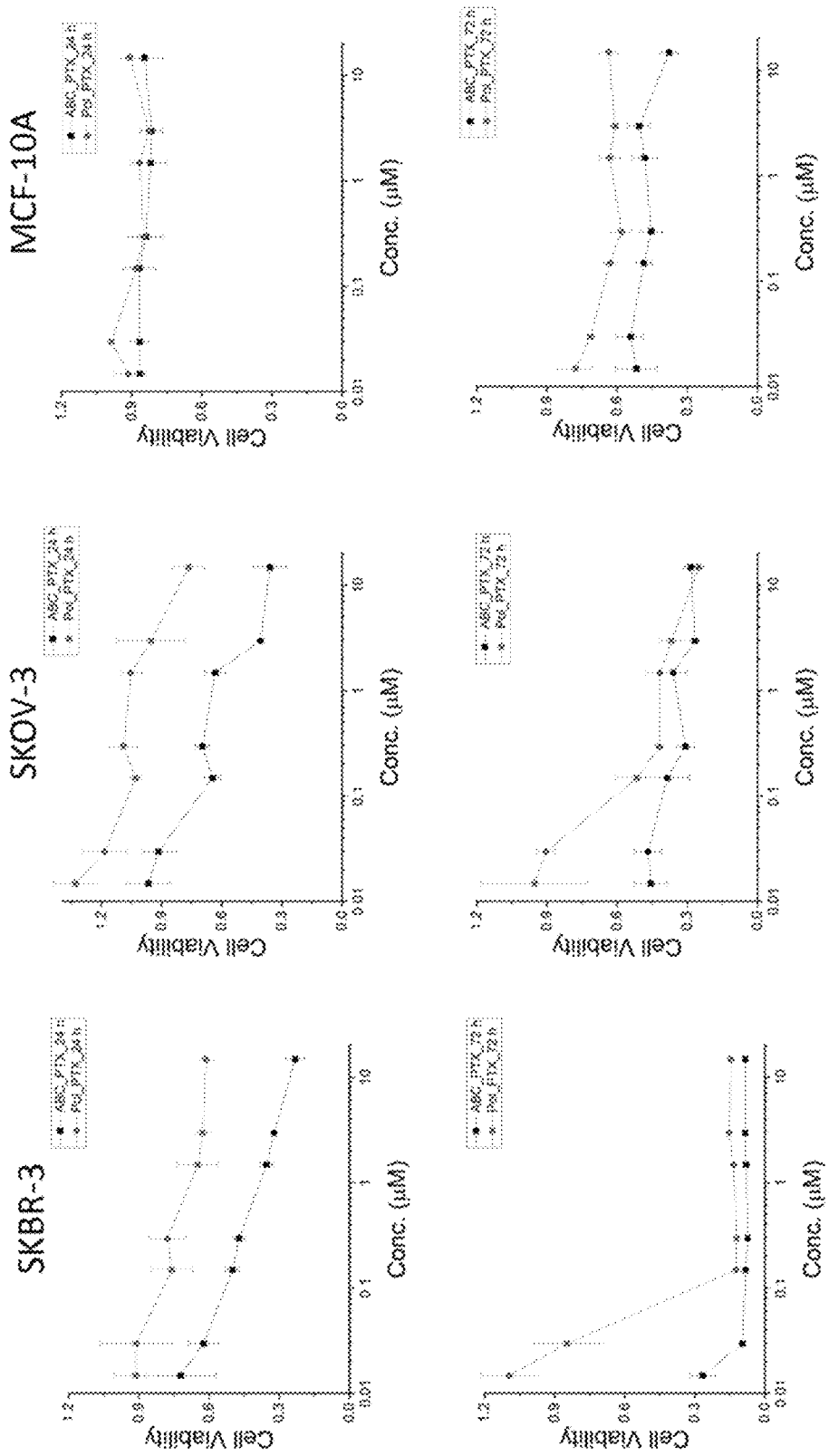
FIGS. 10A to 10B show cell toxicity studies on drug conjugated ABCs. Results show that ABCs can induce significantly higher toxicity compared to brush polymers (Pol) toward the HER2 expression cell lines, while they exhibited similar toxicity toward the control cell line (MCF-10A).
Figure 10B:
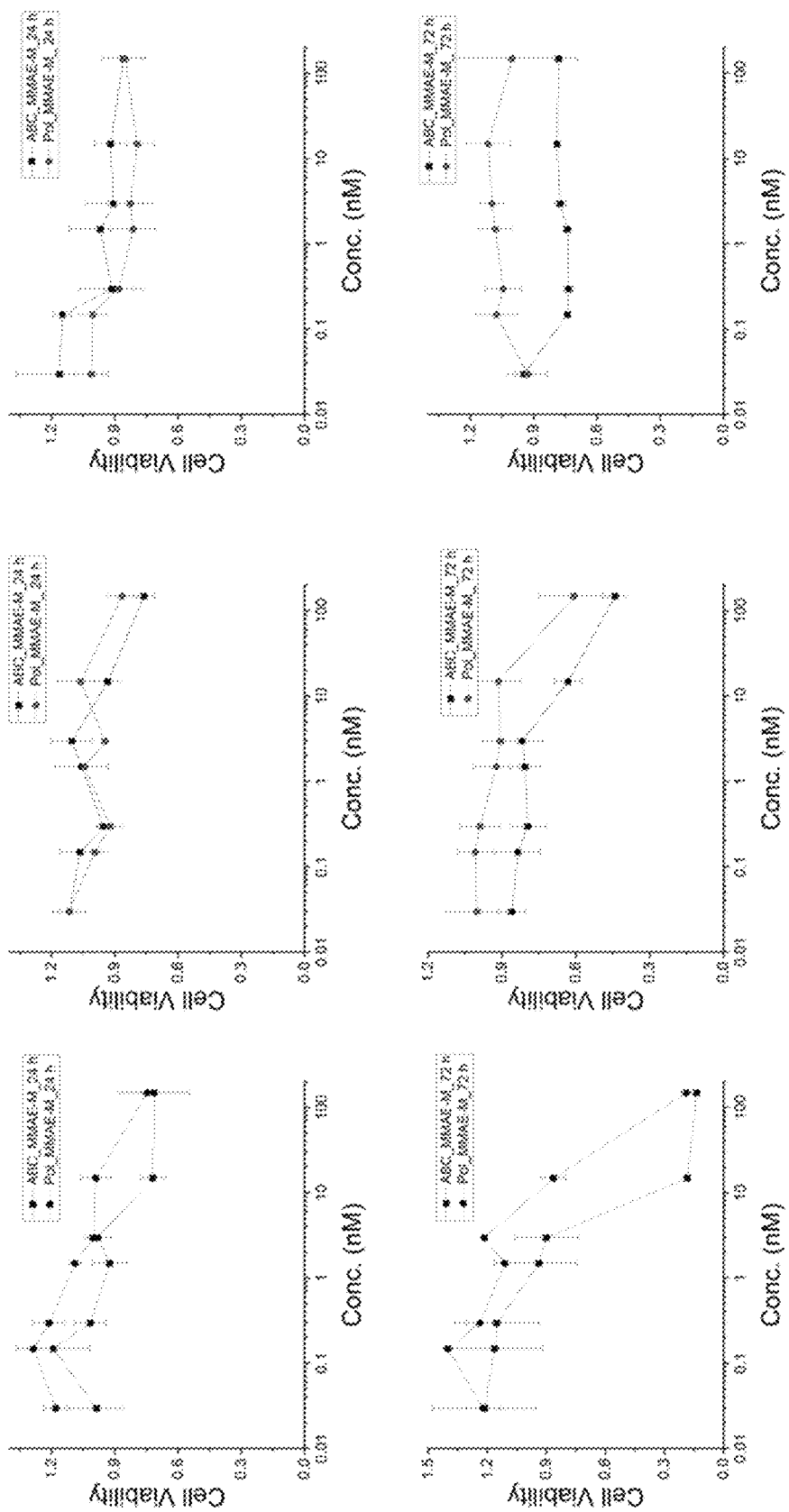
Figure 11A:
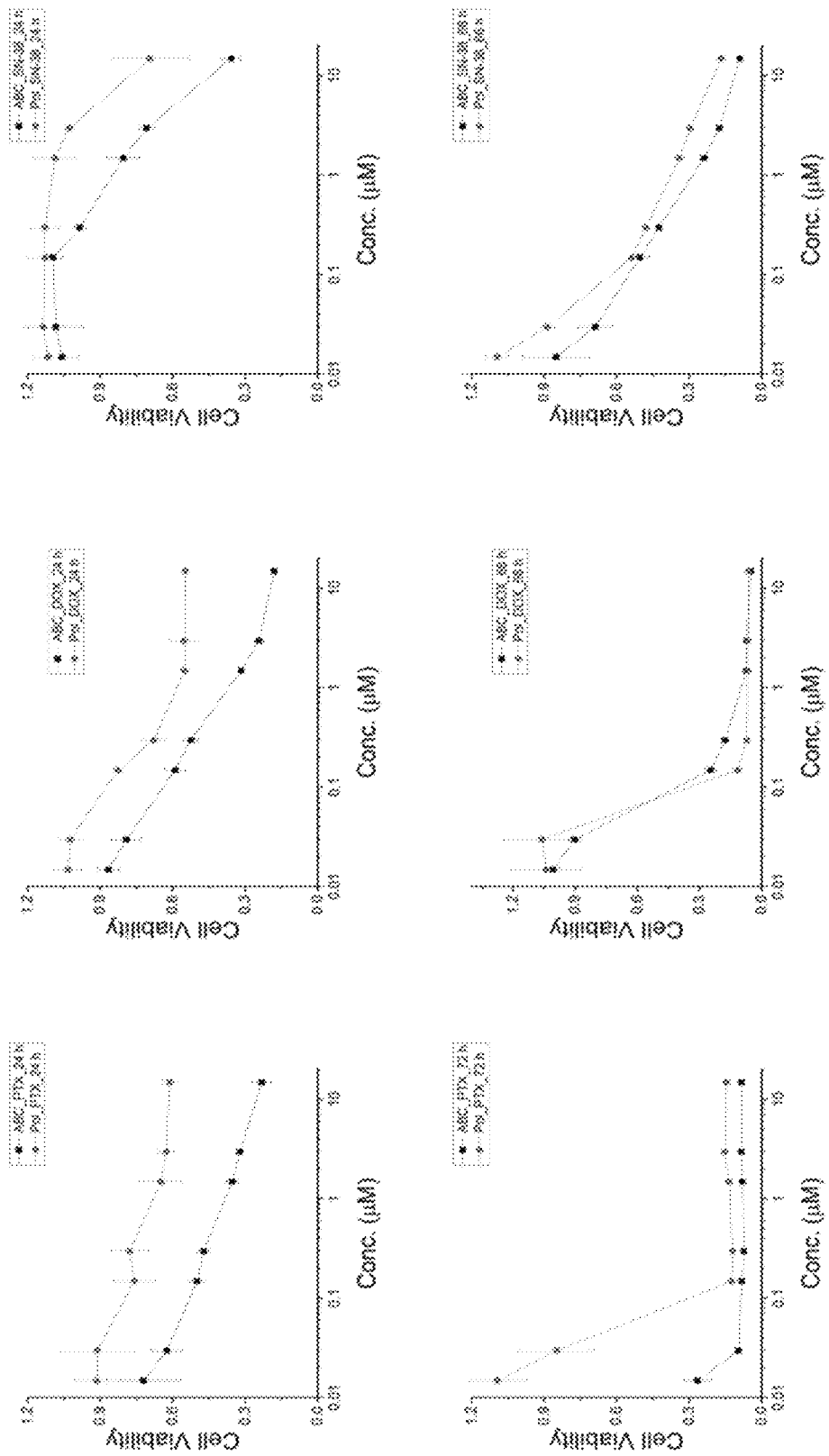
FIGS. 11A to 11D show cell toxicity studies in the SKBR-3 cell line. Results show that ABCs can induce significantly higher toxicity compared to brush polymers (Pol) and free drugs toward HER2 expression cell lines.
Figure 11B:
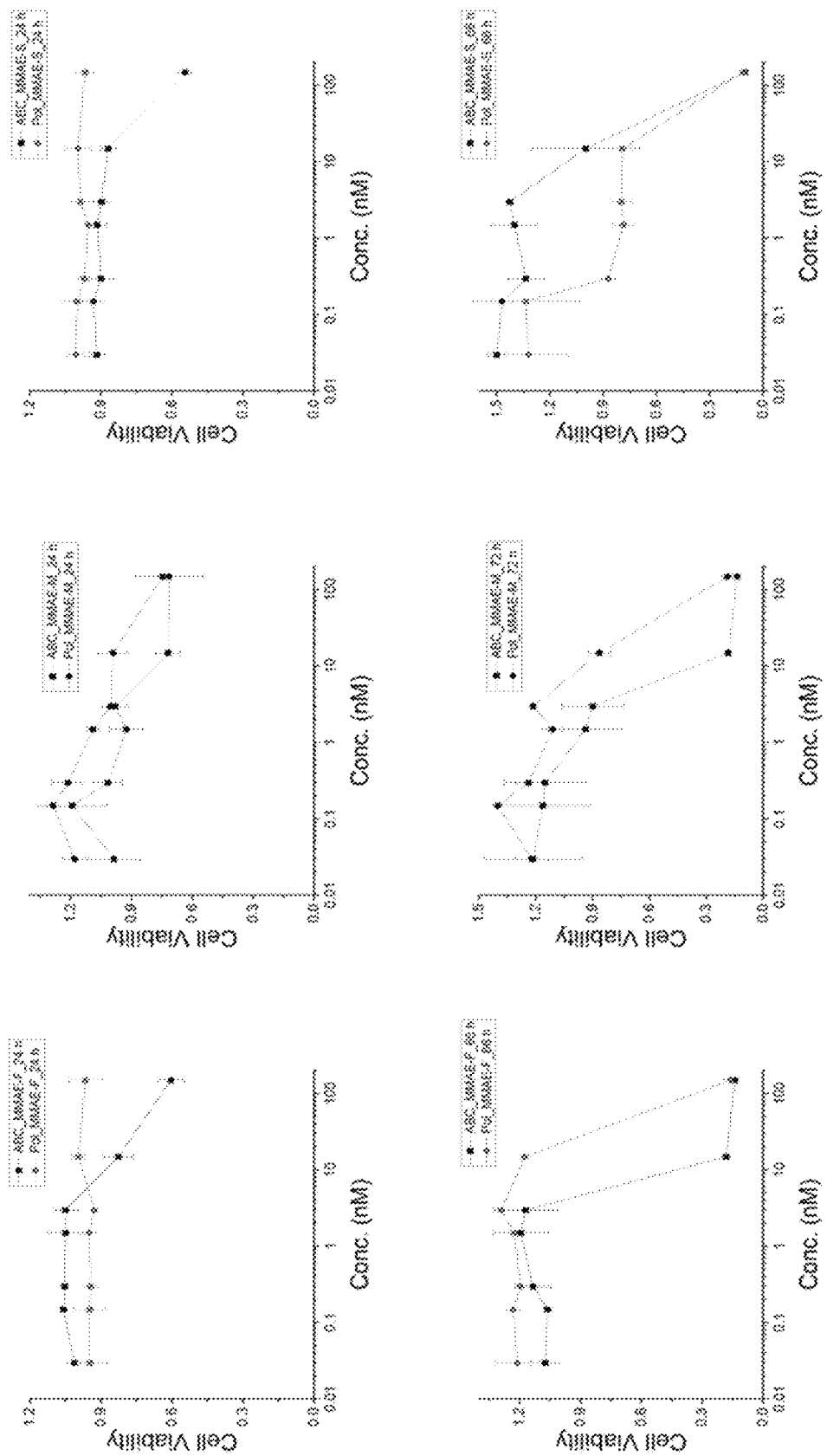
Figure 11C:
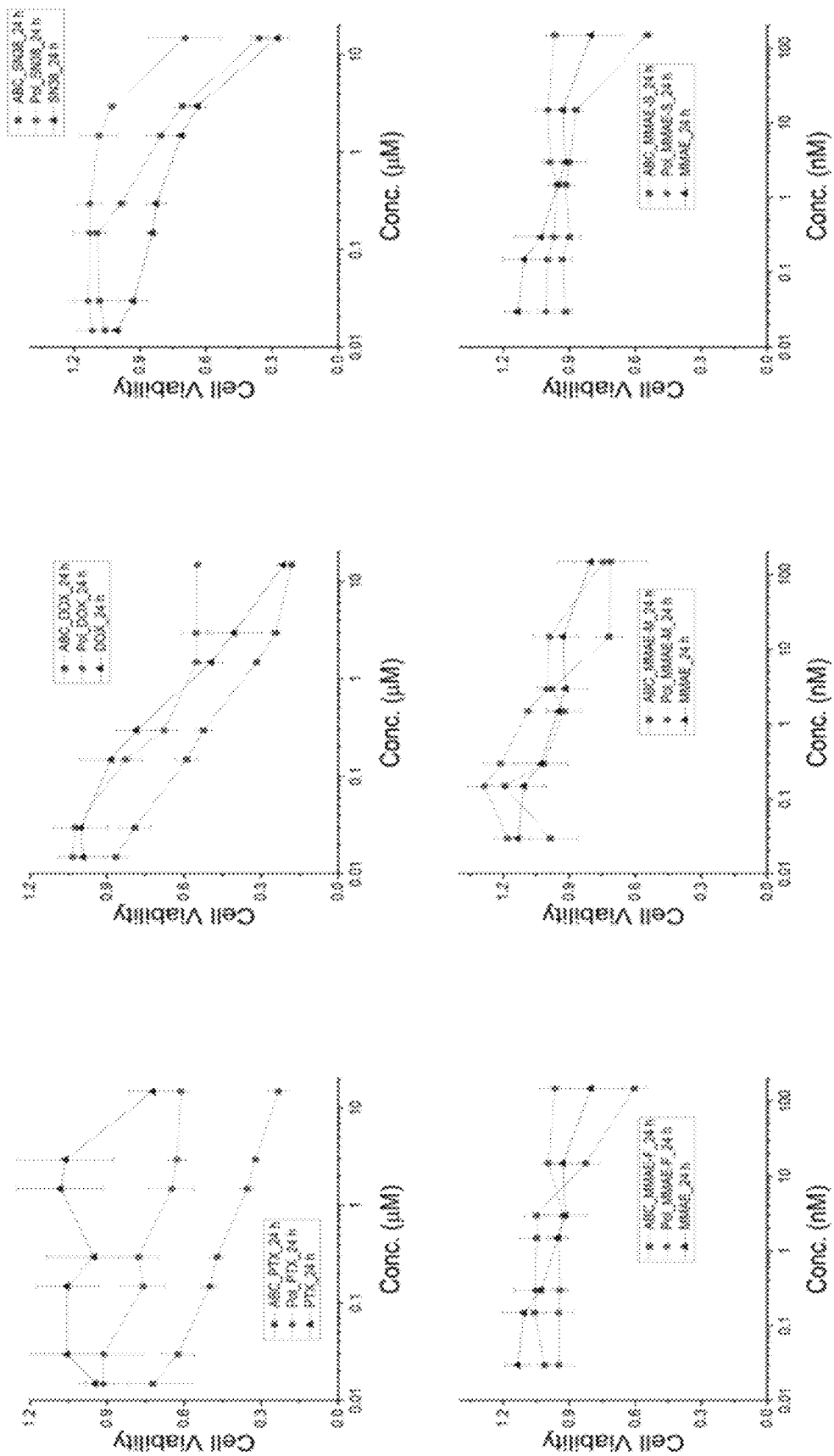
Figure 11D:
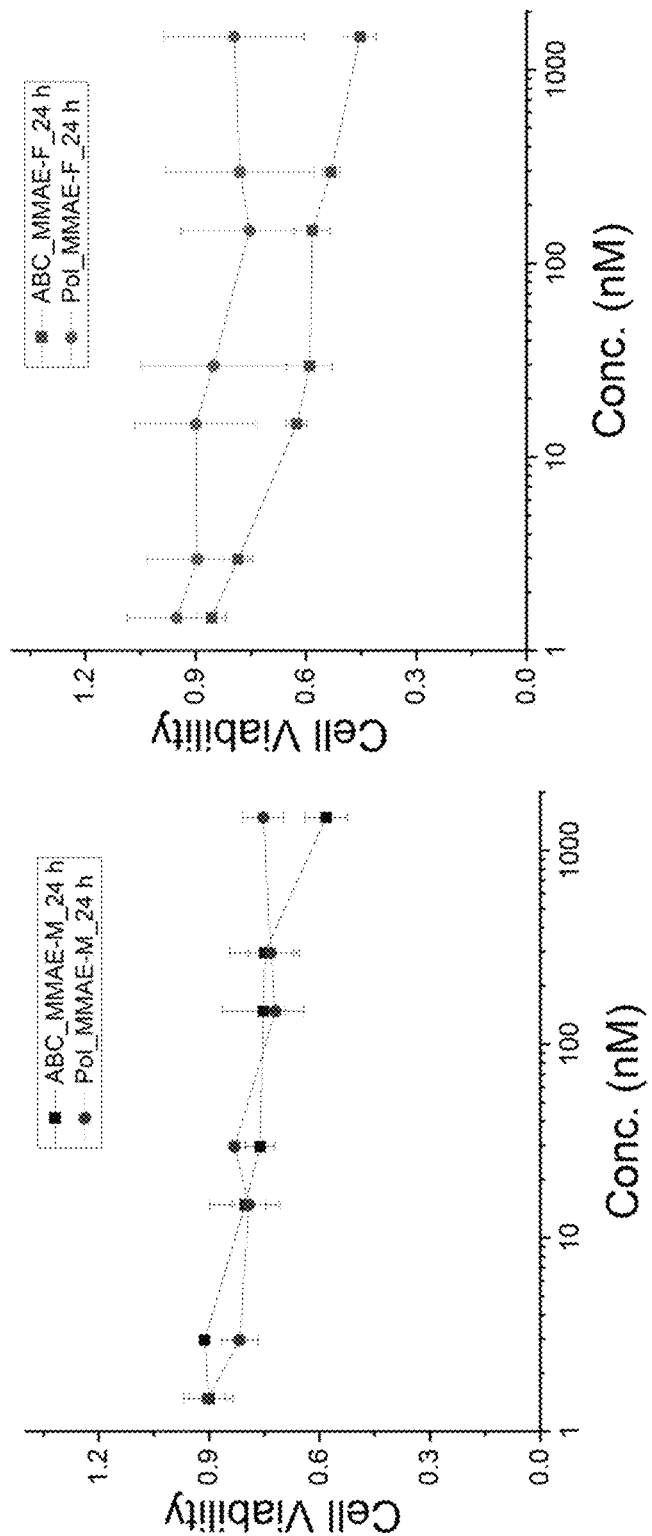

ABCs induced significantly higher toxicity compared to brush polymers in HER2 expression cell lines (SKBR-3, SKOV-3), but exhibited similar toxicity toward the control cell line (MCF-10A) (FIGS. 10A to 10B).

Cell toxicity was evaluated using different conditions in the SKBR-3 (high HER2 expression) cell line. Results show that ABCs can induce significantly higher toxicity compared to brush polymers and free drugs in HER2 expression cell lines. (FIGS. 11A to 11D)

Figure 12A:
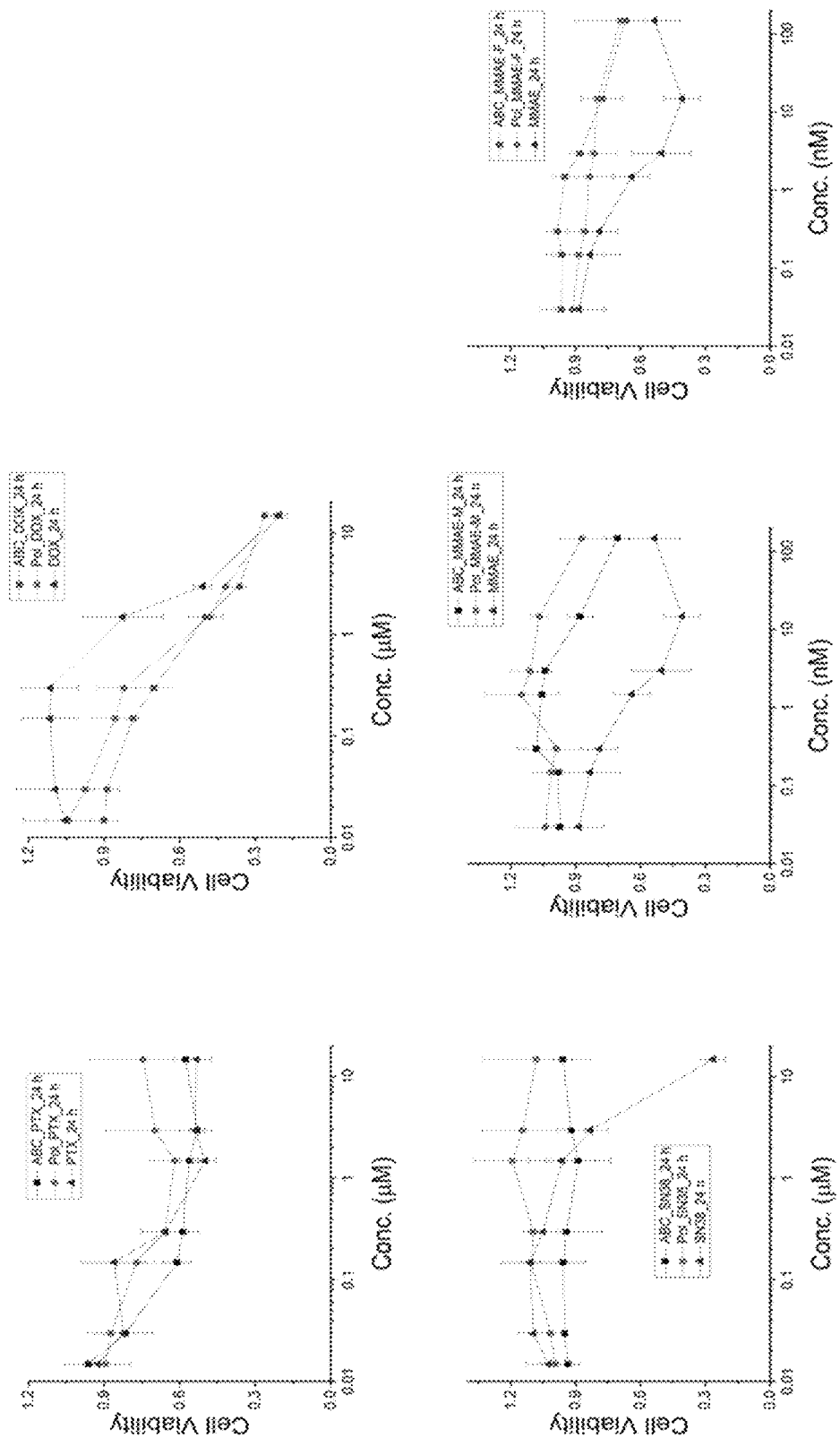
FIGS. 12A to 12B show cell toxicity studies in the HCC-1954 cell line. Results show that ABCs can induce significantly higher toxicity compared to brush polymers (Pol) toward low HER2 expression cell lines.
Figure 12B:
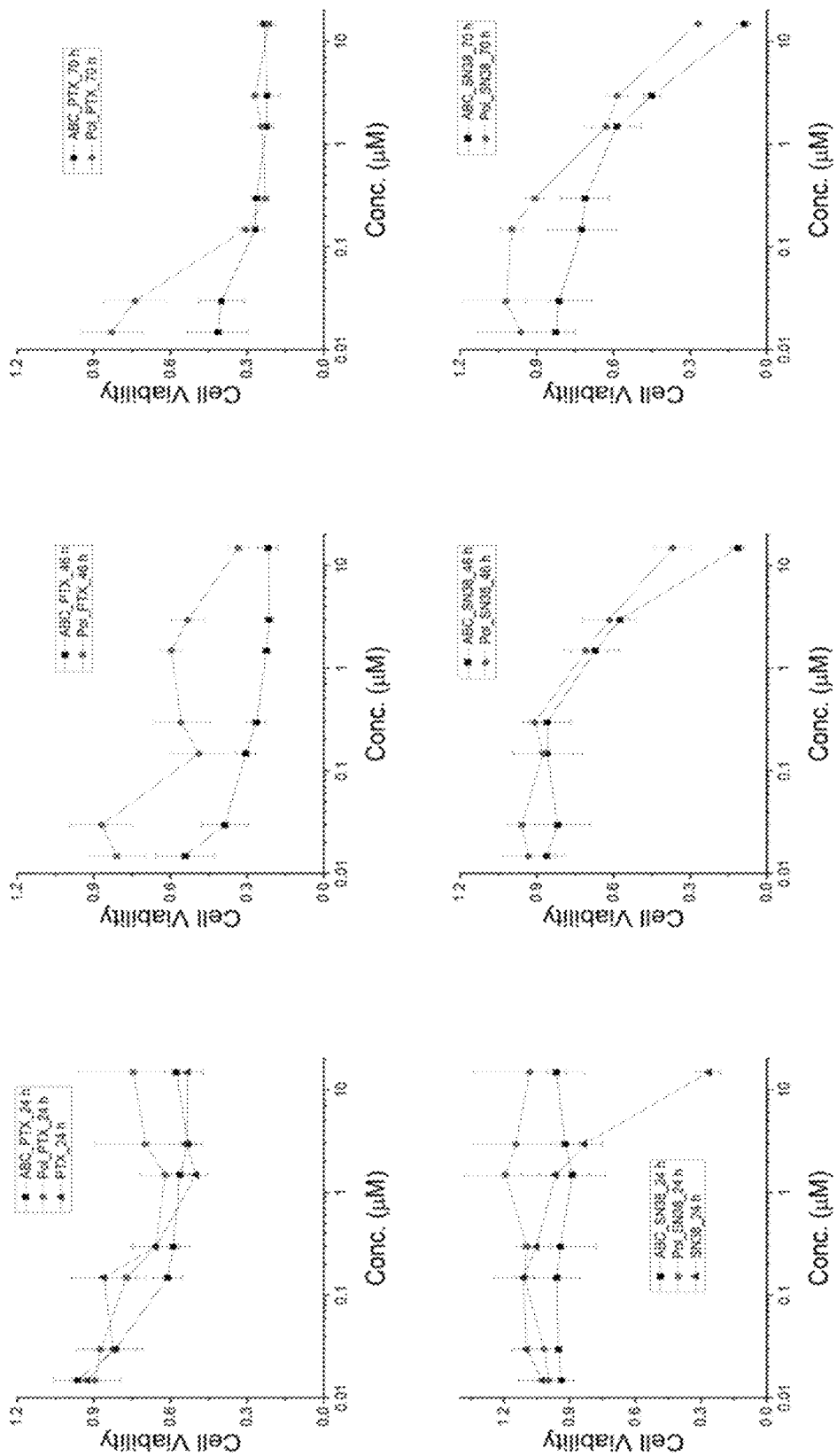
Figure 13:
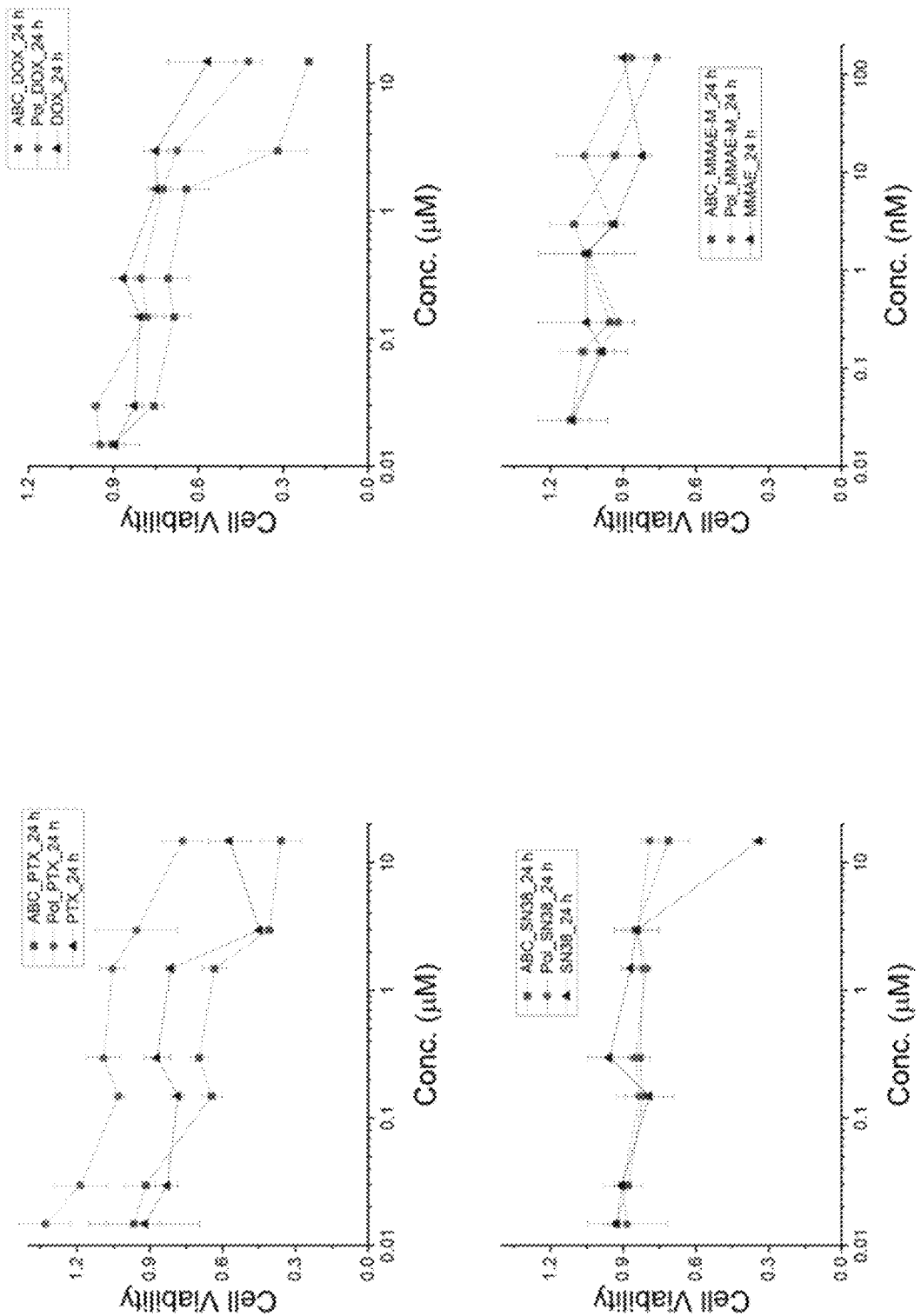
FIG. 13 shows cell toxicity studies in the SKOV-3 cell line. Results show that ABCs can induce significantly higher toxicity compared to brush polymers (Pol) toward medium HER2 expression cell lines.
Figure 14:
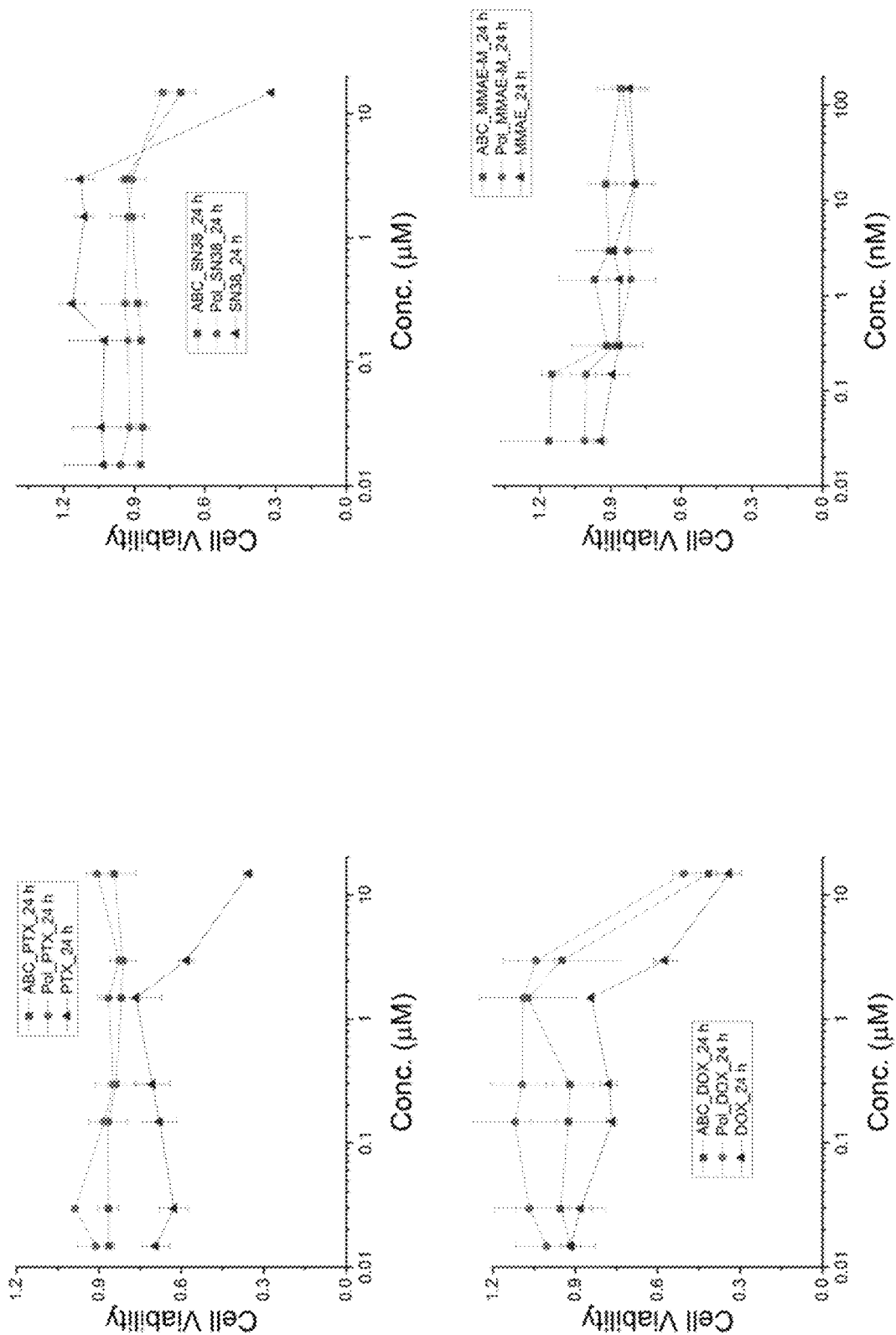
FIG. 14 shows cell toxicity studies in the MCF-10A (control) cell line. Results show that ABCs exhibited similar toxicity to brush polymers (Pol) toward the control cell line without HER2 expression.

Cell toxicity was also evaluated in the HCC-1954 and SKOV-3 cell line. Results show that ABCs can induce significantly higher toxicity compared to brush polymers in low and medium HER2 expression cell lines (FIGS. 12A to 12B. FIG. 13). ABCs exhibited similar toxicity to brush polymers in the control cell line (MCF-10A) without HER2 expression (FIG. 14).

Cell toxicity studies were performed in SKBR-3 (FIG. 15A), HCC-1954 (FIG. 15B) and BT-474 (FIG. 15C) cell lines with the free antibody as a control. Results show that the antibody itself has no toxicity toward these cell lines. The brush polymer or physical mixture of antibody and brush polymer have similar toxicity, significantly lower than ABCs.

Figure 16A:
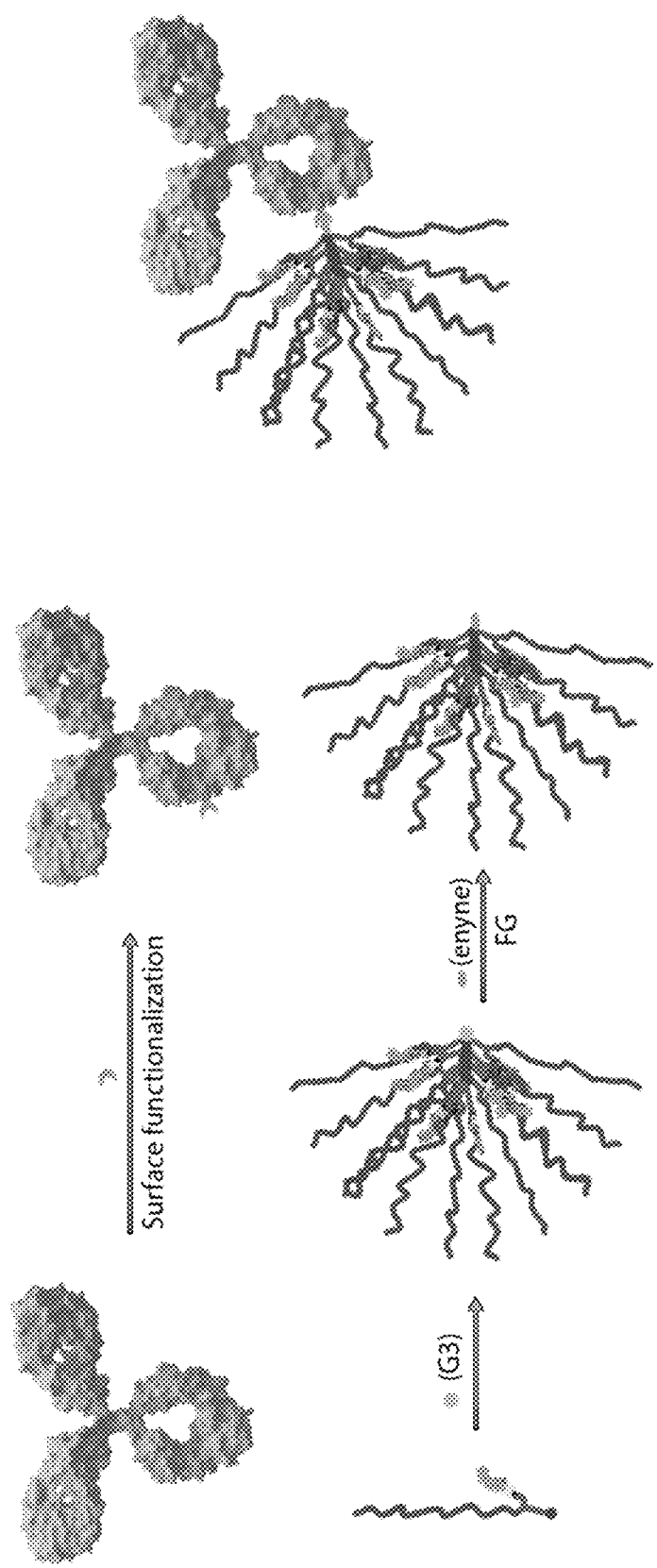
FIGS. 16A to 16D show anti-BCMA based ABCs for targeted delivery.
Figures 16B, 16C, 16D:
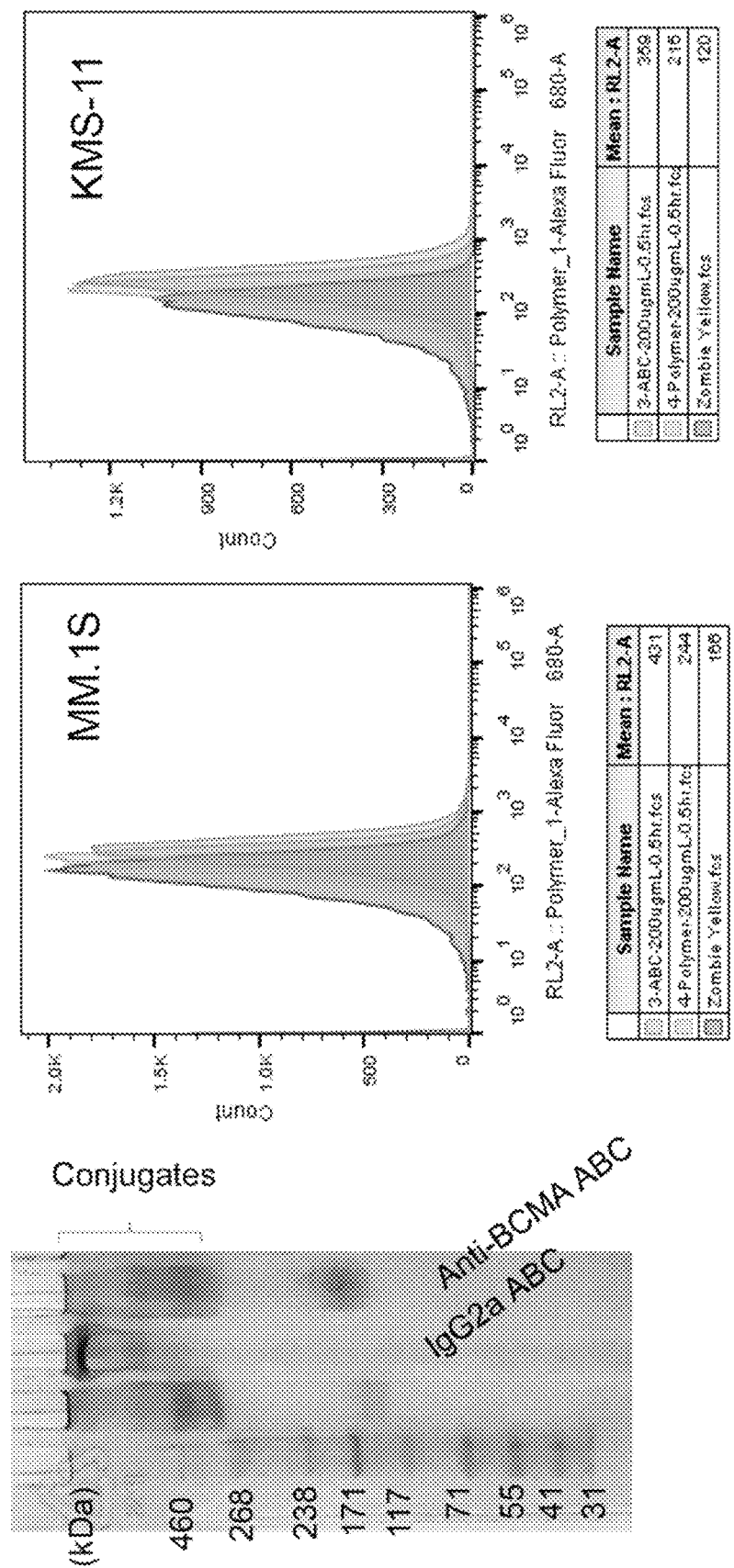

Further, we used Anti-BCMA based ABCs for targeted delivery by flow cytometry. Exemplary results are shown in FIGS. 16B to 16D. The ABCs show much higher cell uptake than BPD in two different cell lines (MM.1S and KMS-11).

Example 3. Cell Experiments

Cell Culture

Different cell lines (including SKBR-3, SKOV-3, MCF-10A, HCC-1954, BT-474) were cultured in T75 cell culture flask containing RMPI or Dulbecco's Modified Eagle Medium/Nutrient Mixture F-12 (DMEM/F12) in a humidified S26 incubator with 5% $CO_2$ at 37° C. Culture media was supplemented with 10% fetal bovine serum (FBS), 1% 1-glutamine, and 1% antibiotic-antimycotic (100 units/mL of penicillin, 100 μg/mL of streptomycin, and 0.25 μg/mL of amphotericin B).

Cellular Uptake Studies Based on Flow Cytometry

Cell uptake studies were performed with different cell lines, seeded at 150 000 cells/mL 24 well plate and cultured for 24 h at 37° C. in a 5% $CO_2$ incubator. The medium was discarded and cells were then incubated with 0.5 mL of medium containing different materials (including ABCs, brush polymers or control ABCs) for different times. After washing the cells with cold PBS, the mean fluorescence intensity within the cells was quantified using flow cytometry.

Cell Viability by MTT Assay

Different cells (including SKBR-3, SKOV-3, MCF-10A, HCC-1954, BT-474) were seeded into 96-well tissue culture plates at a density of 10 000 cells/well/100 μL sample and incubated at 37° C. After 24 h, culture media was replaced and cells were treated with different concentrations of brush polymers in 100 μL media (10 μL protein containing solution with different concentrations+90 μL medium). At the desired time interval, the medium was removed and the cells were cultured by 100 μL 10% MTT (5 mg/mL) in medium solution for another 4 h. Then, the solution was discarded and the remaining crystal was dissolved by 100 μL DMSO. The solution was subjected to absorbance measurement with SpectraMax M5 at 590 nm. Cell death was measured by the MTT assay in triplicate.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

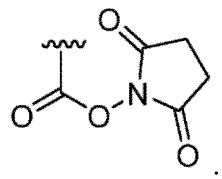

What is claimed is:

1. An end-functionalized polymer of Formula (III):

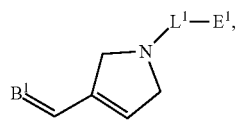

(III)

or a tautomer, isotopically labeled polymer, or salt thereof, wherein:
$B^1$ is a brush polymer or star polymer;

$L^1$ is substituted or unsubstituted, $C_{1-1000}$ alkylene, substituted or unsubstituted, $C_{2-1000}$ alkenylene, substituted or unsubstituted, $C_{2-1000}$ alkynylene, substituted or unsubstituted, $C_{1-1000}$ heteroalkylene, substituted or unsubstituted, $C_{2-1000}$ heteroalkenylene, or substituted or unsubstituted, $C_{2-1000}$ heteroalkynylene;

optionally wherein one or more backbone carbon atoms of the $C_{1-1000}$ alkylene, $C_{2-1000}$ alkenylene, $C_{2-1000}$ alkynylene, $C_{1-1000}$ heteroalkylene, $C_{2-1000}$ heteroalkenylene, or $C_{2-1000}$ heteroalkynylene are independently replaced with substituted or unsubstituted carbocyclylene, substituted or unsubstituted heterocyclylene, substituted or unsubstituted arylene, or substituted or unsubstituted heteroarylene, as valency permits;

$E^1$ is a thiophile, a first click-chemistry handle, a nucleophile, an electrophile, or a leaving group, H, halogen, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted carbocyclyl, substituted or unsubstituted heterocyclyl, substituted or unsubstituted aryl, substituted or unsubstituted heteroaryl, —OR$^a$, —N(R$^a$)$_2$, —SR$^a$, —CN, —SCN, —C(=O)R$^a$, —C(=O)OR$^a$, —C(=O)N(R$^a$)$_2$, —C(=NR$^a$)R$^a$, —C(=NR$^a$)OR$^a$, —C(=NR$^a$)N(R$^a$)$_2$, —NO$_2$, —N$_3$, —NR$^a$C(=O)R$^a$, —NR$^a$C(=O)OR$^a$, —NR$^a$C(=O)N(R$^a$)$_2$, —NR$^a$C(=NR$^a$)R$^a$, —NR$^a$C(=NR$^a$)OR$^a$, —NR$^a$C(=NR$^a$)N(R$^a$)$_2$, —OC(=O)R$^a$, —OC(=O)OR$^a$, —OC(=O)N(R$^a$)$_2$, —OC(=NR$^a$)R$^a$, —OC(=NR$^a$)OR$^a$, —OC(=NR$^a$)N(R$^a$)$_2$, —NR$^a$S(=O)$_2$R$^a$, —NR$^a$S(=O)$_2$OR$^a$, —NR$^a$S(=O)$_2$N(R$^a$)$_2$, —OS(=O)R$^a$, —OS(=O)OR$^a$, —OS(=O)N(R$^a$)$_2$, —S(=O)R$^a$, —S(=O)OR$^a$, —S(=O)N(R$^a$)$_2$, —OS(=O)$_2$R$^a$, —OS(=O)$_2$OR$^a$, —OS(=O)$_2$N(R$^a$)$_2$, —S(=O)$_2$R$^a$, —S(=O)$_2$OR$^a$, —S(=O)$_2$N(R$^a$)$_2$, or —P(=O)(R$^a$)$_2$; and each instance of $R^a$ is independently H, substituted or unsubstituted, $C_{1-6}$ alkyl, substituted or unsubstituted, $C_{2-6}$ alkenyl, substituted or unsubstituted, $C_{2-6}$ alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^a$ attached to a nitrogen atom are joined with the nitrogen atom to form substituted or unsubstituted heterocyclyl or substituted or unsubstituted heteroaryl.

2. A method of preparing an end-functionalized polymer of claim 1, or a tautomer, isotopically labeled polymer, or salt thereof, the method comprising reacting a living polymer of Formula (B):

(B)

with an enyne of Formula II:

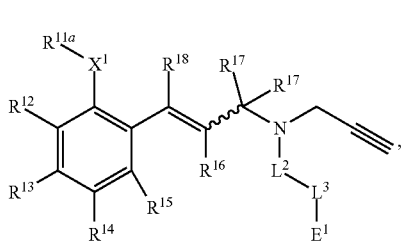

or a tautomer, isotopically labeled compound, salt, solvate, polymorph, or co-crystal thereof, wherein:
$X^1$ is S, O, Se, or a single bond;
$R^{11}$ is substituted or unsubstituted, $C_{1-18}$ alkyl;
each of $R^{12}$, $R^{13}$, $R^{14}$, and $R^{15}$ is independently H, halogen, substituted or unsubstituted, $C_{1-6}$ alkyl, —O-(substituted or unsubstituted, $C_{1-6}$ alkyl), substituted or unsubstituted carbocyclyl, or substituted or unsubstituted aryl;
$R^{16}$ is H or substituted or unsubstituted, $C_{1-6}$ alkyl;
$R^{18}$ is H or substituted or unsubstituted, $C_{1-6}$ alkyl;
each instance of $R^{17}$ is independently H or substituted or unsubstituted, $C_{1-6}$ alkyl;
or $R^{16}$ and one instance of $R^{17}$ are joined with their intervening atoms to form substituted or unsubstituted carbocyclyl or substituted or unsubstituted heterocyclyl;
$L^2$ is —C(=O)—, —S(=O)$_2$—, —S(=O)—, or a single bond;
$L^3$ is substituted or unsubstituted, $C_{1-1000}$ alkylene, substituted or unsubstituted, $C_{2-1000}$ alkenylene, substituted or unsubstituted, $C_{2-1000}$ alkynylene, substituted or unsubstituted, $C_{1-1000}$ heteroalkylene, substituted or unsubstituted, $C_{2-1000}$ heteroalkenylene, substituted or unsubstituted, $C_{2-1000}$ heteroalkynylene, or a single bond;
optionally wherein one or more backbone carbon atoms of the $C_{1-1000}$ alkylene, $C_{2-1000}$ alkenylene, $C_{2-1000}$ alkynylene, $C_{1-1000}$ heteroalkylene, $C_{2-1000}$ heteroalkenylene, or $C_{2-1000}$ heteroalkynylene are independently replaced with substituted or unsubstituted carbocyclylene, substituted or unsubstituted heterocyclylene, substituted or unsubstituted arylene, or substituted or unsubstituted heteroarylene, as valency permits; and
at least one of $L^2$ and $L^3$ is not a single bond.

3. The end-functionalized polymer or a tautomer, isotopically labeled polymer, or salt thereof of claim 1 prepared by a method comprising:
(a) metathesis polymerizing one or more types of monomers in the presence of a metathesis catalyst to form a living polymer of Formula (B):

wherein each instance of the monomers comprises one or more non-aromatic alkenyl and/or one or more alkynyl; and (b) reacting the living polymer with an enyne of Formula II:

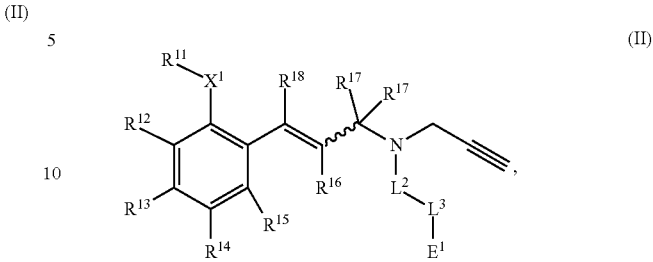

or a tautomer, isotopically labeled compound, salt, solvate, polymorph, or co-crystal thereof, wherein:
$X^1$ is S, O, Se, or a single bond;
$R^{11}$ is substituted or unsubstituted, $C_{1-18}$ alkyl;
each of $R^{12}$, $R^{13}$, $R^{14}$, and $R^{15}$ is independently H, halogen, substituted or unsubstituted, $C_{1-6}$ alkyl, —O-(substituted or unsubstituted, $C_{1-6}$ alkyl), substituted or unsubstituted carbocyclyl, or substituted or unsubstituted aryl;
$R^{16}$ is H or substituted or unsubstituted, $C_{1-6}$ alkyl;
$R^{18}$ is H or substituted or unsubstituted, $C_{1-6}$ alkyl;
each instance of $R^{17}$ is independently H or substituted or unsubstituted, $C_{1-6}$ alkyl;
or $R^{16}$ and one instance of $R^{17}$ are joined with their intervening atoms to form substituted or unsubstituted carbocyclyl or substituted or unsubstituted heterocyclyl;
$L^2$ is —C(=O)—, —S(=O)$_2$—, —S(=O)—, or a single bond;
$L^3$ is substituted or unsubstituted, $C_{1-1000}$ alkylene, substituted or unsubstituted, $C_{2-1000}$ alkenylene, substituted or unsubstituted, $C_{2-1000}$ alkynylene, substituted or unsubstituted, $C_{1-1000}$ heteroalkylene, substituted or unsubstituted, $C_{2-1000}$ heteroalkenylene, substituted or unsubstituted, $C_{2-1000}$ heteroalkynylene, or a single bond;
optionally wherein one or more backbone carbon atoms of the $C_{1-1000}$ alkylene, $C_2$-1000 alkenylene, $C_{2-1000}$ alkynylene, $C_{1-1000}$ heteroalkylene, $C_{2-1000}$ heteroalkenylene, or $C_{2-1000}$ heteroalkynylene are independently replaced with substituted or unsubstituted carbocyclylene, substituted or unsubstituted heterocyclylene, substituted or unsubstituted arylene, or substituted or unsubstituted heteroarylene, as valency permits; and
at least one of $L^2$ and $L^3$ is not a single bond.

4. The end-functionalized polymer of claim 1, or a tautomer, isotopically labeled polymer, or salt thereof, wherein $B^1$ is a brush polymer.

5. The end-functionalized polymer of claim 3, or a tautomer, isotopically labeled polymer, or salt thereof, wherein at least one instance of the monomers is of Formula (A):

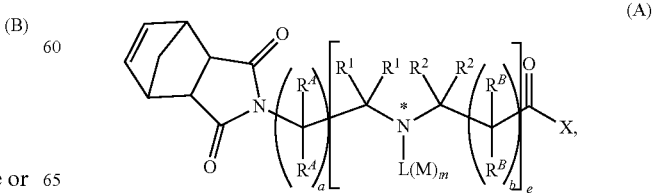

or a tautomer, isotopically labeled compound, salt, solvate, polymorph, or co-crystal thereof, wherein:

each instance of $R^A$ is independently H, halogen, or substituted or unsubstituted, $C_{1-6}$ alkyl;

each instance of a is independently an integer from 0 to 20, inclusive;

each instance of $R^1$ is independently H, halogen, or substituted or unsubstituted, $C_{1-6}$ alkyl, or two $R^1$ attached to the same carbon atom are taken together to form oxo;

each instance of $R^2$ is independently H, halogen, or substituted or unsubstituted, $C_{1-6}$ alkyl, or two $R^2$ attached to the same carbon atom are taken together to form oxo;

each instance of L is substituted or unsubstituted, $C_{1-1000}$ alkylene, substituted or unsubstituted, $C_{2-1000}$ alkenylene, substituted or unsubstituted, $C_{2-1000}$ alkynylene, substituted or unsubstituted, $C_{1-1000}$ heteroalkylene, substituted or unsubstituted, $C_{2-1000}$ heteroalkenylene, or substituted or unsubstituted, $C_{2-1000}$ heteroalkynylene;

optionally wherein one or more backbone carbon atoms of the $C_{1-1000}$ alkylene, $C_2$-1000 alkenylene, $C_{2-1000}$ alkynylene, $C_{1-1000}$ heteroalkylene, $C_{2-1000}$ heteroalkenylene, or $C_{2-1000}$ heteroalkynylene are independently replaced with substituted or unsubstituted carbocyclylene, substituted or unsubstituted heterocyclylene, substituted or unsubstituted arylene, or substituted or unsubstituted heteroarylene, as valency permits;

each instance of M is independently a pharmaceutical agent;

each instance of m is independently an integer from 1 to 10, inclusive;

each instance of RB is independently H, halogen, or substituted or unsubstituted, $C_{1-6}$ alkyl;

each instance of b is independently an integer from 0 to 20, inclusive;

each instance of e is independently an integer from 1 to 10, inclusive;

each instance of X is —ORC or —N($R^D$)$_2$;

each instance of $R^C$ is independently H, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, an oxygen protecting group, or a leaving group; and each instance of $R^D$ is independently H, substituted or unsubstituted, $C_{1-1000}$ alkyl, substituted or unsubstituted, $C_{2-1000}$ alkenyl, substituted or unsubstituted, $C_{2-1000}$ alkynyl, substituted or unsubstituted, $C_{1-1000}$ heteroalkyl, substituted or unsubstituted, $C_{2-1000}$ heteroalkenyl, substituted or unsubstituted, $C_{2-1000}$ heteroalkynyl, or a nitrogen protecting group, or two $R^D$ attached to the same nitrogen atom are taken together with the nitrogen atom to form substituted or unsubstituted heterocyclyl or substituted or unsubstituted heteroaryl.

6. The end-functionalized polymer of claim 4, or a tautomer, isotopically labeled polymer, or salt thereof, wherein $L^1$ is

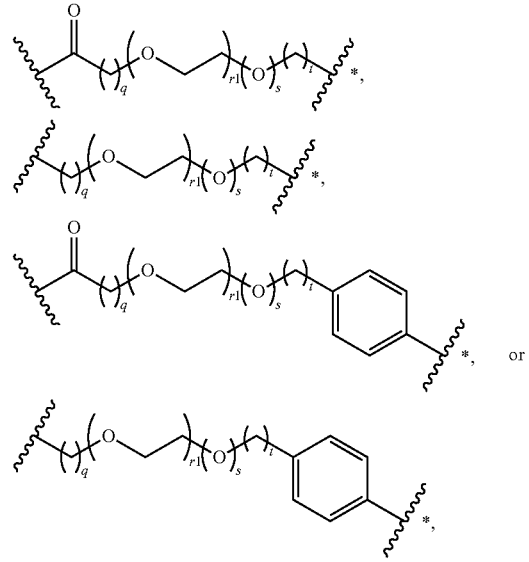

wherein:

each instance of q is independently an integer from 1 to 10, inclusive;

each instance of r1 is independently an integer from 2 to 40, inclusive;

each instance of s is independently 0 or 1;

each instance of t is independently an integer from 0 to 10, inclusive; and the attachment point marked with "*" is attached to $E^1$.

7. The end-functionalized polymer claim 4, or a tautomer, isotopically labeled polymer, or salt thereof, wherein $E^1$ is

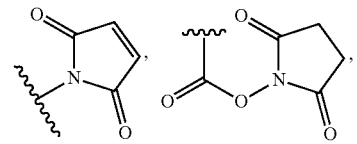

or —OS(=O)$_2$(substituted or unsubstituted phenyl or substituted or unsubstituted, $C_{1-6}$ alkyl).

8. The end-functionalized polymer of claim 4, or a tautomer, isotopically labeled polymer, or salt thereof, wherein $E^1$ is a first click-chemistry handle.

9. The end-functionalized polymer of claim 4, or a tautomer, isotopically labeled polymer, or salt thereof, wherein $E^1$ is —N$_3$.

10. The end-functionalized polymer of claim 4, or a tautomer, isotopically labeled polymer, or salt thereof, wherein $E^1$ is trans-cyclooctenyl.

11. The end-functionalized polymer of claim 4, or a tautomer, isotopically labeled polymer, or salt thereof, wherein $E^1$ is

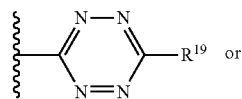

-continued

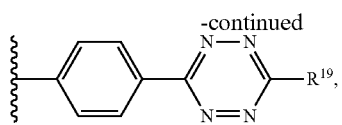

wherein R[19] is H, halogen, unsubstituted $C_{1-6}$ alkyl, or —O-(unsubstituted $C_{1-6}$ alkyl).

12. The end-functionalized polymer of claim 4, or a tautomer, isotopically labeled polymer, or salt thereof, wherein L[1] is unsubstituted $C_{1-1000}$ heteroalkylene.

13. The end-functionalized polymer of claim 12, or a tautomer, isotopically labeled polymer, or salt thereof, wherein E[1] is substituted or unsubstituted carbocyclyl.

14. The end-functionalized polymer of claim 12, or a tautomer, isotopically labeled polymer, or salt thereof, wherein E[1] is a thiophile or a first click-chemistry handle.

15. The end-functionalized polymer of claim 5, or a tautomer, isotopically labeled polymer, or salt thereof, wherein L[1] is unsubstituted $C_{1-1000}$ heteroalkylene.

16. The end-functionalized polymer of claim 15, or a tautomer, isotopically labeled polymer, or salt thereof, wherein E[1] is substituted or unsubstituted carbocyclyl.

17. The end-functionalized polymer of claim 15, or a tautomer, isotopically labeled polymer, or salt thereof, wherein E[1] is a thiophile or a first click-chemistry handle.

18. The end-functionalized polymer of claim 4, or a tautomer, isotopically labeled polymer, or salt thereof, wherein end-functionalized polymer is of the formula:

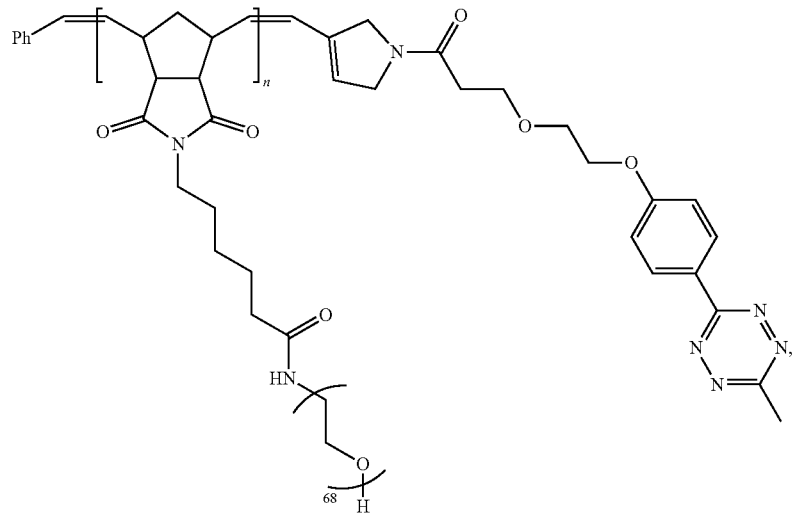

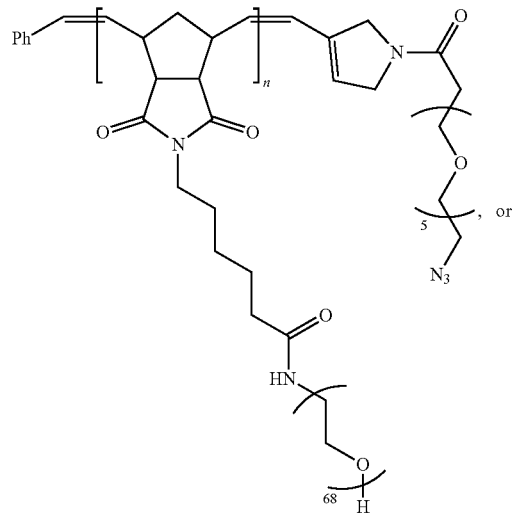

-continued
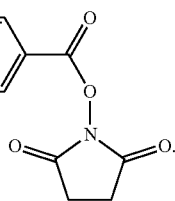
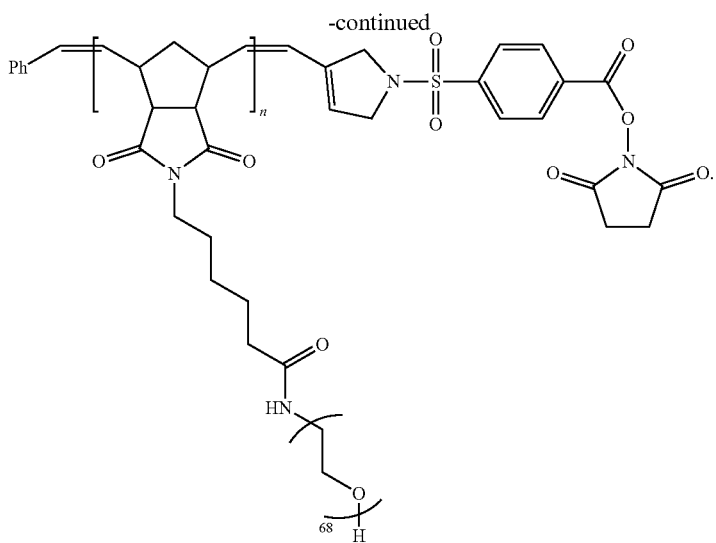
19. The end-functionalized polymer of claim 18, or a tautomer, isotopically labeled polymer, or salt thereof, wherein the end-functionalized polymer is of the formula:
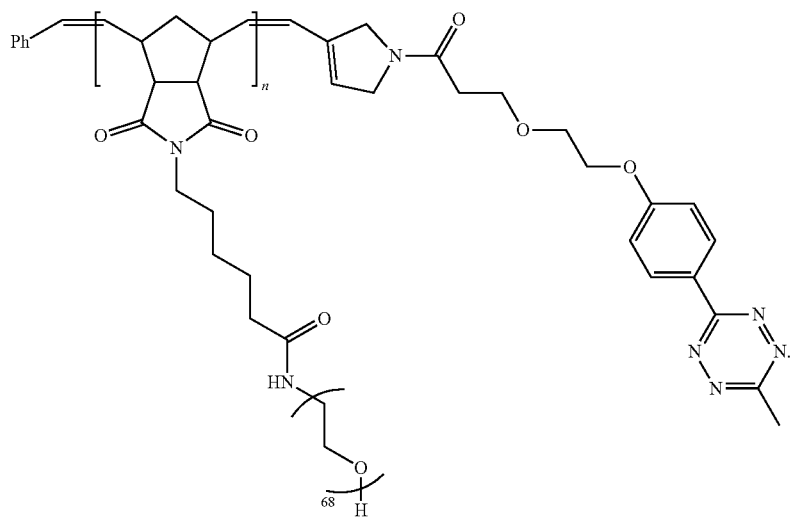
20. The end-functionalized polymer of claim 7, or a tautomer, isotopically labeled polymer, or salt thereof, wherein $L^1$ is
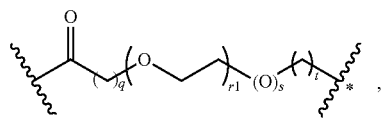
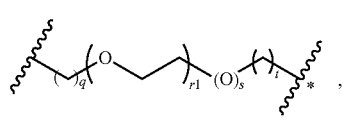
-continued
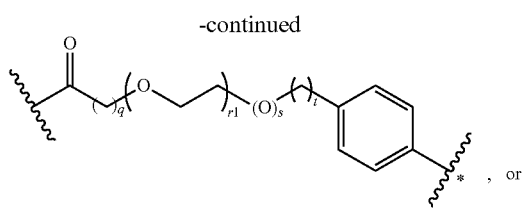, or
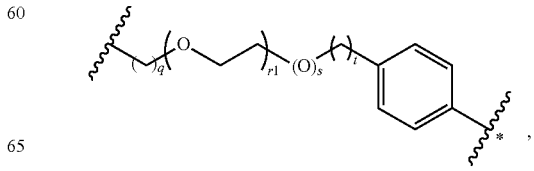

wherein:
  each instance of q is independently an integer from 1 to 10, inclusive;
  each instance of r1 is independently an integer from 2 to 40, inclusive;
  each instance of s is independently 0 or 1;
  each instance of t is independently an integer from 0 to 10, inclusive; and
  the attachment point marked with "*" is attached to $E^1$.

21. The end-functionalized polymer of claim 8, or a tautomer, isotopically labeled polymer, or salt thereof, wherein $L^1$ is

[chemical structures]

wherein:
  each instance of q is independently an integer from 1 to 10, inclusive;
  each instance of r1 is independently an integer from 2 to 40, inclusive;
  each instance of s is independently 0 or 1;
  each instance of t is independently an integer from 0 to 10, inclusive; and
  the attachment point marked with "*" is attached to $E^1$.

22. The end-functionalized polymer of claim 9, or a tautomer, isotopically labeled polymer, or salt thereof, wherein $L^1$ is

[chemical structures]

wherein:
  each instance of q is independently an integer from 1 to 10, inclusive;
  each instance of r1 is independently an integer from 2 to 40, inclusive;
  each instance of s is independently 0 or 1;
  each instance of t is independently an integer from 0 to 10, inclusive; and
  the attachment point marked with "*" is attached to $E^1$.

23. The end-functionalized polymer of claim 10, or a tautomer, isotopically labeled polymer, or salt thereof, wherein $L^1$ is

[chemical structures]

wherein:
  each instance of q is independently an integer from 1 to 10, inclusive;
  each instance of r1 is independently an integer from 2 to 40, inclusive;
  each instance of s is independently 0 or 1;
  each instance of t is independently an integer from 0 to 10, inclusive; and
  the attachment point marked with "*" is attached to $E^1$.

24. The end-functionalized polymer of claim 11, or a tautomer, isotopically labeled polymer, or salt thereof, wherein $L^1$ is

[chemical structure]

-continued

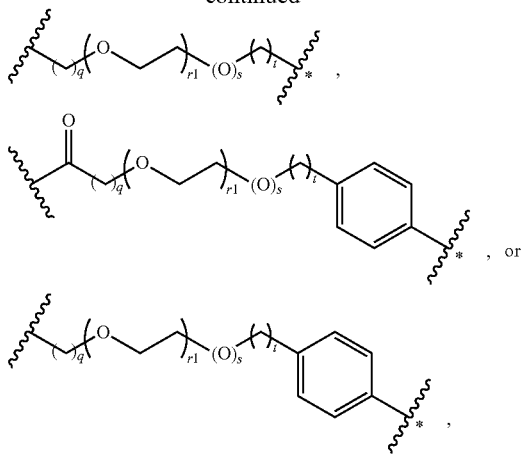

wherein:
each instance of q is independently an integer from 1 to 10, inclusive;
each instance of r1 is independently an integer from 2 to 40, inclusive;
each instance of s is independently 0 or 1;
each instance of t is independently an integer from 0 to 10, inclusive; and
the attachment point marked with "*" is attached to $E^1$.

25. The end-functionalized polymer of claim 5, or a tautomer, isotopically labeled polymer, or salt thereof, wherein $L^1$ is:

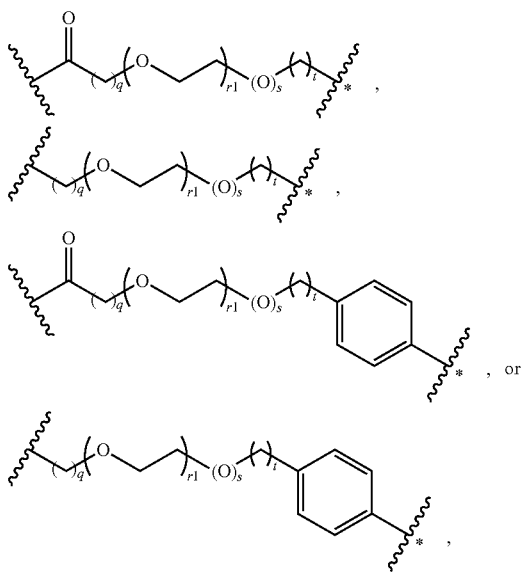

wherein:
each instance of q is independently an integer from 1 to 10, inclusive;
each instance of r1 is independently an integer from 2 to 40, inclusive;
each instance of s is independently 0 or 1;
each instance of t is independently an integer from 0 to 10, inclusive; and
the attachment point marked with "*" is attached to $E^1$.

26. The end-functionalized polymer of claim 25, or a tautomer, isotopically labeled polymer, or salt thereof, wherein $E^1$ is

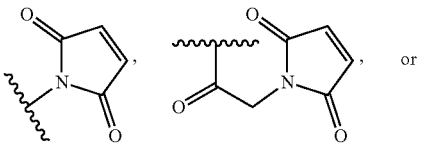 [SMILES: *N1C(=O)C=CC1=O ; "," ; *C(=O)CN1C(=O)C=CC1=O ; "," ; "or"]

—OS(=O)$_2$(substituted or unsubstituted phenyl or substituted or unsubstituted, $C_{1-6}$ alkyl).

27. The end-functionalized polymer of claim 25, or a tautomer, isotopically labeled polymer, or salt thereof, wherein $E^1$ is a first click-chemistry handle.

28. The end-functionalized polymer of claim 25, or a tautomer, isotopically labeled polymer, or salt thereof, wherein $E^1$ is $-N_3$.

29. The end-functionalized polymer of claim 25, or a tautomer, isotopically labeled polymer, or salt thereof, wherein $E^1$ is trans-cyclooctenyl.

30. The end-functionalized polymer of claim 25, or a tautomer, isotopically labeled polymer, or salt thereof, wherein $E^1$ is

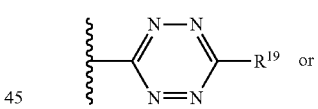

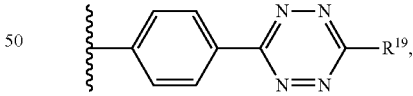

wherein $R^{19}$ is H, halogen, unsubstituted $C_{1-6}$ alkyl, or —O—(unsubstituted $C_{1-6}$ alkyl).

* * * * *

UNITED STATES PATENT AND TRADEMARK OFFICE
CERTIFICATE OF CORRECTION

PATENT NO. : 12,084,415 B2
APPLICATION NO. : 17/970533
DATED : September 10, 2024
INVENTOR(S) : Jeremiah A. Johnson et al.

It is certified that error appears in the above-identified patent and that said Letters Patent is hereby corrected as shown below:

In the Claims

In Claim 2, at Column 135, Lines 5-12, the formula:

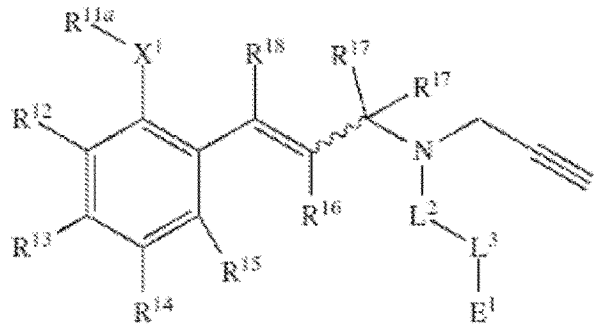

Should be replaced with the formula:

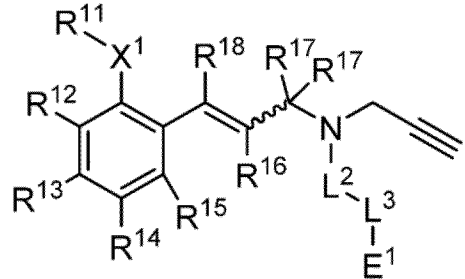

In Claim 26, at Column 146, Lines 17-22, the formula:

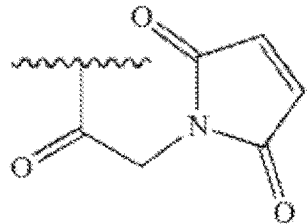

Signed and Sealed this
Second Day of September, 2025

Coke Morgan Stewart
*Acting Director of the United States Patent and Trademark Office*

CERTIFICATE OF CORRECTION (continued)
U.S. Pat. No. 12,084,415 B2

Should be replaced with the formula: